US008445645B2

(12) United States Patent
Stavenhagen et al.

(10) Patent No.: US 8,445,645 B2
(45) Date of Patent: *May 21, 2013

(54) IDENTIFICATION AND ENGINEERING OF ANTIBODIES WITH VARIANT FC REGIONS AND METHODS OF USING SAME

(75) Inventors: Jeffrey Stavenhagen, Brookville, MD (US); Sujata Vijh, Gaithersburg, MD (US); Christopher Rankin, Clarksburg, MD (US); Sergey Gorlatov, Gaithersburg, MD (US); Ling Huang, Gaithersburg, MD (US)

(73) Assignee: MacroGenics, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/158,169

(22) Filed: Jun. 10, 2011

(65) Prior Publication Data
US 2011/0243941 A1  Oct. 6, 2011

Related U.S. Application Data

(63) Continuation of application No. 10/902,588, filed on Jul. 28, 2004, now Pat. No. 7,960,512, which is a continuation-in-part of application No. 10/754,922, filed on Jan. 9, 2004, now Pat. No. 7,355,008.

(60) Provisional application No. 60/439,498, filed on Jan. 9, 2003, provisional application No. 60/456,041, filed on Mar. 19, 2003, provisional application No. 60/514,549, filed on Oct. 23, 2003, provisional application No. 60/587,251, filed on Jul. 12, 2004.

(51) Int. Cl.
*C07K 16/00* (2006.01)
*C12P 21/08* (2006.01)
*A61K 39/395* (2006.01)
*A61K 39/40* (2006.01)

(52) U.S. Cl.
USPC .......... 530/387.1; 530/387.3; 530/388.1; 530/388.22; 530/388.7; 424/130.1; 424/133.1; 424/134.1; 424/141.1; 424/144.1; 424/152.1; 424/153.1

(58) Field of Classification Search
None
See application file for complete search history.

(56) References Cited

U.S. PATENT DOCUMENTS

| | | | | |
|---|---|---|---|---|
| 6,737,056 | B1 * | 5/2004 | Presta ..................... | 424/133.1 |
| 7,960,512 | B2 * | 6/2011 | Stavenhagen et al. ..... | 530/387.1 |
| 8,187,593 | B2 * | 5/2012 | Koenig et al. ............. | 424/130.1 |
| 8,193,318 | B2 * | 6/2012 | Koenig et al. ............. | 530/387.1 |

FOREIGN PATENT DOCUMENTS
WO    WO 03/074679    *  9/2003

OTHER PUBLICATIONS

Lund et al. The Journal of Immunology 1996, 157:4963-4969.*

* cited by examiner

*Primary Examiner* — Chun Dahle
(74) *Attorney, Agent, or Firm* — William C. Schrot; The Auerbach Law Firm, LLC

(57) ABSTRACT

The present invention relates to molecules, particularly polypeptides, more particularly immunoglobulins (e.g., antibodies), comprising a variant Fc region, wherein said variant Fc region comprises at least one amino acid modification relative to a wild-type Fc region, which variant Fc region binds FcγRIIIA and/or FcγRIIA with a greater affinity, relative to a comparable molecule comprising the wild-type Fc region. The molecules of the invention are particularly useful in preventing, treating, or ameliorating one or more symptoms associated with a disease, disorder, or infection. The molecules of the invention are particularly useful for the treatment or prevention of a disease or disorder where an enhanced efficacy of effector cell function (e.g., ADCC) mediated by FcγR is desired, e.g., cancer, infectious disease, and in enhancing the therapeutic efficacy of therapeutic antibodies the effect of which is mediated by ADCC.

8 Claims, 64 Drawing Sheets

Figure 4A:
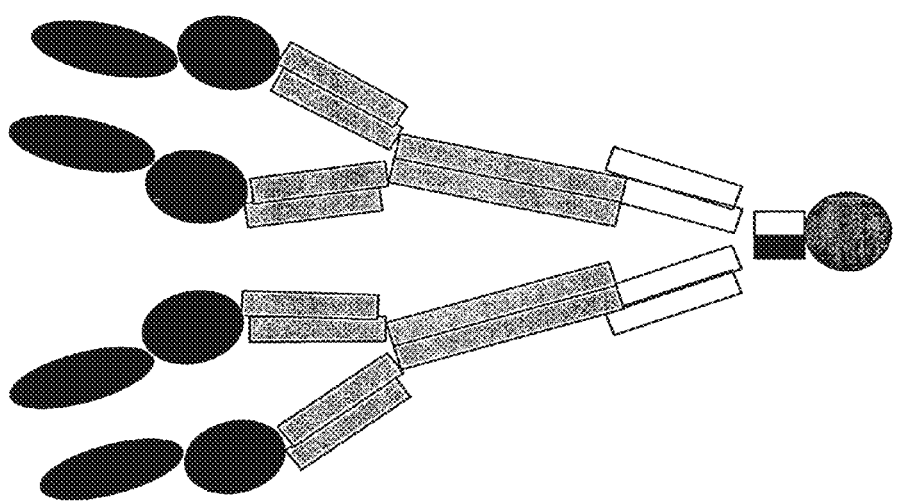

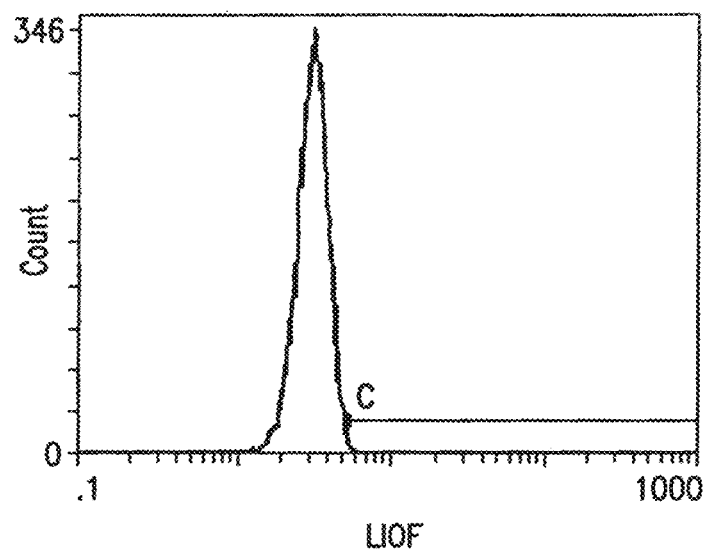
FIG. 4B-A
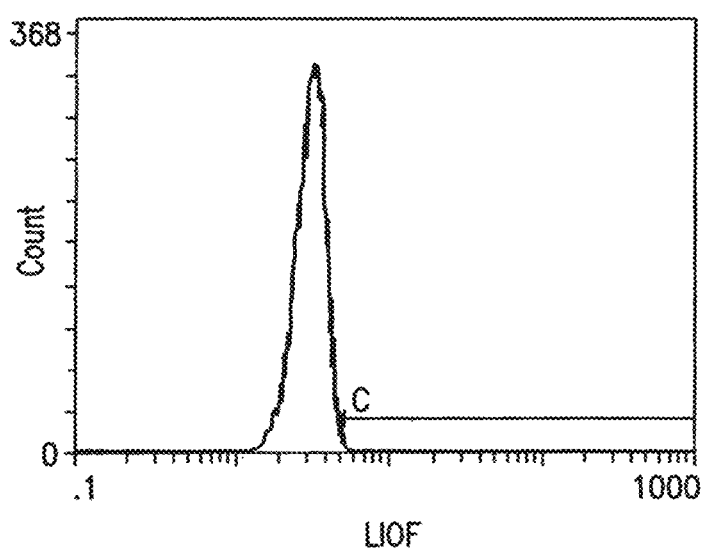
FIG. 4B-B

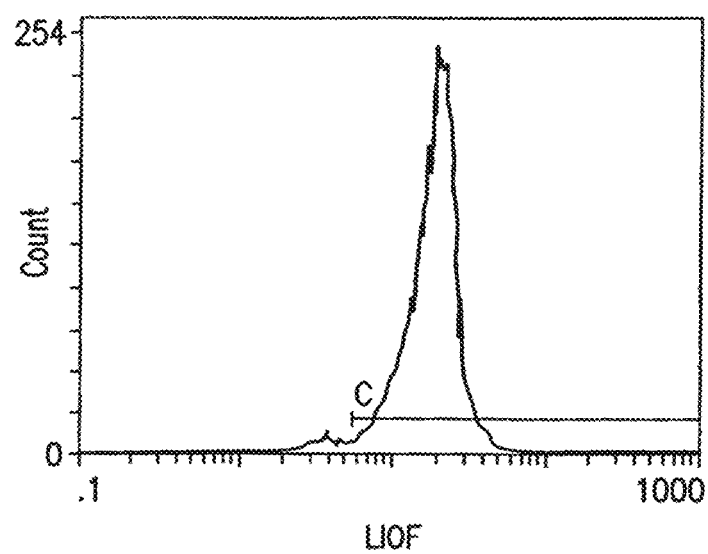
FIG. 4B-C
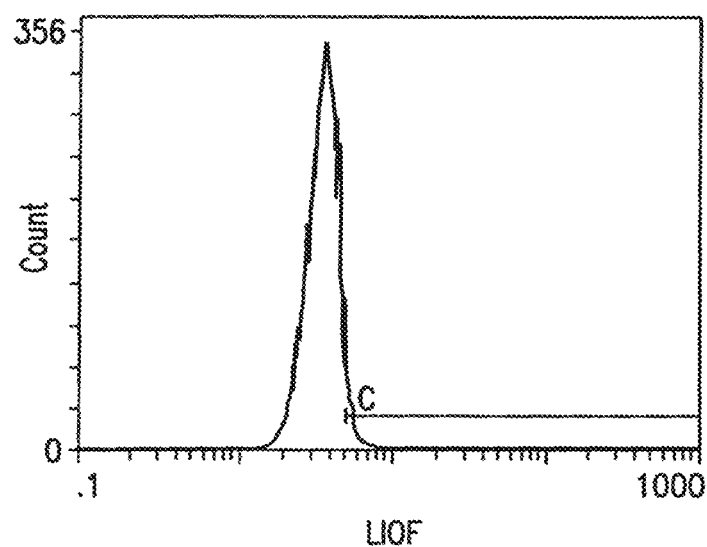
FIG. 4B-D

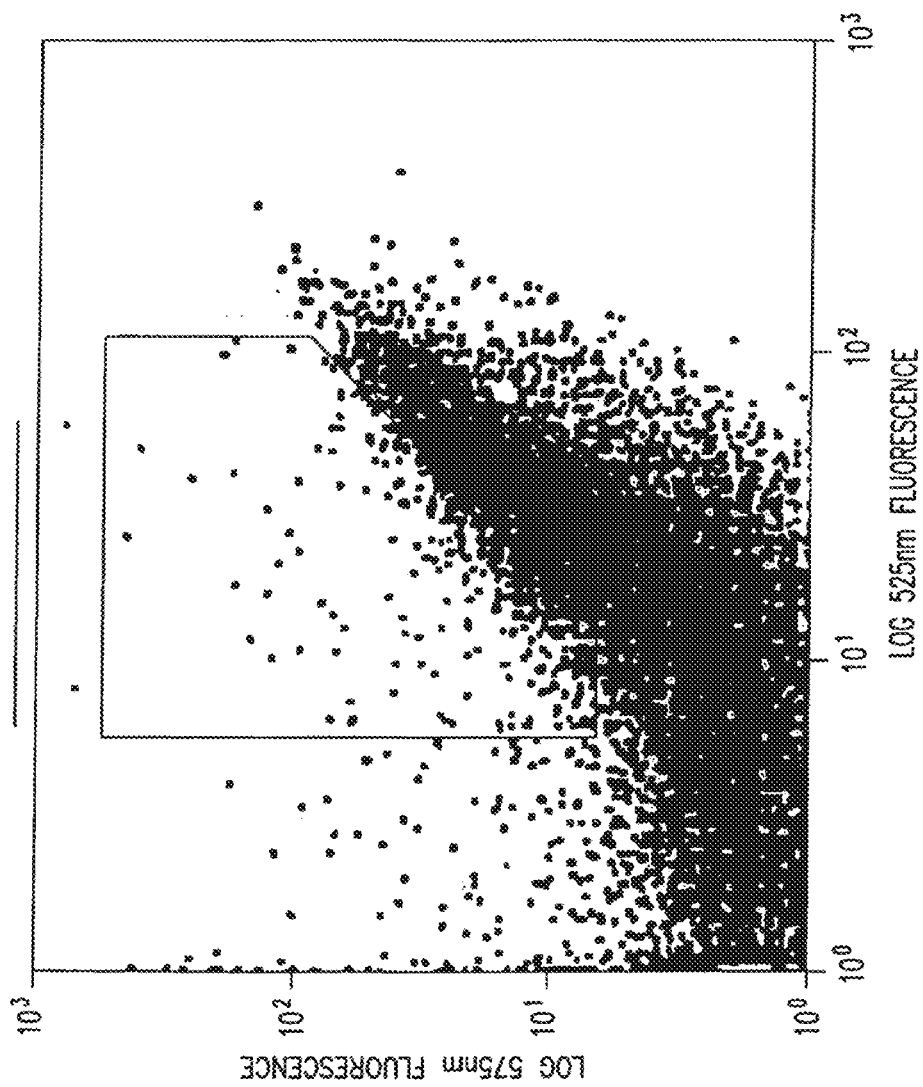

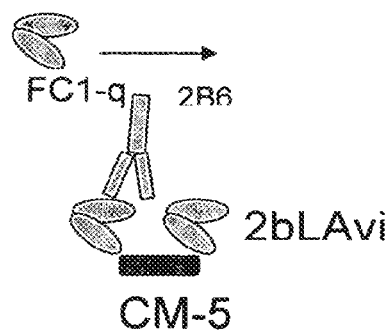
FIG. 34A
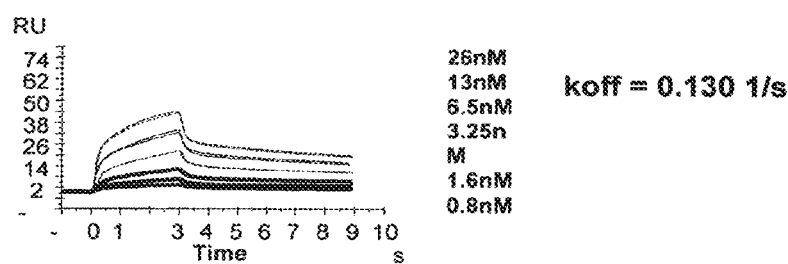
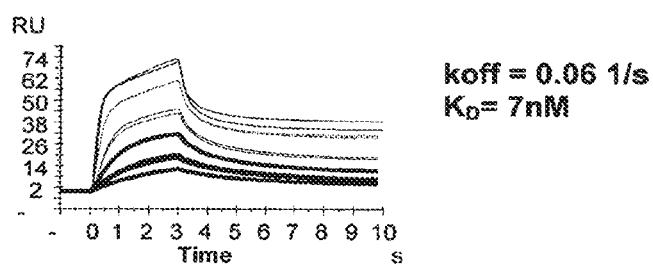
FIG. 34B

IDENTIFICATION AND ENGINEERING OF ANTIBODIES WITH VARIANT FC REGIONS AND METHODS OF USING SAME

CROSS REFERENCE TO RELATED APPLICATIONS

This application is a continuation of U.S. application Ser. No. 10/902,588, filed Jul. 28, 2004, which issued as U.S. Pat. No. 7,960,512, which application is a continuation-in-part of U.S. application Ser. No. 10/754,922, filed Jan. 9, 2004, which issued as U.S. Pat. No. 7,355,008, which is based on and claims priority to U.S. Provisional Application Nos. 60/439,498; 60/456,041; 60/514,549; and 60/587,251, filed on Jan. 9, 2003; Mar. 19, 2003, Oct. 23, 2003, and Jul. 12, 2004, respectively, each of which is incorporated herein by reference in its entirety and to which priority is claimed.

FIELD OF THE INVENTION

The present invention relates to molecules, particularly polypeptides, more particularly immunoglobulins (e.g., antibodies), comprising a variant Fc region, wherein said variant Fc region comprises at least one amino acid modification relative to a wild-type Fc region, which variant Fc region binds FcγRIIIA and/or FcγRIIA with a greater affinity, relative to a comparable molecule comprising the wild-type Fc region. The molecules of the invention are particularly useful in preventing, treating, or ameliorating one or more symptoms associated with a disease, disorder, or infection. The molecules of the invention are particularly useful for the treatment or prevention of a disease or disorder where an enhanced efficacy of effector cell function (e.g., ADCC) mediated by FcγR is desired, e.g., cancer, infectious disease, and in enhancing the therapeutic efficacy of therapeutic antibodies the effect of which is mediated by ADCC.

BACKGROUND OF THE INVENTION 1.1 Fc Receptors and their Roles in the Immune System The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the α chain of the Fc receptor. Fc receptors are defined by their specificity for immunoglobulin subtypes. Fc receptors for IgG are referred to as FcγR, for IgE as FeR, and for IgA as FcαR. Different accessory cells bear Fc receptors for antibodies of different isotype, and the isotype of the antibody determines which accessory cells will be engaged in a given response (reviewed by Ravetch J. V. et al. 1991, *Annu. Rev. Immunol.* 9: 457-92; Gerber J. S. et al. 2001 *Microbes and Infection*, 3: 131-139; Billadeau D. D. et al. 2002, *The Journal of Clinical Investigation*, 2(109): 161-1681; Ravetch J. V. et al. 2000, *Science*, 290: 84-89; Ravetch J. V. et al., 2001 *Annu. Rev. Immunol.* 19:275-90; Ravetch J. V. 1994, *Cell*, 78(4): 553-60). The different Fc receptors, the cells that express them, and their isotype specificity is summarized in Table 1 (adapted from *Immunobiology: The Immune System in Health and Disease*, 4$^{th}$ ed. 1999, Elsevier Science Ltd/Garland Publishing, New York).

Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγRIII(CD16). The three receptors are encoded by distinct genes; however, the extensive homology between the three family members suggest they arose from a common progenitor perhaps by gene duplication.

FcγRII(CD32)

FcγRII proteins are 40 KDa integral membrane glycoproteins which bind only the complexed IgG due to a low affinity for monomeric Ig ($10^6$ M$^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRII-A and FcγRII-B create two functionally heterogenous responses to receptor ligation. The fundamental difference is that the A isoform initiates intracellular signaling leading to cell activation such as phagocytosis and respiratory burst, whereas the β isoform initiates inhibitory signals, e.g., inhibiting B-cell activation.

Signaling Through FcγRs

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI$_3$K). Cellular activation leads to release of proinflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When colligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR-mediated tyrosine kinase activation, consequently preventing the influx of intracellular $Ca^{++}$. Thus crosslinking of FcγRIIB dampens the activating response to FcγR ligation and inhibits cellular responsiveness. B cell activation, B cell proliferation and antibody secretion is thus aborted.

therapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single

TABLE 1

Receptors for the Fc Regions of Immunoglobulin Isotypes

| | Receptor | | | | | | |
|---|---|---|---|---|---|---|---|
| | FcγRI (CD64) | FcγRII-A (CD32) | FcγRII-B2 (CD32) | FcγRII-B1 (CD32) | FcγRIII (CD16) | FcεRI | FcαRI (CD89) |
| Binding | IgG1 $10^8 M^{-1}$ | IgG1 $2 \times 10^6 M^{-1}$ | IgG1 $2 \times 10^6 M^{-1}$ | IgG1 $2 \times 10^6 M^{-1}$ | IgG1 $5 \times 10^5 M^{-1}$ | IgE $1010 M^{-1}$ | IgA1, IgA2 $10^7 M^{-1}$ |
| Cell Type | Macrophages Neutrophils Eosinophils Dendritic cells | Macrophages Neutrophils Eosinophils Dendritic cells Platelets Langerhan cells | Macrophages Neutrophils Eosinophils | B cells Mast cells | NK cells Eosinophil Macrophages Neutrophils Mast Cells | Mast cells Eosinophil Basophils | Macrophages Neutrophils Eosinophils |
| Effect of Ligation | Uptake Stimulation Activation of respiratory burst Induction of killing | Uptake Granule release | Uptake Inhibition of Stimulation | No uptake Inhibition of Stimulation | Induction of Killing | Secretion of granules | Uptake Induction of killing |

1.2 Diseases of Relevance 1.2.1 Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading cause of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

A cure for cancer has yet to be found. Current treatment options, such as surgery, chemotherapy and radiation treatment, are oftentimes either ineffective or present serious side effects.

Cancer Therapy

Currently, cancer therapy may involve surgery, chemotherapy, hormonal therapy and/or radiation treatment to eradicate neoplastic cells in a patient (See, for example, Stockdale, 1998, "Principles of Cancer Patient Management", in *Scientific American: Medicine*, vol. 3, Rubenstein and Federman, eds., Chapter 12, Section IV). Recently, cancer therapy could also involve biological therapy or immunoagent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (See, for example, Gilman et al., Goodman and Gilman's: *The Pharmacological Basis of Therapeutics*, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Major efforts have been directed at harnessing the specificity of the immune response, for example, hybridoma technology has enabled the development of tumor selective monoclonal antibodies (See Green M. C. et al., 2000 *Cancer Treat Rev.*, 26: 269-286; Weiner L M, 1999 *Semin Oncol.* 26 (suppl. 14):43-51), and in the past few years, the Food and Drug Administration has approved the first MAbs for cancer therapy: Rituxin (anti-CD20) for non-Hodgkin's Lymphoma and Herceptin [anti-(c-erb-2/HER-2)] for metastatic breast cancer (Suzanne A. Eccles, 2001, *Breast Cancer Res.*, 3: 86-90). However, the potency of antibody effector function, e.g., to mediate antibody dependent cellular cytotoxicity ("ADCC") is an obstacle to such treatment. Methods to improve the efficacy of such immunotherapy are thus needed.

1.2.2 Inflammatory Diseases and Autoimmune Diseases

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T-cell stimulation, cytokine secretion, synovial cell activation, and joint destruction. The disease has a major impact on both the individual and society, causing significant pain, impaired function and disability, as well as costing millions of dollars in healthcare expenses and lost wages. (See, for example, the NIH website and the NIAID website).

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors for tumor necrosis factor (TNF)-α have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

1.2.3 Infectious Diseases

Infectious agents that cause disease fall into five groups: viruses, bacteria, fungi, protozoa, and helminths (worms). The remarkable variety of these pathogens has caused the natural selection of two crucial features of adaptive immunity. First, the advantage of being able to recognize a wide range of different pathogens has driven the development of receptors on B and T cells of equal or greater diversity. Second, the distinct habitats and life cycles of pathogens have to be countered by a range of distinct effector mechanisms. The characteristic features of each pathogen are its mode of transmission, its mechanism of replication, its pathogenesis or the means by which it causes disease, and the response it elicits.

The record of human suffering and death caused by smallpox, cholera, typhus, dysentery, malaria, etc. establishes the eminence of the infectious diseases. Despite the outstanding successes in control afforded by improved sanitation, immunization, and antimicrobial therapy, the infectious diseases continue to be a common and significant problem of modern medicine. The most common disease of mankind, the common cold, is an infectious disease, as is the feared modern disease AIDS. Some chronic neurological diseases that were thought formerly to be degenerative diseases have proven to be infectious. There is little doubt that the future will continue to reveal the infectious diseases as major medical problems.

An enormous number of human and animal diseases result from virulent and opportunistic infections from any of the above mentioned infectious agents (see Belshe (Ed.) 1984 *Textbook of Human Virology*, PSG Publishing, Littleton, Mass.).

One category of infectious diseases are viral infections for example. Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, 18$^{th}$ Ed., W.B. Saunders Co., Philadelphia, pp. 1750-1753). Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya et al., 1991, *FASEB J.* 5:2369-2381, discussing HIV). However, a common drawback associated with using of many current anti-viral drugs is their deleterious side effects, such as toxicity to the host or resistance by certain viral strains.

2. SUMMARY OF THE INVENTION

The present invention is based, in part, on the identification of mutant human IgG1 heavy chain Fc regions, with altered affinities for FcγR receptors (e.g., activating FcγRs, inhibitory FcγRs), using a yeast display system. In vivo animal modeling and clinical experiments indicate that the Fc region plays an essential role in determining the outcome of monoclonal antibody therapy. Current approaches to optimize the Fc region function (e.g., antibody-dependent cell mediated cytotoxicity (ADCC), complement dependent cytotoxicity (CDC) activity) in therapeutic monoclonal antibodies and soluble polypeptides fused to Fc regions have focused on a limited number of single amino acid changes based on structural analysis and/or computer aided designs. Alternative approaches in engineering Fc regions have focused on the glycosylation of the Fc region to optimize Fc region function. The present invention is based, in part, on selecting possible mutants for alteration in one or more Fc functional activities, such as but not limited to ADCC and CDC, from an unbiased library of Fc variants. The present invention provides methods for engineering Fc regions and identification and screening of novel Fc variants outside the expected regions identified by structural studies. Expected regions as used herein refer to those regions that based on structural and/or biochemical studies are in contact with an Fc ligand.

The present invention provides a discovery platform for the identification of Fc variants with improvement in one or more Fc effector function by combining cell based functional assays and combinatorial library construction with state of the art automation. The present invention assembles complete combinatorial libraries by saturating regions of interest within the Fc with modifications that cover all possible amino acid changes. Combinatorial libraries will be tested using a set of binding and functional assays to select mutants based on improved biological function.

Accordingly, the invention relates to molecules, preferably polypeptides, and more preferably immunoglobulins (e.g., antibodies), comprising a variant Fc region, having one or more amino acid modifications (e.g., substitutions, but also including insertions or deletions) in one or more regions, which modifications alter, e.g., increase or decrease, the affinity of the variant Fc region for an FcγR. Preferably, said one or more amino acid modification increases the affinity of the variant Fc region for FcγRIIIA and/or FcγRIIA. In a preferred embodiment, the molecules of the invention further specifically bind FcγRIIB (via the Fc region) with a lower affinity than a comparable molecule (i.e., having the same amino acid sequence as the molecule of the invention except for the one or more amino acid modifications in the Fc region) comprising the wild-type Fc region binds FcγRIIB. In some embodiments, the invention encompasses molecules with variant Fc regions, having one or more amino acid modifications, which modifications increase the affinity of the variant Fc region for FcγRIIIA and/or FcγRIIA and enhance the affinity of the variant Fc region for FcγRIIB relative to a comparable molecule with a wild type Fc region. In other embodiments, the invention encompasses molecules with variant Fc regions, having one or more amino acid modifications, which modifications increase the affinity of the variant Fc region for FcγRIIIA and/or FcγRIIA but do not alter the affinity of the variant Fc regions for FcγRIIB relative to a comparable molecule with a wild type Fc region. A preferred embodiment is a variant Fc region that has enhanced affinity for FcγRIIIA and FcγRIIA but reduced affinity for FcγRIIB relative to a comparable molecule with a wild type Fc region.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably, the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:49634969; Armour et al., 1999, Eur J Immunol 29:2613-2624; Idusogie et al, 2000, J Immunol 164:41784184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. No. 5,624,821; U.S. Pat. No. 5,885,573; U.S. Pat. No. 6,194,551; PCT WO 00/42072; PCT WO 99/58572; each of which is incorporated herein by reference in its entirety.

The invention encompasses molecules that are homodimers or heterodimers of Fc regions. Heterodimers comprising Fc regions refer to molecules where the two Fc chains have the same or different sequences. In some embodiments, in the heterodimeric molecules comprising variant Fc regions, each chain has one or more different modifications from the other chain. In other embodiments, in the heterodimeric molecules comprising variant Fc regions, one chain contains the wild-type Fc region and the other chains comprises one or more modifications. Methods of engineering heterodimeric Fc containing molecules are known in the art and encompassed within the invention.

In some embodiments, the invention encompasses molecules comprising a variant Fc region, wherein said variant Fc region comprises at least one amino acid modification relative to a wild type Fc region, which variant Fc region does not bind any FcγR or binds with a reduced affinity, relative to a comparable molecule comprising the wild-type Fc region, as determined by standard assays (e.g., in vitro assays) known to one skilled in the art. In a specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγIIIA. In another specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIA. In yet another embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIB.

The affinities and binding properties of the molecules of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 5.2.1). Preferably, the binding properties of the molecules of the invention are also characterized by in vitro functional assays for determining one or more FcγR mediator effector cell functions (See Section 5.2.6). In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In a specific embodiment, the invention encompasses a molecule comprising a variant Fc region, wherein said variant Fc region comprises at least one amino acid modification relative to a wild-type Fc region, such that said polypeptide specifically binds FcγRIIIA with a greater affinity than a comparable molecule comprising the wild-type Fc region binds FcγRIIIA, provided that said variant Fc region does not solely have a substitution at any one of positions 329, 331, or 332, and do not include or are not solely substitution with any one of: alanine at any of positions 256, 290, 298, 312, 333, 334, 359, 360, 326, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334; a lysine at position 335.

In another specific embodiment, the invention encompasses a molecule comprising a variant Fc region, wherein said variant Fc region comprises at least one amino acid modification relative to a wild-type Fc region, such that said polypeptide specifically binds FcγRIIA with a greater affinity than a comparable molecule comprising the wild-type Fc region binds FcγRIIA, provided that the one or more amino acid modifications do not include or are not solely substitution with an alanine at any of positions 256, 290, 326, 255, 258, 267, 272, 276, 280, 283, 285, 286, 331, 337, 268, 272, or 430; an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301.

In a preferred specific embodiment, the invention encompasses a molecule comprising a variant Fc region, wherein said variant Fc region comprises at least one amino acid modification relative to a wild-type Fc region, such that said molecule has an altered affinity for an FcγR, provided that said variant Fc region does not have a substitution at positions that make a direct contact with FcγR based on crystallographic and structural analysis of Fc-FcγR interactions such as those disclosed by Sondermann et al., (2000 *Nature*, 406: 267-273, which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that does not make a direct contact with an FcγR based on structural and crystallographic analysis, e.g., is not within the Fc-FcγR binding site.

In another preferred embodiment, the invention encompasses a molecule comprising a variant Fc region, wherein said variant Fc region comprises at least one amino acid modification relative to a wild-type Fc region, such that said molecule binds an FcγR with an altered affinity relative to a molecule comprising a wild-type Fc region, provided that said at least one amino acid modification do not include or are not solely a substitution at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439. In a specific embodiment, the invention encompasses a molecule comprising a variant Fc region, wherein said variant Fc region comprises at least one amino acid modification relative to a wild-type Fc region, such that said molecule binds an FcγR with an altered affinity relative to a molecule comprising a wild-type Fc region, provided that said variant Fc region does not include or are not solely a substitution at any of positions 255, 258, 267, 269, 270, 276, 278, 280, 283, 285, 289, 292, 293, 294, 295, 296, 300, 303, 305, 307, 309, 322, 329, 332, 331, 337, 338, 340, 373, 376, 416, 419, 434, 435, 437, 438, 439 and does not have an alanine at any of positions 256, 290, 298, 312, 333, 334, 359, 360 326, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334; a lysine at position 335 an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301.

In a specific embodiment, the invention encompasses a molecule comprising a variant Fc region, wherein said variant Fc region does not include or are not solely a substitution at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and does not have a histidine, glutamine, or tyrosine at position 280; a serine, glycine, threonine or tyrosine at position 290, a leucine or isoleucine at position 300; an asparagine at position 294, a proline at position 296; a proline, asparagine, aspartic acid, or valine at position 298; a lysine at position 295. In yet another preferred embodiment, the invention encompasses a molecule comprising a variant Fc region, wherein said variant Fc region comprises at least one amino acid modification relative to a wild-type Fc region, such that said molecule binds an FcγR with a reduced affinity relative to a molecule comprising a wild-type Fc region provided that said variant Fc region does not have or are not solely have a substitution at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439. In yet another preferred embodiment, the invention encompasses a molecule comprising a variant Fc region, wherein said variant Fc region comprises at least one amino acid modification relative to a wild-type Fc region, such that said molecule binds an FcγR with an enhanced affinity relative to a molecule comprising a wild-type Fc region provided that said variant Fc region does not have or are not solely a substitution at any of positions 280, 283, 285, 286, 290, 294, 295, 298, 300, 301, 305, 307, 309, 312, 315, 331, 333, 334, 337, 340, 360, 378, 398, or 430.

In a specific embodiment, the invention encompasses a molecule comprising a variant Fc region, wherein said variant Fc region does not include a substitution or does not solely have a substitution at any of positions 330, 243, 247, 298, 241, 240, 244, 263, 262, 235, 269, or 328 and does not have a leucine at position 243, an asparagine at position 298, a leucine at position 241, and isoleucine or an alanine at position 240, a histidine at position 244, a valine at position 330, or an isoleucine at position 328.

In a specific embodiment, molecules of the invention comprise a variant Fc region having one or more amino acid modifications (e.g., substitutions), which modifications increase the affinity of the variant Fc region for FcγRIIIA and/or FcγRIIA by at least 2-fold, relative to a comparable molecule comprising a wild-type Fc region. In certain embodiments, molecules of the invention comprise a variant Fc region having one or more amino acid modifications (e.g., substitutions), which modifications increase the affinity of the variant Fc region for FcγRIIIA and/or FcγRIIA by greater than 2-fold, at least 4-fold, at least 5-fold, at least 6-fold, at least 8-fold, or at least 10-fold relative to a comparable molecule comprising a wild-type Fc region. In other embodiments of the invention, molecules of the invention comprising a variant Fc region specifically bind FcγRIIIA and/or FcγRIIA with at least 65%, at least 75%, at least 85%, at least 95%, at least 100%, at least 150%, at least 200% greater affinity relative to a molecule comprising a wild-type Fc region. Such measurements are preferably in vitro assays.

The invention encompasses molecules with altered affinities for the activating and/or inhibitory Fcγ receptors. In particular, the invention contemplates molecules with variant Fc regions, having one or more amino acid modifications, which modifications increase the affinity of the variant Fc region for FcγRIIB but decrease the affinity of the variant Fc region for FcγRIIIA and/or FcγRIIA, relative to a comparable molecule with a wild-type Fc region. In other embodiments, the invention encompasses molecules with variant Fc regions, having one or more amino acid modifications, which modifications decrease the affinity of the variant Fc region for FcγRIIB and also decrease the affinity of the variant Fc regions for FcγRIIIA and/or FcγRIIA relative to a comparable molecule with a wild-type Fc region. In yet other embodiments, the invention encompasses molecules with variant Fc regions, which modifications decrease the affinity of the variant Fc region for FcγRIIIA and/or FcγRIIA but do not alter the affinity of the variant Fc region for FcγRIIB relative to a comparable molecule with a wild-type Fc region. In yet other embodiments, the invention encompasses molecules with variant Fc regions, which modifications increase the affinity of the variant Fc region for FcγRIIIA and/or FcγRIIA but reduce the affinity of the variant Fc region for FcγRIIB relative to a comparable molecule with a wild-type Fc region.

In a specific embodiment, the molecules of the invention comprise a variant Fc region, having one or more amino acid modifications (e.g., substitutions), which one or more modifications increase the affinity of the variant Fc region for FcγRIIIA and decrease the affinity of the variant Fc region for FcγRIIB, relative to a comparable molecule comprising a wild-type Fc region which binds FcγRIIIA and FcγRIIB with wild-type affinity. In a certain embodiment, the one or more amino acid modifications are not a substitution with alanine at any of positions 256, 298, 333, or 334.

In another specific embodiment, the molecules of the invention comprise a variant Fc region, having one or more amino acid modifications (e.g., substitutions), which one or more modifications increase the affinity of the variant Fc region for FcγRIIA and decrease the affinity of the variant Fc region for FcγRIIB, relative to a comparable molecule comprising a wild-type Fc region which binds FcγRIIA and FcγRIIB with wild-type affinity. In a certain embodiment, the one or more amino acid modifications is not a substitution with arginine at position 320.

In most preferred embodiments, the molecules of the invention with altered affinities for activating and/or inhibitory receptors having variant Fc regions, have one or more amino acid modifications, wherein said one or more amino acid modification is a substitution at position 288 with asparagine, at position 330 with serine and at position 396 with leucine (MgFc10) (See Table 5); or a substitution at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 392 with threonine, and at position 396 with leucine (MgFc38); or a substitution at position 221 with glutamic acid, at position 270 with glutamic acid, at position 308 with alanine, at position 311 with histidine, at position 396 with leucine, and at position 402 with aspartic acid (MgFc42); or a substitution at position 240 with alanine, and at position 396 with leucine (MgFc52); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid and at position 396 with leucine (MgFc59).

The preferred method for screening and identifying molecules comprising variant Fc regions with altered FcγR affinities (e.g., enhanced FcγRIIIA affinity) is yeast surface display technology (for review see Boder and Wittrup, 2000, *Methods in Enzymology*, 328: 430-444, which is incorporated herein by reference in its entirety). Specifically, the yeast surface display is a genetic method whereby polypeptides comprising Fc mutants are expressed on the yeast cell wall in a form accessible for interacting with FcγR. Yeast surface display of the mutant Fc containing polypeptides of the invention may be performed in accordance with any of the techniques known to those skilled in the art or the specific methods described herein. Yeast display offers the advantage of utilizing actual binding to a desired receptor to identify variant Fc regions that have enhanced binding to that receptor.

One aspect of the invention provides a method for selecting mutant Fc fusion proteins with a desirable binding property, e.g., the ability of the mutant Fc fusion protein to bind FcγRIIIA with a greater affinity than a comparable polypeptide comprising a wild-type Fc region binds FcγRIIIA Yeast cells displaying the mutant Fc fusion proteins can be screened and characterized by any biochemical or immunological based assays known to those skilled in the art for assessing binding interactions. In a specific embodiment, screening of mutant Fc fusion proteins is done using one or more biochemical based assays, e.g., an ELISA assay.

In preferred embodiments, screening and identifying molecules comprising variant Fc regions with altered FcγR affinities (e.g., enhanced FcγRIIIA affinity) are done using the yeast display technology as described herein in combination with one or more biochemical based assays, preferably in a high throughput manner. The one or more biochemical assays can be any assay known in the art for identifying Fc-FcγR interaction, i.e., specific binding of an Fc region to an FcγR, including, but not limited to, an ELISA assay, surface plasmon resonance assays, immunoprecipitation assay, affinity chromatography, and equilibrium dialysis. In some embodiments, screening and identifying molecules comprising variant Fc regions with altered FcγR affinities (e.g., enhanced FcγRIIIA affinity) are done using the yeast display technology as described herein in combination with one or more functional based assays, preferably in a high throughput manner. The functional based assays can be any assay known in the art for characterizing one or more FcγR mediated effector cell function such as those described herein in Section 5.2.6. Non-limiting examples of effector cell functions that can be used in accordance with the methods of the invention, include but are not limited to, antibody-dependent cell mediated cytotoxicity (ADCC), antibody-dependent phagocytosis, phagocytosis, opsonization, opsonophagocytosis, cell binding, rosetting, C1q binding, and complement dependent cell mediated cytotoxicity. In some embodiments, screening and identifying molecules comprising variant Fc regions with altered FcγR affinities (e.g., enhanced FcγRIIIA affinity) are done using the yeast display technology as described herein in combination with one or more biochemical based assays in combination or in parallel with one or more functional based assays, preferably in a high throughput manner.

A preferred method for measuring the FcγR-Fc interaction in accordance with the invention is an assay developed by the inventors, which allows detection and quantitation of the interaction, despite the inherently weak affinity of the receptor for its ligand, e.g., in the micromolar range for FcγRIIB and FcγRIIIA The method involves the formation of an FcγR complex (e.g., FcγRIIIA, FcγRIIB) that has an improved avidity for an Fc region, relative to an uncomplexed FcγR. In a specific embodiment, the invention encompasses a method for producing a tetrameric FcγR complex, wherein said tetrameric complex has an enhanced affinity for an Fc region, relative to the affinity of a monomeric FcγR for the Fc region, said method comprising: (i) producing a fusion protein, such that a 15 amino acid AVITAG sequence operably linked to the soluble region of FcγR; (ii) biotinylating the protein produced using an *E. coli* BirA enzyme; (iii) mixing the biotinylated protein produced with streptaividn-phycoerythrin in an appropriate molar ratio, such that a tetrameric FcγR complex is formed.

In a preferred embodiment of the invention, polypeptides comprising Fc regions bind the tetrameric FcγR complexes, formed according to the methods of the invention, with at least an 8-fold higher affinity than they bind the monomeric uncomplexed FcγR. The binding of polypeptides comprising Fc regions to the tetrameric FcγR complexes may be determined using standard techniques known to those skilled in the art, such as for example, fluorescence activated cell sorting (FACS), radioimmunoassays, ELISA assays, etc.

The invention encompasses the use of the immune complexes formed according to the methods described above for determining the functionality of molecules comprising an Fc region in cell-based or cell-free assays.

In a specific embodiment, the invention provides modified immunoglobulins comprising a variant Fc region with an enhanced affinity for FcγRIIIA and/or FcγRIIA. Such immunoglobulins include IgG molecules that naturally contain FcγR binding regions (e.g., FcγRIIIA and/or FcγRIIB binding regions), or immunoglobulin derivatives that have been engineered to contain an FcγR binding region (e.g., FcγRIIIA and/or FcγRIIB binding regions). The modified immunoglobulins of the invention include any immunoglobulin molecule that binds, preferably, immunospecifically, i.e., competes off non-specific binding as determined by immunoassays well known in the art for assaying specific antigen-antibody binding, an antigen and contains an FcγR binding region (e.g., a FcγRIIIA and/or FcγRIIB binding region). Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an FcγR binding region.

In certain embodiment, the invention encompasses immunoglobulins comprising a variant Fc region with an enhanced affinity for FcγRIIIA and/or FcγRIIA such that the immunoglobulin has an enhanced effector function, e.g., antibody dependent cell mediated cytotoxicity. The effector function of the molecules of the invention can be assayed using any assay described herein or known to those skilled in the art. In some embodiments, immunoglobulins comprising a variant Fc region with an enhanced affinity for FcγRIIIA and/or FcγRIIA have an enhanced ADCC activity relative to wild-type by at least 2-fold, at least 4-fold, at least 8-fold, at least 10-fold, at least 50-fold, or at least 100-fold.

The invention encompasses engineering human or humanized therapeutic antibodies (e.g., tumor specific monoclonal antibodies) in the Fc region by modification (e.g., substitution, insertion, deletion) of one or more amino acid residues, which modifications modulate the affinity of the therapeutic antibody for an FcγR activating receptor and/or an FcγR inhibitory receptor. In one embodiment, the invention relates to engineering human or humanized therapeutic antibodies (e.g., tumor specific monoclonal antibodies) in the Fc region by modification of one or more amino acid residues, which modifications increase the affinity of the Fc region for FcγRIIIA and/or FcγRIIA. In another embodiment, the invention relates to engineering human or humanized therapeutic antibodies (e.g., tumor specific monoclonal antibodies) in the Fc region by modification of one or more amino acid residues, which modification increases the affinity of the Fc region for FcγRIIIA and/or FcγRIIA and further decreases the affinity of the Fc region for FcγRIIB. The engineered therapeutic antibodies may further have an enhanced effector function, e.g., enhanced ADCC activity, phagocytosis activity, etc., as determined by standard assays known to those skilled in the art.

In a specific embodiment, the invention encompasses engineering a humanized monoclonal antibody specific for Her2/neu protooncogene (e.g., Ab4D5 humanized antibody as disclosed in Carter et al., 1992, *Proc. Natl. Acad. Sci. USA* 89:4285-9) by modification (e.g., substitution, insertion, deletion) of at least one amino acid residue which modification increases the affinity of the Fc region for FcγRIIIA and/or FcγRIIA. In another specific embodiment, modification of the humanized Her2/neu monoclonal antibody may also further decrease the affinity of the Fc region for FcγRIIB. In yet another specific embodiment, the engineered humanized monoclonal antibodies specific for Her2/neu may further have an enhanced effector function as determined by standard assays known in the art and disclosed and exemplified herein.

In another specific embodiment, the invention encompasses engineering a mouse human chimeric anti-CD20 monoclonal antibody, 2H7 by modification (e.g., substitution, insertion, deletion) of at least one amino acid residue which modification increases the affinity of the Fc region for FcγRIIIA and/or FcγRIIA. In another specific embodiment, modification of the anti-CD20 monoclonal antibody, 2H7 may also further decrease the affinity of the Fc region for FcγRIIB. In yet another specific embodiment, the engineered anti-CD20 monoclonal antibody, 2H7 may further have an enhanced effector function as determined by standard assays known in the art and disclosed and exemplified herein.

In another specific embodiment, the invention encompasses engineering an anti-FcγRIIB antibody including but not limited to any of the antibodies disclosed in U.S. Provisional Application No. 60/403,266 filed on Aug. 12, 2002 and U.S. application Ser. No. 10/643,857 filed on Aug. 14, 2003, by modification (e.g., substitution, insertion, deletion) of at least one amino acid residue which modification increases the affinity of the Fc region for FcγRIIIA and/or FcγRIIA. Examples of anti-FcγRIIB antibodies that may be engineered in accordance with the methods of the invention are 2B6 monoclonal antibody having ATCC accession number PTA-4591 and 3H7 having ATCC accession number PTA-4592 (deposited at ATCC, 10801 University Boulevard, Manassas, Va. 02209-2011, which are incorporated herein by reference. In another specific embodiment, modification of the anti-FcγRIIB antibody may also further decrease the affinity of the Fc region for FcγRIIB. In yet another specific embodiment, the engineered anti-FcγRIIB antibody may further have an enhanced effector function as determined by standard assays known in the art and disclosed and exemplified herein. In a specific embodiment, the 2B6 monoclonal antibody comprises a modification at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 243 with isoleucine, at position 379 with leucine, and at position 420 with valine (MgFc29); or a substitution at position 392 with threonine and at position 396 with leucine (MgFc38); or a substitution at position 221 with glutamic acid, at position 270 with glutamic acid, at position 308 with alanine, at position 311 with histidine, at position 396 with leucine, and at position 402 with aspartic (MgFc42); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid, and at position 396 with leucine (MgFc59).

The present invention also includes polynucleotides that encode a molecule of the invention, including polypeptides and antibodies, identified by the methods of the invention. The polynucleotides encoding the molecules of the invention may be obtained, and the nucleotide sequence of the polynucleotides determined, by any method known in the art. The invention relates to an isolated nucleic acid encoding a molecule of the invention. The invention also provides a vector comprising said nucleic acid. The invention further provides host cells containing the vectors or polynucleotides of the invention.

The invention further provides methods for the production of the molecules of the invention. The molecules of the invention, including polypeptides and antibodies, can be produced by any method known to those skilled in the art, in particular, by recombinant expression. In a specific embodiment, the invention relates to a method for recombinantly producing a molecule of the invention, said method comprising: (i) culturing in a medium a host cell comprising a nucleic acid encoding said molecule, under conditions suitable for the expression of said molecule; and (ii) recovery of said molecule from said medium.

The molecules identified in accordance with the methods of the invention are useful in preventing, treating, or ameliorating one or more symptoms associated with a disease, disorder, or infection. The molecules of the invention are particularly useful for the treatment or prevention of a disease or disorder where an enhanced efficacy of effector cell function (e.g., ADCC) mediated by FcγR is desired, e.g., cancer, infectious disease, and in enhancing the therapeutic efficacy of therapeutic antibodies the effect of which is mediated by ADCC.

In one embodiment, the invention encompasses a method of treating cancer in a patient having a cancer characterized by a cancer antigen, said method comprising administering a therapeutically effective amount of a therapeutic antibody that binds the cancer antigen, which has been engineered in accordance with the methods of the invention. In a specific embodiment, the invention encompasses a method for treating cancer in a patient having a cancer characterized by a cancer antigen, said method comprising administering a therapeutically effective amount of a therapeutic antibody that specifically binds said cancer antigen, said therapeutic antibody comprising a variant Fc region, wherein said variant Fc region comprises at least one amino acid modification relative to a wild-type Fc region, such that said therapeutic antibody specifically binds FcγRIIIA with a greater affinity than the therapeutic antibody comprising the wild-type Fc region binds FcγRIIIA, provided that said variant Fc region does not have a substitution at positions 329, 331, or 332, and does not have an alanine at any of positions 256, 290, 298, 312, 333, 334, 359, 360, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334. In another specific embodiment, the invention encompasses a method for treating cancer in a patient having a cancer characterized by a cancer antigen, said method comprising administering a therapeutically effective amount of a therapeutic antibody that specifically binds a cancer antigen, said therapeutic antibody comprising a variant Fc region, wherein said variant Fc region comprises at least one amino acid modification relative to a wild-type Fc region such that said therapeutic antibody specifically binds FcγRIIIA with a greater affinity than a therapeutic antibody comprising the wild-type Fc region binds FcγRIIIA, and said therapeutic antibody further specifically binds FcγRIIB with a lower affinity than a therapeutic antibody comprising the wild-type Fc region binds FcγRIIB, provided that said variant Fc region does not have an alanine at any of positions 256, 298, 333, or 334. The invention encompasses a method for treating cancer in a patient characterized by a cancer antigen, said method comprising administering a therapeutically effective amount of a therapeutic antibody that specifically binds said cancer antigen and said therapeutic antibody comprises a variant Fc region so that the antibody has an enhanced ADCC activity.

The invention encompasses a method of treating an autoimmune disorder and/or inflammatory disorder in a patient in need thereof, said method comprising administering to said patient a therapeutically effective amount of a molecule comprising a variant Fc region, wherein said variant Fc region comprises at least one amino acid modification relative to a wild type Fc region, such that said molecule specifically binds FcγRIIB with a greater affinity than a comparable molecule comprising the wild type Fc region, and said molecule further specifically binds FcγRIIIA with a lower affinity than a comparable molecule comprising the wild type Fc region, and said molecule binds an immune complex (e.g., an antigen/antibody complex). The invention encompasses a method of treating an autoimmune disorder and/or inflammatory disorder further comprising administering one or more additional prophylactic or therapeutic agents, e.g., immunomodulatory agents, anti-inflammatory agents, used for the treatment and/or prevention of such diseases.

The invention also encompasses methods for treating or preventing an infectious disease in a subject comprising administering a therapeutically or prophylactically effective amount of one or more molecules of the invention that bind an infectious agent or cellular receptor therefor. Infectious diseases that can be treated or prevented by the molecules of the invention are caused by infectious agents including but not limited to viruses, bacteria, fungi, protozae, and viruses.

According to one aspect of the invention, molecules of the invention comprising variant Fc regions have an enhanced antibody effector function towards an infectious agent, e.g., a pathogenic protein, relative to a comparable molecule comprising a wild-type Fc region. In a specific embodiment, molecules of the invention enhance the efficacy of treatment of an infectious disease by enhancing phagocytosis and/or opsonization of the infectious agent causing the infectious disease. In another specific embodiment, molecules of the invention enhance the efficacy of treatment of an infectious disease by enhancing ADCC of infected cells causing the infectious disease.

In some embodiments, the molecules of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with antibiotics known to those skilled in the art for the treatment and or prevention of an infectious disease.

The invention provides pharmaceutical compositions comprising a molecule of the invention, e.g., a polypeptide comprising a variant Fc region, an immunoglobulin comprising a variant Fc region, a therapeutic antibody engineered in accordance with the invention, and a pharmaceutically acceptable carrier. The invention additionally provides pharmaceutical compositions further comprising one or more additional therapeutic agents, including but not limited to anti-cancer agents, anti-inflammatory agents, immunomodulatory agents.

2.1 Definitions

As used herein, the term "Fc region" is used to define a C-terminal region of an IgG heavy chain. Although the boundaries may vary slightly, the human IgG heavy chain Fc region is defined to stretch from Cys226 to the carboxy terminus The Fc region of an IgG comprises two constant domains, CH2 and CH3. The CH2 domain of a human IgG Fc region usually extends from amino acids 231 to amino acid 341. The CH3 domain of a human IgG Fc region usually extends from amino acids 342 to 447. The CH2 domain of a human IgG Fc region (also referred to as "Cγ2" domain) usually extends from amino acid 231-340. The CH2 domain is unique in that it is not closely paired with another domain. Rather, two N-linked branched carbohydrate chains are interposed between the two CH2 domains of an intact native IgG.

Throughout the present specification, the numbering of the residues in an IgG heavy chain is that of the EU index as in Kabat et al., *Sequences of Proteins of Immunological Interest*, 5$^{th}$ Ed. Public Health Service, NH1, MD (1991), expressly incorporated herein by references. The "EU index as in Kabat" refers to the numbering of the human IgG1 EU antibody.

The "hinge region" is generally defined as stretching from Glu216 to Pro230 of human IgG1. Hinge regions of other IgG isotypes may be aligned with the IgG1 sequence by placing the first and last cysteine residues forming inter-heavy chain S—S binds in the same positions.

As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "cancer" refers to a neoplasm or tumor resulting from abnormal uncontrolled growth of cells. As used herein, cancer explicitly includes, leukemias and lymphomas. In some embodiments, cancer refers to a benign tumor, which has remained localized. In other embodiments, cancer refers to a malignant tumor, which has invaded and destroyed neighboring body structures and spread to distant sites. In some embodiments, the cancer is associated with a specific cancer antigen.

As used herein, the term "immunomodulatory agent" and variations thereof refer to an agent that modulates a host's immune system. In certain embodiments, an immunomodulatory agent is an immunosuppressant agent. In certain other embodiments, an immunomodulatory agent is an immunostimulatory agent. Immunomodatory agents include, but are not limited to, small molecules, peptides, polypeptides, fusion proteins, antibodies, inorganic molecules, mimetic agents, and organic molecules.

As used herein, the term "epitope" refers to a fragment of a polypeptide or protein or a non-protein molecule having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, a "therapeutically effective amount" refers to that amount of the therapeutic agent sufficient to treat or manage a disease or disorder. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

"Effector function" as used herein is meant a biochemical event that results from the interaction of an antibody Fc region with an Fc receptor or ligand. Effector functions include but are not limited to antibody dependent cell mediated cytotoxicity (ADCC), antibody dependent cell mediated phagocytosis (ADCP), and complement dependent cytotoxicity (CDC). Effector functions include both those that operate after the binding of an antigen and those that operate independent of antigen binding.

"Effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and may be from any organism including but not limited to humans, mice, rats, rabbits, and monkeys.

"Fc ligand" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, staphylococcal protein A, streptococcal protein G, and viral FcγR. Fc ligands may include undiscovered molecules that bind Fc.

3. BRIEF DESCRIPTION OF THE DRAWINGS

Figure 1:
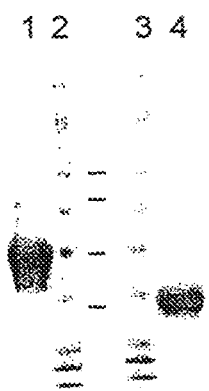

FIG. 1 SDS-PAGE ANALYSIS OF RECOMBINANT SOLUBLE FcγR

The purity of recombinant soluble FcγR proteins was assessed by 10% polyacrylamide gel electrophoresis. The gels were stained with Coomassie blue. Lane 1: purified recombinant soluble FcγRIIIA; Lane 2: molecular weight marker; Lane 3: molecular weight marker; Lane 4: purified recombinant soluble FcγRIIB. The dashes refer to the molecular weight of the markers, from top to bottom, they correspond to a molecular weight of 98, 50, 36, and 22 KDa respectively.

Figure 2:
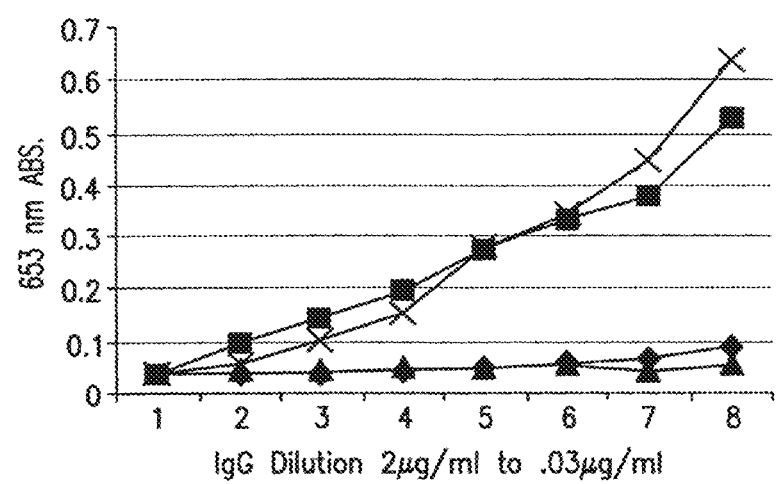

FIG. 2 ELISA ASSAY OF RECOMBINANT SOLUBLE FcγR

The direct binding of purified recombinant soluble FcγRIIIA to aggregated and monomeric IgG was determined using an ELISA assay. Binding of (▲) aggregated IgG with 3G8; (♦) Biotinylated IgG; (■) aggregated IgG; (X) aggregated IgG with mouse IgG1.

Figure 3A:
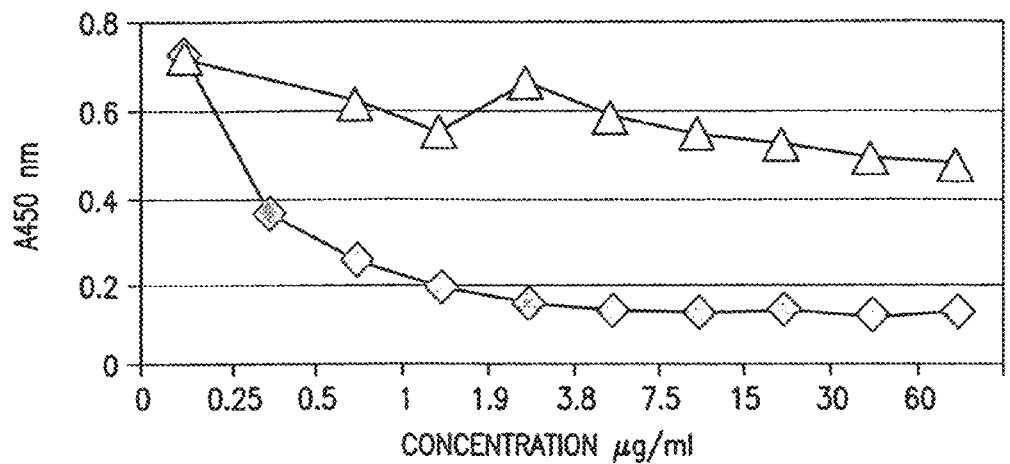

FIGS. 3A and B CHARACTERIZATION OF FcγRIIIA TETRAMERIC COMPLEX USING AN ELISA ASSAY A. Soluble tetrameric FcγRIIIA complex binds soluble monomeric human IgG specifically. Binding of soluble tetrameric FcγRIIIA to human IgG is blocked by 3G8 (▲), a mouse anti-FcγIIIA monoclonal antibody; the 4-4-20 monoclonal antibody harboring the D265A mutation was not able to block the binding of soluble tetrameric FcγRIIIA to aggregated human IgG (Δ).

B. Binding of soluble tetrameric FcγRIIIA complex to soluble monomeric human IgG (■) is compared to the binding of monomeric soluble FcγRIIIA to soluble monomeric human IgG (♦).

FIGS. 4A and B CHARACTERIZATION OF FcγRIIIA TETRAMERIC COMPLEX USING A MAGNETIC BEAD ASSAY A. FcγRIIIA Complex: two FcγRIIIA (filled shape) are joined by a monoclonal antibody DJ130c ($1^{st}$ Ab); the anti-mouse $F(ab)_2$ is conjugated to PE (circle).

B. FACS analysis of FcγRIIIA bound to Fc coated beads: (a) beads alone; (b) complex without FcγRIIIA; (c) complex with FcγRIIIA; (d) complex with FcγRIIIA and LNK16.

Figure 5:
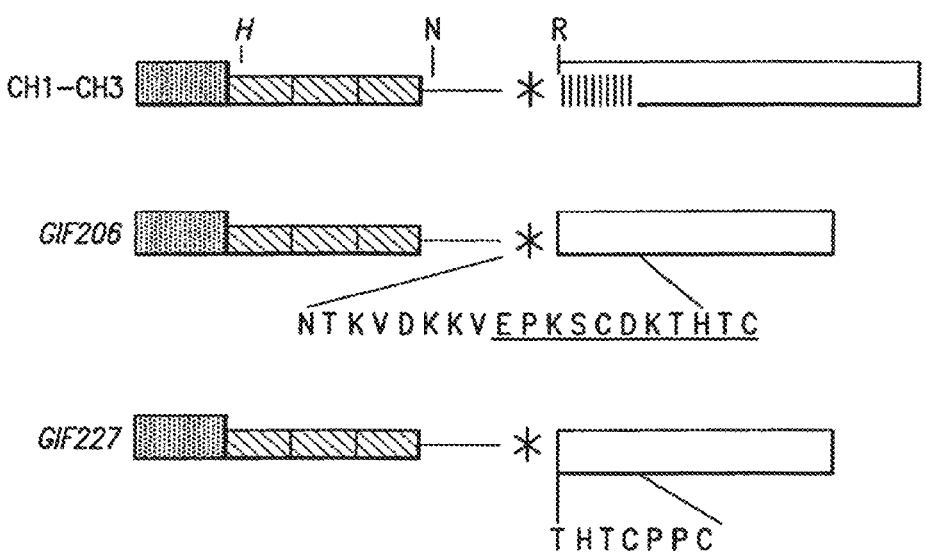

FIG. 5 SCHEMATIC PRESENTATION OF Fc CONTAINING CONSTRUCTS

A schematic diagram of the IgG1 Fc domains cloned into pYD1 is presented. The open box represents the hinge-CH2-CH3 domains; parallel vertical lines represent the CH1 domain. In the case of the GIF206 and 227 constructs; the N-terminal amino acids are shown. The underlined residues correspond to the hinge region; the * represents the Xpress epitope tag; hatched boxes represent the Gly4-Ser linker, and the stippled boxes represent the Aga2p gene.

FIGS. 6A-H FACS ANALYSIS OF THE Fc FUSION PROTEINS ON THE YEAST CELL WALL

Cells were incubated with either a PE-conjugated polyclonal goat anti-human Fc antibody (FIGS. 6A-D) or with HP6017 (Sigma), a mouse anti-human IgG1 Fc (CH3) specific monoclonal antibody (FIGS. 6E-H). A and E represent vector alone; Panels B and F represent the CH1-CH3 construct; Panels C and G represent the GIF227; and Panels D and H represent the GIF 206 construct.

Figure 7A:
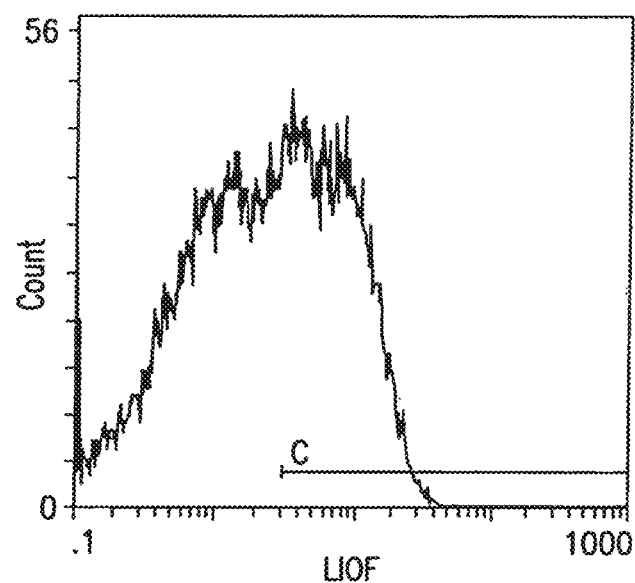
Figure 7B:
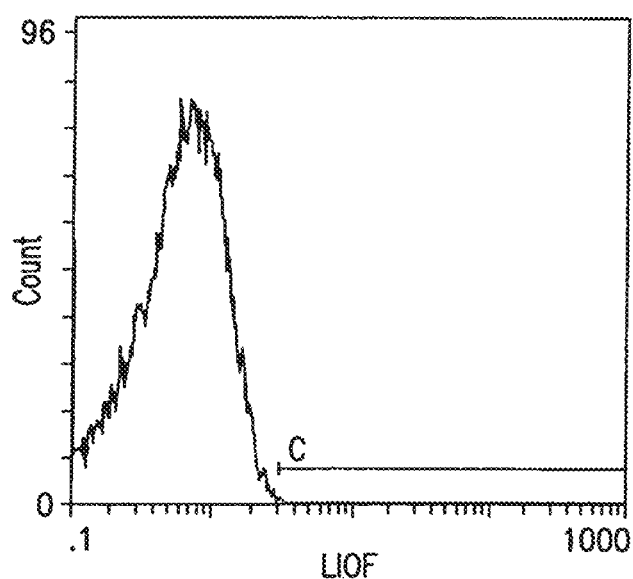
Figure 7C:
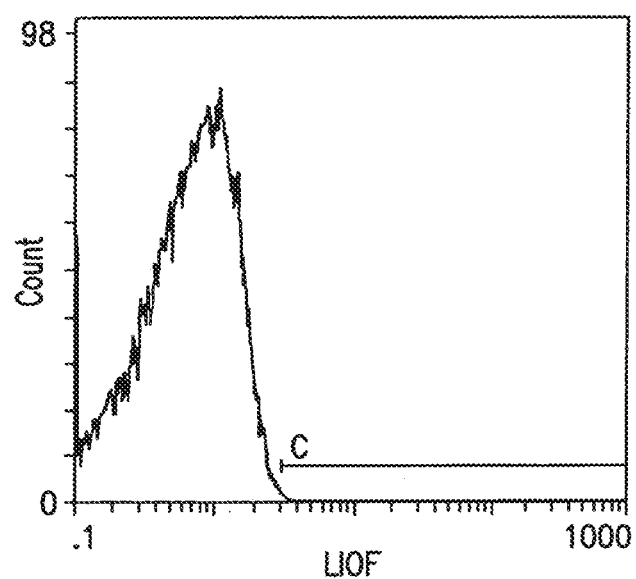

FIGS. 7A-C BINDING OF SOLUBLE TETRAMERIC FcγRIIIA TO THE SURFACE DISPLAYED Fc FUSION PROTEINS

Cells containing pYD1-CH1 (A); pYD-CH1-D265A (B); and pYD vector (C) were grown under conditions to express Aga2p fusion proteins on the cell surface. Cells were incubated with FcγRIIIA at 0.15 mM, 7.5 mM, and 7.5 mM, respectively, and analyzed by FACS.

Figure 8:
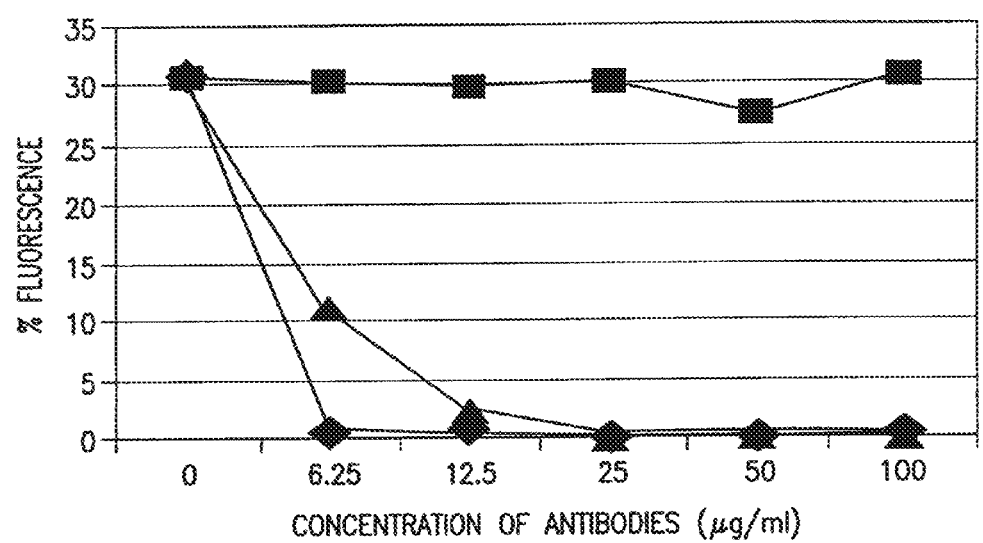

FIG. 8 CHARACTERIZATION OF THE BINDING OF SOLUBLE TETRAMERIC FcγRIIIA TO THE SURFACE DISPLAYED Fc FUSION PROTEINS

Binding of FcγRIIIA tetrameric complex to Fc fusion proteins on the yeast cell surface was analyzed. PE-conjugated FcγRIIIA tetrameric complexes were pre-incubated with different concentrations of 3G8 (♦), LNK (▲) or an irrelevant isotype control (■), and subsequently incubated with the yeast cells. Cells were analyzed by FACS for PE fluorescence. The percent cells that bound the FcγRIIIA tetrameric complex were plotted on the y-axis.

FIG. 9 EXAMPLE OF SORT GATE FOR SELECTING Fc MUTANTS WITH INCREASED BINDING TO FcγRIIIA

Cells were stained with PE-conjugated FcγRIIIA tetrameric complexes (y-axis) and anti-Fc-FITC conjugated antibody α-axis). Boxed area represents sort gate set to select ~1.0% of the cell population.

Figure 10A:
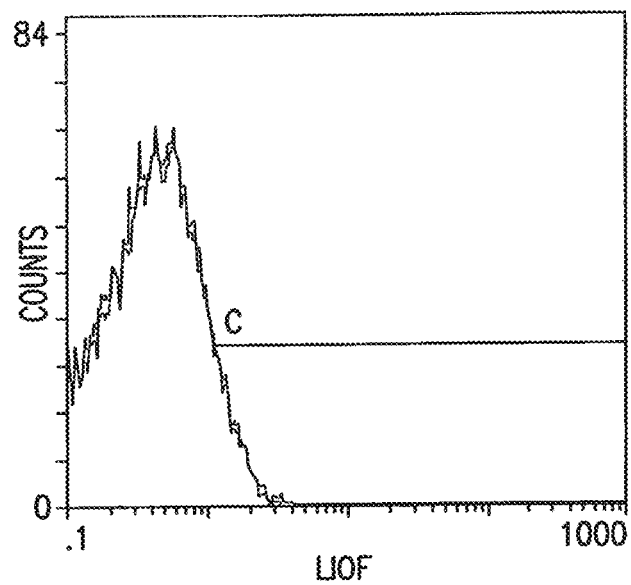
Figure 10B:
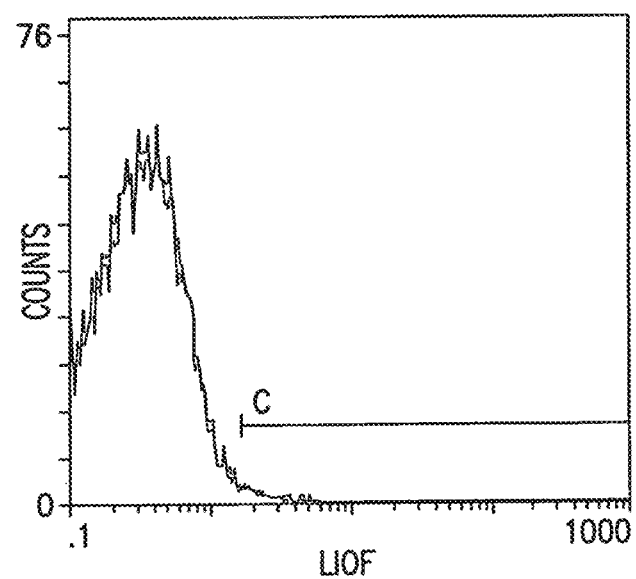
Figure 10C:
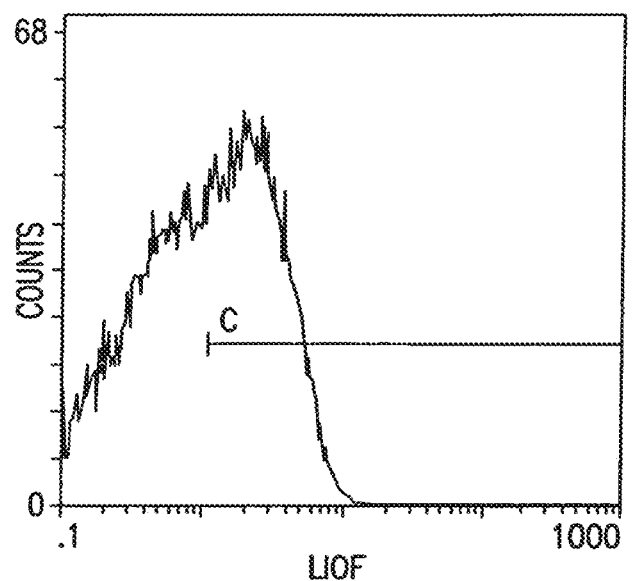
Figure 10D:
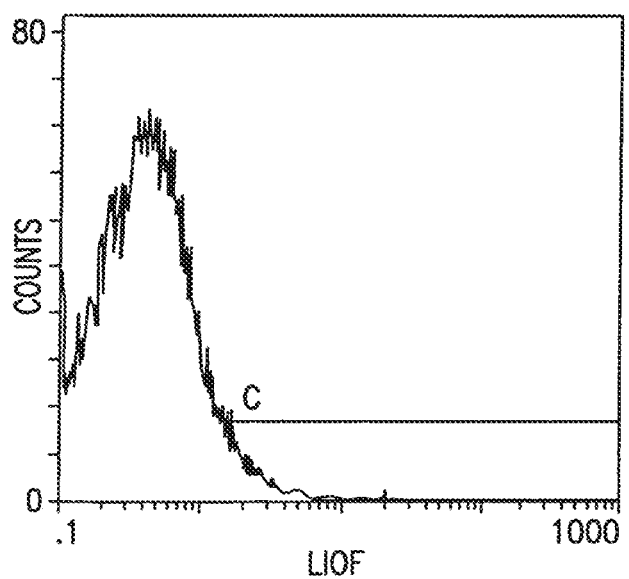
Figure 10E:
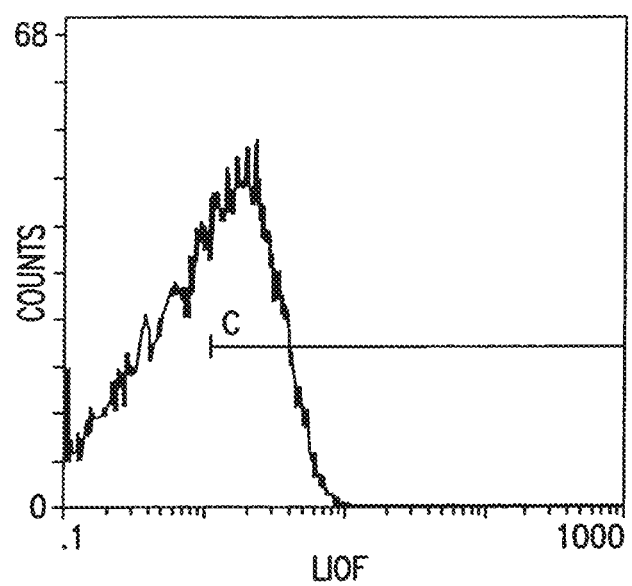
Figure 10F:
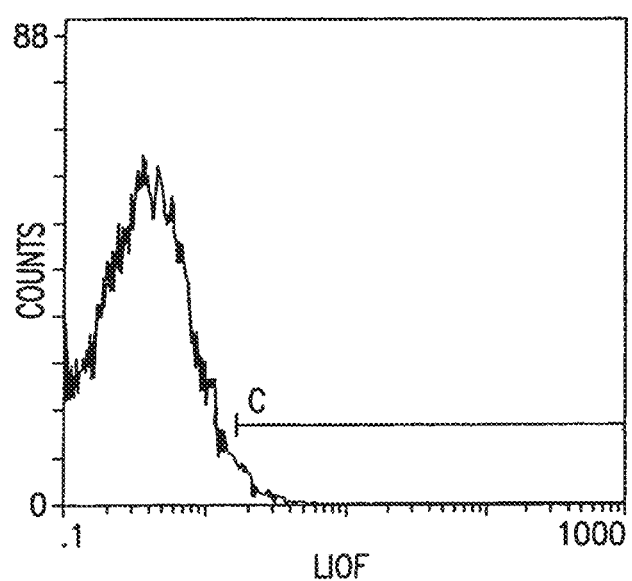
Figure 10G:
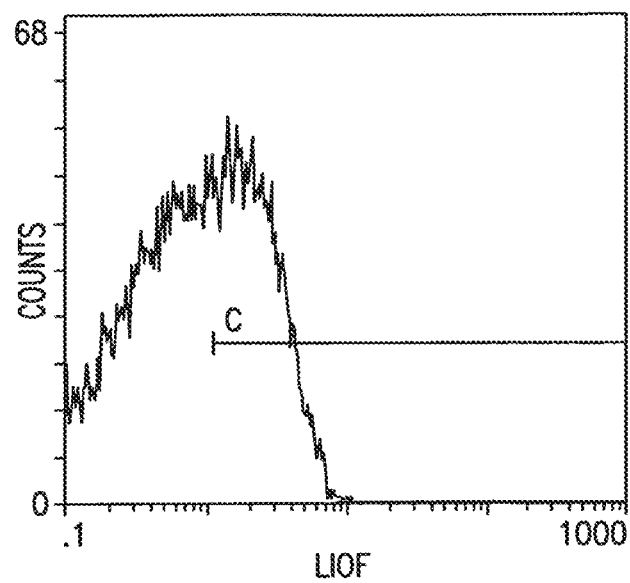
Figure 10H:
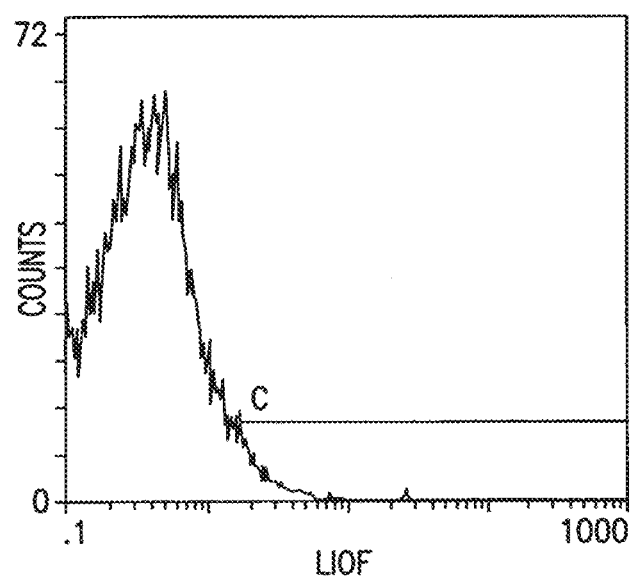
Figure 10I:
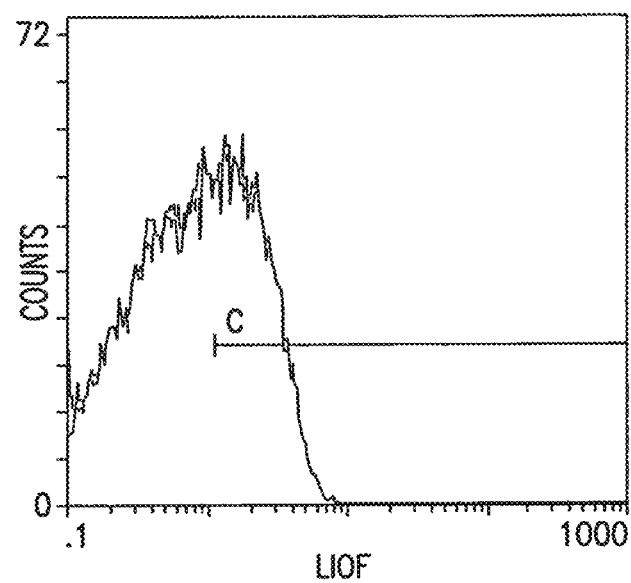
Figure 10J:
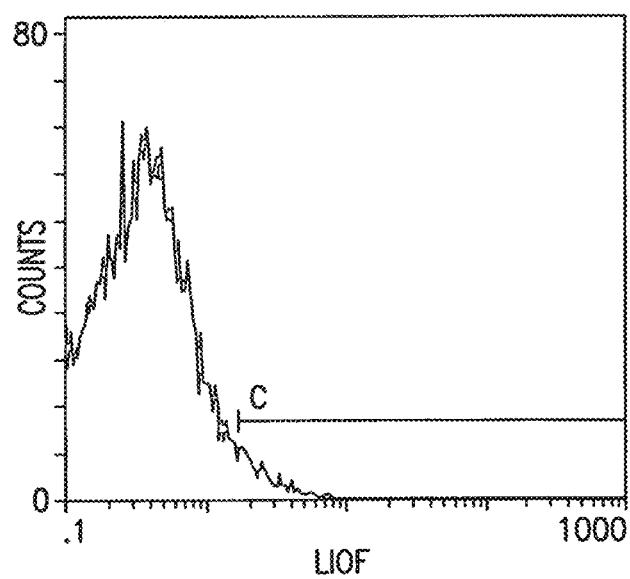
Figure 10K:
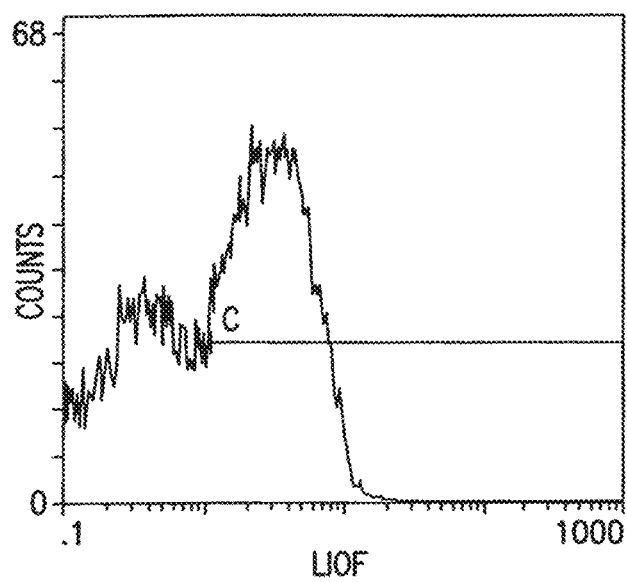
Figure 10L:
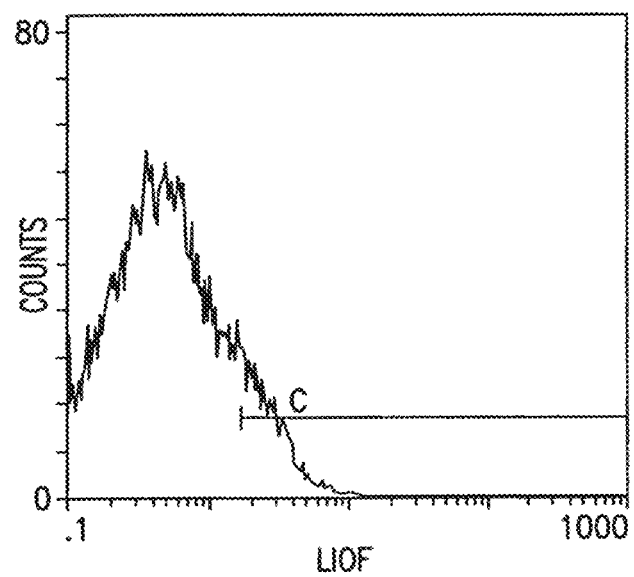
Figure 10M:
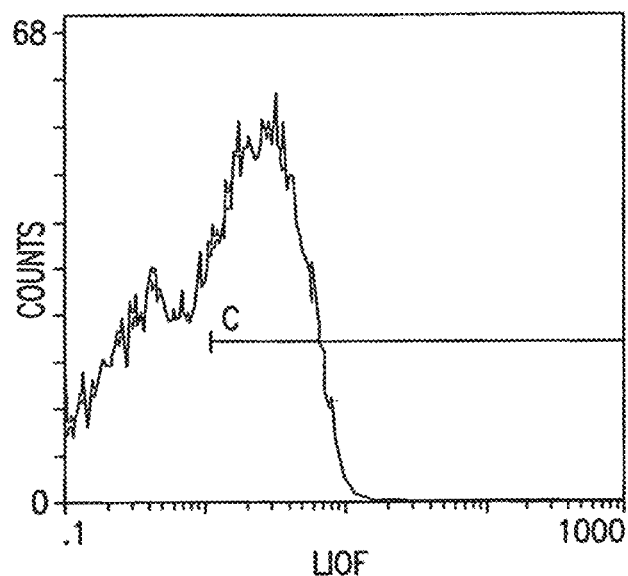
Figure 10N:
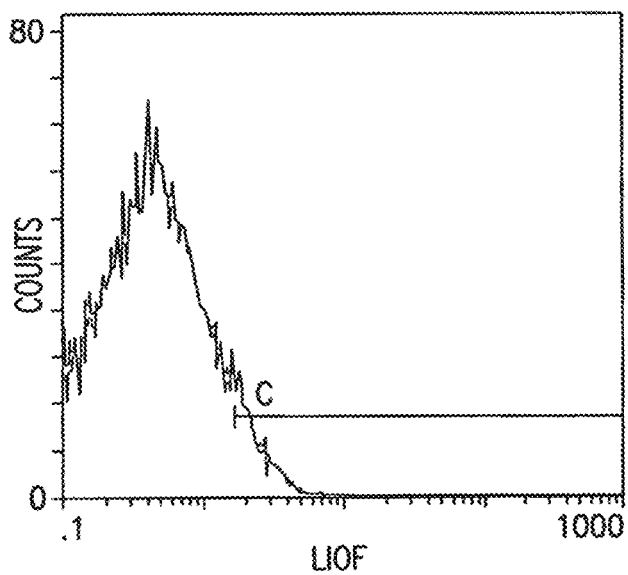

FIGS. 10A-N FACS ANALYSIS OF SOME OF THE Fc MUTANTS IDENTIFIED HAVING AN INCREASED AFFINITY FOR FcγRIIIA TETRAMERIC COMPLEXES

Individual clones harboring the pYD-CH1 plasmid containing independent Fc mutations were amplified in selective media containing glucose, induced for Fc expression in selective media containing galactose, and subsequently analyzed by FACs. FIGS. 10A and B represent cells harboring wild-type Fc; FIGS. 10C and D represent mutant #5; FIGS. 10E and F represent mutant #20; FIGS. 10G and H represent mutant #21; FIGS. 10I and J represent mutant #24; FIGS. 10K and L represent mutant #25; FIGS. 10M and N represent mutant #27. Cells were stained with FcγRIIIA tetrameric complex (FIGS. 10A, C, E, G, I, K, and M) or FcγRIIB tetrameric complex (FIGS. 10B, D, F, H, J, L, and N).

Figure 11A:
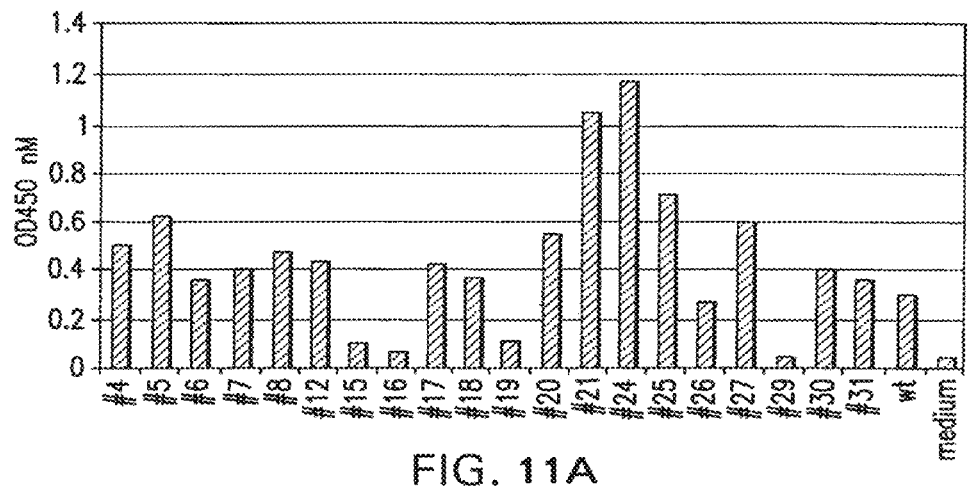
Figure 11B:
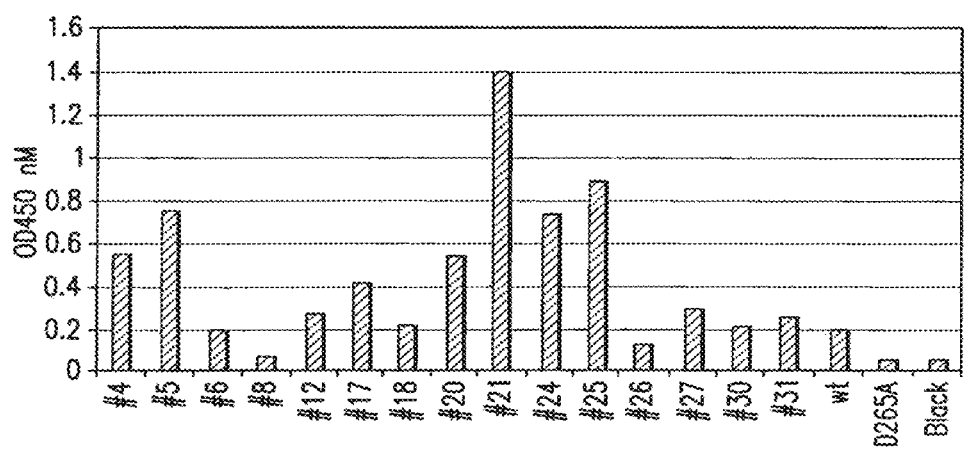

FIGS. 11A-B CHARACTERIZATION OF Fc MUTANTS IN THE 4-4-20 MONOCLONAL ANTIBODY BY ELISA

Fc domains from the pYD-CH1 plasmids were cloned into the heavy chain of the chimeric 4-4-20 monoclonal antibody. The 4-4-20 monoclonal antibody was expressed in 293 cells and supernatants were collected. ELISA plates were coated with fluoresceine conjugated BSA to capture the chimeric 4-4-20 mutant antibodies. FcγRIIIA (A) and FcγRIIB (B) receptors were then coated onto the ELISA plates to which the 4-4-20 monoclonal antibodies had been absorbed in order to determine the relative affinities of the variant receptors to the Fc domains. Mutants #15 and #29 were non-binding isolates included as controls.

Figure 12:
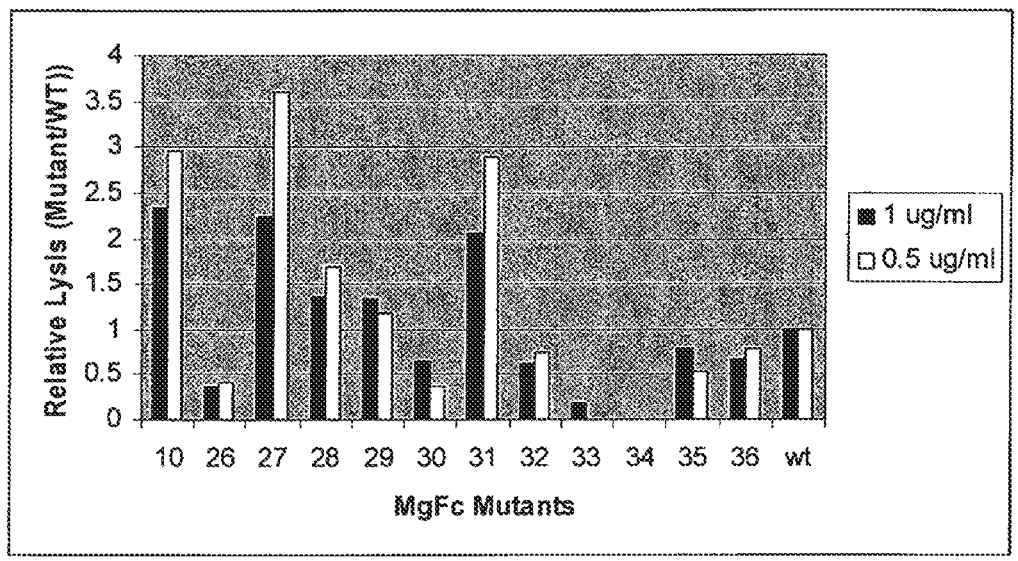

FIG. 12 ADCC ACTIVITY OF MUTANTS IN THE 4-4-20 MONOCLONAL ANTIBODY 4-4-20 antibodies containing mutant Fc regions were assessed for their ADCC activity, and compared to the ADCC activity of a wild type 4-4-20 antibody. The mutants analyzed are as follows: MGFc-10 (K288N, A330S, P396L), MGFc-26 (D265A), MGFc-27 (G316D, A378V, D399E), MGFc28 (N315I, A379M, D399E), MGFc29 (F243I, V379L, G420V), MGFc30 (F275V), MGFc-31 (P247L, N421K), MGFc-32 (D280E, S354F, A431D, L441I), MGFc-33 (K317N, F423 deleted), MGFc-34 (F241L, E258G), MGFc-35 (R255Q, K326E), MGFc-36 (K218R, G281D, G385R)

Figure 13A:
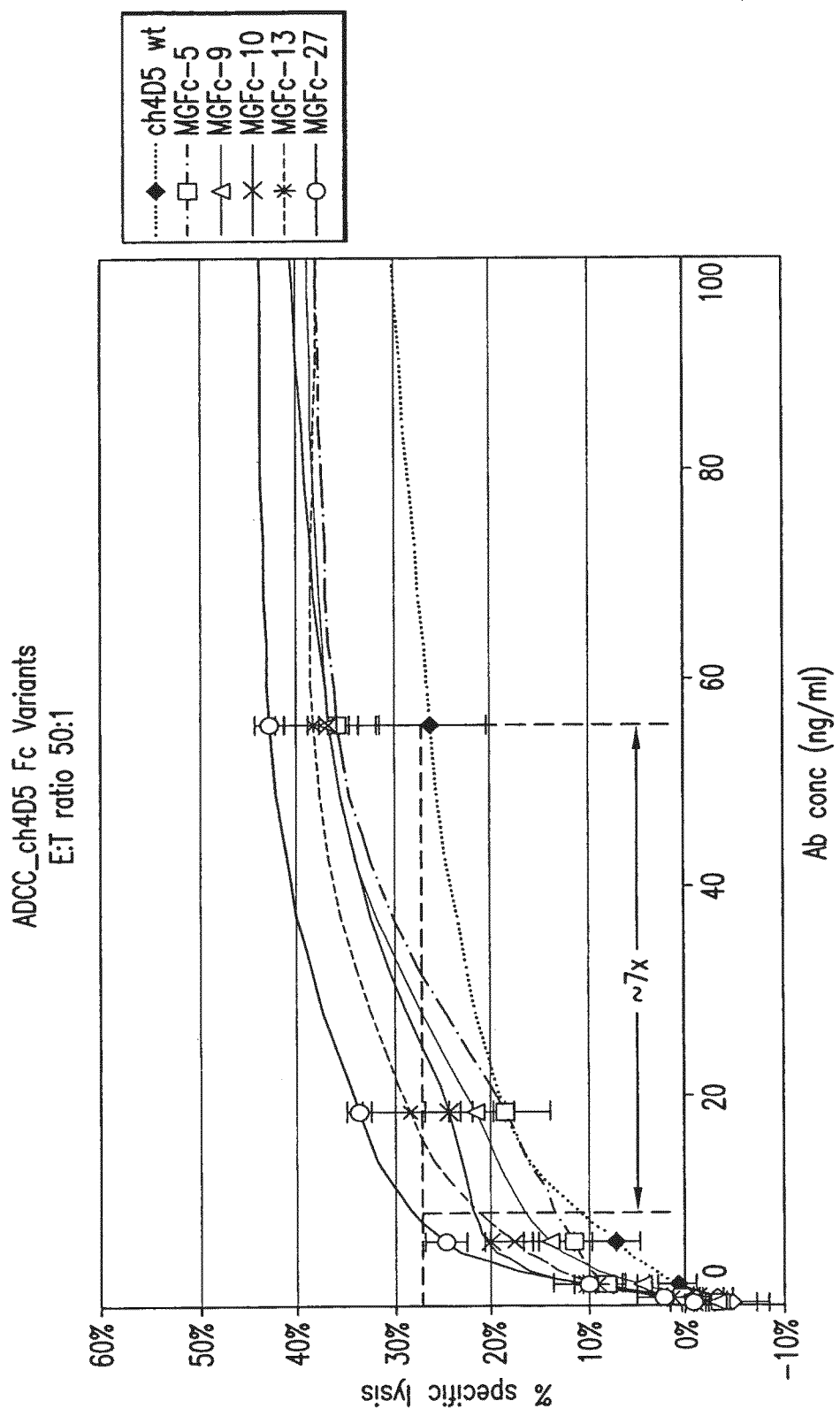

FIGS. 13A and B ADCC ACTIVITY OF MUTANTS IN THE HER2/NEU HUMANIZED MONOCLONAL ANTIBODY A. Humanized HER2/neu monoclonal antibodies containing mutant Fc regions were assessed for their ADCC activity and compared to the ADCC activity of a wild type Her2/neu antibody. The mutants analyzed are as follows: MGFc-5 (V379M), MGFc-9 (F243I, V379L), MGFc-10 (K288N, A330S, P396L), MGFc-13 (K334E, T359N, T366S), MGFc-27 (G316D, A378V, D399E).

B. ADCC activity of additional mutants in the context of the humanized Her2/neu monoclonal antibody MGFc-37 (K248M), MGFc-39 (E293V Q295E, A327T), MGFc-38 (K392T, P396L), MGFc-41 (H268N, P396L), MGFc-23 (K334E, R292L), MGFc-44, MGFc-45. Two independent clones were tested for each mutant.

FIG. 14 CAPTURE OF CH 4-4-20 ANTIBODY ON BSA-FITC SURFACE

6 μL of antibody at a concentration of approximately 20 μg/mL was injected at 5 μL/min over a BSA-fluoroscein isothiocyanate (FITC) surface. BIAcore sensogram of the binding of ch 4-4-20 antibodies with mutant Fc regions on the surface of the BSA-FITC immobilized sensor ship is shown. The marker was set on wild-type captured antibody response.

Figure 15:
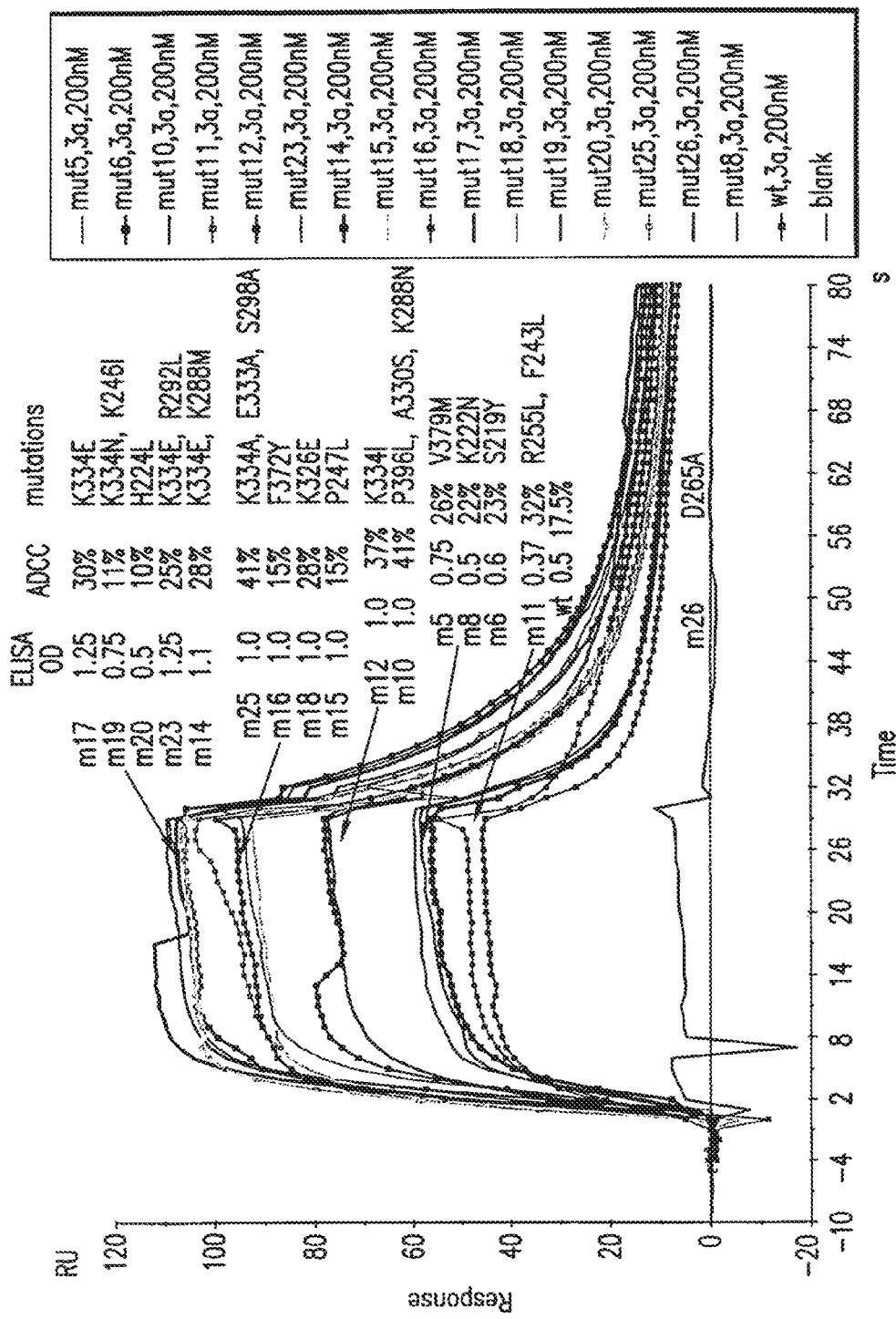
Figure 16A:
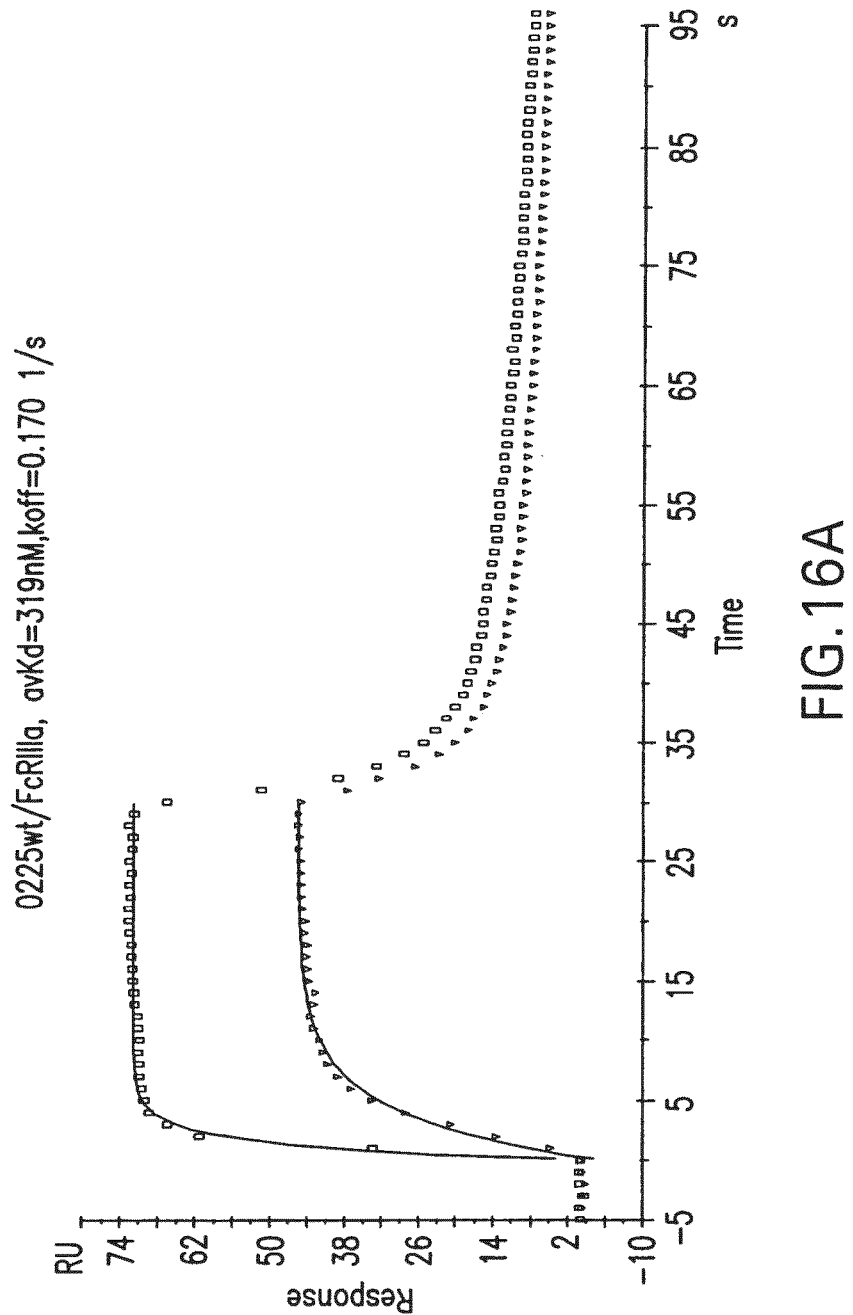
Figure 16B:
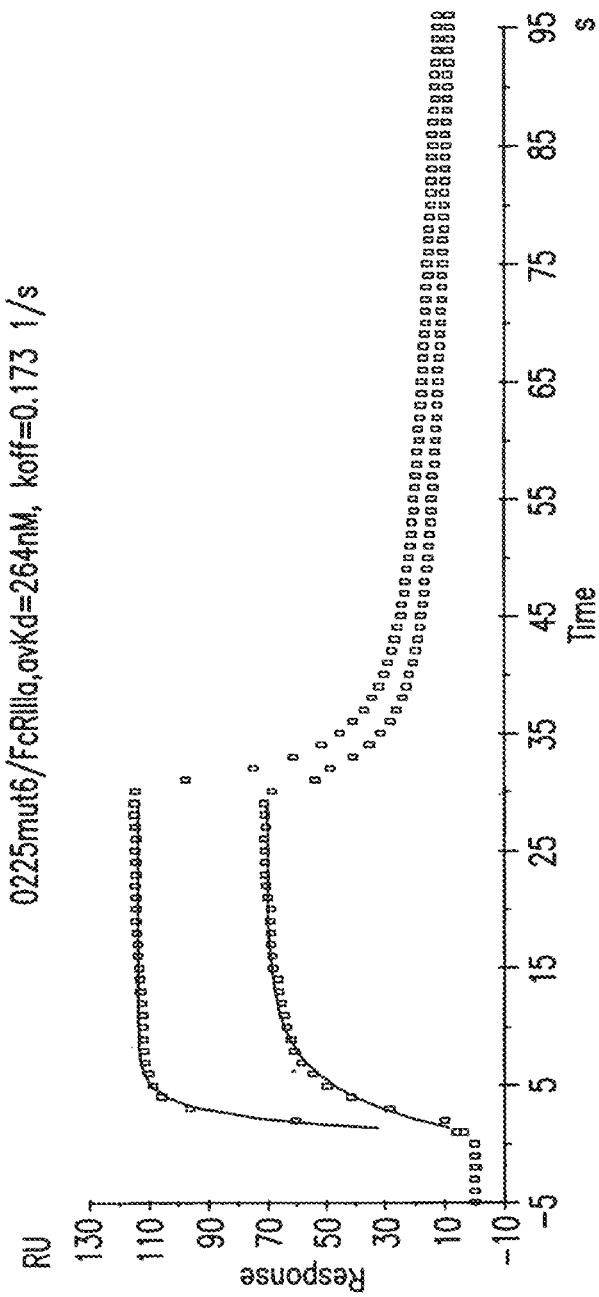
Figure 16C:
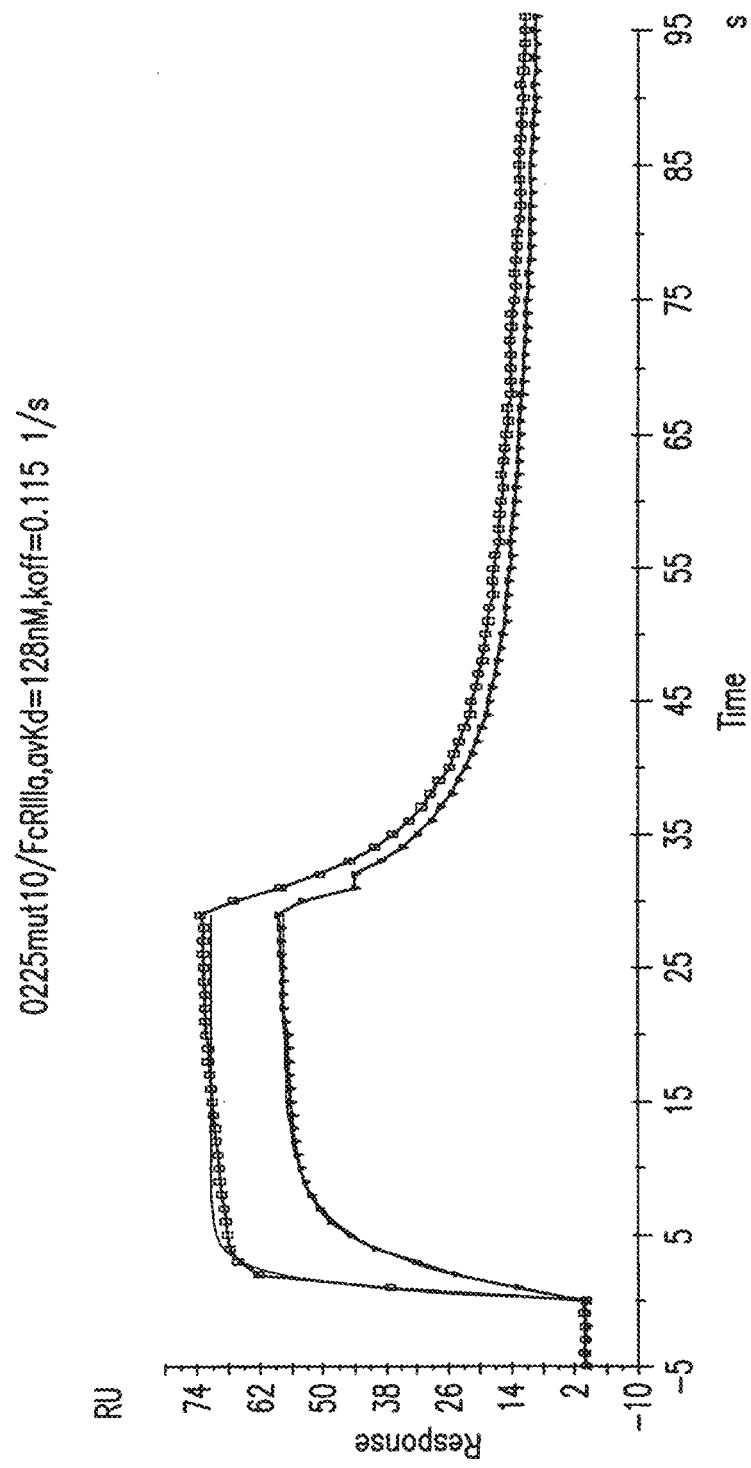
Figure 16D:
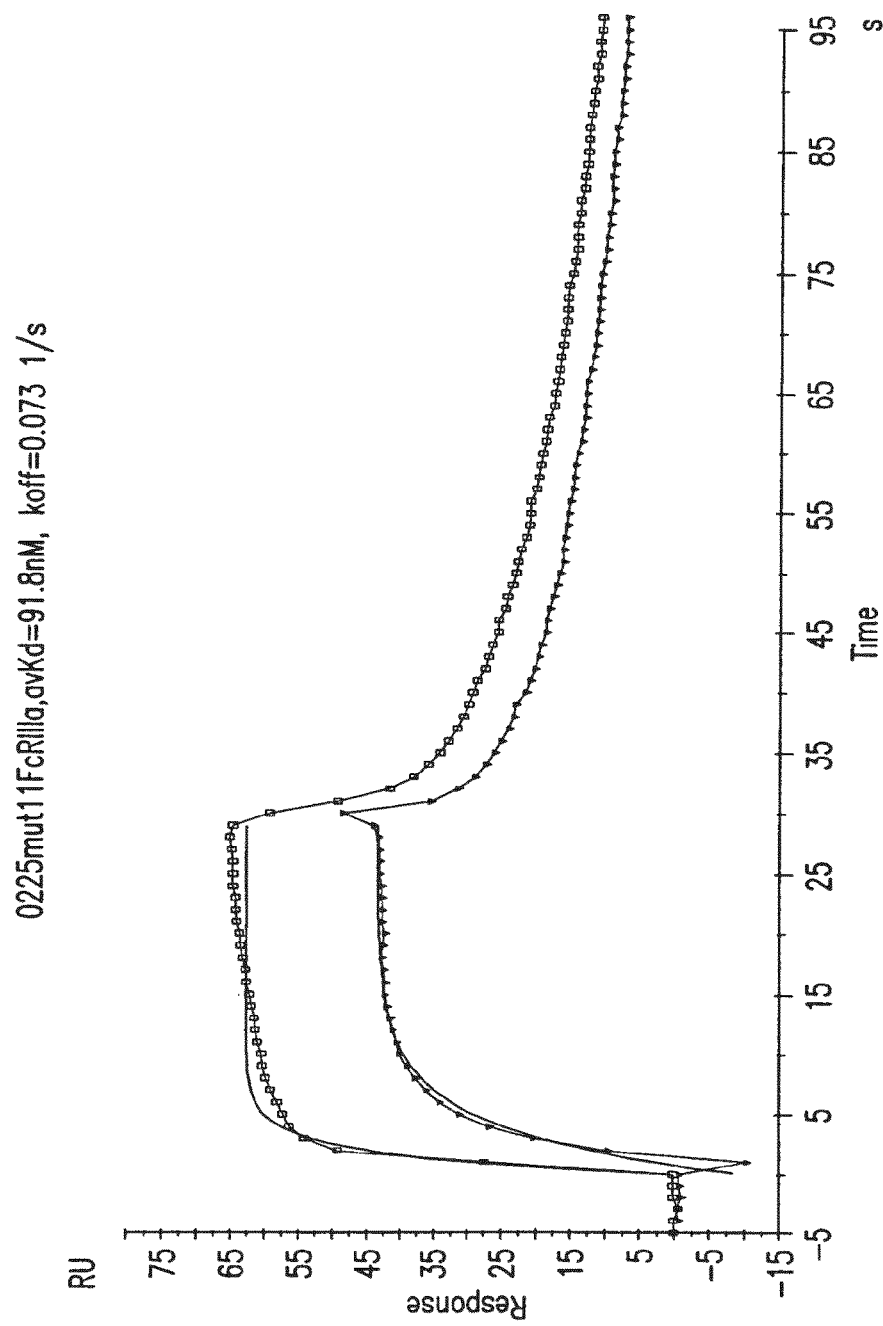
Figure 16E:
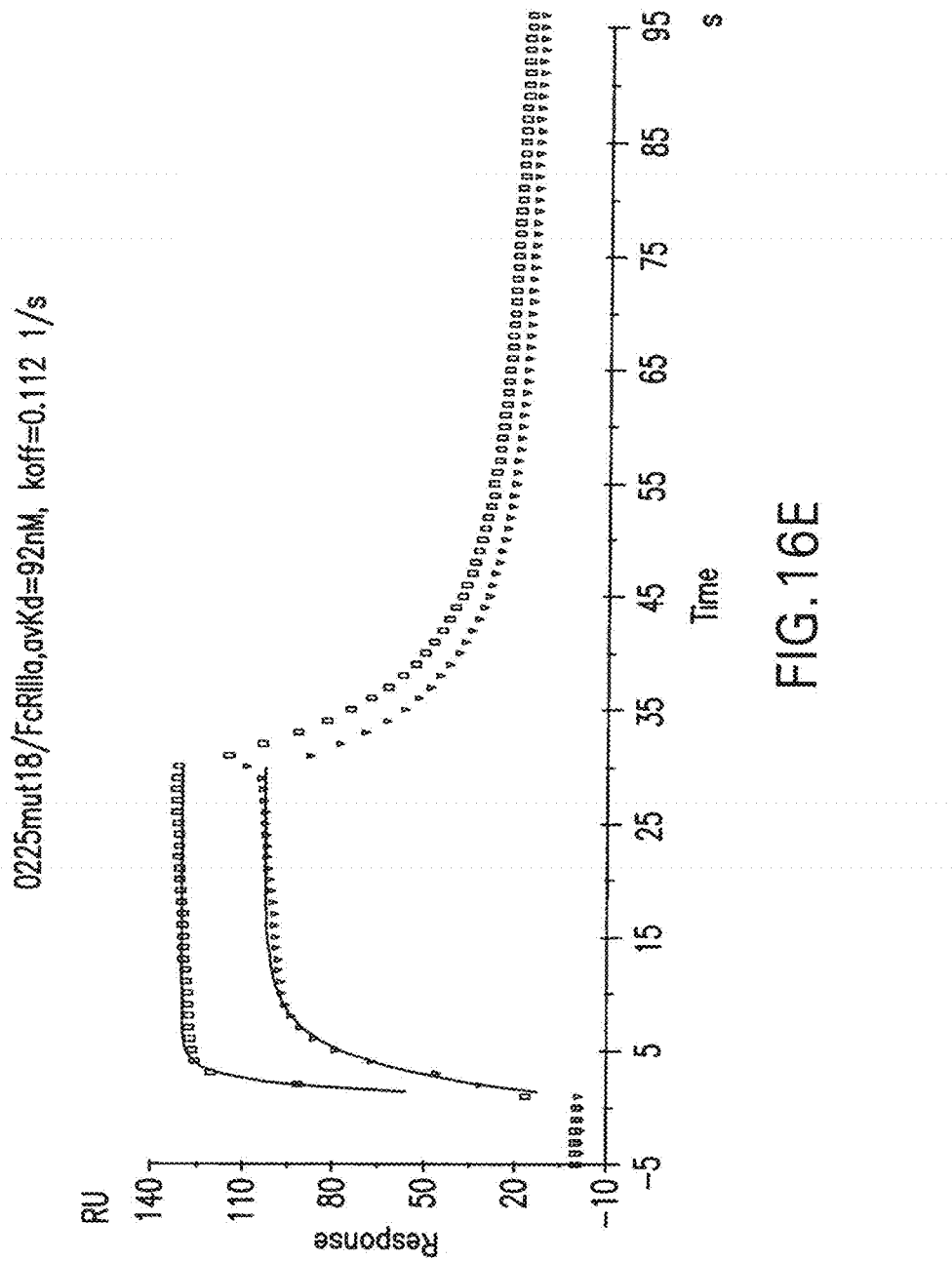
Figure 16F:
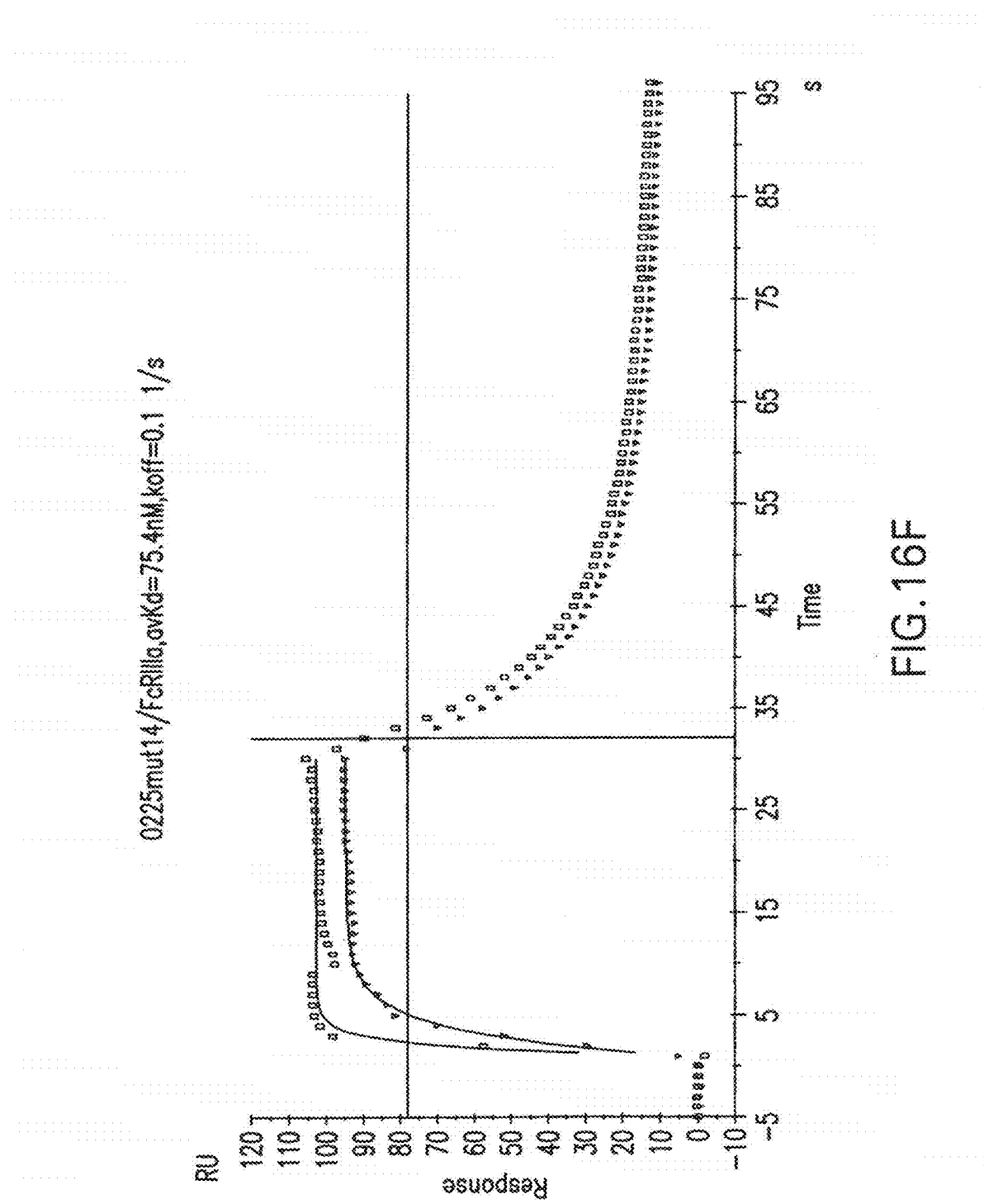
Figure 16G:
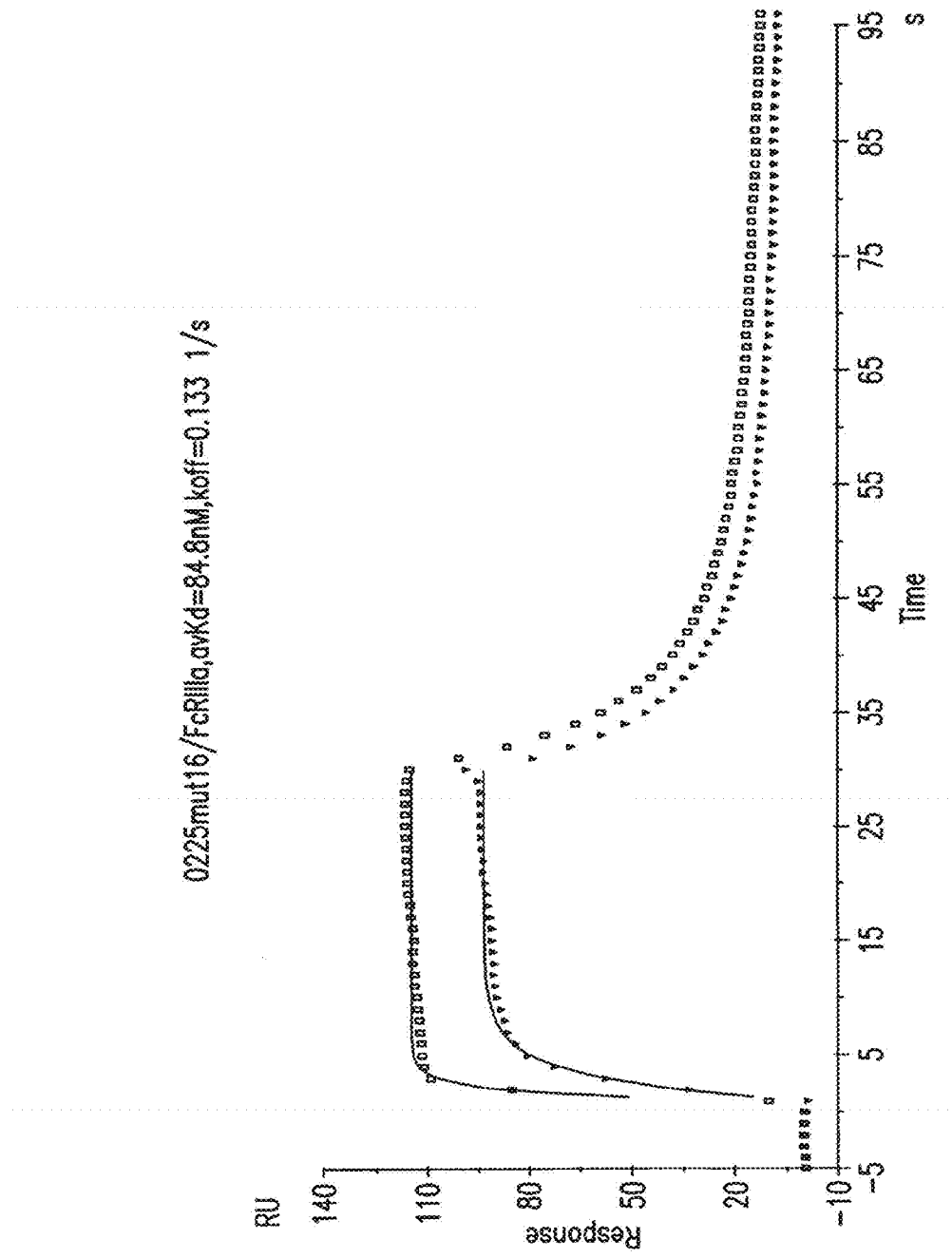
Figure 16H:
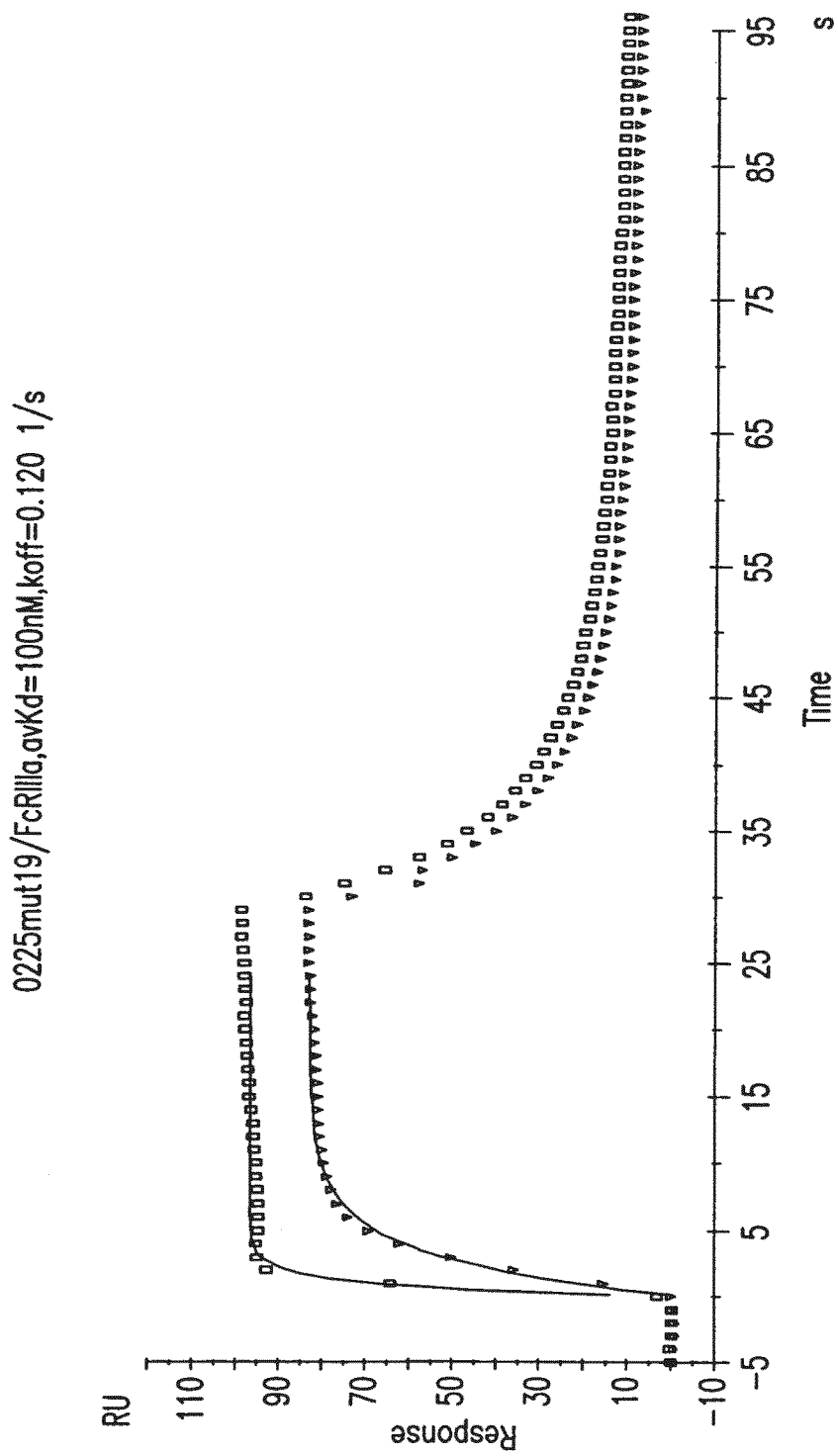

FIG. 15 SENSOGRAM OF REAL TIME BINDING OF FcγRIIIA TO CH 4-4-20 ANTIBODIES CARRYING VARIANT Fc REGIONS

Binding of FcγRIIIA to ch-4-4-20 antibodies carrying variant Fc regions was analyzed at 200 nM concentration. Responses were normalized at the level of ch-4-4-20 antibody obtained for wild-type.

Mutants used were as follows: Mut 6 (S219V), Mut 10 (P396L, A330S, K288N); Mut 18 (K326E); Mut 14 (K334E, K288N); Mut 11 (R255L, F243L); Mut 16 (F372Y); Mut 19 (K334N, K246I).

FIGS. 16A-H ANALYSIS OF KINETIC PARAMETERS OF FcγRIIIA BINDING TO ANTIBODIES CARRYING VARIANT Fc REGIONS

Kinetic parameters for FcγRIIIA binding to antibodies carrying variant Fc regions were obtained by generating separate best fit curves for 200 nM and 800 nM. Solid line indicates an association fit which was obtained based on the $k_{off}$ values calculated for the dissociation curves in the 32-34 sec interval. $K_d$ and $k_{off}$ values represent the average from two concentrations.

Figure 17:
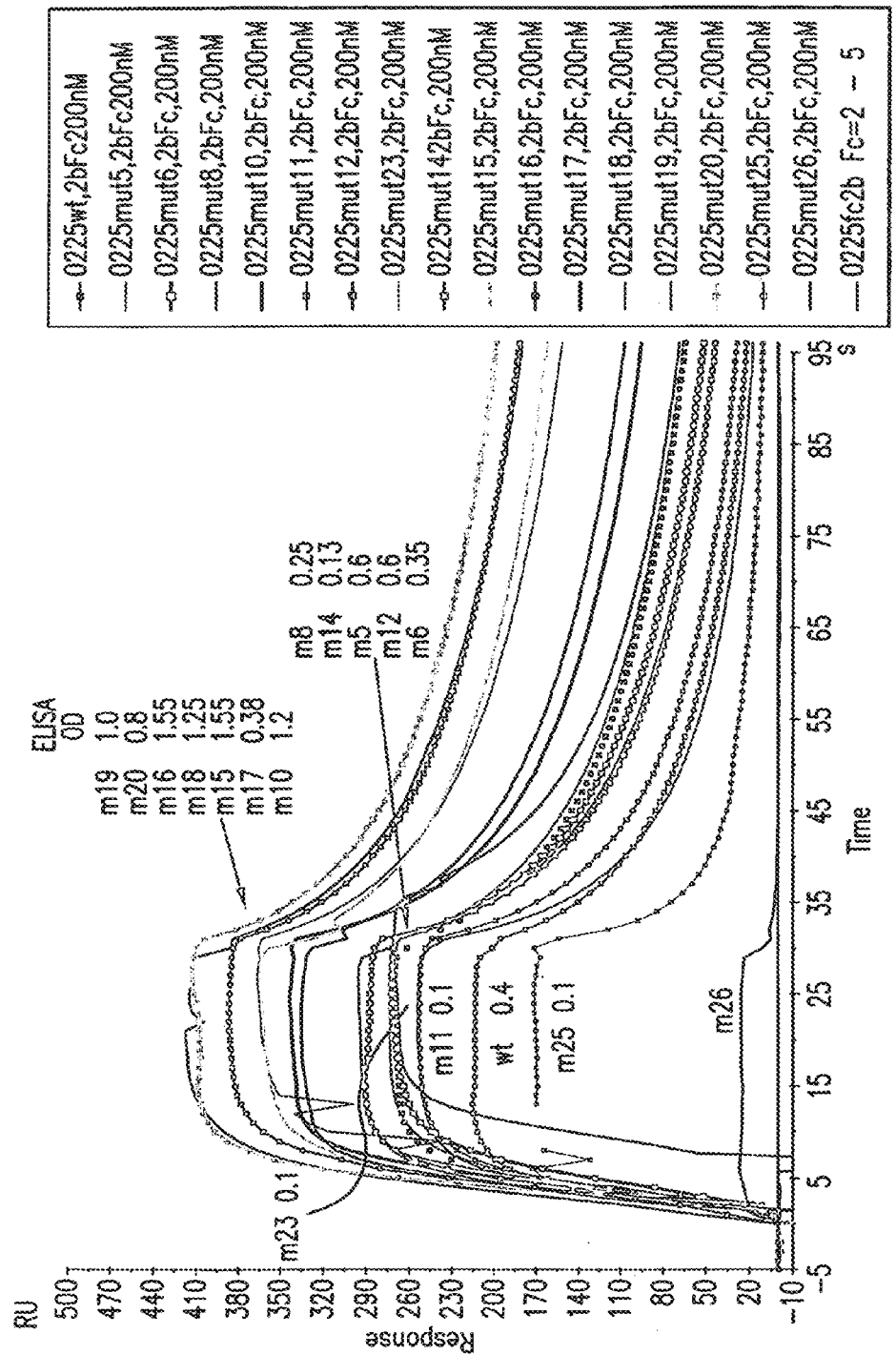

FIG. 17 SENSOGRAM OF REAL TIME BINDING OF FcγRIIB-Fc FUSION PROTEINS TO ANTIBODIES CARRYING VARIANT Fc REGIONS

Binding of FcγRIIB-Fc fusion proteins to ch-4-4-20 antibodies carrying variant Fc regions was analyzed at 200 nM concentration. Responses were normalized at the level of ch-4-4-20 antibody obtained for wild type.

Figure 18A:
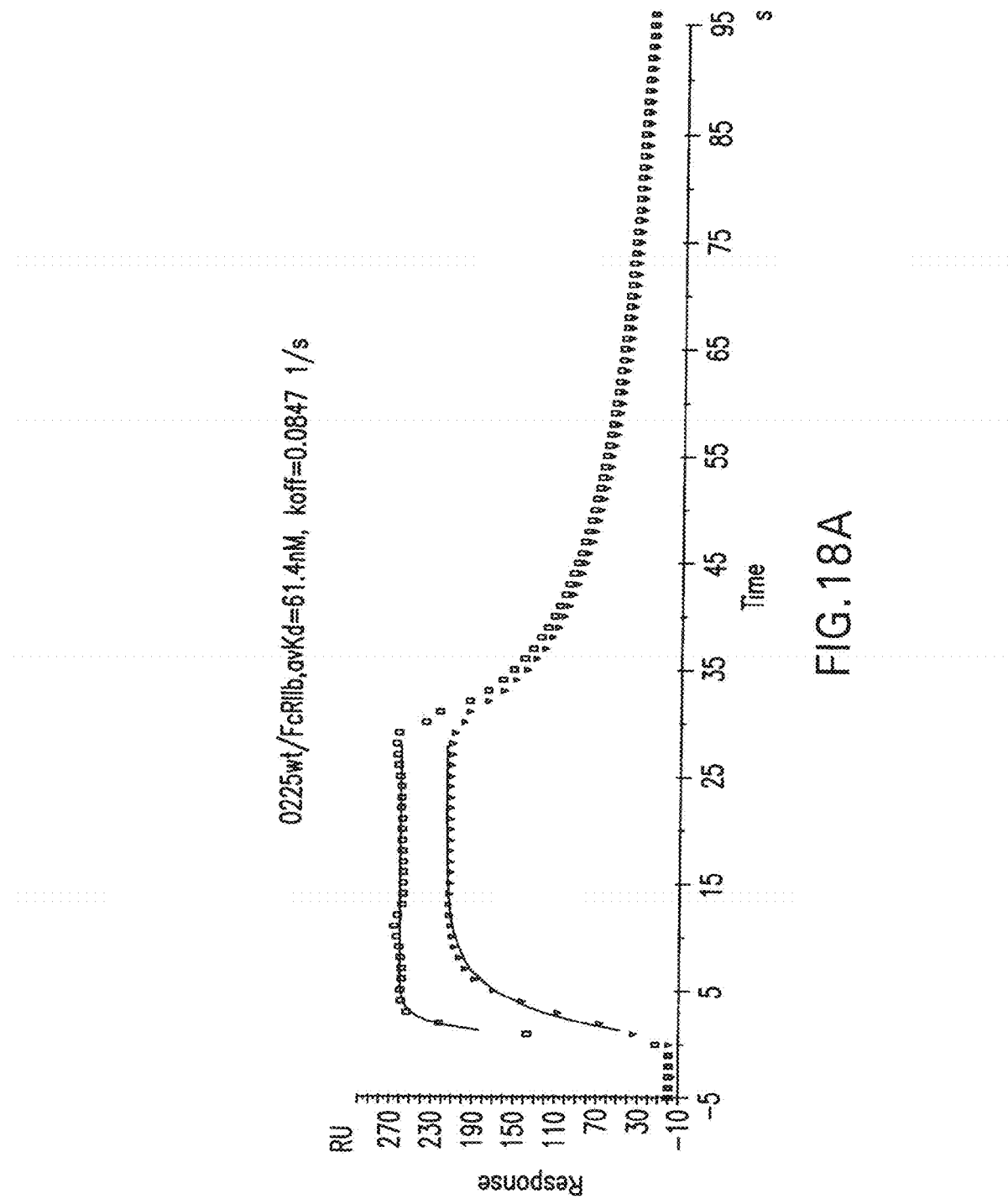
Figure 18B:
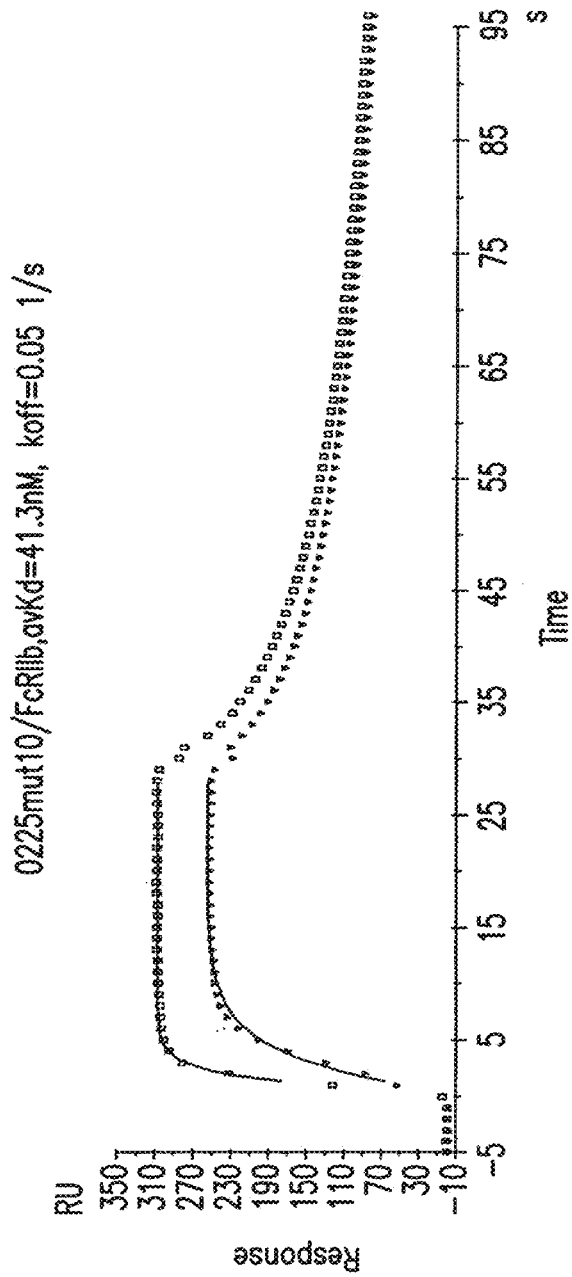
Figure 18C:
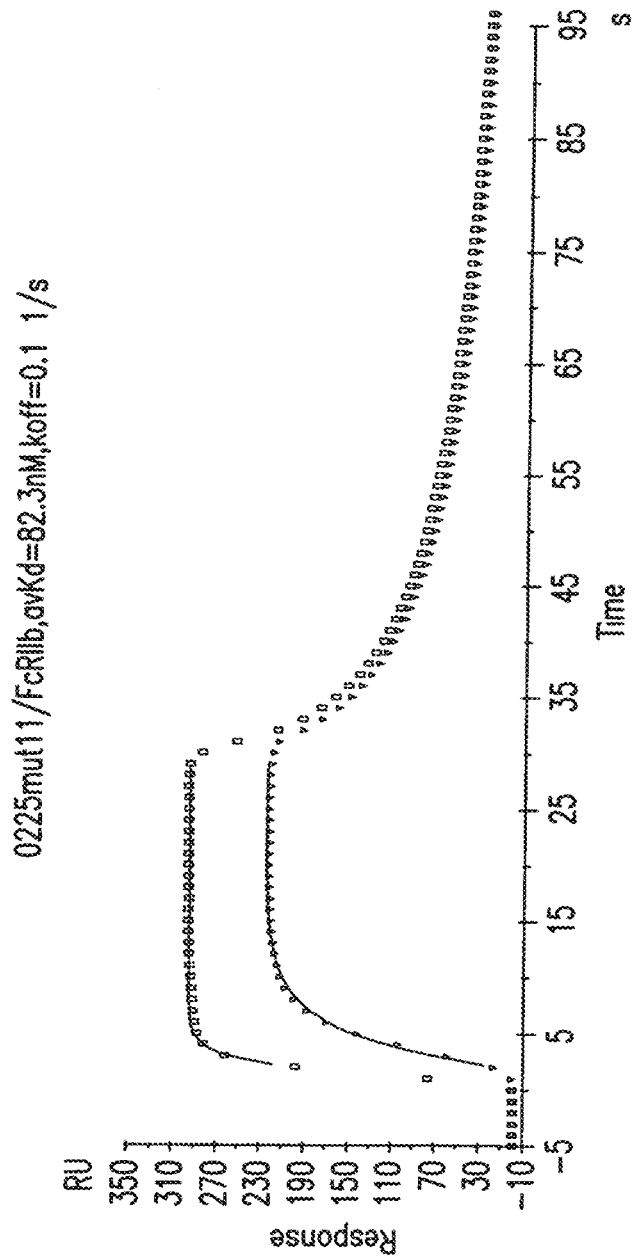

FIGS. 18A-C ANALYSIS OF KINETIC PARAMETERS FcγRIIB-Fc FUSION PROTEINS TO ANTIBODIES CARRYING VARIANT Fc REGIONS

Kinetic parameters for FcγRIIB-Fc binding to antibodies carrying variant Fc regions were obtained by generating separate best fit curves for 200 nM and 800 nM. Solid line indicates an association fit which was obtained based on the $k_{off}$ values calculated for the dissociation curves in the 32-34 sec. interval. $K_d$ and $K_{off}$ values represent the average from two concentrations.

Mutants used were as follows: Mut 6 (S219V), Mut 10 (P396L, A330S, K288N); Mut 18 (K326E); Mut 14 (K334E, K288N); Mut 11 (R255L, F243L); Mut 16 (F372Y); Mut 19 (K334N, K246I).

Figure 19:
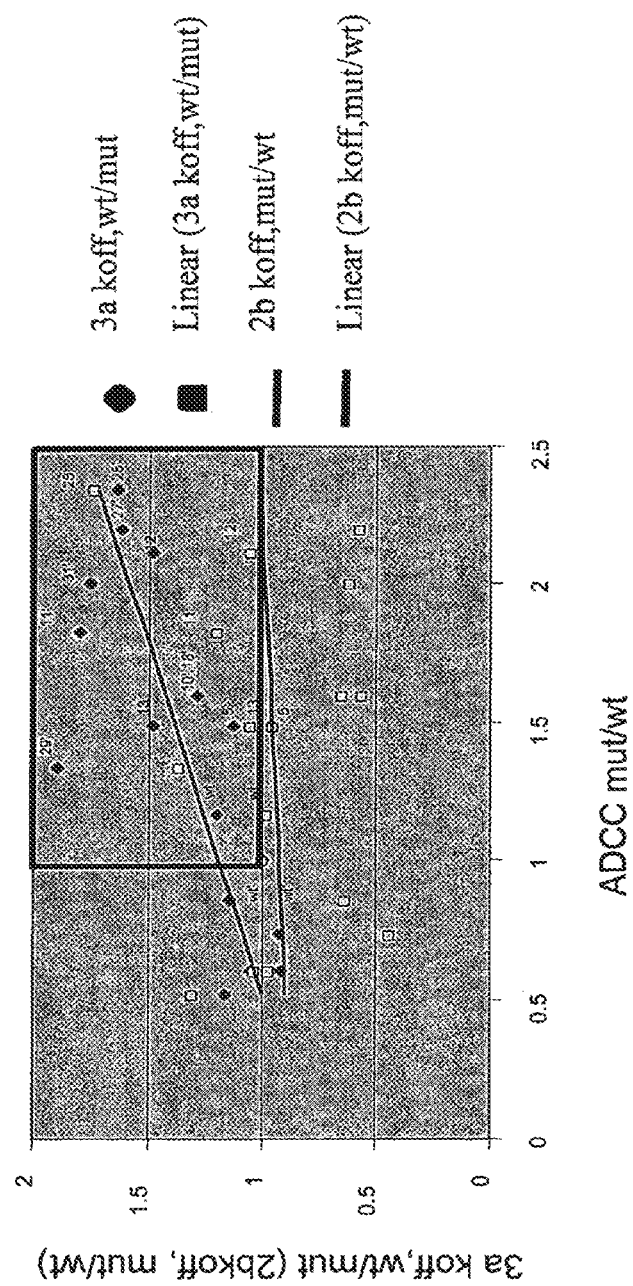

FIG. 19 RATIOS OF $K_{off}$ (WT)/$K_{off}$ (MUT) FOR FcγRIIIA-Fc PLOTTED AGAINST ADCC DATA Numbers higher than one show a decreased dissociation rate for FcγRIIIA binding and increased dissociation rate for FcγRIIB-Fc binding relative to wild-type. Mutants in the box have lower off rate for FcγRIIIA binding and higher off rate for FcγRIIB-Fc binding.

Figure 20:
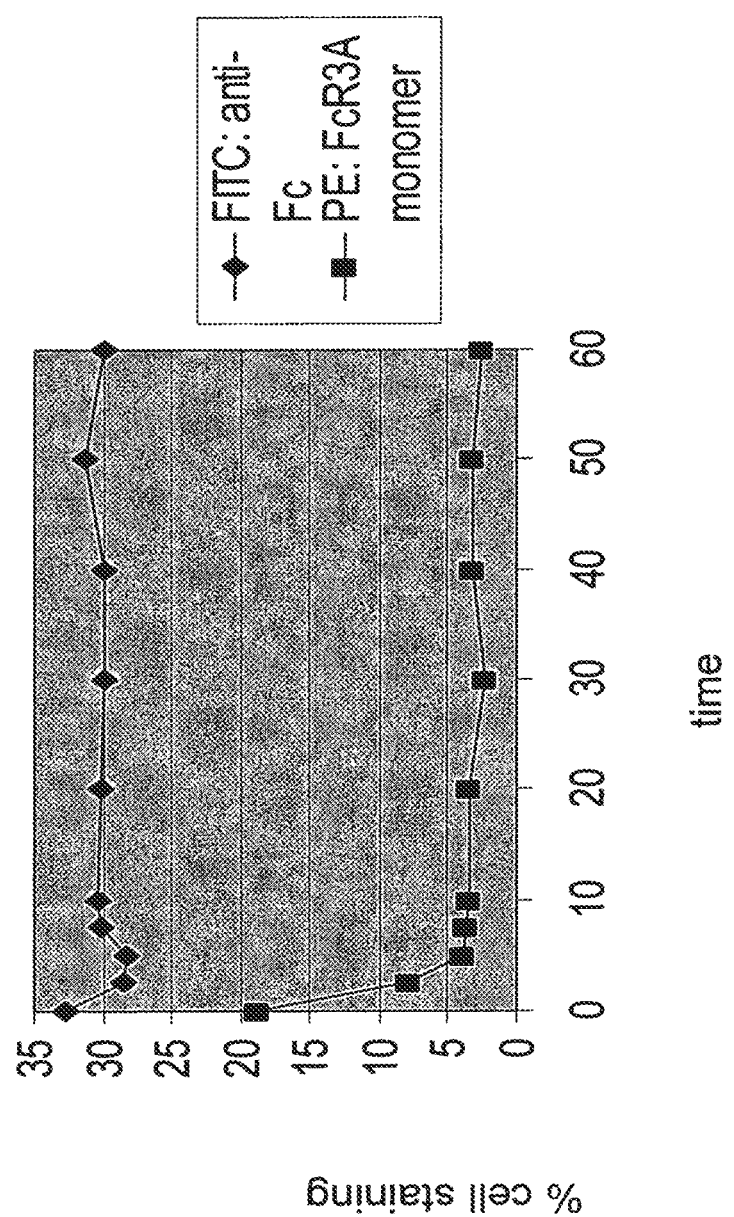

FIG. 20 COMPETITION WITH UNLABELED FcγRIIIA

A kinetic screen was implemented to identify Fc region mutants with improved $K_{off}$ rates for binding FcγRIIIA A library of Fc region variants containing P396L mutation was incubated with 0.1 μM biotinylated FcγRIIIA-Linker-Avitag for one hour and then washed. Subsequently 0.8 μM unlabeled FcγRIIIA was incubated with the labeled yeast for different time points. Yeast was spun down and unlabeled FcγRIIIA was removed. Receptor bound yeast was stained with SA (streptavidin):PE (phycoerythrin) for FACS analysis.

FIGS. 21A-C FACS ANALYSIS BASED ON THE KINETIC SCREEN

Based on the calculated $K_{off}$ from the data presented in FIG. 20, a one minute time point selection was chosen. A 10-fold excess of library was incubated with 0.1 M biotinylated FcγRIIIA-Linker-Avitag™ monomer; cells were washed and incubated with unlabeled ligand for one minute; then washed and labeled with SA:PE. The cells were then sorted by FACS, selecting the top 0.3% binders. The nonselected P396L library was compared to the yeast cells selected for improved binding by FACS. The histograms show the percentage of cells that are costained with both FcγRIIIA/PE and goat anti-human Fc/FITC.

Figures 1, 22A:
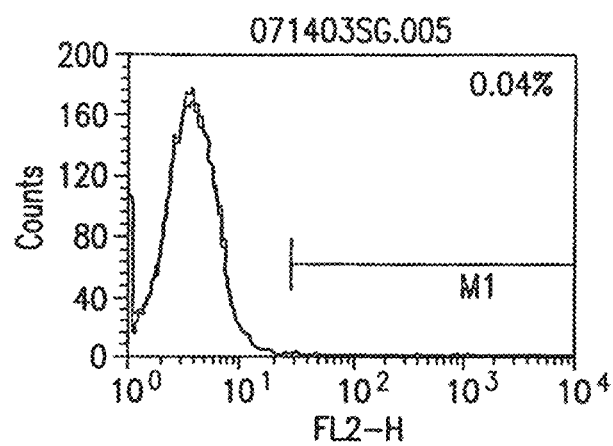
Figures 2, 22A:
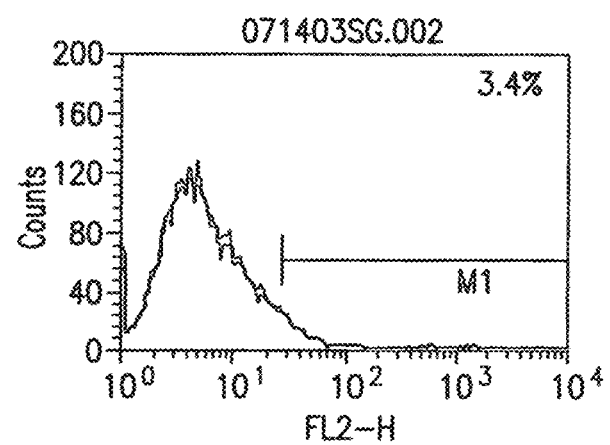
Figures 3, 22A:
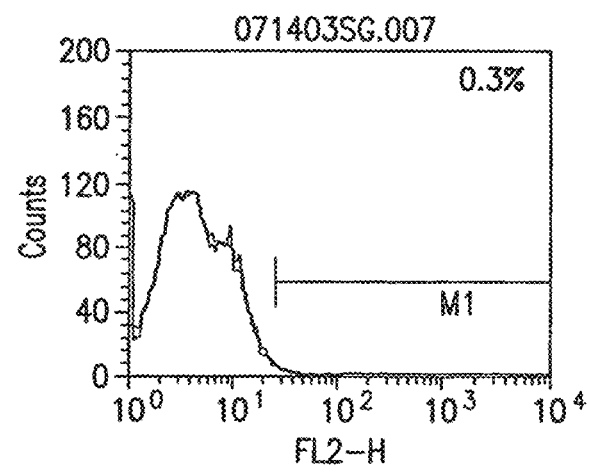
Figures 4, 22A:
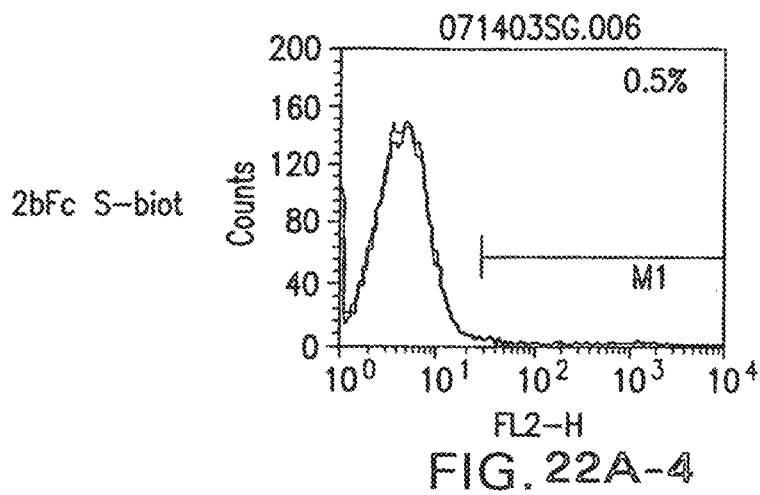
Figures 5, 22A:
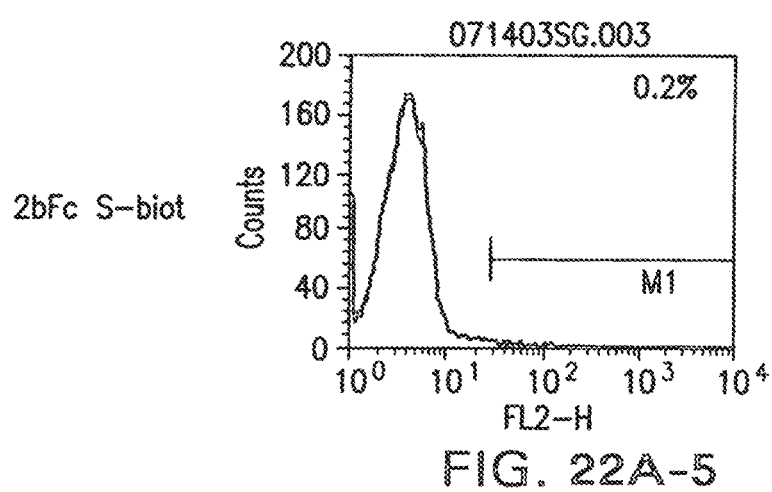
Figures 6, 22A:
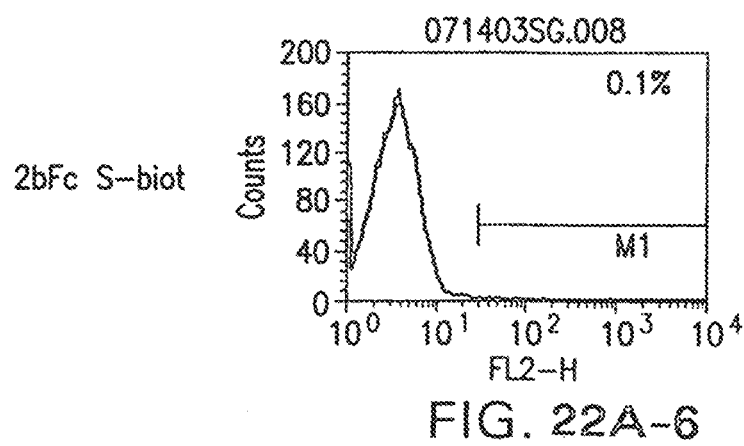
Figures 1, 22B:
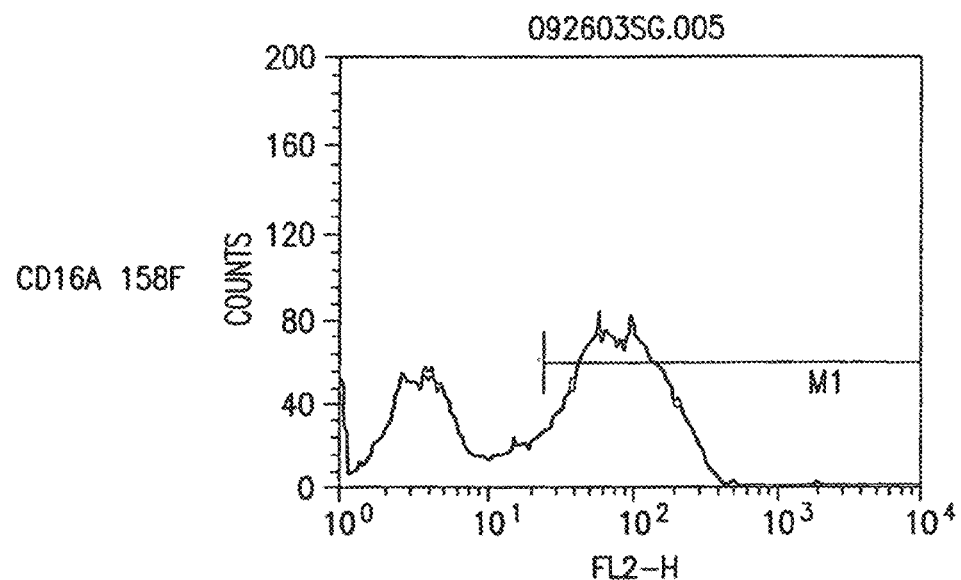
Figures 2, 22B:
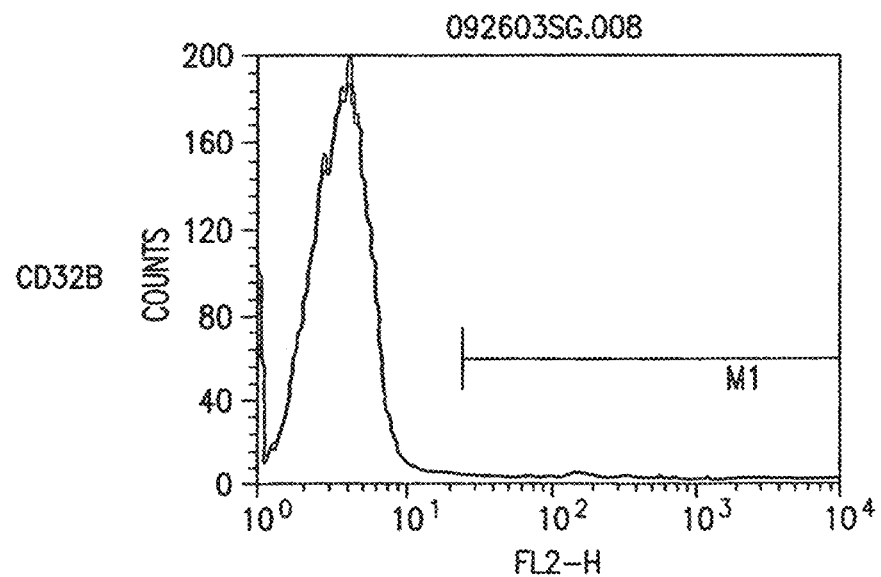
Figures 3, 22B:
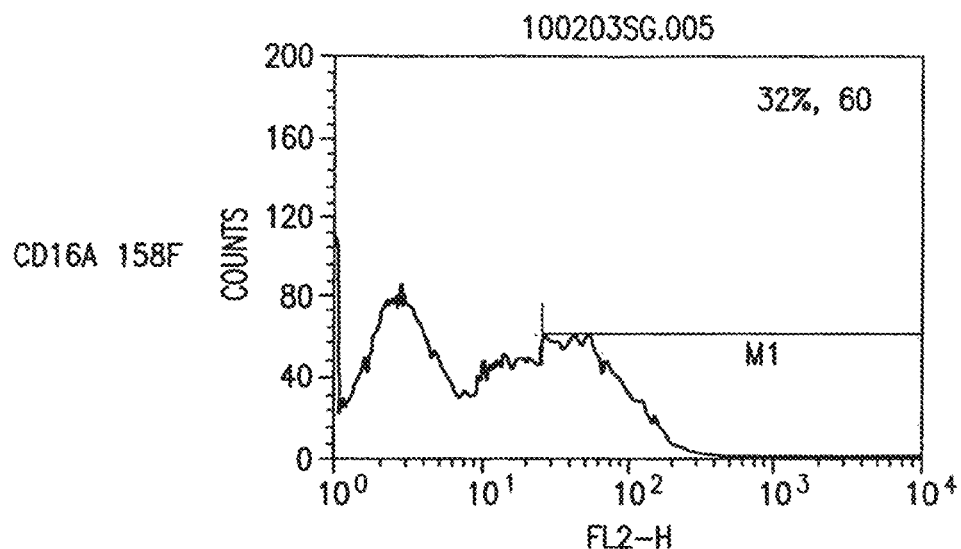
Figures 4, 22B:
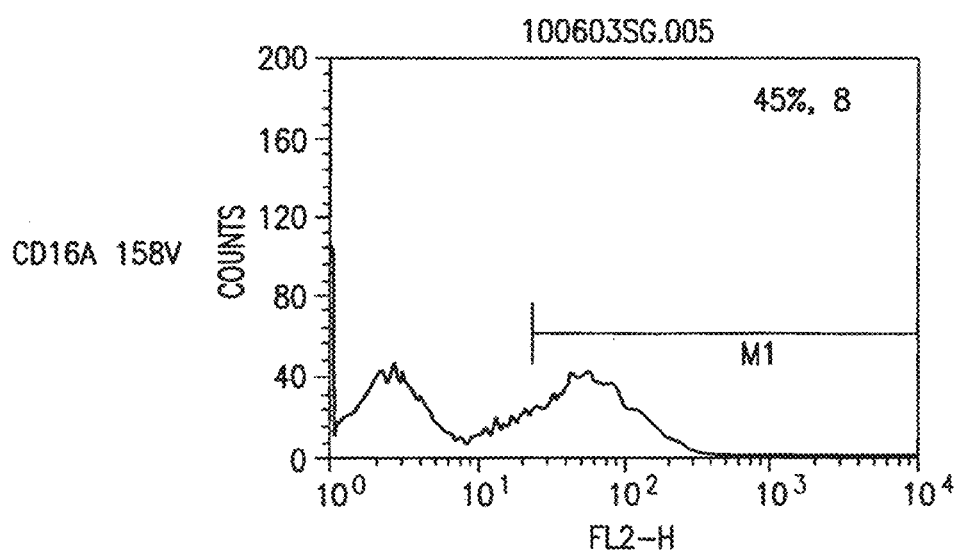
Figures 5, 22B:
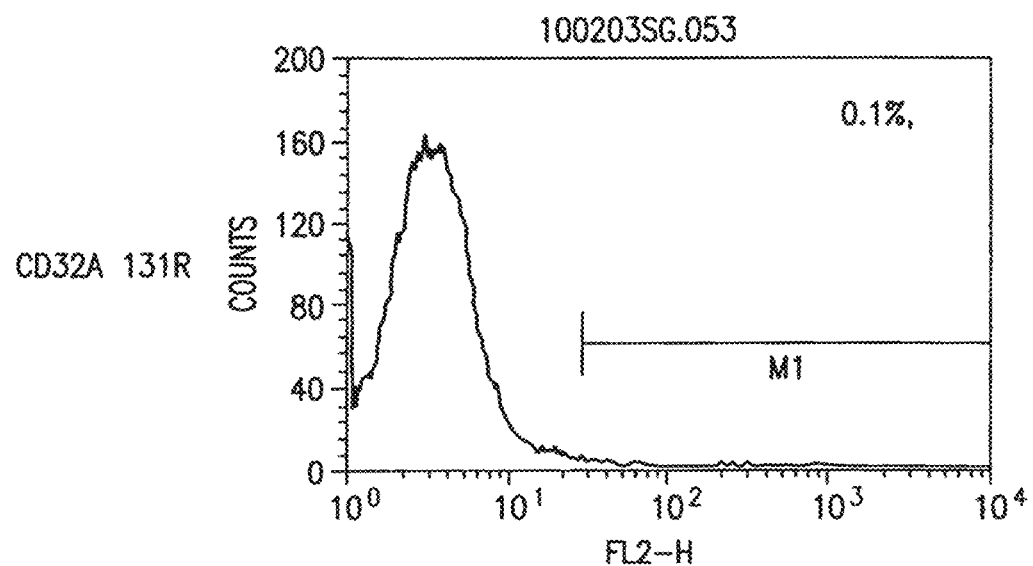
Figures 6, 22B:
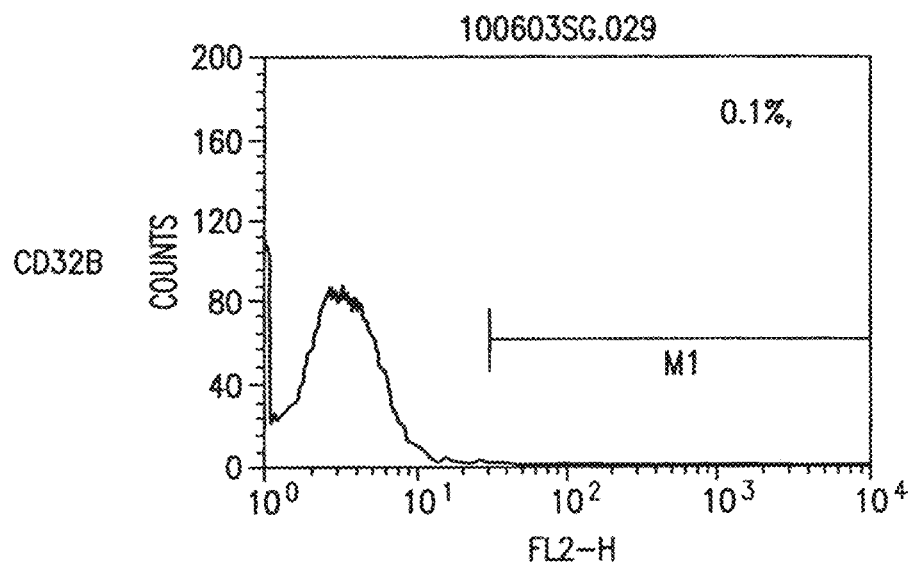

FIGS. 22A-B SELECTION BASED ON SOLID PHASE DEPLETION OF FcγRIIB Fc BINDERS

A. The P396L library was screened based on FcγRIIB depletion and FcγRIIIA selection using magnetic beads. The FcγRIIB depletion by magnetic beads was repeated 5 times. The resulting yeast population was analyzed and found to show greater than 50% cell staining with goat anti-human Fc and a very small percentage of cells stained with FcγRIIIA Subsequently cells were selected twice by FACS using 0.1 μM biotinylated FcγRIIIA linker Avitag™. Yeast cells were analyzed for both FcγRIIIA and FcγRIIB binding after each sort and compared to wild type binding.

B. Fc Mutants were selected from the FcγRIIB depleted yeast population using biotinylated FcγRIIIA 158F linker Avitag™ monomer as a ligand. The sort gate was set to select the top 0.25% FcγRIIIA 158F binders. The resulting enriched population was analyzed by FACS for binding to the different FcγRIIIA (158F and 158V), FcγRIIIB and FcγRIIA (131R).

Figure 23:
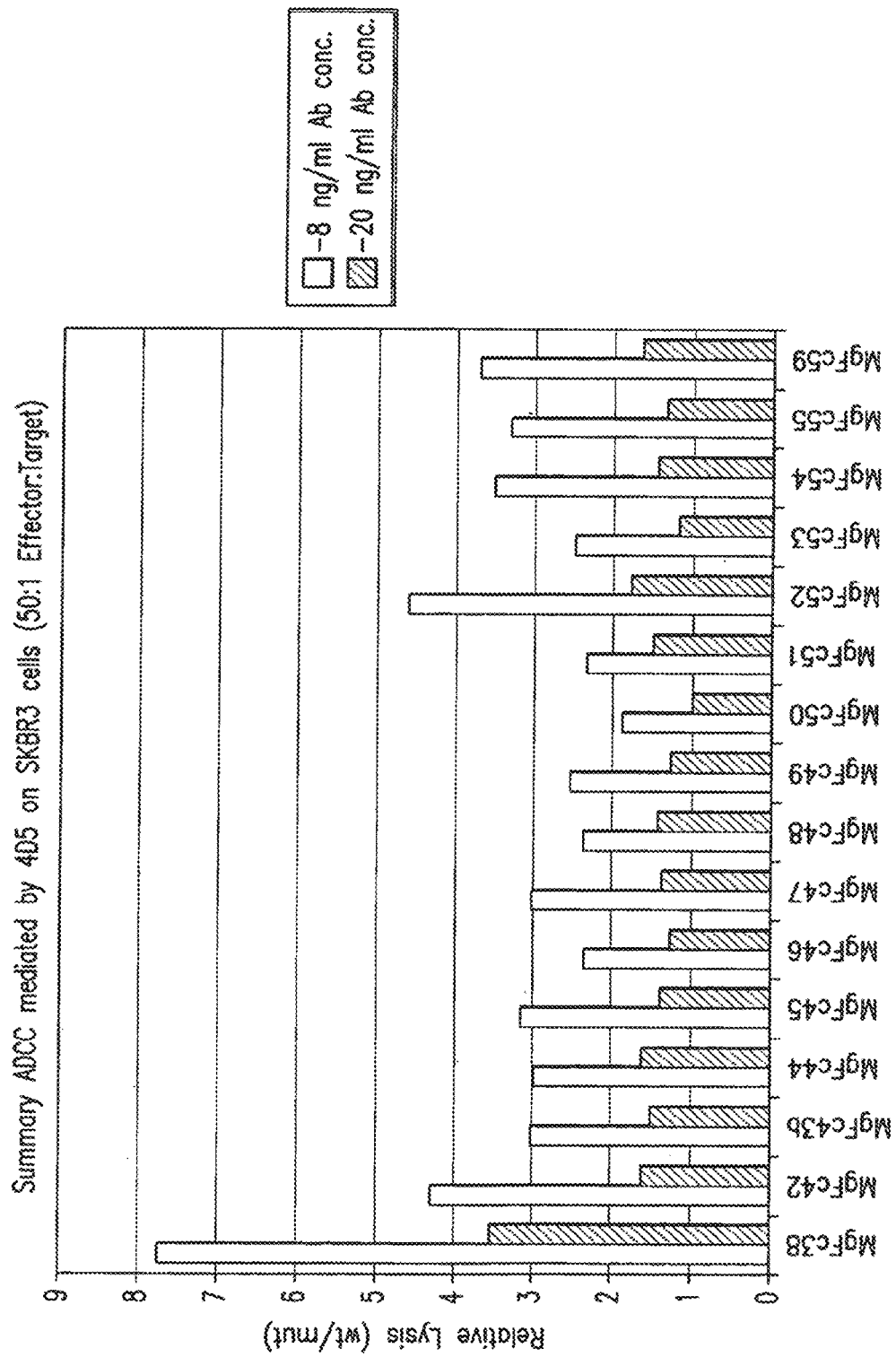

FIG. 23 RELATIVE RATES OF SKBR3 TARGET CELL LYSIS MEDIATED BY CHIMERIC 4D5 HARBORING Fc MUTANTS

Relative rates of lysis was calculated for each Fc mutant tested. Lysis rates for 4D5 antibody with Fc mutants were divided by the rate of lysis mediated by wild type 4D5 antibody. Data from at least 2 independent assays were averaged and plotted on the histogram. For each Fc mutant data from two different antibody concentrations are shown. The antibody concentrations were chosen to flank the point along the curve at which lysis was ~50%.

Figure 24:
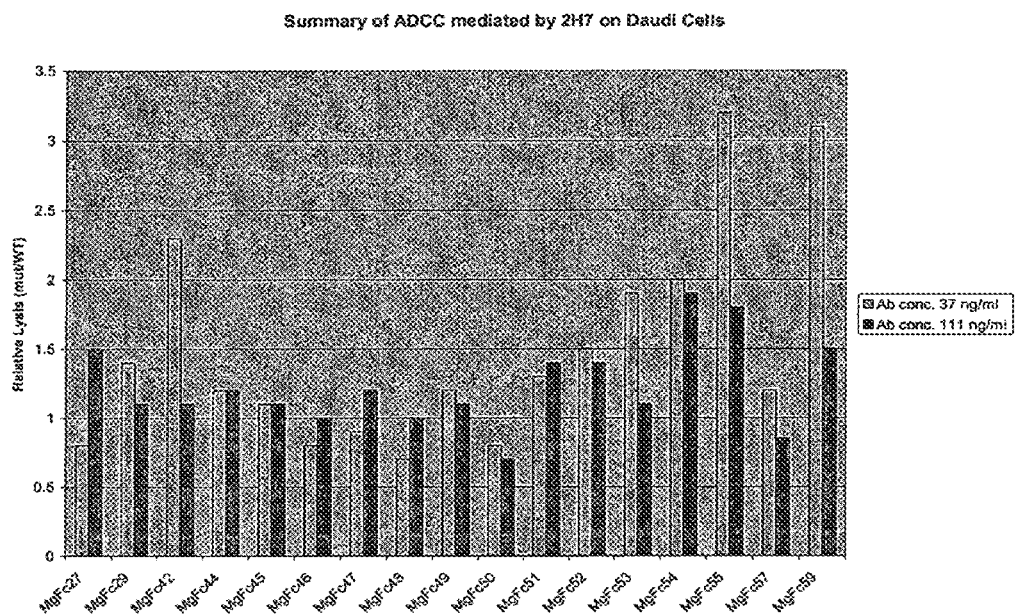

FIG. 24 RELATIVE RATES OF DAUDI CELL LYSIS MEDIATED BY CHIMERIC 2H7 HARBORING FC MUTANTS

Relative rates of lysis were calculated for each Fc mutant tested. Lysis rates for 2H7 antibody with Fc mutants were divided by the rate of lysis mediated by wild type 2H7 antibody. Data from at least 1-2 independent assays were averaged and plotted on the histogram. For each Fc mutant, data from two different antibody concentrations are shown The antibody concentrations were chosen based on the point along the curve at which lysis was ~50%.

FIG. 25 SCHEME FOR LIBRARY PRODUCTION.

DNA strands are represented. Forward arrows represent primers containing mutant codons. Reverse arrow represent reverse gene specific oligo.

FIG. 26 STRATEGY FOR PRODUCTION OF LIBRARIES BY BUILD A GENE PROTOCOL.

The rectangular boxes represent the hinge, CH2, and CH3 domains, respectively. The short black lines represent the double stranded oligos with 5' overhangs.

Figure 27:
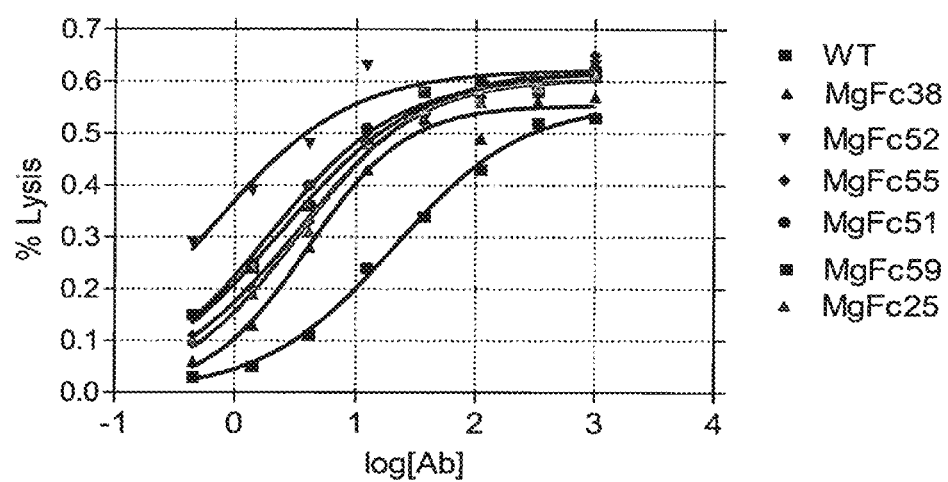

FIG. 27 NOVEL Fc MUTANTS IMPROVE PBMC MEDIATED ADCC IN SKBR3 CELLS.

The plot shows linear regression analysis of a standard ADCC assay. Antibody was titrated over 3 logs using an effector to target ratio of 75:1. % lysis=(Experimental release−SR)/(MR−SR)*100.

Figure 28:
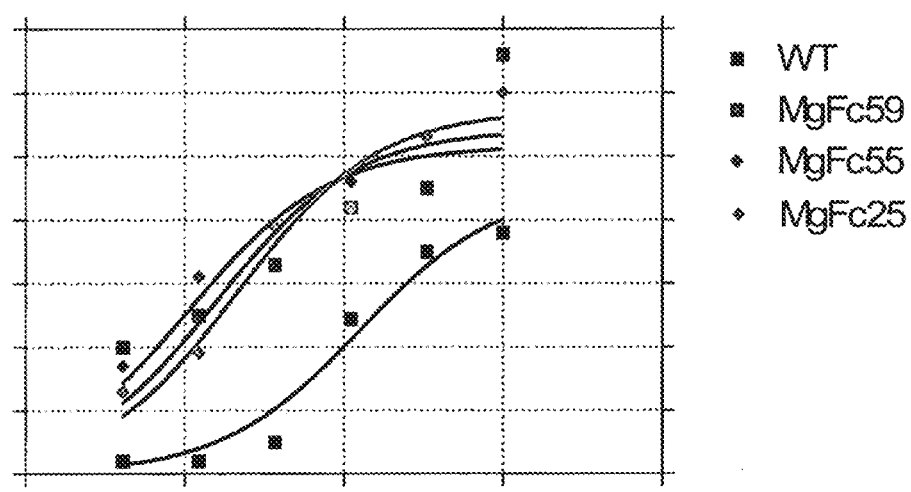

FIG. 28 NOVEL Fc MUTANTS IMPROVE PBMC MEDIATED ADCC IN DAUDI CELLS.

The plot shows linear regression analysis of a standard ADCC assay. Antibody was titrated over 3 logs using an effector to target ratio of 75:1. % lysis=(Experimental release−SR)/(MR−SR)*100.

Figure 29:
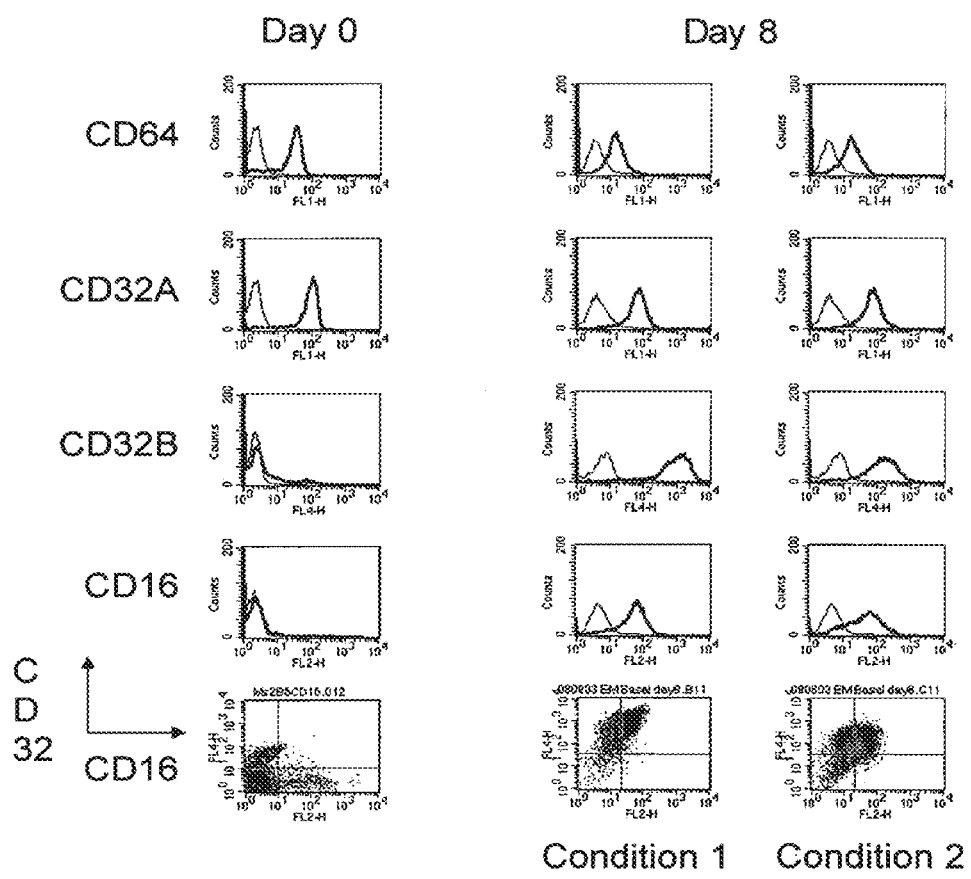

FIG. 29 Fc RECEPTOR PROFILES VIA FACS UPON CYTOKINE TREATMENT OF MONOCYTES.

Cytokine treatment of monocytes increases low affinity Fc receptor expression Elutriated monocytes were cultured using specific cytokines in serum free media. Fc receptor profiles were assayed using FACS.

Figure 30:
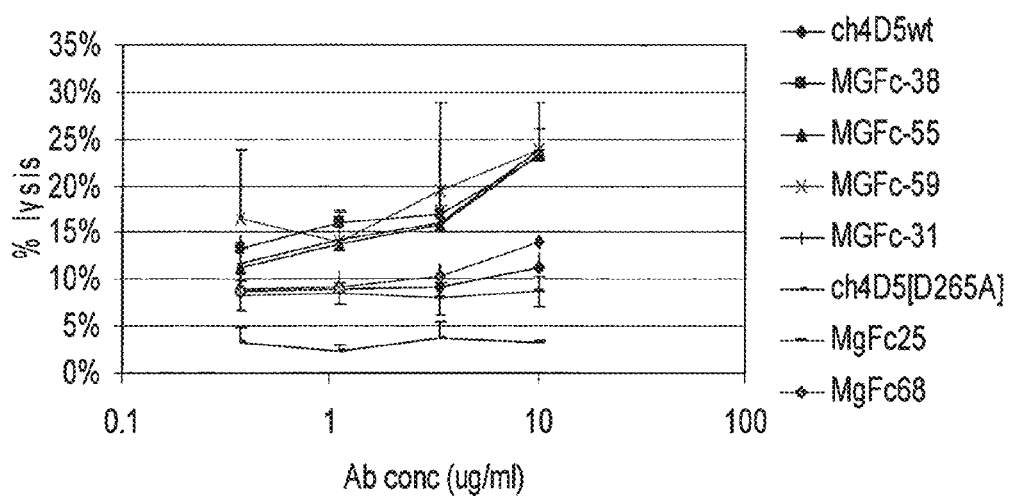

FIG. 30 IMPROVED TUMOR CELL KILLING USING Fc MUTANTS IN MACROPHAGE-DERIVED MONOCYTES BASED ADCC.

Ch4D5 MAb concentration over 2 logs was tested using effector:target ratio of 35:1. Percent lysis was calculated as in FIG. 28.

FIG. 31 COMPLEMENT DEPENDENT CYTOTOXICITY ASSAY FLOW CHART.

The flow chart summarizes the CDC assays used.

FIG. 32 COMPLEMENT DEPENDENT CYTOTOXICITY ACTIVITY

Fc mutants that show enhanced binding to FcγRIIIA also showed improved complement activity. Anti-CD20 ChMAb over 3 orders of magnitude was titrated. Percent lysis was calculated as in as in FIG. 28.

Figure 33:
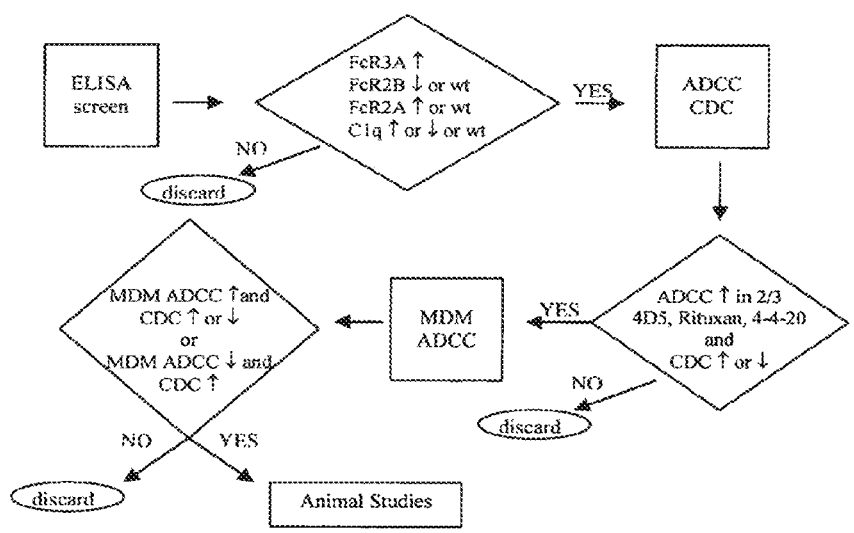

FIG. 33 DECISION TREE FOR SELECTION OF Fc MUTANTS

An exemplary protocol for selecting Fc mutants.

FIG. 34 C1q BINDING TO 2B6 ANTIBODY

A. The diagram depicts the BIAcore format for analysis of 2B6 binding to the first component of the complement cascade.

B. Sensogram of real time binding of 2B6 antibody carrying variant Fc regions to C1q.

FIGS. 35A-D C1q BINDING TO 2B6 MUTANT ANTIBODY.

Sensogram of real time binding of 2B6 mutants to C1q (3.25 nM). Mutants depicted at MgFc51 (Q419H, P396L); MgFc51/60 in Panel A; MgFc55 and MgFc55/60 (Panel B), MgFc59 and MgFc59/60 (Panel C); and MgFc31/60 (Panel D).

FIGS. 36A-D Fc VARIANTS WITH DECREASED BINDING TO FcγRIIB

Binding of FcR to ch4D5 antibodies to compare effect of D270E (60) on R255L, P396L double mutant (MgFc55). K$_D$ was analyzed at different concentrations of FcR; 400 nM CD16A 158V; 800 nM CD16A 158F; 200 nM CD32B; 200 nM CD32A 131H. Analysis was performed using separate K$_D$ using Biacore 3000 software.

FIGS. 37A-D KINETIC CHARACTERISTICS OF 4D5 MUTANTS SELECTED FROM FcγRIIB DEPLETIONS/FcγRIIAH131 SELECTION

Binding of FcR to ch4D5 antibodies carrying different Fc mutations selected by CD32B depletion and CD32A H131 screening strategy. K$_D$ was analyzed at different concentrations of FcR; 400 nM CD16A 158V; 800 nM CD16A 158F; 200 nM CD32B; 200 nM CD32A 131H. Analysis was performed using separate K$_D$ using Biacore 3000 software.

Figure 38:
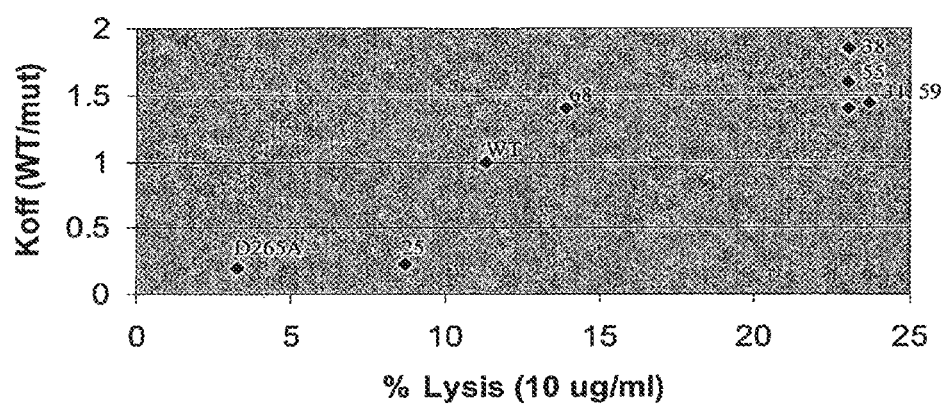

FIG. 38. PLOT OF MDM ADCC DATA AGAINST THE K$_{OFF}$ DETERMINED FOR CD32A 131H BINDING AS DETERMINED BY BIACORE.

The mutants are as follows: MgFc 25 (E333A, K334A, S298A); MgFc68 (D270E); MgFc38 (K392T, P396L); MgFc55 (R255L, P396L); MgFc31 (P247L, N421K); MgFc59 (K370E, P396L).

4. DESCRIPTION OF THE PREFERRED EMBODIMENTS

The present invention relates to molecules, preferably polypeptides, and more preferably immunoglobulins (e.g., antibodies), comprising a variant Fc region, having one or more amino acid modifications (e.g., substitutions, but also including insertions or deletions) in one or more regions, which modifications alter, e.g., increase or decrease, the affinity of the variant Fc region for an FcγR. In some embodiments, the invention provides molecules comprising a variant Fc region, wherein said variant Fc region comprises at least one amino acid modification relative to a wild-type Fc region, which variant Fc region binds FcγRIIIA with a greater affinity, relative to a comparable molecule, i.e., being the same as said molecule with a variant Fc region but not having the one or more amino acid modifications, comprising the wild-type Fc region as determined by methods known to one skilled in the art for determining Fc-FcγR interactions and methods disclosed herein, for example, an ELISA assay or a surface plasmon resonance assay. In yet other embodiments, the invention encompasses molecules comprising a variant Fc region, wherein said variant Fc region comprises at least one amino acid modification relative to a wild-type Fc region, which variant Fc region binds FcγRIIIA with a reduced affinity relative to a comparable molecule comprising the wild-type Fc region. In a preferred embodiment, the molecules of the invention further specifically bind FcγRIIB (via the Fc region) with a lower affinity than a comparable molecule comprising the wild-type Fc region binds FcγRIIB. In some embodiments, the invention encompasses molecules comprising a variant Fc region, wherein said variant Fc region comprises at least one amino acid modification relative to a wild-type Fc region, which variant Fc region binds FcγRIIIA and FcγRIIB with a greater affinity, relative to a comparable molecule comprising the wild-type Fc region. In other embodiments, the invention encompasses molecules comprising a variant Fc region, wherein said variant Fc region comprises at least one amino acid modification relative to a wild-type Fc region, which variant Fc region binds FcγRIIB with a greater affinity, relative to a comparable molecule comprising the wild-type Fc region. In other embodiments, the invention encompasses molecules comprising variant Fc region, wherein said variant Fc region comprises at least one amino acid modification relative to a wild-type Fc region, which variant Fc region binds FcγRIIB with a reduced affinity, relative to a comparable molecule comprising the wild-type Fc region.

In some embodiments, the invention encompasses molecules comprising a variant Fc region, wherein said variant Fc region comprises at least one amino acid modification relative to a wild type Fc region, which variant Fc region does not show a detectable binding to any FcγR (e.g., does not bind FcγRIIA, FcγRIIB, or FcγRIIIA, as determined by, for example, an ELISA assay), relative to a comparable molecule comprising the wild-type Fc region.

In a specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγIIIA. In another specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIA. In yet another embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIB. The invention particularly relates to the modification of human or humanized therapeutic antibodies (e.g., tumor specific anti-angiogenic or anti-inflammatory monoclonal antibodies) for enhancing the efficacy of therapeutic antibodies by enhancing, for example, the effector function of the therapeutic antibodies, e.g., enhancing ADCC.

The affinities and binding properties of the molecules of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 5.2.1). Preferably, the binding properties of the molecules of the invention are also characterized by in vitro functional assays for determining one or more FcγR mediator effector cell functions (See Section 5.2.6). In most preferred embodiments, the molecules of the invention have similar binding properties in in vivo models (such as those described and disclosed herein) as those in in vitro based assays However, the present invention does not exclude molecules of the invention that do not exhibit the desired phenotype in in vitro based assays but do exhibit the desired phenotype in vivo.

In some embodiments, the molecules of the invention comprising a variant Fc region comprise at least one amino acid modification in the CH3 domain of the Fc region, which is defined as extending from amino acids 342-447. In other embodiments, the molecules of the invention comprising a variant Fc region comprise at least one amino acid modification in the CH2 domain of the Fc region, which is defined as extending from amino acids 231-341. In some embodiments, the molecules of the invention comprise at least two amino acid modifications, wherein one modification is in the CH3 region and one modification is in the CH2 region. The invention further encompasses amino acid modification in the hinge region. Molecules of the invention with one or more amino acid modifications in the CH2 and/or CH3 domains have altered affinities for an FcγR as determined using methods described herein or known to one skilled in the art.

In a particular embodiment, the invention encompasses amino acid modification in the CH1 domain of the Fc region.

In particularly preferred embodiments, the invention encompasses molecules comprising a variant Fc region wherein said variant has an increased binding to FcγRIIA (CD32A) and/or an increased ADCC activity, as measured using methods known to one skilled in the art and exemplified herein. The ADCC assays used in accordance with the methods of the invention may be NK dependent or macrophage dependent.

The Fc variants of the present invention may be combined with other known Fc modifications including but not limited to modifications which alter effector function and modification which alter FcγR binding affinity. In a particular embodiment, an Fc variant of the invention comprising a first amino acid modification in the CH3 domain, CH2 domain or the hinge region may be combined with a second Fc modification such that the second Fc modification is not in the same domain as the first so that the first Fc modification confers an additive, synergistic or novel property on the second Fc modification. In some embodiments, the Fc variants of the invention do not have any amino acid modification in the CH2 domain.

The Fc variants of the present invention may be combined with any of the known Fc modifications in the art such as those disclosed in Table 2 below.

TABLE 2

| Substitution(s) |
| --- |
| V264A |
| V264L |
| V264I |
| F241W |
| F241L |
| F243W |
| F243L |
| F241L/F243L/V262I/V264I |
| F241W/F243W |
| F241W/F243W/V262A/V264A |
| F241L/V262I |
| F243L/V264I |
| F243L/V262I/V264W |
| F241Y/F243Y/V262T/V264T |
| F241E/F243R/V262E/V264R |
| F241E/F243Q/V262T/V264E |
| F241R/F243Q/V262T/V264R |
| F241E/F243Y/V262T/V264R |
| L328M |
| L328E |
| L328F |
| I332E |
| L328M/I332E |
| P244H |
| P245A |
| P247V |
| W313F |
| P244H/P245A/P247V |
| P247G |
| V264I/I332E |
| F241E/F243R/V262E/V264R/I332E |
| F241E/F243Q/V262T/V264E/I332E |
| F241R/F243Q/V262T/V264R/I332E |
| F241E/F243Y/V262T/V264R/I332E |
| S298A |
| S298A/I332E |
| S298A/E333A/K334A |
| S239E/I332E |
| S239Q/I332E |
| S239E |
| D265G |
| D265N |

TABLE 2-continued

| Substitution(s) |
| --- |
| S239E/D265G |
| S239E/D265N |
| S239E/D265Q |
| Y296E |
| Y296Q |
| S298T |
| S298N |
| T299I |
| A327S |
| A327N |
| S267Q/A327S |
| S267L/A327S |
| A327L |
| P329F |
| A330L |
| A330Y |
| I332D |
| N297S |
| N297D |
| N297S/I332E |
| N297D/I332E |
| N297E/I332E |
| D265Y/N297D/I332E |
| D265Y/N297D/T299L/I332E |
| D265F/N297E/I332E |
| L328I/I332E |
| L328Q/I332E |
| I332N |
| I332Q |
| V264T |
| V264F |
| V240I |
| V263I |
| V266I |
| T299A |
| T299S |
| T299V |
| N325Q |
| N325L |
| N325I |
| S239D |
| S239N |
| S239F |
| S239D/I332D |
| S239D/I332E |
| S239D/I332N |
| S239D/I332Q |
| S239E/I332D |
| S239E/I332N |
| S239E/I332Q |
| S239N/I332D |
| S239N/I332E |
| S239N/I332N |
| S239N/I332Q |
| S239Q/I332D |
| S239Q/I332N |
| S239Q/I332Q |
| K326E |
| Y296D |
| Y296N |
| F241Y/F243Y/V262T/V264T/N297D/I332E |
| A330Y/I332E |
| V264I/A330Y/I332E |
| A330L/I332E |
| V264I/A330L/I332E |
| L234D |
| L234E |
| L234N |
| L234Q |
| L234T |
| L234H |
| L234Y |
| L234I |
| L234V |
| L234F |
| L235D |
| L235S |
| L235N |

TABLE 2-continued

| Substitution(s) |
|---|
| L235Q |
| L235T |
| L235H |
| L235Y |
| L235I |
| L235V |
| L235F |
| S239T |
| S239H |
| S239Y |
| V240A |
| V240T |
| V240M |
| V263A |
| V263T |
| V263M |
| V264M |
| V264Y |
| V266A |
| V266T |
| V266M |
| E269H |
| E269Y |
| E269F |
| E269R |
| Y296S |
| Y296T |
| Y296L |
| Y296I |
| A298H |
| T299H |
| A330V |
| A330I |
| A330F |
| A330R |
| A330H |
| N325D |
| N325E |
| N325A |
| N325T |
| N325V |
| N325H |
| L328D/I332E |
| L328E/I332E |
| L328N/I332E |
| L328Q/I332E |
| L328V/I332E |
| L328T/I332E |
| L328H/I332E |
| L328I/I332E |
| L328A |
| I332T |
| I332H |
| I332Y |
| I332A |
| S239E/V264I/I332E |
| S239Q/V264I/I332E |
| S239E/V264I/A330Y/I332E |
| S239E/V264I/S298A/A330Y/I332E |
| S239D/N297D/I332E |
| S239E/N297D/I332E |
| S239D/D265V/N297D/I332E |
| S239D/D265I/N297D/I332E |
| S239D/D265L/N297D/I332E |
| S239D/D265F/N297D/I332E |
| S239D/D265Y/N297D/I332E |
| S239D/D265H/N297D/I332E |
| S239D/D265T/N297D/I332E |
| V264I/N297D/I332E |
| Y296D/N297D/I332E |
| Y296E/N297D/I332E |
| Y296N/N297D/I332E |
| Y296Q/N297D/I332E |
| Y296H/N297D/I332E |
| Y296T/N297D/I332E |
| N297D/T299V/I332E |
| N297D/T299I/I332E |
| N297D/T299L/I332E |

TABLE 2-continued

| Substitution(s) |
|---|
| N297D/T299F/I332E |
| N297D/T299H/I332E |
| N297D/T299E/I332E |
| N297D/A330Y/I332E |
| N297D/S298A/A330Y/I332E |
| S239D/A330Y/I332E |
| S239N/A330Y/I332E |
| S239D/A330L/I332E |
| S239N/A330L/I332E |
| V264I/S298A/I332E |
| S239D/S298A/I332E |
| S239N/S298A/I332E |
| S239D/V264I/I332E |
| S239D/V264I/S298A/I332E |
| S239D/V264I/A330L/I332E |
| T256A |
| K290A |
| D312A |
| *K326A |
| S298A |
| E333A |
| K334A |
| E430A |
| T359A |
| K360A |
| E430A |
| K320M |
| K326S |
| K326N |
| K326D |
| K326E |
| K334Q |
| K334E |
| K334M |
| K334H |
| K334V |
| K334L |
| A330K |
| T335K |
| A339T |
| E333A, K334A |
| T256A, S298A |
| T256A, D280A, S298A, T307A |
| S298A, E333A, K334A S298A, K334A |
| S298A, E333A |
| T256A |
| K290A |
| K326A |
| R255A |
| E258A |
| S267A |
| E272A |
| N276A |
| D280A |
| E283A |
| H285A |
| N286A |
| P331A |
| S337A |
| H268A |
| E272A |
| E430A |
| A330K |
| R301M |
| H268N |
| H268S |
| E272Q |
| N286Q |
| N286S |
| N286D |
| K290S |
| K320M |
| K320Q |
| K320E |
| K320R |
| K322E |
| K326S |
| K326D |

TABLE 2-continued

| Substitution(s) |
| --- |
| K326E |
| A330K |
| T335E |
| S267A, E258A |
| S267A, R255A |
| S267A, D280A |
| S267A, E272A |
| S267A, E293A |
| S267A, E258A, D280A, R255A |
| P238A |
| D265A |
| E269A |
| D270A |
| N297A |
| P329A |
| A327Q |
| S239A |
| E294A |
| Q295A |
| V303A |
| K246A |
| I253A |
| T260A |
| K274A |
| V282A |
| K288A |
| Q311A |
| K317A |
| E318A |
| K338A |
| K340A |
| Q342A |
| R344A |
| E345A |
| Q347A |
| R355A |
| E356A |
| M358A |
| K360A |
| N361A |
| Q362A |
| Y373A |
| S375A |
| D376A |
| E380A |
| E382A |
| S383A |
| N384A |
| Q386A |
| E388A |
| N389A |
| N390A |
| Y391A |
| K392A |
| L398A |
| S400A |
| D401A |
| D413A |
| K414A |
| S415A |
| R416A |
| Q418A |
| Q419A |
| N421A |
| V422A |
| S424A |
| E430A |
| H433A |
| N434A |
| H435A |
| Y436A |
| T437A |
| Q438A |
| K439A |
| S440A |
| S442A |
| S444A |
| K447A |
| K246M |
| K248M |
| Y300F |
| A330Q |
| K338M |
| K340M |
| A378Q |
| Y391F |

In other embodiments, the Fc variants of the present invention may be combined with any of the known Fc modifications in the art such as those disclosed in Tables 3 A and B below.

TABLE 3A

| Starting Variant | Position 300 | Position 298 | Position 296 | Position 295 | Position 294 |
| --- | --- | --- | --- | --- | --- |
| Y300I + → | — | S298N, S298V, S298D, S298P, S298A, S298G, S298T, or S298L. | Y296P, Y296F, or N276Q. | Q295K, Q295L, or Q295A. | E294N, E294A, E294Q, or E294D. |
| Y300L + → | — | S298N, S298V, S298D, S298P, S298A, S298G, S298T, or S298L. | Y296P, Y296F, or N276Q. | Q295K, Q295L, or Q295A. | E294N, E294A, E294Q, or E294D. |
| S298N + → | Y300I, Y300L, or Y300F. | — | Y296P, Y296F, or N276Q. | Q295K, Q295L, or Q295A. | E294N, E294A, E294Q, or E294D. |
| S298V + → | Y300I, Y300L, or Y300F. | — | Y296P, Y296F, or N276Q. | Q295K, Q295L, or Q295A. | E294N, E294A, E294Q, or E294D. |
| S298D + → | Y300I, Y300L, or Y300F. | — | Y296P, Y296F, or N276Q. | Q295K, Q295L, or Q295A. | E294N, E294A, E294Q, or E294D. |
| S298P + → | Y300I, Y300L, or Y300F. | — | Y296P, Y296F, or N276Q. | Q295K, Q295L, or Q295A. | E294N, E294A, E294Q, or E294D. |
| Y296P + → | Y300I, Y300L, or Y300F. | S298N, S298V, S298D, S298P, S298A, S298G, S298T, or S298L. | — | Q295K, Q295L, or Q295A. | E294N, E294A, E294Q, or E294D. |
| Q295K + → | Y300I, Y300L, or Y300F. | S298N, S298V, S298D, S298P, S298A, S298G, S298T, or S298L. | Y296P, Y296F, or N276Q. | — | E294N, E294A, E294Q, or E294D. |
| Q295L + → | Y300I, Y300L, or Y300F. | S298N, S298V, S298D, S298P, S298A, S298G, S298T, or S298L. | Y296P, Y296F, or N276Q. | — | E294N, E294A, E294Q, or E294D. |

TABLE 3A-continued

| Starting Variant | Position 300 | Position 298 | Position 296 | Position 295 | Position 294 |
|---|---|---|---|---|---|
| E294N + → | Y300I, Y300L, or Y300F. | S298N, S298V, S298D, S298P, S298A, S298G, S298T, or S298L. | Y296P, Y296F, or N276Q. | Q295K, Q295L, or Q295A. | — |

**Note that table uses EU numbering as in Kabat.

TABLE 3B

| Starting Variant | Position 334 | Position 333 | Position 324 | Position 286 | Position 276 |
|---|---|---|---|---|---|
| Y300I + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Y300L + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298N + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298V + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298D + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298P + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Y296P + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Q295K + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Q295L + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| E294N + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |

**Note that table uses EU numbering as in Kabat.

In a preferred specific embodiment, the invention encompasses a molecule comprising a variant Fc region, wherein said variant Fc region comprises at least one amino acid modification relative to a wild-type Fc region, such that said molecule has an altered affinity for an FcγR, provided that said variant Fc region does not have a substitution at positions that make a direct contact with FcγR based on crystallographic and structural analysis of Fc-FcγR interactions such as those disclosed by Sondermann et al., 2000 (*Nature*, 406: 267-273 which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that makes a direct contact with an FcγR based on structural and crystallographic analysis.

The FcγR interacting domain maps to the lower hinge region and select sites within the CH2 and CH3 domains of the IgG heavy chain. Amino acid residues flanking the actual contact positions and amino acid residues in the CH3 domain play a role in IgG/FcγR interactions as indicated by mutagenesis studies and studies using small peptide inhibitors, respectively (Sondermann et al., 2000 *Nature*, 406: 267-273; Diesenhofer et al., 1981, Biochemistry, 20: 2361-2370; Shields et al., 2001, J. Biol. Chem. 276: 6591-6604; each of which is incorporated herein by reference in its entirety). Direct contact as used herein refers to those amino acids that are within at least 1 A, at least 2, or at least 3 angstroms of each other or within 1 Å, 1.2 Å, 1.5 Å, 1.7 Å or 2 Å Van Der Waals radius. An exemplary list of previously identified sites on the Fc that effect binding of Fc interacting proteins is listed in the Table 4 below. In some embodiments, the invention encompasses Fc variants that do not have any modifications at the sites listed below. In other embodiments, the invention encompasses Fc variants comprising amino acid modifications at one or more sites listed below in combination with other modifications disclosed herein such that such modification has a synergistic or additive effect on the property of the mutant.

TABLE 4

PREVIOUSLY IDENTIFIED SITES ON THE Fc THAT EFFECT BINDING OF Fc INTERACTING PROTEINS.

| FcR-Fc | Domain | residue | FcRI | FcRII | FcRIII | C1q | FcRn |
|---|---|---|---|---|---|---|---|
|  | CH2 | 233 | C | C | C |  | C |
| A, B | CH2 | 234 | C | C | C | G | C |
| A, B | CH2 | 235 | C | C | C | G | C |
| A, B | CH2 | 236 | C | C | C |  | C |
| A, B | CH2 | 237 |  |  |  |  |  |
| A, B | CH2 | 238 | D |  |  |  |  |
| A, B | CH2 | 239 |  |  | C |  |  |
|  | CH2 | 241 | D |  |  |  |  |
|  | CH2 | 243 | D |  |  |  |  |
|  | CH2 | 246 | D |  |  |  |  |
|  | CH2 | 250 |  |  |  |  | E |
|  | CH2 | 254 |  |  |  |  | C |
|  | CH2 | 255 |  | C |  |  |  |
|  | CH2 | 256 |  | C | C |  |  |
|  | CH2 | 258 |  | C |  |  |  |
| B | CH2 | 265 | C | C | C | F | C |
| B | CH2 | 267 |  | C |  |  |  |
|  | CH2 | 268 |  | C | C |  |  |
| B | CH2 | 269 |  |  | C |  |  |
|  | CH2 | 270 |  | C | C | F |  |
|  | CH2 | 272 |  | C |  |  |  |
|  | CH2 | 276 |  | C |  |  |  |
|  | CH2 | 285 |  | C |  |  |  |
|  | CH2 | 286 |  | C |  |  |  |
|  | CH2 | 288 |  |  |  |  | C |
|  | CH2 | 290 |  | C | C |  |  |
|  | CH2 | 292 |  | C |  |  |  |
|  | CH2 | 293 |  |  | C |  |  |
|  | CH2 | 295 |  | C | C |  |  |
|  | CH2 | 296 |  |  | C |  |  |
| B | CH2 | 297 | X | X | X | X |  |
| B | CH2 | 298 |  |  |  |  |  |
| B | CH2 | 299 |  |  |  |  |  |
|  | CH2 | 301 | D | C | C |  |  |
|  | CH2 | 311 |  |  |  |  | C |
|  | CH2 | 312 |  |  |  |  | C |
|  | CH2 | 315 |  | C |  |  |  |
|  | CH2 | 317 |  |  |  |  | C |
|  | CH2 | 322 |  | C | C | F |  |
|  | CH2 | 326 |  | C |  | F |  |
| A, B | CH2 | 327 | D, C | C | C |  |  |
| A | CH2 | 328 |  |  |  |  |  |
| A | CH2 | 329 | D, C | C | C | F |  |
| A | CH2 | 330 |  |  |  |  |  |
|  | CH2 | 331 |  | C |  | F |  |
| A | CH2 | 332 |  |  |  |  |  |
|  | CH2 | 333 |  |  | C | F |  |
|  | CH2 | 334 |  |  | C |  |  |
|  | CH2 | 337 |  | C |  |  |  |
|  | CH2 | 338 |  |  | C |  |  |
|  | CH3 | 339 |  |  | C |  |  |
|  | CH3 | 360 |  |  |  |  | C |
|  | CH3 | 362 |  |  |  |  | C |
|  | CH3 | 376 |  |  | C |  |  |
|  | CH3 | 378 |  | C |  |  |  |
|  | CH3 | 380 |  |  |  |  | C |
|  | CH3 | 382 |  |  |  |  | C |
|  | CH3 | 414 |  | C |  |  |  |
|  | CH3 | 415 |  |  |  |  | C |
|  | CH3 | 424 |  |  |  |  | C |
|  | CH3 | 428 |  |  |  |  | E |
|  | CH3 | 430 |  | C |  |  |  |
|  | CH3 | 433 |  |  |  |  | C |
|  | CH3 | 434 |  |  |  |  | C |
|  | CH3 | 435 |  |  |  |  | C |
|  | CH3 | 436 |  |  |  |  | C |

Table 4 lists sites within the Fc region that have previously been identified to be important for the Fc-FcR interaction. Columns labeled FcR-Fc identifies the Fc chain contacted by the FcR. Letters identify the reference in which the data was cited. C is Shields et al., 2001, J. Biol. Chem. 276: 6591-6604; D is Jefferis et al., 1995, Immunol. Lett. 44: 111-7; E is Hinton et al; 2004, J. Biol. Chem. 279(8): 6213-6; F is Idusogie et al., 2000, J. Immunol. 164: 4178-4184; each of which is incorporated herein by reference in its entirety.

In another preferred embodiment, the invention encompasses a molecule. comprising a variant Fc region, wherein said variant Fc region comprises at least one amino acid modification relative to a wild-type Fc region, such that said molecule binds an FcγR with an altered affinity relative to a molecule comprising a wild-type Fc region, provided that said variant Fc region does not have or is not solely a substitution at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439. In a specific embodiment, the invention encompasses a molecule comprising a variant Fc region, wherein said variant Fc region comprises at least one amino acid modification relative to a wild-type Fc region, such that said molecule binds an FcγR with an altered affinity relative to a molecule comprising a wild-type Fc region, provided that said variant Fc region does not have or is not solely a substitution at any of positions 255, 258, 267, 269, 270, 276, 278, 280, 283, 285, 289, 292, 293, 294, 295, 296, 300, 303, 305, 307, 309, 322, 329, 332, 331, 337, 338, 340, 373, 376, 416, 419, 434, 435, 437, 438, 439 and does not have an alanine at any of positions 256, 290, 298, 312, 333, 334, 359, 360 326, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334; a lysine at position 335 an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301.

In a specific embodiment, the invention encompasses a molecule comprising a variant Fc region, wherein said variant Fc region does not have or is not solely a substitution at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and does not have a histidine, glutamine, or tyrosine at position 280; a serine, glycine, threonine or tyrosine at position 290, a leucine or isoleucine at position 300; an asparagine at position 294, a proline at position 296; a proline, asparagine, aspartic acid, or valine at position 298; a lysine at position 295. In yet another preferred embodiment, the invention encompasses a molecule comprising a variant Fc region, wherein said variant Fc region comprises at least one amino acid modification relative to a wild-type Fc region, such that said molecule binds an FcγR with a reduced affinity relative to a molecule comprising a wild-type Fc region provided that said variant Fc region does not have or is not solely a substitution at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439. In yet another preferred embodiment, the invention encompasses a molecule comprising a variant Fc region, wherein said variant Fc region comprises at least one amino acid modification relative to a wild-type Fc region, such that said molecule binds an FcγR with an enhanced affinity relative to a molecule comprising a wild-type Fc region provided that said variant Fc region does not have or is not solely a substitution at any of positions 280, 283, 285, 286, 290, 294, 295, 298, 300, 301, 305, 307, 309, 312, 315, 331, 333, 334, 337, 340, 360, 378, 398, or 430.

In a specific embodiment, the invention encompasses a molecule comprising a variant Fc region, wherein said variant Fc region does not include or are not solely a substitution at any of positions 330, 243, 247, 298, 241, 240, 244, 263, 262, 235, 269, or 328 and does not have a leucine at position 243, an asparagine at position 298, a leucine at position 241, and isoleucine or an alanine at position 240, a histidine at position 244, a valine at position 330, or an isoleucine at position 328.

In most preferred embodiments, the molecules of the invention with altered affinities for activating and/or inhibitory receptors having variant Fc regions, have one or more amino acid modifications, wherein said one or more amino acid modification is a substitution at position 288 with asparagine, at position 330 with serine and at position 396 with leucine (MgFc10)(See Table 5); or a substitution at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 392 with threonine, and at position 396 with leucine (MgFc38); or a substitution at position 221 with glutamic acid, at position 270 with glutamic acid, at position 308 with alanine, at position 311 with histidine, at position 396 with leucine, and at position 402 with aspartic acid (MgFc42); or a substitution at position 240 with alanine, and at position 396 with leucine (MgFc52); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid and at position 396 with leucine (MgFc59).

In one specific embodiment, the invention encompasses a molecule comprising a variant Fc region wherein said variant Fc region comprises a substitution at position 396 with leucine, at position 270 with glutamic acid and at position 243 with leucine. In another specific embodiment the molecule further comprises one or more amino acid modification such as those disclosed herein.

In some embodiments, the invention encompasses molecules comprising a variant Fc region having an amino acid modification at one or more of the following positions: 185, 142, 192, 141, 132, 149, 133, 125, 162, 147, 119, 166, 251, 292, 290, 291, 252, 288, 268, 256, 262, 218, 214, 205, 215, 247, 275, 202, 289, 258, 219, 279, 222, 246, 233, 246, 268, 244, 217, 253, 246, 224, 298, 280, 255, 218, 281, 284, 216, 223, 235, 221, 252, 241, 258, 227, 231, 215, 274, 287, 244, 229, 287, 291, 240, 281, 232, 269, 225, 246, 246, 293, 295, 248, 276, 268, 210, 288, 227, 221, 217, 261, 210, 242, 255, 240, 250, 247, 258, 246, 282, 219, 225, 270, 263, 272, 292, 233, 247, 254, 243, 347, 339, 392, 399, 301, 315, 383, 396, 385, 348, 333, 334, 310, 337, 371, 359, 366, 359, 379, 330, 318, 395, 319, 380, 305, 309, 335, 370, 378, 394, 386, 377, 358, 384, 397, 372, 326, 320, 375, 327, 381, 354, 385, 335, 387, 353, 375, 383, 397, 345, 375, 389, 335, 394, 316, 399, 315, 394, 382, 390, 369, 377, 304, 323, 313, 388, 339, 317, 365, 367, 340, 311, 312, 398, 343, 352, 362, 303, 308, 327, 307, 344, 328, 393, 355, 360, 306, 361, 355, 415, 408, 409, 407, 424, 401, 402, 435, 421, 431, 441, 440, 435, 431, 442, 400, 422, 406, 411, 422, 433, 406, 423, 420, 412, 447, 443, 414, 433, 428, 446, 402, 419, 410, 404, 427, 417, 433, 436, 438, 416. Preferably such mutations result in molecules that have an altered affinity for an FcγR and/or have an altered effector cell mediated function as determined using methods disclosed and exemplified herein and known to one skilled in the art.

The invention encompasses molecules comprising variant Fc regions consisting of or comprising any of the mutations listed in the table below in Table 5.

TABLE 5

EXEMPLARY MUTATIONS

| SINGLE SITE MUTANTS | DOUBLE SITE MUTANTS |
|---|---|
| K392R | Q347H, A339V |
| N315I | S415I, L251F |
| S132I | K290E, L142P |
| P396L | G285E, P247H |
| P396H | K409R, S166N |
| A162V | E334A, K334A |
| R292L | R292L. K334E |
| T359N | K288N, A330S |
| T366S | R255L, E318K |
| V379L | F243L, E318K |
| K288N | V279L, P395S |
| A330S | K246T, Y319F |
| F243L | F243I, V379L |
| E318K | K288M, K334E |
| V379M | K334E, E308D |
| S219Y | E233D, K334E |
| V282M | K246T, P396H |
| D401V | H268D, E318D |
| K222N | K246I, K334N |
| K334I | K320E, K326E |
| K334E | S375C, P396L |
| I377F | K288N, K326N |
| P247L | P247L, N421K |
| F372Y | S298N, W381R |
| K326E | R255Q, K326E |
| H224L | V284A, F372L |
| F275Y | T394M. V397M |
| L398V | P247L, E389G |
| K334N | K290T, G371D |
| S400P | P247L, L398Q |
| S407I | P247L, I377F |
| F372Y | K326E, G385E |
| T366N | S298N, S407R |
| K414N | E258D, N384K |
| M352L | F241L, E258G |
| T225S | K370N, S440N |
| I377N | K317N, F423-DELETED |
| K248M | P227S, K290E |
| R292G | K334E, E380D |
| S298N | P291S, P353Q |
| D270E | V240I, V281M |
| E233G | P232S, S304G |
| | P247L, L406F |
| | D399E, M428L |
| | L251F, F372L |
| | D399E, G402D |
| | D399E, M428L |
| | K392T, P396L |
| | H268N, P396L |
| | K326I, P396L |
| | H268D, P396L |
| | K210M, P396L |
| | L358P, P396L |
| | K334N, P396L |
| | V379M, P396L |
| | P227S, P396L |
| | P217S, P396L |

TABLE 5-continued

EXEMPLARY MUTATIONS

| SINGLE SITE MUTANTS | DOUBLE SITE MUTANTS |
|---|---|
| | Q419H, P396L |
| | K370E, P396L |
| | L242F, P396L |
| | R255L, P396L |
| | V240A, P396L |
| | T250A, P396L |
| | P247S, P396L |
| | L410H, P396L |
| | Q419L, P396L |
| | V427A, P396L |
| | E258D, P396L |
| | N384K, P396L |
| | V323I, P396L |
| | P244H, P396L |
| | V305L, P396L |
| | S400F, P396L |
| | V303I, P396L |
| | A330V, Q419H |
| | V263Q, E272D |
| | K326E, A330T |

In yet other embodiments, the invention encompasses molecules comprising variant Fc regions having more than two amino acid modifications. A non-limiting example of such variants is listed in the table below (Table 6). The invention encompasses mutations listed in Table 6 which further comprise one or more amino acid modifications such as those disclosed herein.

TABLE 6

EXEMPLARY COMBINATION VARIANTS

D399E, R292L, V185M
R301C, M252L, S192T
P291S, K288E, H268L, A141V
S383N, N384K, T256N, V262L, K218E, R214I, K205E, F149Y, K133M
S408I, V215I, V125L
G385E, P247H
V348M, K334N, F275I, Y202M, K147T
H310Y, T289A, Y407V, E258D
R292L, P396L, T359N
F275I, K334N, V348M
F243L, R255L, E318K
K334E, T359N, T366S
T256S, V305I, K334E, N390S
T335N, K370E, A378V, T394M, S424L
K334E, T359N, T366S, Q386R
K288N, A330S, P396L
P244H, L358M, V379M, N384K, V397M
P217S, A378V, S408R
P247L, I253N, K334N
D312E, K327N, I378S
D280E, S354F, A431D, L441I
K218R, G281D, G385R
P247L, A330T, S440G
T355N, P387S, H435Q
P247L, A431V, S442F
P343S, P353L, S375I, S383N
E216D, E345K, S375I
K288N, A330S, P396L
K222N, T335N, K370E, A378V, T394M
G316D, A378V, D399E
N315I, V379M, T394M
K326Q, K334E, T359N, T366S
A378V, N390I, V422I
V282E, V369I, L406F
V397M, T411A, S415N
T223I, T256S, L406F
L235P, V382M, S304G, V305I, V323I
P247L, W313R, E388G
D221Y, M252I, A330G, A339T, T359N, V422I, H433L
F243I, V379L, G420V

TABLE 6-continued

EXEMPLARY COMBINATION VARIANTS

A231V, Q386H, V412M
T215P, K274N, A287G, K334N, L365V, P396L
P244A, K326I, C367R, S375I, K447T
R301H, K340E, D399E
C229Y, A287T, V379M, P396L, L443V
E269K, K290N, Q311R, H433Y
E216D, K334R, S375I
T335N, P387S, H435Q
K246I, Q362H, K370E
K334E, E380D, G446V
V303I, V369F, M428L
K246E, V284M, V308A
E293V, Q295E, A327T
Y319F, P352L, P396L
D221E, D270E, V308A, Q311H, P396L, G402D
K290T, N390I, P396L
K288R, T307A, K344E, P396L
V273I, K326E, L328I, P396L
K326I, S408N, P396L
K261N, K210M, P396L
F243L, V305I, A378D, F404S, P396L
K290E, V369A, T393A, P396L
K210N, K222I, K320M, P396L
P217S, V305I, I309L, N390H, P396L
K246N, Q419R, P396L
P217A, T359A, P396L
V215I, K290V, P396L
F275L, Q362H, N384K, P396L
A330V, H433Q, V427M
V263Q, E272D, Q419H
N276Y, T393N, W417R
V282L, A330V, H433Y, T436R
V284M, S298N, K334E, R355W
A330V, G427M, K438R
S219T, T225K, D270E, K360R
K222E, V263Q, S298N
E233G, P247S, L306P
S219T, T225K, D270E
S254T, A330V, N361D, P243L
V284M, S298N, K334E, R355W R416T
D270E, G316D, R416G
K392T, P396L, D270E
R255L, P396L, D270E
V240A, P396L, D270E
Q419H, P396L, D270E
K370E, P396L, D270E
P247L, N421K, D270E
R292P, V305I
R292P, V305I, F243L
V284M, R292L, K370N

In some embodiments, the molecules, preferably the immunoglobulins of the invention further comprise one or more glycosylation sites, so that one or more carbohydrate moieties are covalently attached to the molecule. Preferably, the antibodies of the invention with one or more glycosylation sites and/or one or more modifications in the Fc region have an enhanced antibody mediated effector function, e.g., enhanced ADCC activity. In some embodiments, the invention further comprises antibodies comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301 Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

The invention encompasses antibodies that have been modified by introducing one or more glycosylation sites into one or more sites of the antibodies, preferably without altering the functionality of the antibody, e.g., binding activity to FcγR. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "*In Vitro Mutagenesis,*" *Recombinant DNA: A Short Course*, J. D. Watson, et al. W.H. Freeman and Company, New York, 1983, chapter 8, pp. 106-116, which is incorporated herein by reference in its entirety. An exemplary method for introducing a glycosylation site into an antibody of the invention may comprise: modifying or mutating an amino acid sequence of the antibody so that the desired Asn-X-Thr/Ser sequence is obtained.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of an antibody of the invention by deleting one or more endogenous carbohydrate moieties of the antibody. In a specific embodiment, the invention encompasses shifting the glycosylation site of the Fc region of an antibody, by modifying positions adjacent to 297. In a specific embodiment, the invention encompasses modifying position 296 so that position 296 and not position 297 is glycosylated.

4.1 Polypeptides and Antibodies with Variant Fc Regions

The present invention is based, in part, on the identification of mutant human IgG1 heavy chain Fc regions, with altered affinities for different FcγR receptors, using a yeast display system. Accordingly, the invention relates to molecules, preferably polypeptides, and more preferably immunoglobulins (e.g., antibodies), comprising a variant Fc region, having one or more amino acid modifications (e.g., substitutions, but also including insertions or deletions) in one or more regions, which modifications alter the affinity of the variant Fc region for an FcγR.

It will be appreciated by one skilled in the art that aside from amino acid substitutions, the present invention contemplates other modifications of the Fc region amino acid sequence in order to generate an Fc region variant with one or more altered properties, e.g., altered effector function. The invention contemplates deletion of one or more amino acid residues of the Fc region in order to reduce binding to an FcγR. Preferably, no more than 5, no more than 10, no more than 20, no more than 30, no more than 50 Fc region residues will be deleted according to this embodiment of the invention. The Fc region herein comprising one or more amino acid deletions will preferably retain at least about 80%, and preferably at least about 90%, and most preferably at least about 95%, of the wild type Fc region. In some embodiments, one or more properties of the molecules are maintained such as for example, non-immunogenicity, FcγRIIIA binding, FcγRIIA binding, or a combination of these properties.

In alternate embodiments, the invention encompasses amino acid insertion to generate the Fc region variants, which variants have altered properties including altered effector function. In one specific embodiment, the invention encompasses introducing at least one amino acid residue, for example one to two amino acid residues and preferably no more than 10 amino acid residues adjacent to one or more of the Fc region positions identified herein. In alternate embodiments, the invention further encompasses introducing at least one amino acid residue, for example one to two amino acid residues and preferably no more than 10 amino acid residues adjacent to one or more of the Fc region positions known in the art as impacting FcγR interaction and/or binding.

The invention further encompasses incorporation of unnatural amino acids to generate the Fc variants of the invention. Such methods are known to those skilled in the art such as those using the natural biosynthetic machinery to allow incorporation of unnatural amino acids into proteins, see, e.g., Wang et al., 2002 Chem. Comm. 1:1-11; Wang et al., 2001, Science, 292: 498-500; van Hest et al., 2001. Chem. Comm. 19: 1897-1904, each of which is incorporated herein by reference in its entirety. Alternative strategies focus on the enzymes responsible for the biosynthesis of amino acyl-tRNA, see, e.g., Tang et al., 2001, J. Am. Chem. 123(44): 11089-11090; Kiick et al., 2001, FEBS Lett. 505(3): 465; each of which is incorporated herein by reference in its entirety.

The affinities and binding properties of the molecules of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 5.2.1). Preferably, the binding properties of the molecules of the invention are also characterized by in vitro functional assays for determining one or more FcγR mediator effector cell functions (See Section 5.2.6). In most preferred embodiments, the molecules of the invention have similar binding properties in in vivo models (such as those described and disclosed herein) as those in in vitro based assays However, the present invention does not exclude molecules of the invention that do not exhibit the desired phenotype in in vitro based assays but do exhibit the desired phenotype in vivo. A representative flow chart of the screening and characterization of molecules of the invention is described in FIG. 33.

The invention encompasses molecules comprising a variant Fc region that binds with a greater affinity to one or more FcγRs. Such molecules preferably mediate effector function more effectively as discussed infra. In other embodiments, the invention encompasses molecules comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Reduction or elimination of effector function would be desirable in cases of autoimmune disease where one would block FcγR activating receptors in effector cells (This type of function would be present in the host cells). In general increased effector function would be directed to tumor and foreign cells.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:49634969; Armour et al., 1999, Eur J Immunol 29:2613-2624; Idusogie et al, 2000, J Immunol 164:41784184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. No. 5,624,821; U.S. Pat. No. 5,885,573; U.S. Pat. No. 6,194,551; PCT WO 00/42072; PCT WO 99/58572; each of which is incorporated herein by reference in its entirety.

In some embodiments, the Fc variants of the present invention are incorporated into an antibody or Fc fusion that comprises one or more engineered glycoforms, i.e., a carbohydrate composition that is covalently attached to a molecule comprising an Fc region, wherein said carbohydrate composition differs chemically from that of a parent molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277: 26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, JMB, 336: 1239-49 each of which is incorporated herein by reference in its entirety.

The Fc variants of the present invention may be optimized for a variety of properties. Properties that may be optimized include but are not limited to enhanced or reduced affinity for an FcγR, enhanced or reduced effector function. In a preferred embodiment, the Fc variants of the present invention are optimized to possess enhanced affinity for a human activating FcγR, preferably FcγR, FcγRIIA, FcγRIIc, FcγRIIIA, and FcγRIIIB, most preferably FcγRIIIA In an alternate preferred embodiment, the Fc variants are optimized to possess reduced affinity for the human inhibitory receptor FcγRIIB. These preferred embodiments are anticipated to provide antibodies and Fc fusions with enhanced therapeutic properties in humans, for example enhanced effector function and greater anti-cancer potency as described and exemplified herein. These preferred embodiments are anticipated to provide antibodies and Fc fusions with enhanced tumor elimination in mouse xenograft tumor models.

In an alternate embodiment the Fc variants of the present invention are optimized to have reduced affinity for a human FcγR, including but not limited to FcγRI, FcγRIIA, FcγRIIB, FcγRIIc, FcγRIIIA, and FcγRIIIB These embodiments are anticipated to provide antibodies and Fc fusions with enhanced therapeutic properties in humans, for example reduced effector function and reduced toxicity.

In alternate embodiments the Fc variants of the present invention possess enhanced or reduced affinity for FcγRs from non-human organisms, including but not limited to mice, rats, rabbits, and monkeys. Fc variants that are optimized for binding to a non-human FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of antibodies or Fc fusions that comprise Fc variants that are optimized for one or more mouse FcγRs, may provide valuable information with regard to the efficacy of the antibody or Fc fusion, its mechanism of action, and the like.

While it is preferred to alter binding to an FcγR, the instant invention further contemplates Fc variants with altered binding affinity to the neonatal receptor (FcRn). Although not intending to be bound by a particular mechanism of action, Fc region variants with improved affinity for FcRn are anticipated to have longer serum half-lives, and such molecules will have useful applications in methods of treating mammals where long half-life of the administered polypeptide is desired, e.g., to treat a chronic disease or disorder. Although not intending to be bound by a particular mechanism of action, Fc region variants with decreased FcRn binding affinity, on the contrary, are expected to have shorter half-lives, and such molecules may, for example, be administered to a mammal where a shortened circulation time may be advantageous, e.g., for in vivo diagnostic imaging or for polypeptides which have toxic side effects when left circulating in the blood stream for extended periods. Fc region variants with decreased FcRn binding affinity are anticipated to be less likely to cross the placenta, and thus may be utilized in the treatment of diseases or disorders in pregnant women.

In other embodiments, these variants may be combined with other known Fc modifications with altered FcRn affinity such as those disclosed in International Publication Nos. WO 98/23289; and WO 97/34631; and U.S. Pat. No. 6,277,375, each of which is incorporated herein by reference in its entirety.

The invention encompasses any other method known in the art for generating antibodies having an increased half-life in vivo, for example, by introducing one or more amino acid modifications (i.e., substitutions, insertions or deletions) into an IgG constant domain, or FcRn binding fragment thereof (preferably a Fc or hinge-Fc domain fragment). See, e.g., International Publication Nos. WO 98/23289; and WO 97/34631; and U.S. Pat. No. 6,277,375, each of which is incorporated herein by reference in its entirety to be used in combination with the Fc variants of the invention. Further, antibodies of the invention can be conjugated to albumin in order to make the antibody or antibody fragment more stable in vivo or have a longer half-life in vivo. The techniques well-known in the art, see, e.g., International Publication Nos. WO 93/15199, WO 93/15200, and WO 01/77137, and European Patent No. EP 413,622, all of which are incorporated herein by reference in their entirety.

The variant(s) described herein may be subjected to further modifications, often times depending on the intended use of the variant. Such modifications may involve further alteration of the amino acid sequence (substitution, insertion and/or deletion of amino acid residues), fusion to heterologous polypeptide(s) and/or covalent modifications. Such further modifications may be made prior to, simultaneously with, or following, the amino acid modification(s) disclosed herein which results in altered properties such as an alteration of Fc receptor binding and/or ADCC activity.

Alternatively or additionally, the invention encompasses combining the amino acid modifications disclosed herein with one or more further amino acid modifications that alter C1q binding and/or complement dependent cytoxicity function of the Fc region as determined in vitro and/or in vivo. Preferably, the starting molecule of particular interest herein is usually one that binds to C1q and displays complement dependent cytotoxicity (CDC). The further amino acid substitutions described herein will generally serve to alter the ability of the starting molecule to bind to C1q and/or modify its complement dependent cytotoxicity function, e.g., to reduce and preferably abolish these effector functions. In other embodiments molecules comprising substitutions at one or more of the described positions with improved C1q binding and/or complement dependent cytotoxicity (CDC) function are contemplated herein. For example, the starting molecule may be unable to bind C1q and/or mediate CDC and may be modified according to the teachings herein such that it acquires these further effector functions. Moreover, molecules with preexisting C1q binding activity, optionally further having the ability to mediate CDC may be modified such that one or both of these activities are altered, e.g., enhanced. In some embodiments, the invention encompasses variant Fc regions with altered CDC activity without any alteration in C1q binding. In yet other embodiments, the invention encompasses variant Fc regions with altered CDC activity and altered C1q binding.

To generate an Fc region with altered C1q binding and/or complement dependent cytotoxicity (CDC) function, the amino acid positions to be modified are generally selected from positions 270, 322, 326, 327, 329, 331, 333, and 334, where the numbering of the residues in an IgG heavy chain is that of the EU index as in Kabat et al., Sequences of Proteins of Immunological Interest, 5th Ed. Public Health Service, National Institutes of Health, Bethesda, Md. (199). These amino acid modifications may be combined with one or more Fc modifications disclosed herein to provide a synergistic or additive effect on C1q binding and/or CDC activity. In other embodiments, the invention encompasses Fc variants with altered C1q binding and/or complement dependent cytotoxicity (CDC) function comprising an amino acid substitution at position 396 with leucine and at position 255 with leucine; or an amino acid substitution at position 396 with leucine and at position 419 with histidine; an amino acid substitution at position 396 with leucine and at position 370 with glutamic acid; an amino acid substitution at position 396 with leucine and at position 240 with alanine; an amino acid substitution at position 396 with leucine and at position 392 with threonine; an amino acid substitution at position 247 with leucine and at position 421 with lysine. The invention encompasses any known modification of the Fc region which alters C1q binding and/or complement dependent cytotoxicity (CDC) function such as those disclosed in Idusogie et al., 2001, *J. Immunol.* 166(4) 2571-5; Idusogie et al., *J. Immunol.* 2000 164(8): 4178-4184; each of which is incorporated herein by reference in its entirety.

As disclosed above, the invention encompasses an Fc region with altered effector function, e.g., modified C1q binding and/or FcR binding and thereby altered CDC activity and/or ADCC activity. In specific embodiments, the invention encompasses variant Fc regions with improved C1q binding and improved FcγRIII binding; e.g. having both improved ADCC activity and improved CDC activity. In alternative embodiments, the invention encompasses a variant Fc region with reduced CDC activity and/or reduced ADCC activity. In other embodiments, one may increase only one of these activities, and optionally also reduce the other activity, e.g. to generate an Fc region variant with improved ADCC activity, but reduced CDC activity and vice versa.

A. Mutants with Enhanced Altered Affinities for FcγRIIIA and/or FcγRIIA

The invention encompasses molecules comprising a variant Fc region, having one or more amino acid modifications (e.g., substitutions) in one or more regions, wherein such modifications alter the affinity of the variant Fc region for an activating FcγR. In some embodiments, molecules of the invention comprise a variant Fc region, having one or more amino acid modifications (e.g., substitutions) in one or more regions, which modifications increase the affinity of the variant Fc region for FcγRIIIA and/or FcγRIIA by at least 2-fold, relative to a comparable molecule comprising a wild-type Fc region. In another specific embodiment, molecules of the invention comprise a variant Fc region, having one or more amino acid modifications (e.g., substitutions) in one or more regions, which modifications increase the affinity of the variant Fc region for FcγRIIIA and/or FcγRIIA by greater than 2 fold, relative to a comparable molecule comprising a wild-type Fc region. In other embodiments of the invention the one or more amino acid modifications increase the affinity of the variant Fc region for FcγRIIIA and/or FcγRIIA by at least 3-fold, 4-fold, 5-fold, 6-fold, 8-fold, or 10-fold relative to a comparable molecule comprising a wild-type Fc region. In yet other embodiments of the invention the one or more amino acid modifications decrease the affinity of the variant Fc region for FcγRIIIA and/or FcγRIIA by at least 3-fold, 4-fold, 5-fold, 6-fold, 8-fold, or 10-fold relative to a comparable molecule comprising a wild-type Fc region. Such fold increases are preferably determined by an ELISA or surface plasmon resonance assays. In a specific embodiment, the one or more amino acid modifications do not include or are not solely a substitution at any one of positions 329, 331, or 322 with any amino acid. In certain embodiments, the one or more amino acid modifications do not include or are not solely a substitution with any one of alanine at positions 256, 290, 298, 312, 333, 334, 359, 360, or 430; with lysine at position 330; with threonine at position 339; with methionine at position 320; with serine, asparagine, aspartic acid, or glutamic acid at position 326 with glutamine, glutamic acid, methionine, histidine, valine, or leucine at position 334. In another specific embodiment, the one or more amino acid modifications do not include or are not solely a substitution at any of positions 280, 290, 300, 294, or 295. In another more specific embodiment, the one or more amino acid modifications do not include or are not solely a substitution at position 300 with leucine or isoleucine; at position 295 with lysine; at position 294 with asparagine; at position 298 with valine; aspartic acid proline, aspargine, or valine; at position 280 with histidine, glutamine or tyrosine; at position 290 with serine, glycine, theonine or tyrosine.

In another specific embodiment, the invention encompasses a molecule comprising a variant Fc region, wherein said variant Fc region comprises at least one amino acid modification relative to a wild-type Fc region, such that said polypeptide specifically binds FcγRIIA with a greater affinity than a comparable molecule comprising the wild-type Fc region binds FcγRIIA, provided that said variant Fc region does not have an alanine at any of positions 256, 290, 326, 255, 258, 267, 272, 276, 280, 283, 285, 286, 331, 337, 268, 272, or 430; an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301. In a specific embodiment, molecules of the invention comprise a variant Fc region, having one or more amino acid modifications (e.g., substitutions) in one or more regions, which modifications increase the affinity of the variant Fc region for FcγRIIA by at least 2-fold, relative to a comparable molecule comprising a wild-type Fc region. In another specific embodiment, molecules of the invention comprise a variant Fc region, having one or more amino acid modifications (e.g., substitutions) in one or more regions, which modifications increase the affinity of the variant Fc region for FcγRIIA by greater than 2 fold, relative to a comparable molecule comprising a wild-type Fc region. In other embodiments of the invention the one or more amino acid modifications increase the affinity of the variant Fc region for FcγRIIA by at least 3-fold, 4-fold, 5-fold, 6-fold, 8-fold, or 10-fold relative to a comparable molecule comprising a wild-type Fc region In a specific embodiment, the invention encompasses molecules, preferably polypeptides, and more preferably immunoglobulins (e.g., antibodies), comprising a variant Fc region, having one or more amino acid modifications (e.g., substitutions but also include insertions or deletions), which modifications increase the affinity of the variant Fc region for FcγRIIIA and/or FcγRIIA by at least 65%, at least 70%, at least 75%, at least 85%, at least 90%, at least 95%, at least 99%, at least 100%, at least 150%, and at least 200%, relative to a comparable molecule comprising a wild-type Fc region.

In a specific embodiment, the one or more amino acid modifications which increase the affinity of the variant Fc region comprise a substitution at position 347 with histidine, and at position 339 with valine; or a substitution at position 425 with isoleucine and at position 215 with phenylalanine; or a substitution at position 408 with isoleucine, at position 215 with isoleucine, and at position 125 with leucine; or a substitution at position 385 with glutamic acid and at position 247 with histidine; or a substitution at position 348 with methionine, at position 334 with asparagine, at position 275 with isoleucine, at position 202 with methionine, and at position 147 with threonine; or a substitution at position 275 with isoleucine, at position 334 with asparagine, and at position 348 with methionine; or a substitution at position 279 with leucine and at position 395 with serine; or a substitution at position 246 with threonine and at position 319 with phenylalanine; or a substitution at position 243 with isoleucine and at position 379 with leucine; or a substitution at position 243 with leucine, at position 255 with leucine and at position 318 with lysine; or a substitution at position 334 with glutamic acid, at position 359 with asparagine, and at position 366 with serine; or a substitution at position 288 with methionine and at position 334 with glutamic acid; or a substitution at position 334 with glutamic acid and at position 380 with aspartic acid; or a substitution at position 256 with serine, at position 305 with isoleucine, at position 334 with glutamic acid and at position 390 with serine; or a substitution at position 335 with asparagine, at position 370 with glutamic acid, at position 378 with valine, at position 394 with methionine, and at position 424 with leucine; or a substitution at position 233 with aspartic acid and at position 334 with glutamic acid; or a substitution at position 334 with glutamic acid, at position 359 with asparagine, at position 366 with serine, and at position 386 with arginine; or a substitution at position 246 with threonine and at position 396 with histidine; or a substitution at position 268 with aspartic acid and at position 318 with aspartic acid; or a substitution at position 288 with asparagine, at position 330 with serine, and at position 396 with leucine; or a substitution at position 244 with histidine, at position 358 with methionine, at position 379 with methionine, at position 384 with lysine and at position 397 with methionine; or a substitution at position 217 with serine, at position 378 with valine, and at position 408 with arginine; or a substitution at position 247 with leucine, at position 253 with asparagine, and at position 334 with asparagine; or a substitution at position 246 with isoleucine, and at position 334 with asparagine; or a substitution at position 320 with glutamic acid and at position 326 with glutamic acid; or a substitution at position 375 with cysteine and at position 396 with leucine. Examples of other amino acid substitutions that results in an enhanced affinity for FcγRIIIA in vitro are disclosed below and summarized in Table 5.

The invention encompasses a molecule comprising a variant Fc region, wherein said variant Fc region comprises a substitution at position 243 with isoleucine and at position 379 with leucine, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 288 with asparagine, at position 330 with serine, and at position 396 with leucine, such that said molecule binds FcγRIIIA with about a 5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 243 with leucine and at position 255 with leucine such that said molecule binds FcγRIIIA with about a 1 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 334 with glutamic acid, at position 359 with asparagine, and at position 366 with serine, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 288 with methionine and at position 334 with glutamic acid, such that said molecule binds FcγRIIIA with about a 3 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 316 with aspartic acid, at position 378 with valine, and at position 399 with glutamic acid, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 315 with isoleucine, at position 379 with methionine, and at position 399 with glutamic acid, such that said molecule binds FcγRIIIA with about a 1 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 243 with isoleucine, at position 379 with leucine, and at position 420 with valine, such that said molecule binds FcγRIIIA with about a 2.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 247 with leucine, and at position 421 with lysine, such that said molecule binds FcγRIIIA with about a 3 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 392 with threonine and at position 396 with leucine such that said molecule binds FcγRIIIA with about a 4.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 293 with valine, at position 295 with glutamic acid, and at position 327 with threonine, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 268 with asparagine and at position 396 with leucine, such that said molecule binds FcγRIIIA with about a 2 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 319 with phenylalanine, at position 352 with leucine, and at position 396 with leucine, such that said molecule binds FcγRIIIA with about a 2 fold higher affinity than a comparable molecule comprising the wild type Fc region binds FcγRIIIA, as determined by an ELISA assay.

In a specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 396 with histidine. In a specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 248 with methionine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 392 with arginine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 315 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 132 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 162 with valine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 379 with methionine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 219 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 282 with methionine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 401 with valine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 222 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 334 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 377 with phenylalanine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 334 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 247 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 326 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 372 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 224 with leucine.

The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 275 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 398 with valine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 334 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 400 with proline. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 407 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 372 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 366 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a reduced affinity than a comparable polypeptide comprising the wild-type Fc region, wherein said at least one amino acid modification comprises substitution at position 414 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a reduced affinity than a comparable polypeptide comprising the wild-type Fc region, wherein said at least one amino acid modification comprises substitution at position 225 with serine. The invention encompasses an isolated polypeptide comprising a variant Fc region, wherein said variant Fc region comprises at least one amino acid modification relative to a wild-type Fc region, such that said polypeptide specifically binds FcγRIIIA with a reduced affinity than a comparable polypeptide comprising the wild-type Fc region, wherein said at least one amino acid modification comprises substitution at position 377 with asparagine.

In a specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with about a 2 fold greater affinity than a comparable polypeptide comprising the wild-type Fc region as determined by an ELISA assay, wherein said at least one amino acid modification comprises substitution at position 379 with methionine. In another specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with about a 1.5 fold greater affinity than a comparable polypeptide comprising the wild-type Fc region as determined by an ELISA assay, wherein said at least one amino acid modification comprises substitution at position 248 with methionine.

In some embodiments, the molecules of the invention have an altered affinity for FcγRIIIA and/or FcγRIIA as determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 5.2.1). Preferably, the binding properties of these molecules with altered affinities for activating FcγR receptors are also correlated to their activity as determined by in vitro functional assays for determining one or more FcγR mediator effector cell functions (See Section 5.2.6), e.g., molecules with variant Fc regions with enhanced affinity for FcγRIIIA have an enhanced ADCC activity. In most preferred embodiments, the molecules of the invention that have an altered binding property for an activating Fc receptor, e.g., FcγRIIIA in an in vitro assay also have an altered binding property in in vivo models (such as those described and disclosed herein). However, the present invention does not exclude molecules of the invention that do not exhibit an altered FcγR binding in in vitro based assays but do exhibit the desired phenotype in vivo.

B. Mutants with Enhanced Affinity for FcγRIIIA and Reduced or No Affinity for FcγRIIB In a specific embodiment, the molecules of the invention comprise a variant Fc region, having one or more amino acid modifications (i.e., substitutions) in one or more regions, which one or more modifications increase the affinity of the variant Fc region for FcγRIIIA and decreases the affinity of the variant Fc region for FcγRIIB, relative to a comparable molecule comprising a wild-type Fc region which binds FcγRIIIA and FcγRIIB with wild-type affinity. In a certain embodiment, the one or more amino acid modifications do not include or are not solely a substitution with alanine at any of positions 256, 298, 333, 334, 280, 290, 294, 298, or 296; or a substitution at position 298 with asparagine, valine, aspartic acid, or proline; or a substitution 290 with serine. In certain amino embodiments, the one or more amino acid modifications increases the affinity of the variant Fc region for FcγRIIIA by at least 65%, at least 70%, at least 75%, at least 85%, at least 90%, at least 95%, at least 99%, at least 100%, at least 200%, at least 300%, at least 400% and decreases the affinity of the variant Fc region for FcγRIIB by at least 65%, at least 70%, at least 75%, at least 85%, at least 90%, at least 95%, at least 99%, at least 100%, at least 200%, at least 300%, at least 400%.

In a specific embodiment, the molecule of the invention comprising a variant Fc region with an enhanced affinity for FcγRIIIA and a lowered affinity or no affinity for FcγRIIB, as determined based on an ELISA assay and/or an ADCC based assay using ch-4-4-20 antibody carrying the variant Fc region comprises a substitution at any of the following of position 275 with isoleucine, at position 334 with asparagine, and at position 348 with methionine; or a substitution at position 279 with leucine and at position 395 with serine; or a substitution at position 246 with threonine and at position 319 with phenylalanine; or a substitution at position 243 with leucine, at position 255 with leucine, and at position 318 with lysine; or a substitution at position 334 with glutamic acid, at position 359 with asparagine and at position 366 with serine; or a substitution at position 334 with glutamic acid and at position 380 with aspartic acid; or a substitution at position 256 with serine, at position 305 with isoleucine, at position 334 with glutamic acid, and at position 390 with serine; or a substitution at position 335 with asparagine, at position 370 with glutamic acid, at position 378 with valine, at position 394 with methionine and at position 424 with leucine; or a substitution at position 233 with aspartic acid and at position 334 with glutamic acid; or a substitution at position 334 with glutamic acid, at position 359 with asparagine, at position 366 with serine and at position 386 with arginine; or a substitution at position 312 with glutamic acid, at position 327 with asparagine, and at position 378 with serine; or a substitution at position 288 with asparagine and at position 326 with asparagine; or a substitution at position 247 with leucine and at position 421 with lysine; or a substitution at position 298 with asparagine and at position 381 with arginine; or a substitution at position 280 with glutamic acid, at position 354 with phenylalanine, at position 431 with aspartic acid, and at position 441 with isoleucine; or a substitution at position 255 with glutamine and at position 326 with glutamic acid; or a substitution at position 218 with arginine, at position 281 with aspartic acid and at position 385 with arginine; or a substitution at position 247 with leucine, at position 330 with threonine and at position 440 with glycine; or a substitution at position 284 with alanine and at position 372 with leucine; or a substitution at position 335 with asparagine, as position 387 with serine and at position 435 with glutamine; or a substitution at position 247 with leucine, at position 431 with valine and at position 442 with phenylalanine.

In a specific embodiment, the molecule of the invention comprising a variant Fc region with an enhanced affinity for FcγRIIIA and a lowered affinity or no affinity for FcγRIIB as determined based on an ELISA assay and/or an ADCC based assay using ch-4-4-20 antibody carrying the variant Fc region comprises a substitution at position 379 with methionine; at position 219 with tyrosine; at position 282 with methionine; at position 401 with valine; at position 222 with asparagine; at position 334 with isoleucine; at position 334 with glutamic acid; at position 275 with tyrosine; at position 398 with valine.

The invention encompasses an isolated polypeptide comprising a variant Fc region, wherein said variant Fc region comprises at least one amino acid modification relative to a wild-type Fc region, such that said polypeptide specifically binds FcγRIIB with about a 3 fold lower affinity than a comparable polypeptide comprising the wild-type Fc region as determined by an ELISA assay, wherein said at least one amino acid modification comprises substitution at position 288 with asparagine, at position 330 with serine, and at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIB with about a 10-15 fold lower affinity than a comparable polypeptide comprising the wild-type Fc region as determined by an ELISA assay, wherein said at least one amino acid modification comprises substitution at position 316 with aspartic acid, at position 378 with valine, and at position 399 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIB with about a 10 fold lower affinity than a comparable polypeptide comprising the wild-type Fc region as determined by an ELISA assay, wherein said at least one amino acid modification comprises substitution at position 315 with isoleucine, at position 379 with methionine, and at position 399 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIB with about a 7 fold lower affinity than a comparable polypeptide comprising the wild-type Fc region as determined by an ELISA assay, wherein said at least one amino acid modification comprises substitution at position 243 with isoleucine, at position 379 with leucine, and at position 420 with valine. The invention encompasses an isolated polypeptide comprising a variant Fc region, wherein said variant Fc region comprises at least one amino acid modification relative to a wild-type Fc region, such that said polypeptide specifically binds FcγRIIB with about a 3 fold lower affinity than a comparable polypeptide comprising the wild-type Fc region as determined by an ELISA assay, wherein said at least one amino acid modification comprises substitution at position 392 with threonine and at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIB with about a 5 fold lower affinity than a comparable polypeptide comprising the wild-type Fc region as determined by an ELISA assay, wherein said at least one amino acid modification comprises substitution at position 268 with asparagine and at position 396 with leucine. The invention also encompasses an isolated polypeptide comprising a variant Fc region, wherein said variant Fc region comprises at least one amino acid modification relative to a wild-type Fc region, such that said polypeptide specifically binds FcγRIIB with about a 2 fold lower affinity than a comparable polypeptide comprising the wild-type Fc region as determined by an ELISA assay, wherein said at least one amino acid modification comprises substitution at position 319 with phenylalanine, at position 352 with leucine, and at position 396 with leucine.

C. Mutants with Enhanced Affinity to FcγRIIIA and FcγRIIB

The invention encompasses molecules comprising variant Fc regions, having one or more amino acid modifications, which modifications increase the affinity of the variant Fc region for FcγRIIIA and FcγRIIB by at least 65%, at least 70%, at least 75%, at least 85%, at least 90%, at least 95%, at least 99%, at least 100%, at least 200%, at least 300%, at least 400% and decreases the affinity of the variant Fc region for FcγRIIB by at least 65%, at least 70%, at least 75%, at least 85%, at least 90%, at least 95%, at least 99%, at least 100%, at least 200%, at least 300%, at least 400%. In a specific embodiment, the molecule of the invention comprising a variant Fc region with an enhanced affinity for FcγRIIIA and an enhanced affinity for FcγRIIB (as determined based on an ELISA assay and/or an ADCC based assay using ch-4-4-20 antibody carrying the variant Fc region as described herein) comprises a substitution at position 415 with isoleucine and at position 251 with phenylalanine; or a substitution at position 399 with glutamic acid, at position 292 with leucine, and at position 185 with methionine; or a substitution at position 408 with isoleucine, at position 215 with isoleucine, and at position 125 with leucine; or a substitution at position 385 with glutamic acid and at position 247 with histidine; or a substitution at position 348 with methionine, at position 334 with asparagine, at position 275 with isoleucine, at position 202 with methionine and at position 147 with threonine; or a substitution at position 246 with threonine and at position 396 with histidine; or a substitution at position 268 with aspartic acid and at position 318 with aspartic acid; or a substitution at position 288 with asparagine, at position 330 with serine and at position 396 with leucine; or a substitution at position 244 with histidine, at position 358 with methionine, at position 379 with methionine, at position 384 with lysine and at position 397 with methionine; or a substitution at position 217 with serine, at position 378 with valine, and at position 408 with arginine; or a substitution at position 247 with leucine, at position 253 with asparagine, and at position 334 with asparagine; or a substitution at position 246 with isoleucine and at position 334 with asparagine; or a substitution at position 320 with glutamic acid and at position 326 with glutamic acid; or a substitution at position 375 with cysteine and at position 396 with leucine; or a substitution at position 343 with serine, at position 353 with leucine, at position 375 with isoleucine, at position 383 with asparagine; or a substitution at position 394 with methionine and at position 397 with methionine; or a substitution at position 216 with aspartic acid, at position 345 with lysine and at position 375 with isoleucine; or a substitution at position 288 with asparagine, at position 330 with serine, and at position 396 with leucine; or a substitution at position 247 with leucine and at position 389 with glycine; or a substitution at position 222 with asparagine, at position 335 with asparagine, at position 370 with glutamic acid, at position 378 with valine and at position 394 with methionine; or a substitution at position 316 with aspartic acid, at position 378 with valine and at position 399 with glutamic acid; or a substitution at position 315 with isoleucine, at position 379 with methionine, and at position 394 with methionine; or a substitution at position 290 with threonine and at position 371 with aspartic acid; or a substitution at position 247 with leucine and at position 398 with glutamine; or a substitution at position 326 with glutamine; at position 334 with glutamic acid, at position 359 with asparagine, and at position 366 with serine; or a substitution at position 247 with leucine and at position 377 with phenylalanine; or a substitution at position 378 with valine, at position 390 with isoleucine and at position 422 with isoleucine; or a substitution at position 326 with glutamic acid and at position 385 with glutamic acid; or a substitution at position 282 with glutamic acid, at position 369 with isoleucine and at position 406 with phenylalanine; or a substitution at position 397 with methionine; at position 411 with alanine and at position 415 with asparagine; or a substitution at position 223 with isoleucine, at position 256 with serine and at position 406 with phenylalanine; or a substitution at position 298 with asparagine and at position 407 with arginine; or a substitution at position 246 with arginine, at position 298 with asparagine, and at position 377 with phenylalanine; or a substitution at position 235 with proline, at position 382 with methionine, at position 304 with glycine, at position 305 with isoleucine, and at position 323 with isoleucine; or a substitution at position 247 with leucine, at position 313 with arginine, and at position 388 with glycine; or a substitution at position 221 with tyrosine, at position 252 with isoleucine, at position 330 with glycine, at position 339 with threonine, at position 359 with asparagine, at position 422 with isoleucine, and at position 433 with leucine; or a substitution at position 258 with aspartic acid, and at position 384 with lysine; or a substitution at position 241 with leucine and at position 258 with glycine; or a substitution at position 370 with asparagine and at position 440 with asparagine; or a substitution at position 317 with asparagine and a deletion at position 423; or a substitution at position 243 with isoleucine, at position 379 with leucine and at position 420 with valine; or a substitution at position 227 with serine and at position 290 with glutamic acid; or a substitution at position 231 with valine, at position 386 with histidine, and at position 412 with methionine; or a substitution at position 215 with proline, at position 274 with asparagine, at position 287 with glycine, at position 334 with asparagine, at position 365 with valine and at position 396 with leucine; or a substitution at position 293 with valine, at position 295 with glutamic acid and at position 327 with threonine; or a substitution at position 319 with phenylalanine, at position 352 with leucine, and at position 396 with leucine; or a substitution at position 392 with threonine and at position 396 with leucine; at a substitution at position 268 with asparagine and at position 396 with leucine; or a substitution at position 290 with threonine, at position 390 with isoleucine, and at position 396 with leucine; or a substitution at position 326 with isoleucine and at position 396 with leucine; or a substitution at position 268 with aspartic acid and at position 396 with leucine; or a substitution at position 210 with methionine and at position 396 with leucine; or a substitution at position 358 with proline and at position 396 with leucine; or a substitution at position 288 with arginine, at position 307 with alanine, at position 344 with glutamic acid, and at position 396 with leucine; or a substitution at position 273 with isoleucine, at position 326 with glutamic acid, at position 328 with isoleucine and at position 396 with leucine; or a substitution at position 326 with isoleucine, at position 408 with asparagine and at position 396 with leucine; or a substitution at position 334 with asparagine and at position 396 with leucine; or a substitution at position 379 with methionine and at position 396 with leucine; or a substitution at position 227 with serine and at position 396 with leucine; or a substitution at position 217 with serine and at position 396 with leucine; or a substitution at position 261 with asparagine, at position 210 with methionine and at position 396 with leucine; or a substitution at position 419 with histidine and at position 396 with leucine; or a substitution at position 370 with glutamic acid and at position 396 with leucine; or a substitution at position 242 with phenylalanine and at position 396 with leucine; or a substitution at position 255 with leucine and at position 396 with leucine; or a substitution at position 240 with alanine and at position 396 with leucine; or a substitution at position 250 with serine and at position 396 with leucine; or a substitution at position 247 with serine and at position 396 with leucine; or a substitution at position 410 with histidine and at position 396 with leucine; or a substitution at position 419 with leucine and at position 396 with leucine; or a substitution at position 427 with alanine and at position 396 with leucine; or a substitution at position 258 with aspartic acid and at position 396 with leucine; or a substitution at position 384 with lysine and at position 396 with leucine; or a substitution at position 323 with isoleucine and at position 396 with leucine; or a substitution at position 244 with histidine and at position 396 with leucine; or a substitution at position 305 with leucine and at position 396 with leucine; or a substitution at position 400 with phenylalanine and at position 396 with leucine; or a substitution at position 303 with isoleucine and at position 396 with leucine; or a substitution at position 243 with leucine, at position 305 with isoleucine, at position 378 with aspartic acid, at position 404 with serine and at position 396 with leucine; or a substitution at position 290 with glutamic acid, at position 369 with alanine, at position 393 with alanine and at position 396 with leucine; or a substitution at position 210 with asparagine, at position 222 with isoleucine, at position 320 with methionine and at position 396 with leucine; or a substitution at position 217 with serine, at position 305 with isoleucine, at position 309 with leucine, at position 390 with histidine and at position 396 with leucine; or a substitution at position 246 with asparagine; at position 419 with arginine and at position 396 with leucine; or a substitution at position 217 with alanine, at position 359 with alanine and at position 396 with leucine; or a substitution at position 215 with isoleucine, at position 290 with valine and at position 396 with leucine; or a substitution at position 275 with leucine, at position 362 with histidine, at position 384 with lysine and at position 396 with leucine; or a substitution at position 334 with asparagine; or a substitution at position 400 with proline; or a substitution at position 407 with isoleucine; or a substitution at position 372 with tyrosine; or a substitution at position 366 with asparagine; or a substitution at position 414 with asparagine; or a substitution at position 352 with leucine; or a substitution at position 225 with serine; or a substitution at position 377 with asparagine; or a substitution at position 248 with methionine.

D. Mutants that do not Bind any FcγR

In some embodiments, the invention encompasses molecules comprising a variant Fc region, wherein said variant Fc region comprises at least one amino acid modification relative to a wild-type Fc region, which variant Fc region does not bind any FcγR, as determined by standard assays known in the art and disclosed herein, relative to a comparable molecule comprising the wild type Fc region. In a specific embodiment, the one or more amino acid modifications which abolish binding to all FcγRs comprise a substitution at position 232 with serine and at position 304 with glycine; or a substitution at position 269 with lysine, at position 290 with asparagine, at position 311 with arginine, and at position 433 with tyrosine; or a substitution at position 252 with leucine; or a substitution at position 216 with aspartic acid, at position 334 with arginine, and at position 375 with isoleucine; or a substitution at position 247 with leucine and at position 406 with phenylalanine, or a substitution at position 335 with asparagine, at position 387 with serine, and at position 435 with glutamine; or a substitution at position 334 with glutamic acid, at position 380 with aspartic acid, and at position 446 with valine; or a substitution at position 303 with isoleucine, at position 369 with phenylalanine, and at position 428 with leucine; or a substitution at position 251 with phenylalanine and at position 372 with leucine; or a substitution at position 246 with glutamic acid, at position 284 with methionine and at position 308 with alanine; or a substitution at position 399 with glutamic acid and at position 402 with aspartic acid; or a substitution at position 399 with glutamic acid and at position 428 with leucine.

D. Mutants with Altered FcγR-Mediated Effector Functions

The invention encompasses immunoglobulin comprising Fc variants with altered effector functions. In some embodiments, immunoglobulins comprising Fc variants mediate effector function more effectively in the presence of effector cells as determined using assays known in the art and exemplified herein. In other embodiments, immunoglobulins comprising Fc variants mediate effector function less effectively in the presence of effector cells as determined using assays known in the art and exemplified herein. In specific embodiments, the Fc variants of the invention may be combined with other known Fc modifications that alter effector function, such that the combination has an additive, synergistic effect. The Fc variants of the invention have altered effector function in vitro and/or in vivo.

In a specific embodiment, the immunoglobulins of the invention with enhanced affinity for FcγRIIIA and/or FcγRIIA have an enhanced FcγR-mediated effector function as determined using ADCC activity assays disclosed herein. Examples of effector functions that could be mediated by the molecules of the invention include, but are not limited to, C1q binding, complement-dependent cytotoxicity, antibody-dependent cell mediate cytotoxicity (ADCC), phagocytosis, etc. The effector functions of the molecules of the invention can be assayed using standard methods known in the art, examples of which are disclosed in Section 5.2.6. In a specific embodiment, the immunoglobulins of the invention comprising a variant Fc region with enhanced affinity for FcγRIIIA and/or FcγRIIA mediate antibody dependent cell mediated cytotoxicity (ADCC) 2-fold more effectively, than an immunoglobulin comprising a wild-type Fc region. In other embodiments, the immunoglobulins of the invention comprising a variant Fc region with enhanced affinity for FcγRIIIA and/or FcγRIIA mediate antibody dependent cell mediated cytotoxicity (ADCC) at least 4-fold, at least 8-fold, at least 10-fold, at least 100-fold, at least 1000-fold, at least $10^4$-fold, at least $10^5$-fold more effectively, than an immunoglobulin comprising a wild-type Fc region. In another specific embodiment, the immunoglobulins of the invention with enhanced affinity for FcγRIIIA and/or FcγRIIA have altered C1q binding activity. In some embodiments, the immunoglobulins of the invention with enhanced affinity for FcγRIIIA and/or FcγRIIA have at least 2-fold, at least 4-fold, at least 8-fold, at least 10-fold, at least 100-fold, at least 1000-fold, at least $10^4$-fold, at least $10^5$-fold higher C1q binding activity than an immunoglobulin comprising a wild-type Fc region. In yet another specific embodiment, the immunoglobulins of the invention with enhanced affinity for FcγRIIIA and/or FcγRIIA have altered complement dependent cytotoxicity. In yet another specific embodiment, the immunoglobulins of the invention with enhanced affinity for FcγRIIIA and/or FcγRIIA have an enhanced complement dependent cytotoxicity than an immunoglobulin comprising a wild-type Fc region. In some embodiments, the immunoglobulins of the invention with enhanced affinity for FcγRIIIA and/or FcγRIIA have at least 2-fold, at least 4-fold, at least 8-fold, at least 10-fold, at least 100-fold, at least 1000-fold, at least $10^4$-fold, at least $10^5$-fold higher complement dependent cytotoxicity than an immunoglobulin comprising a wild-type Fc region.

In other embodiments, immunoglobulins of the invention with enhanced affinity for FcγRIIIA and/or FcγRIIA have enhanced phagocytosis activity relative to an immunoglobulin comprising a wild-type Fc region, as determined by standard assays known to one skilled in the art or disclosed herein. In some embodiments, the immunoglobulins of the invention with enhanced affinity for FcγRIIIA and/or FcγRIIA have at least 2-fold, at least 4-fold, at least 8-fold, at least 10-fold higher phagocytosis activity relative to an immunoglobulin comprising a wild-type Fc region.

In a specific embodiment, the invention encompasses an immunoglobulin comprising a variant Fc region with one or more amino acid modifications, with an enhanced affinity for FcγRIIIA and/or FcγRIIA such that the immunoglobulin has an enhanced effector function, e.g., antibody dependent cell mediated cytotoxicity, or phagocytosis. In a specific embodiment, the one or more amino acid modifications which increase the affinity of the variant Fc region for FcγRIIIA and/or FcγRIIA and increase the ADCC activity of the immunoglobulin comprise a substitution at position 379 with methionine; or a substitution at position 243 with isoleucine and at position 379 with leucine; or a substitution at position 288 with asparagine, at position 330 with serine, and at position 396 with leucine; or a substitution at position 243 leucine and at position 255 with leucine; or a substitution at position 334 with glutamic acid, at position 359 with asparagine, and at position 366 with serine; or a substitution at position 288 with methionine and at position 334 with glutamic acid; or a substitution at position 334 with glutamic acid and at position 292 with leucine; or a substitution at position 316 with aspartic acid, at position 378 with valine, and at position 399 with glutamic acid; or a substitution at position 315 with isoleucine, at position 379 with methionine, and at position 399 with glutamic acid; or a substitution at position 243 with isoleucine, at position 379 with leucine, and at position 420 with valine; or a substitution at position 247 with leucine and at position 421 with lysine; or a substitution at position 248 with methionine; or a substitution at position 392 with threonine and at position 396 with leucine; or a substitution at position 293 with valine, at position 295 with glutamic acid, and at position 327 with threonine; or a substitution at position 268 with asparagine and at position 396 with leucine; or a substitution at position 319 with phenylalanine, at position 352 with leucine, and at position 396 with leucine.

In another specific embodiment, the one or more amino acid modifications which increase the ADCC activity of the immunoglobulin is any of the mutations listed below, in table 7.

TABLE 7

| AMINO ACID MODIFICATION WHICH INCREASE ADCC |
|---|
| E333A, K334A |
| R292L, K334E |
| V379M |
| S219Y |
| V282M |
| K222N |
| F243I, V379L |
| F243L, R255L, E318K |
| K334I |
| K334E, T359N, T366S |
| K288M, K334E |
| K288N, A330S, P396L |
| K326E |

TABLE 7-continued

| AMINO ACID MODIFICATION WHICH INCREASE ADCC |
|---|
| G316D, A378V, D399E |
| N315I, V379M, T394M |
| F243I, V379L, G420V |
| E293V, Q295E, A327T |
| Y319F, P352L, P396L |
| K392T, P396L |
| K248M |
| H268N, P396L |
| K290T, N390I, P396L |
| K326I, P396L |
| H268D, P396L |
| K210M, P396L |
| L358P, P396L |
| K288R, T307A, K344E, P396L |
| V273I, K326E, L328I, P396L |
| K326I, S408N, P396L |
| K334N, P396L |
| V379M, P396L |
| P227S, P396L |
| P217S, P396L |
| K261N, K210M, P396L |
| Q419H, P396L |
| K370E, P396L |
| L242F, P396L |
| F243L, V305I, A378D, F404S, P396L |
| R255L, P396L |
| V240A, P396L |
| T250S, P396L |
| P247S, P396L |
| K290E, V369A, T393A, P396L |
| K210N, K222I, K320M, P396L |
| L410H, P396L |
| Q419L, P396L |
| V427A, P396L |
| P217S, V305I, I309L, N390H, P396L |
| E258D, P396L |
| N384K, P396L |
| V323I, P396L |
| K246N, Q419R, P396L |
| P217A, T359A, P396L |
| P244H, P396L |
| V215I, K290V, P396L |
| F275L, Q362H, N384K, P396L |
| V305L, P396L |
| S400F, P396L |
| V303I, P396L |
| D270E, G316D, R416G |
| P247L, N421K |
| P247L, N421K, D270E |
| Q419H, P396L, D270E |
| K370E, P396L, D270E |
| R255L, P396L, D270E |
| V240A, P396L, D270E |
| K392T, P396L, D270E |

Alternatively or additionally, it may be useful to combine the above amino acid modifications or any other amino acid modifications disclosed herein with one or more further amino acid modifications that alter C1q binding and/or complement dependent cytoxicity function of the Fc region. The starting molecule of particular interest herein is usually one that binds to C1q and displays complement dependent cytotoxicity (CDC). The further amino acid substitutions described herein will generally serve to alter the ability of the starting molecule to bind to C1q and/or modify its complement dependent cytotoxicity function, e.g., to reduce and preferably abolish these effector functions. However, molecules comprising substitutions at one or more of the described positions with improved C1q binding and/or complement dependent cytotoxicity (CDC) function are contemplated herein. For example, the starting molecule may be unable to bind C1q and/or mediate CDC and may be modified according to the teachings herein such that it acquires these further effector functions. Moreover, molecules with preexisting C1q binding activity, optionally further having the ability to mediate CDC may be modified such that one or both of these activities are enhanced.

As disclosed above, one can design an Fc region with altered effector function, e.g., by modifying C1q binding and/or FcR binding and thereby changing CDC activity and/or ADCC activity. For example, one can generate a variant Fc region with improved C1q binding and improved FcγRIII binding; e.g., having both improved ADCC activity and improved CDC activity. Alternatively, where one desires that effector function be reduced or ablated, one may engineer a variant Fc region with reduced CDC activity and/or reduced ADCC activity. In other embodiments, one may increase only one of these activities, and optionally also reduce the other activity, e.g., to generate an Fc region variant with improved ADCC activity, but reduced CDC activity and vice versa.

The invention encompasses specific variants of the Fc region that have been identified using the methods of the invention from a yeast library of mutants after 2nd-4th-round of sorting are listed in Table 8. Table 8 summarizes the various mutants that were identified using the methods of the invention. The mutants were assayed using an ELISA assay for determining binding to FcγRIIIA and FcγRIIB. The mutants were also tested in an ADCC assay, by cloning the Fc variants into a ch 4-4-20 antibody using methods disclosed and exemplified herein. Bolded items refer to experiments, in which the ch4-4-20 were purified prior the ADCC assay. The antibody concentration used was in the range 0.5 μg/mL-1.0 μg/mL.

TABLE 8

MUTATIONS IDENTIFIED IN THE Fc REGION

| Mutations | Domain | Binding to FcγRIIIA (ELISA) | Binding to FcγRIIB (ELISA) | 4-4-20 ADCC (Relative Lysis (Mut/Wt) |
|---|---|---|---|---|
| pYD-CH1 library FACS screen with 3A tetramer | | | | |
| Q347H; A339V | CH3 | ↑ 0.5x | NT | |
| S415I; L251F | CH2, CH3 | ↑ 0.5x | ↑ .75x | 0.82 |
| K392R | CH3 | N/C | NT | |
| D399E; R292L; V185M | CH1, CH2, CH3 | N/C | ↑ 0.5x | 0.65<br>0.9 |
| K290E; L142P | CH1, CH2 | N/C | NT | |
| R301C; M252L; S192T | CH1, CH2 | ↓ .5x | NT | |
| P291S; K288E; H268L: A141V | CH1, CH2 | ↓ .5x | NT | |
| N315I | CH2 | N/C | ↑ .75x | |

TABLE 8-continued

MUTATIONS IDENTIFIED IN THE Fc REGION

| Mutations | Domain | Binding to FcγRIIIA (ELISA) | Binding to FcγRIIB (ELISA) | 4-4-20 ADCC (Relative Lysis (Mut/Wt) |
|---|---|---|---|---|
| S132I | CH1 | N/C | NT | |
| S383N; N384K; T256N; V262L; K218E; R214I; K205E; F149Y; K133M | All | ↑ 0.5x | NT | |
| S408I; V215I; V125L | CH1, CH2, CH3 | ↑ 0.5x | ↑ .75x | 0.62 |
| P396L | CH3 | ↑ 1x | ↑1x | 0.55 |
| G385E; P247H; | CH2, CH3 | ↑ 1x | ↑ .75x | 0.44 |
| P396H | CH3 | ↑ 1x | ↑1x | 0.58 |
| A162V | CH1 | N/C | NT | |
| V348M; K334N; F275I; Y202M; K147T | CH1, CH2, CH3 | ↑ 0.5x | ↑.75x | 0.33 |
| H310Y; T289A; G337E | CH2 | ↑ .5x | NT | |
| S119F; G371S; Y407V; E258D | CH1, CH2, CH3 | N/C | N/C | 0.29 |
| K409R; S166N | CH1, CH3 | N/C | NT | |
| in vitro Site Directed mutants | | | | |
| R292L | CH2 | NT | NT | 0.82 |
| T359N | CH3 | NT | NT | 1.06 |
| T366S | CH3 | NT | NT | 0.93 |
| E333A, K334A | CH2 | NT | NT | 1.41 |
| R292L, K334E | CH2 | NT | NT | 1.41; 1.64 |
| R292L, P396L, T359N | CH2, CH3 | NT | NT | 0.89; 1.15 |
| V379L | CH3 | NT | NT | 0.83 |
| K288N | CH2 | NT | NT | 0.78 |
| A330S | CH2 | NT | NT | 0.52 |
| F243L | CH2 | NT | NT | 0.38 |
| E318K | CH2 | NT | NT | 0.86 |
| K288N, A330S | CH2 | NT | NT | 0.08 |
| R255L, E318K | CH2 | NT | NT | 0.82 |
| F243L, E318K | CH2 | NT | NT | 0.07 |
| Mutants in 4-4-20 mini-library | | | | |
| Increased FcγRIIIA binding, decreased or no change to FcγRIIB binding | | | | |
| N/C means no change; N/B means no binding; | | | | |
| NT means not tested | | | | |
| V379M | CH3 | ↑2x | N/C | 1.47 |
| S219Y | Hinge | ↑1x | ↓ or N/B | 1.28 |
| V282M | CH2 | ↑1x | ↓ or N/B | 1.25; 1 |
| F275I, K334N, V348M | CH2 | ↑0.5x | N/C | |
| D401V | CH3 | ↑ 0.5x | N/C | |
| V279L, P395S | CH2 | ↑ 1x | N/C | |
| K222N | Hinge | ↑ 1x | ↓or N/B | 1.33; 0.63 |
| K246T, Y319F | CH2 | ↑ 1x | N/C | |
| F243I, V379L | CH2, CH3 | ↑1.5x | ↓ or N/B | 1.86; 1.35 |
| F243L, R255L, E318K | CH2 | ↑ 1x | ↓ or N/B | 1.81; 1.45 |
| K334I | CH2 | ↑ 1x | N/C | 2.1; 1.97 |
| K334E, T359N, T366S | CH2, CH3 | ↑1.5x | N/C | 1.49; 1.45 |
| K288M, K334E | CH2 | ↑ 3x | ↓ or N/B | 1.61; 1.69 |
| K334E, E380D | CH2, CH3 | ↑1.5x | N/C | |
| T256S, V305I, K334E, N390S | CH2, CH3 | ↑1.5x | N/C | |
| K334E | CH2 | ↑2.5x | N/C | 1.75; 2.18 |
| T335N, K370E, A378V, T394M, S424L | CH2, CH3 | ↑0.5x | N/C | |
| E233D, K334E | CH2 | ↑1.5x | N/C | 0.94; 1.02 |
| K334E, T359N, T366S, Q386R | CH2 | ↑ 1x | N/C | |
| Increased Binding to FcγIIIA and FcγRIIB | | | | |
| K246T, P396H | CH2, CH3 | ↑ 1x | ↑ 2.5x | |
| H268D, E318D | CH2 | ↑1.5x | ↑ 5x | |
| K288N, A330S, P396L | CH2, CH3 | ↑ 5x | ↑ 3x | 2.34; 1.66; 2.54 |
| I377F | CH3 | ↑1.5x | ↑0.5x | |
| P244H, L358M, V379M, N384K, V397M | CH2, CH3 | ↑1.75x | ↑1.5x | |
| P217S, A378V, S408R | Hinge, CH3 | ↑ 2x | ↑4.5x | |
| P247L, I253N, K334N | CH2 | ↑ 3x | ↑ 2.5x | |
| P247L | CH2 | ↑0.5x | ↑ 4x | 0.91; 0.84 |
| F372Y | CH3 | ↑0.75x | ↑5.5x | 0.88; 0.59 |
| K326E | CH2 | ↑ 2x | ↑ 3.5x | 1.63; 2 |
| K246I, K334N | CH2 | ↑0.5x | ↑ 4x | 0.66; 0.6 |
| K320E, K326E | CH2 | ↑ 1x | ↑ 1x | |
| H224L | Hinge | ↑0.5x | ↑ 5x | 0.55; 0.53 |
| S375C, P396L | CH3 | ↑1.5x | ↑4.5x | |
| D312E, K327N, I378S | CH2, CH3 | ↑0.5x | N/C | |
| K288N, K326N | CH2 | ↑ 1x | N/C | |
| F275Y | CH2 | ↑ 3x | N/C | 0.64 |

TABLE 8-continued

MUTATIONS IDENTIFIED IN THE Fc REGION

| Mutations | Domain | Binding to FcγRIIIA (ELISA) | Binding to FcγRIIB (ELISA) | 4-4-20 ADCC (Relative Lysis (Mut/Wt) |
|---|---|---|---|---|
| P247L, N421K | CH2, CH3 | ↑ 3x | N/C | 2.0 |
| S298N, W381R | CH2, CH3 | ↑ 2x | N/C | |
| D280E, S354F, A431D, L441I | CH2, CH3 | ↑ 3x | N/C | 0.62 |
| R255Q, K326E | CH2 | ↑ 2x | N/C | 0.79 |
| K218R, G281D, G385R | H, CH2, CH3 | ↑3.5x | N/C | 0.67 |
| L398V | CH3 | ↑1.5x | N/C | |
| P247L, A330T, S440G | CH2, CH3 | ↑0.75x | ↓0.25x | |
| V284A, F372L | CH2, CH3 | 1x | N/C | |
| T335N, P387S, H435Q | CH2, CH3 | 1.25x | N/C | |
| P247L, A431V, S442F | CH2, CH3 | 1x | N/C | |
| Increased Binding to FcγRIIIA and FcγRIIB | | | | |
| P343S, P353L, S375I, S383N | CH3 | ↑ 0.5x | ↑ 6x | |
| T394M, V397M | CH3 | ↑0.5x | ↑ 3x | |
| E216D, E345K, S375I | H, CH2, CH3 | ↑ 0.5x | ↑ 4x | |
| K334N, | CH2 | ↑0.5x | ↑ 2x | |
| K288N, A330S, P396L | CH2, CH3 | ↑0.5x | ↑ 9x | |
| P247L, E389G | CH2, CH3 | ↑1.5x | ↑ 9x | |
| K222N, T335N, K370E, A378V, T394M | H, CH2, CH3 | ↑ 1x | ↑ 7x | |
| G316D, A378V, D399E | CH2, CH3 | ↑1.5x | ↑ 14x | 2.24 |
| N315I, V379M, T394M | CH2, CH3 | ↑ 1x | ↑ 9x | 1.37 |
| K290T, G371D, | CH2, CH3 | ↑ 0.25x | ↑ 6x | |
| P247L, L398Q | CH2, CH3 | ↑ 1.25x | ↑ 10x | |
| K326Q, K334E, T359N, T366S | CH2, CH3 | ↑ 1.5x | ↑ 5x | |
| S400P | CH3 | ↑ 1x | ↑ 6x | |
| P247L, I377F | CH2, CH3 | ↑ 1x | ↑ 5x | |
| A378V, N390I, V422I | CH3 | ↑ 0.5x | ↑ 5x | |
| K326E, G385E | CH2, CH3 | ↑0.5x | ↑15x | |
| V282E, V369I, L406F | CH2, CH3 | ↑ 0.5x | ↑ 7x | |
| V397M, T411A, S415N | CH3 | ↑ 0.25x | ↑5x | |
| T223I, T256S, L406F | H, CH2, CH3 | ↑ 0.25x | ↑ 6x | |
| S298N, S407R | CH2, CH3 | ↑0.5x | ↑ 7x | |
| K246R, S298N, I377F | CH2, CH3 | ↑ 1x | ↑ 5x | |
| S407I | CH3 | ↑ 0.5x | ↑4x | |
| F372Y | CH3 | ↑0.5x | ↑4x | |
| L235P, V382M, S304G, V305I, V323I | CH2, CH3 | ↑ 2x | ↑ 2x | |
| P247L, W313R, E388G | CH2, CH3 | ↑1.5x | ↑1x | |
| D221Y, M252I, A330G, A339T, T359N, V422I, H433L | H, CH2, CH3 | ↑2.5x | ↑ 6x | |
| E258D, N384K | CH2, CH3 | ↑1.25x | ↑4x | |
| F241L, E258G | CH2 | ↑ 2x | ↑ 2.5x | −0.08 |
| K370N, S440N | CH3 | ↑1x | ↑ 3.5x | |
| K317N, F423-deleted | CH2, CH3 | ↑ 2.5x | ↑ 7x | 0.18 |
| F243I, V379L, G420V | CH2, CH3 | ↑ 2.5x | ↑3.5x | 1.35 |
| P227S, K290E | H, CH2 | ↑ 1x | ↑ 0.5x | |
| A231V, Q386H, V412M | CH2, CH3 | ↑1.5x | ↑ 6x | |
| T215V, K274N, A287G, K334N, L365V, P396L | H, CH2, CH3 | ↑2x | ↑ 4x | |
| Increased Binding to FcγRIIB but not FcγRIIIA | | | | |
| K334E, E380D | CH2, CH3 | N/C | ↑4.5x | |
| T366N | CH3 | N/C | ↑ 5x | |
| P244A, K326I, C367R, S375I, K447T | CH2, CH3 | N/C | ↑ 3x | |
| C229Y, A287T, V379M, P396L, L443V | H, CH2, CH3 | ↓ 0.25x | ↑10x | |
| Decreased binding to FcγRIIIA and FcγRIIB | | | | |
| R301H, K340E, D399E | CH2, CH3 | ↓ 0.50x | ↓ 0.25x | |
| K414N | CH3 | ↓ 0.25x | N/B | |
| P291S, P353Q | CH2, CH3 | ↓ 0.50x | ↓ 0.25x | |
| V240I, V281M | CH2 | ↓ 0.25x | ↓ 0.25x | |
| P232S, S304G | CH2 | N/B | N/B | |
| E269K, K290N, Q311R, H433Y | CH2, CH3 | N/B | N/B | |
| M352L | CH3 | N/B | N/B | |
| E216D, K334R, S375I | H, CH2, CH3 | N/B | N/B | |
| P247L, L406F | CH2, CH3 | N/B | N/B | |
| T335N, P387S, H435Q | CH2, CH3 | N/B | N/B | |
| T225S | CH2 | ↓ 0.25x | ↓ 0.50x | |
| D399E, M428L | CH3 | ↓ 0.50x | ↓ 0.50x | |
| K246I, Q362H, K370E | CH2, CH3 | N/B | ↓ 0.50x | |
| K334E, E380D, G446V | CH2, CH3 | N/B | N/B | |
| I377N | CH3 | ↓ 0.50x | N/B | |
| V303I, V369F, M428L | CH2, CH3 | N/B | N/B | |
| L251F, F372L | CH2, CH3 | N/B | N/B | |
| K246E, V284M, V308A | CH2, CH3 | N/B | N/B | |

TABLE 8-continued

MUTATIONS IDENTIFIED IN THE Fc REGION

| Mutations | Domain | Binding to FcγRIIIA (ELISA) | Binding to FcγRIIB (ELISA) | 4-4-20 ADCC (Relative Lysis (Mut/Wt) |
|---|---|---|---|---|
| D399E, G402D | CH3 | N/B | N/B | |
| D399E, M428L | CH3 | N/B | N/B | |
| FcγRIIB depletion/FcγRIIIA selection: Naive Fc library. | | | | |
| E293V, Q295E, A327T | CH2 | ↑0.4x | ↓ or N/B | 4.29 |
| Y319F, P352L, P396L | CH2, CH3 | ↑3.4x | ↑2x | 1.09 |
| K392T, P396L | CH3 | ↑ 4.5x | ↑ 2.5x | 3.07 |
| K248M | CH2 | ↑0.4x | ↓ or N/B | 4.03 |
| H268N, P396L | CH2, CH3 | ↑ 2.2x | ↑ 4.5x | 2.24 |
| Solution competition 40X FcγRIIB-G2: P396L Library | | | | |
| D221E, D270E, V308A, Q311H, P396L, G402D | | ↑3.6x | ↑0.1x | 3.17 |
| Equilibrium Screen: 0.8 µM FcγRIIIA monomer: P396L library | | | | |
| K290T, N390I, P396L | CH2, CH3 | ↑2.8x | ↑ 6.1x | 1.93 |
| K326I, P396L | CH2, CH3 | ↑2.9x | ↑ 5.9x | 1.16 |
| H268D, P396L | CH2, CH3 | ↑3.8x | ↑ 13.7x | 2.15 |
| K210M, P396L | CH1, CH3 | ↑1.9x | ↑ 4.6x | 2.02 |
| L358P, P396L | CH3 | ↑1.9x | ↑ 4.2x | 1.58 |
| K288R, T307A, K344E, P396L | CH2, CH3 | ↑ 4.1x | ↑ 2.3x | 3.3 |
| V273I, K326E, L328I, P396L | CH2, CH3 | ↑ 1.3x | ↑ 10.8x | 0.78 |
| K326I, S408N, P396L | CH2, CH3 | ↑4x | ↑ 9.3x | 1.65 |
| K334N, P396L | CH2, CH3 | ↑3.1x | ↑ 3x | 2.43 |
| V379M, P396L | CH3 | ↑1.9x | ↑5.6x | 2.01 |
| P227S, P396L | CH2, CH3 | ↑1.5x | ↑ 4x | 2.01 |
| P217S, P396L | H, CH3 | ↑1.6x | ↑4.5x | 2.04 |
| K261N, K210M, P396L | CH2, CH3 | ↑ 2x | ↑ 4.2x | 2.06 |
| Kinetic Screen: 0.8 µM, 1′ with cold 8 µM FcγRIIIA: P396L Library | | | | |
| term is M, P396L | CH3 | ↑1.9x | ↑ 7.2x | 3.09 |
| Q419H, P396L | CH3 | ↑ 2x | ↑ 6.9x | 2.24 |
| K370E, P396L | CH3 | ↑2x | ↑6.6x | 2.47 |
| L242F, P396L | CH2, CH3 | ↑ 2.5x | ↑ 4.1x | 2.4 |
| F243L, V305I, A378D, F404S, P396L | CH2, CH3 | ↑1.6x | ↑5.4x | 3.59 |
| R255L, P396L | CH2, CH3 | ↑1.8x | ↑ 6x | 2.79 |
| V240A, P396L | CH2, CH3 | ↑ 1.3x | ↑ 4.2x | 2.35 |
| T250S, P396L | CH2, CH3 | ↑ 1.5x | ↑6.8x | 1.60 |
| P247S, P396L | CH2, CH3 | ↑ 1.2x | ↑ 4.2x | 2.10 |
| K290E, V369A, T393A, P396L | CH2, CH3 | ↑ 1.3x | ↑ 6.7x | 1.55 |
| K210N, K222I, K320M, P396L | H, CH2, CH3 | ↑ 2.7x | ↑ 8.7x | 1.88 |
| L410H, P396L | CH3 | ↑ 1.7x | ↑ 4.5x | 2.00 |
| Q419L, P396L | CH3 | ↑ 2.2x | ↑ 6.1x | 1.70 |
| V427A, P396L | CH3 | ↑ 1.9x | ↑4.7x | 1.67 |
| P217S, V305I, I309L, N390H, P396L | H, CH2, CH3 | ↑2x | ↑ 7x | 1.54 |
| E258D, P396L | CH2, CH3 | ↑ 1.9x | ↑ 4.9x | 1.54 |
| N384K, P396L | CH3 | ↑ 2.2x | ↑5.2x | 1.49 |
| V323I, P396L | CH2, CH3 | ↑ 1.1x | ↑ 8.2x | 1.29 |
| K246N, Q419R, P396L | CH2, CH3 | ↑1.1x | ↑ 4.8x | 1.10 |
| P217A, T359A, P396L | H, CH2, CH3 | ↑1.5x | ↑ 4.8x | 1.17 |
| P244H, P396L | CH2, CH3 | ↑2.5x | ↑ 4x | 1.40 |
| V215I, K290V, P396L | H, CH2, CH3 | ↑2.2x | ↑ 4.6x | 1.74 |
| F275L, Q362H, N384K, P396L | CH2, CH3 | ↑ 2.2x | ↑ 3.7x | 1.51 |
| V305L, P396L | CH2, CH3 | ↑1.3x | ↑ 5.5x | 1.50 |
| S400F, P396L | CH3 | ↑1.5x | ↑4.7x | 1.19 |
| V303I, P396L | CH3 | ↑1.1x | ↑ 4x | 1.01 |
| FcγRIIB depletion FcγRIIIA 158V solid phase selection: Naive Library | | | | |
| A330V, H433Q, V427M | CH2, CH3 | NT | NT | NT |
| V263Q, E272D, Q419H | CH2, CH3 | NT | NT | NT |
| N276Y, T393N, W417R | CH2, CH3 | NT | NT | NT |
| V282L, A330V, H433Y, T436R | CH2, CH3 | NT | NT | NT |
| A330V, Q419H | CH2, CH3 | NT | NT | NT |
| V284M, S298N, K334E, R355W | CH2, CH3 | NT | NT | NT |
| A330V, G427M, K438R | CH2, CH3 | NT | NT | NT |
| S219T, T225K, D270E, K360R | CH2, CH3 | NT | NT | NT |
| K222E, V263Q, S298N | CH2 | NT | NT | NT |
| V263Q, E272D | CH2 | NT | NT | NT |
| R292G | CH2 | NT | NT | NT |
| S298N | CH2 | NT | NT | NT |
| E233G, P247S, L306P | CH2 | NT | NT | NT |

TABLE 8-continued

MUTATIONS IDENTIFIED IN THE Fc REGION

| Mutations | Domain | Binding to FcγRIIIA (ELISA) | Binding to FcγRIIB (ELISA) | 4-4-20 ADCC (Relative Lysis (Mut/Wt) |
|---|---|---|---|---|
| D270E | CH2 | NT | NT | NT |
| S219T, T225K, D270E | CH2 | NT | NT | NT |
| K326E, A330T | CH2 | NT | NT | NT |
| E233G | CH2 | NT | NT | NT |
| S254T, A330V, N361D, P243L | CH2, CH3 | NT | NT | NT |
| FcγRIIB depletion FcγRIIIA 158F solid phase selection: Naïve Library 158F by FACS top 0.2% | | | | |
| V284M, S298N, K334E, R355W R416T | CH2, CH3 | NT | NT | |
| FcγRIIB depletion FcgRIIA 131H solid phase selection: Naïve Library | | | | |
| R292P, V305I | CH2, CH2 | NT | NT | |
| D270E, G316D, R416G | CH2, CH3 | NT | NT | |
| V284M, R292L, K370N | CH2, CH3 | NT | NT | |
| R292P, V305I, F243L | CH2 | NT | NT | |

In preferred embodiments, the invention provides modified immunoglobulin molecules (e.g., antibodies) with variant Fc regions, having one or more amino acid modifications, which one or more amino acid modifications increase the affinity of the molecule for FcγRIIIA and/or FcγRIIA. Such immunoglobulins include IgG molecules that naturally contain FcγR binding regions (e.g., FcγRIIIA and/or FcγRIIB binding region), or immunoglobulin derivatives that have been engineered to contain an FcγR binding region (e.g., FcγRIIIA and/or FcγRIIB binding region). The modified immunoglobulins of the invention include any immunoglobulin molecule that binds, preferably, immunospecifically, i.e., competes off non-specific binding as determined by immunoassays well known in the art for assaying specific antigen-antibody binding, an antigen and contains an FcγR binding region (e.g., a FcγRIIIA and/or FcγRIIB binding region). Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an FcγR binding region.

In some embodiments, the molecules of the invention comprise portions of an Fc region. As used herein the term "portion of an Fc region" refers to fragments of the Fc region, preferably a portion with effector activity and/or FcγR binding activity (or a comparable region of a mutant lacking such activity). The fragment of an Fc region may range in size from 5 amino acids to the entire Fc region minus one amino acid. The portion of an Fc region may be missing up to 10, up to 20, up to 30 amino acids from the N-terminus or C-terminus.

The IgG molecules of the invention are preferably IgG1 subclass of IgGs, but may also be any other IgG subclasses of given animals. For example, in humans, the IgG class includes IgG1, IgG2, IgG3, and IgG4; and mouse IgG includes IgG1, IgG2a, IgG2b, IgG2c and IgG3.

The immunoglobulins (and other polypeptides used herein) may be from any animal origin including birds and mammals. Preferably, the antibodies are human, rodent (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example, in U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide or may be specific for heterologous epitopes, such as a heterologous polypeptide or solid support material. See, e.g., PCT publications WO 93/17715; WO 92/08802; WO 91/00360; WO 92/05793; Tutt, et al., J. Immunol., 147: 60-69, 1991; U.S. Pat. Nos. 4,474,893; 4,714,681; 4,925,648; 5,573,920; 5,601,819; Kostelny et al., J. Immunol., 148:1547-1553, 1992.

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against a tumor cell antigen and the other arm directed against a cytotoxic molecule.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983); which is incorporated herein by reference in its entirety). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986). According to another approach described in WO96/27011, a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies are contemplated. For example, trispecific antibodies can be prepared. See, e.g., Tutt et al. J. Immunol. 147: 60 (1991), which is incorporated herein by reference.

The antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, *Science*, 229:1202, 1985; Oi et al., *BioTechniques*, 4:214 1986; Gillies et al., *J. Immunol. Methods*, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions and constant domains from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., *Nature*, 332: 323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, *Molecular Immunology*, 28(4/5):489-498, 1991; Studnicka et al., *Protein Engineering*, 7(6):805-814, 1994; Roguska et al., *Proc Natl. Acad. Sci. USA*, 91:969-973, 1994), and chain shuffling (U.S. Pat. No. 5,565,332), all of which are hereby incorporated by reference in their entireties. Humanized antibodies may be generated using any of the methods disclosed in U.S. Pat. Nos. 5,693,762 (Protein Design Labs), 5,693,761, (Protein Design Labs) 5,585,089 (Protein Design Labs), 6,180, 370 (Protein Design Labs), and U.S. Publication Nos. 20040049014, 200300229208, each of which is incorporated herein by reference in its entirety.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, *Int. Rev. Immunol.*, 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885,793; 5,916,771; and 5,939,598, which are incorporated by reference herein in their entireties. In addition, companies such as Abgenix, Inc. (Freemont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., *Bio/technology,* 12:899-903, 1988).

The invention encompasses engineering human or humanized therapeutic antibodies (e.g., tumor specific monoclonal antibodies) in the Fc region, by modification (e.g., substitution, insertion, deletion) of at least one amino acid residue, which modification increases the affinity of the Fc region for FcγRIIIA and/or FcγRIIA. In another embodiment, the invention relates to engineering human or humanized therapeutic antibodies (e.g., tumor specific monoclonal antibodies) in the Fc region, by modification of at least one amino acid residue, which modification increases the affinity of the Fc region for FcγRIIIA and/or FcγRIIA and further decreases the affinity of the Fc region for FcγRIIB. The engineered therapeutic antibodies may further have an enhanced effector function, e.g., enhanced ADCC activity, phagocytosis activity, etc., as determined by standard assays known to those skilled in the art.

In a specific embodiment, the invention encompasses engineering a humanized monoclonal antibody specific for Her2/neu protooncogene (e.g., Ab4D5 humanized antibody as disclosed in Carter et al., 1992, *Proc. Natl. Acad. Sci. USA* 89:4285-9) by modification (e.g., substitution, insertion, deletion) of at least one amino acid residue which modification increases the affinity of the Fc region for FcγRIIIA and/or FcγRIIA. In another specific embodiment, modification of the humanized Her2/neu monoclonal antibody may also further decrease the affinity of the Fc region for FcγRIIB. In yet another specific embodiment, the engineered humanized monoclonal antibodies specific for Her2/neu may further have an enhanced effector function as determined by standard assays known in the art and disclosed and exemplified herein.

In another specific embodiment, the invention encompasses engineering a mouse human chimeric anti-CD20 monoclonal antibody, 2H7 by modification (e.g., substitution, insertion, deletion) of at least one amino acid residue which modification increases the affinity of the Fc region for FcγRIIIA and/or FcγRIIA. In another specific embodiment, modification of the anti-CD20 monoclonal antibody, 2H7 may also further decrease the affinity of the Fc region for FcγRIIB. In yet another specific embodiment, the engineered anti-CD20 monoclonal antibody, 2H7 may further have an enhanced effector function as determined by standard assays known in the art and disclosed and exemplified herein.

In another specific embodiment, the invention encompasses engineering an anti-FcγRIIB antibody including but not limited to any of the antibodies disclosed in U.S. Provisional Application No. 60/403,266 filed on Aug. 12, 2002 and U.S. application Ser. No. 10/643,857 filed on Aug. 14, 2003, U.S. Provisional Application No. 60/562,804 filed on Apr. 16, 2004; U.S. Provisional Application No. 60/569,882 filed on May 10, 2004 and U.S. Provisional Application Nos. 60/582, 044, 60/582,045 and 60/582,043 filed on Jun. 21, 2004, by modification (e.g., substitution, insertion, deletion) of at least one amino acid residue which modification increases the affinity of the Fc region for FcγRIIIA and/or FcγRIIA. Each of the above mentioned applications are incorporated herein by reference in their entireties. Examples of anti-FcγRIIB antibodies that may be engineered in accordance with the methods of the invention are 2B6 monoclonal antibody having ATCC accession number PTA-4591 and 3H7 having ATCC accession number PTA-4592, 1D5 monoclonal antibody having ATCC accession number PTA-5958, 1F2 monoclonal antibody having ATCC accession number PTA-5959, 2D11 monoclonal antibody having ATCC accession number PTA-5960, 2E1 monoclonal antibody having ATCC accession number PTA-5961 and 2H9 monoclonal antibody having ATCC accession number PTA-5962 (all deposited at University Boulevard, Manassas, Va. 02209-2011), which are incorporated herein by reference. In another specific embodiment, modification of the anti-FcγRIIB antibody may also further decrease the affinity of the Fc region for FcγRIIB. In yet another specific embodiment, the engineered anti-FcγRIIB antibody may further have an enhanced effector function as determined by standard assays known in the art and disclosed and exemplified herein. In a specific embodiment, the 2B6 monoclonal antibody comprises a modification at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 243 with isoleucine, at position 379 with leucine, and at position 420 with valine (MgFc29); or a substitution at position 392 with threonine and at position 396 with leucine (MgFc38); or a substitution at position 221 with glutamic acid, at position 270 with glutamic acid, at position 308 with alanine, at position 311 with histidine, at position 396 with leucine, and at position 402 with aspartic (MgFc42); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid, and at position 396 with leucine (MgFc59) (See Table 5).

4.1.1 Polypeptide and Antibody Conjugates

Molecules of the invention (i.e., polypeptides, antibodies) comprising variant Fc regions may be recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences.

Further, molecules of the invention (i.e., polypeptides, antibodies) comprising variant Fc regions may be conjugated to a therapeutic agent or a drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., *J. Immunol.*, 6:1567-1574, 1994), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF"), macrophage colony stimulating factor, ("M-CSF"), or a growth factor (e.g., growth hormone ("GH"); proteases, or ribonucleases.

Molecules of the invention (i.e., polypeptides, antibodies) can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, *Proc. Natl. Acad. Sci. USA,* 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., *Cell,* 37:767 1984) and the "flag" tag (Knappik et al., *Biotechniques,* 17(4):754-761, 1994).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of molecules of the invention (e.g., antibodies with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Molecules of the invention comprising variant Fc regions, or the nucleic acids encoding the molecules of the invention, may be further altered by being subjected to random mutagenesis by error-prone PCR, random nucleotide insertion or other methods prior to recombination. One or more portions of a polynucleotide encoding a molecule of the invention, may be recombined with one or more components, motifs, sections, parts, domains, fragments, etc. of one or more heterologous molecules.

The present invention also encompasses molecules of the invention comprising variant Fc regions (i.e., antibodies, polypeptides) conjugated to a diagnostic or therapeutic agent or any other molecule for which serum half-life is desired to be increased and/or targeted to a particular subset of cells. The molecules of the invention can be used diagnostically to, for example, monitor the development or progression of a disease, disorder or infection as part of a clinical testing procedure to, e.g., determine the efficacy of a given treatment regimen. Detection can be facilitated by coupling the molecules of the invention to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the molecules of the invention or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the molecules of the invention to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La) lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium $^{201}$Ti) tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

Molecules of the invention (i.e., antibodies, polypeptides) comprising a variant Fc region may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, a molecule of the invention can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraaza-cyclododecane-N,N',N",N"'-tetraacetic acid (DOTA) which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50 each of which is incorporated herein by reference in their entireties.

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., *Immunol. Rev.,* 62:119-58, 1982.

In one embodiment, where the molecule of the invention is an antibody comprising a variant Fc region, it can be administered with or without a therapeutic moiety conjugated to it, administered alone, or in combination with cytotoxic factor(s) and/or cytokine(s) for use as a therapeutic treatment. Alternatively, an antibody of the invention can be conjugated to a second antibody to form an antibody heteroconjugate as described by Segal in U.S. Pat. No. 4,676,980, which is incorporated herein by reference in its entirety. Antibodies of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

4.2 Screening of Molecules with Variant Fc Regions for Enhanced FcγRIII Binding and Characterization of Same In preferred embodiments, screening and identifying molecules comprising variant Fc regions with altered FcγR affinities (e.g., enhanced FcγRIIIA affinity) are done using the yeast display technology as described herein in combination with one or more biochemical based assays, preferably in a high throughput manner. The one or more biochemical assays can be any assay known in the art for identifying Fc-FcγR interaction, i.e., specific binding of an Fc region to an FcγR, including, but not limited to, an ELISA assay, surface plasmon resonance assays, immunoprecipitation assay, affinity chromatography, and equilibrium dialysis. In some embodiments, screening and identifying molecules comprising variant Fc regions with altered FcγR affinities (e.g., enhanced FcγRIIIA affinity) are done using the yeast display technology as described herein in combination with one or more functional based assays, preferably in a high throughput manner. The functional based assays can be any assay known in the art for characterizing one or more FcγR mediated effector cell functions such as those described herein in Section 5.2.7. Non-limiting examples of effector cell functions that can be used in accordance with the methods of the invention, include but are not limited to, antibody-dependent cell mediated cytotoxicity (ADCC), antibody-dependent phagocytosis, phagocytosis, opsonization, opsonophagocytosis, cell binding, rosetting, C1q binding, and complement dependent cell mediated cytotoxicity. In some embodiments, screening and identifying molecules comprising variant Fc regions with altered FcγR affinities (e.g., enhanced FcγRIIIA affinity) are done using the yeast display technology as described herein in combination with one or more biochemical based assays in combination or in parallel with one or more functional based assays, preferably in a high throughput manner.

The term "specific binding" of an Fc region to an FcγR refers to an interaction of the Fc region and a particular FcγR which has an affinity constant of at least about 150 nM, in the case of monomeric FcγRIIIA and at least about 60 nM in the case of dimeric FcγRIIB as determined using, for example, an ELISA or surface plasmon resonance assay (e.g., a BIAcore™). The affinity constant of an Fc region for monomeric FcγRIIIA may be 150 nM, 200 nM or 300 nM. The affinity constant of an Fc region for dimeric FcγRIIB may be 60 nM, 80 nM, 90 nM, or 100 nM. Dimeric FcγRIIB for use in the methods of the invention may be generated using methods known to one skilled in the art. Typically, the extracellular region of FcγRIIB is covalently linked to a heterologous polypeptide which is capable of dimerization, so that the resulting fusion protein is a dimer, e.g., see, U.S. Application No. 60/439,709 filed on Jan. 13, 2003, which is incorporated herein by reference in its entirety. A specific interaction generally is stable under physiological conditions, including, for example, conditions that occur in a living individual such as a human or other vertebrate or invertebrate, as well as conditions that occur in a cell culture such conditions as used for maintaining and culturing mammalian cells or cells from another vertebrate organism or an invertebrate organism.

In a specific embodiment, screening for and identifying molecules comprising variant Fc regions and altered FcγR affinities comprise: displaying the molecule comprising a variant Fc region on the yeast surface; and characterizing the binding of the molecule comprising the variant Fc region to a FcγR (one or more), using a biochemical assay for determining Fc-FcγR interaction, preferably, an ELISA based assay. Once the molecule comprising a variant Fc region has been characterized for its interaction with one or more FcγRs and determined to have an altered affinity for one or more FcγRs, by at least one biochemical based assay, e.g., an ELISA assay, the molecule may be engineered into a complete immunoglobulin, using standard recombinant DNA technology methods known in the art, and the immunoglobulin comprising the variant Fc region expressed in mammalian cells for further biochemical characterization. The immunoglobulin into which a variant Fc region of the invention is introduced (e.g., replacing the Fc region of the immunoglobulin) can be any immunoglobulin including, but not limited to, polyclonal antibodies, monoclonal antibodies, bispecific antibodies, multi-specific antibodies, humanized antibodies, and chimeric antibodies. In preferred embodiments, a variant Fc region is introduced into an immunoglobulin specific for a cell surface receptor, a tumor antigen, or a cancer antigen. The immunoglobulin into which a variant Fc region of the invention is introduced may specifically bind a cancer or tumor antigen for example, including, but not limited to, KS 1/4 pan-carcinoma antigen (Perez and Walker, 1990, *J. Immunol.* 142: 3662-3667; Bumal, 1988, *Hybridoma* 7(4): 407-415), ovarian carcinoma antigen (CA125) (Yu et al., 1991, *Cancer Res.* 51(2): 468-475), prostatic acid phosphate (Tailor et al., 1990, *Nucl. Acids Res.* 18(16): 4928), prostate specific antigen (Henttu and Vihko, 1989, Biochem. Biophys. Res. Comm. 160(2): 903-910; Israeli et al., 1993, Cancer Res. 53: 227-230), melanoma-associated antigen p97 (Estin et al., 1989, *J. Natl. Cancer Instil.* 81(6): 445-446), melanoma antigen gp75 (Vijayasardahl et al., 1990, *J. Exp. Med.* 171(4): 1375-1380), high molecular weight melanoma antigen (HMW-MAA) (Natali et al., 1987, *Cancer* 59: 55-63; Mittelman et al., 1990, *J. Clin. Invest.* 86: 2136-2144), prostate specific membrane antigen, carcinoembryonic antigen (CEA) (Foon et al., 1994, *Proc. Am. Soc. Clin. Oncol.* 13: 294), polymorphic epithelial mucin antigen, human milk fat globule antigen, colorectal tumor-associated antigens such as: CEA, TAG-72 (Yokata et al., 1992, *Cancer Res.* 52: 3402-3408), CO17-1A (Ragnhammar et al., 1993, *Int. J. Cancer* 53: 751-758); GICA 19-9 (Herlyn et al., 1982, *J. Clin. Immunol.* 2: 135), CTA-1 and LEA, Burkitt's lymphoma antigen-38.13, CD19 (Ghetie et al., 1994, *Blood* 83: 1329-1336), human B-lymphoma antigen-CD20 (Reff et al., 1994, *Blood* 83:435-445), CD33 (Sgouros et al., 1993, *J. Nucl. Med.* 34:422-430), melanoma specific antigens such as ganglioside GD2 (Saleh et al., 1993, *J. Immunol.*, 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12: 1036-1044), ganglioside GM3 (Hoon et al., 1993, *Cancer Res.* 53: 5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46: 3917-3923), antigens of fibrosarcoma, human leukemia T cell antigen-Gp37 (Bhattacharya-Chatterjee et al., 1988, *J. of Immun.* 141:1398-1403), neoglycoprotein, sphingolipids, breast cancer antigen such as EGFR (Epidermal growth factor receptor), HER2 antigen (p185$^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, *Science* 245: 301-304), differentiation antigen (Feizi, 1985, *Nature* 314: 53-57) such as I antigen found in fetal erythrocytes, primary endoderm I antigen found in adult erythrocytes, preimplantation embryos, I(Ma) found in gastric adenocarcinomas, M18, M39 found in breast epithelium, SSEA-1 found in myeloid cells, VEP8, VEP9, My1, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group Le$^a$) found in Adenocarcinoma, NS-10 found in adenocarcinomas, CO-43 (blood group Le$^b$), G49 found in EGF receptor of A431 cells, MH2 (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos. In one embodiment, the antigen is a T cell receptor derived peptide from a Cutaneous Tcell Lymphoma (see, Edelson, 1998, *The Cancer Journal* 4:62).

In some embodiments, a variant Fc region of the invention is introduced into an anti-fluoresceine monoclonal antibody, 4-4-20 (Kranz et al., 1982 *J. Biol. Chem.* 257(12): 6987-6995; which is incorporated herein by reference in its entirety). In other embodiments, a variant Fc region of the invention is introduced into a mouse-human chimeric anti-CD20 monoclonal antibody 2H7, which recognizes the CD20 cell surface phosphoprotein on B cells (Liu et al., 1987, *Journal of Immunology*, 139: 3521-6; which is incorporated herein by reference in its entirety). In yet other embodiments, a variant Fc region of the invention is introduced into a humanized anti-body (Ab4D5) against the human epidermal growth factor receptor 2 (p185 HER2) as described by Carter et al. (1992, *Proc. Natl. Acad. Sci. USA* 89: 4285-9; which is incorporated herein by reference in its entirety). In yet other embodiments, a variant Fc region of the invention is introduced into a humanized anti-TAG72 antibody (CC49) (Sha et al., 1994 *Cancer Biother.* 9(4): 341-9). In other embodiments, a variant Fc region of the invention is introduced into Rituxan which is used for treating lymphomas.

In another specific embodiment, the invention encompasses engineering an anti-FcγRIIB antibody including but not limited to any of the antibodies disclosed in U.S. Provisional Application No. 60/403,266 filed on Aug. 12, 2002; U.S. application Ser. No. 10/643,857 filed on Aug. 14, 2003; U.S. Provisional Application No. 60/562,804 filed on Apr. 16, 2004; U.S. Provisional Application No. 60/569,882 filed on May 10, 2004 and U.S. Provisional Application Nos. 60/582,044, 60/582,045, and 60/582,043 filed on Jun. 21, 2004, by modification (e.g., substitution, insertion, deletion) of at least one amino acid residue which modification increases the affinity of the Fc region for FcγRIIIA and/or FcγRIIA. Examples of anti-FcγRIIB antibodies that may be engineered in accordance with the methods of the invention are 2B6 monoclonal antibody having ATCC accession number PTA-4591 and 3H7 having ATCC accession number PTA-4592, 1D5 monoclonal antibody having ATCC accession number PTA-5958, 1F2 monoclonal antibody having ATCC accession number PTA-5959, 2D11 monoclonal antibody having ATCC accession number PTA-5960, 2E1 monoclonal antibody having ATCC accession number PTA-5961 and 2H9 monoclonal antibody having ATCC accession number PTA-5962 (all deposited at 10801 University Boulevard, Manassas, Va. 02209-2011), which are incorporated herein by reference. In another specific embodiment, modification of the anti-FcγRIIB antibody may also further decrease the affinity of the Fc region for FcγRIIB. In yet another specific embodiment, the engineered anti-FcγRIIB antibody may further have an enhanced effector function as determined by standard assays known in the art and disclosed and exemplified herein. In some embodiments, a variant Fc region of the invention is introduced into a therapeutic monoclonal antibody specific for a cancer antigen or cell surface receptor including but not limited to, Erbitux™ (also known as IMC-C225) (ImClone Systems Inc.), a chimerized monoclonal antibody against EGFR; HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); IMC-C225 which is a chimeric anti-EGFR IgG antibody (ImClone System); VITAXINT™ which is a humanized anti-αVβ3 integrin antibody (Applied Molecular Evolution/MedImmune); Campath 1H/LDP-03 which is a humanized anti CD52 IgG1 antibody (Leukosite); Smart M195™ which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10™ which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3™ is a humanized anti-ICAM3 antibody (ICOS Pharm); IDEC-114™ is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151™ is a primatized anti-CD4 antibody (IDEC); IDEC-152™ is a primatized anti-CD23 antibody (IDEC/Seikagaku); SMART anti-CD3™ is a humanized anti-CD3 IgG (Protein Design Lab); 5G1.1™ is a humanized anti-complement factor 5 (C5) antibody (Alexion Pharm); IDEC-151™ is a primatized anti-CD4 IgG1 antibody (IDEC Pharm/SmithKline Beecham); MDX-CD4™ is a human anti-CD4 IgG antibody (Medarex/Eisai/Genmab); CDP571™ is a humanized anti-TNF-α IgG4 antibody (Celltech); LDP-02™ is a humanized anti-α4β7 antibody (LeukoSite/Genentech); OrthoClone™ OKT4A™ is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33™ is a human anti-CD64 (FcγR) antibody (Medarex/Centeon); rhuMab-E25™ is a humanized anti-IgE IgG1 antibody (Genentech/Norvartis/Tanox Biosystems); IDEC-152™ is a primatized anti-CD23 antibody (IDEC Pharm); ABX-CBL™ is a murine anti CD-147 IgM antibody (Abgenix); BTI-322™ is a rat anti-CD2 IgG antibody (Medimmune/Bio Transplant); Orthoclone™/OKT3™ is a murine anti-CD3 IgG2a antibody (ortho Biotech); SIMULECT™ is a chimeric anti-CD25 IgG1 antibody (Novartis Pharm); LDP-01™ is a humanized anti-$β_2$-integrin IgG antibody (LeukoSite); Anti-LFA-1 is a murine anti CD18 F(ab')$_2$ (Pasteur-Merieux/Immunotech); CAT-152™ is a human anti-TGF-$β_2$ antibody (Cambridge Ab Tech); and Corsevin M™ is a chimeric anti-Factor VII antibody (Centocor).

The variant Fc regions of the invention, preferably in the context of an immunoglobulin, can be further characterized using one or more biochemical assays and/or one or more functional assays, preferably in a high throughput manner. In some alternate embodiments, the variant Fc regions of the inventions are not introduced into an immunoglobulin and are further characterized using one or more biochemical assays and/or one or more functional assays, preferably in a high throughput manner. The one or more biochemical assays can be any assay known in the art for identifying Fc-FcγR interactions, including, but not limited to, an ELISA assay, and surface plasmon resonance-based assay for determining the kinetic parameters of Fc-FcγR interaction, e.g., BIAcore assay. The one or more functional assays can be any assay known in the art for characterizing one or more FcγR mediated effector cell function as known to one skilled in the art or described herein. In specific embodiments, the immunoglobulins comprising the variant Fc regions are assayed in an ELISA assay for binding to one or more FcγRs, e.g., FcγRIIIA, FcγRIIA, FcγRIIA; followed by one or more ADCC assays. In some embodiments, the immunoglobulins comprising the variant Fc regions are assayed further using a surface plasmon resonance-based assay, e.g., BIAcore. Surface plasmon resonance-based assays are well known in the art, and are further discussed in Section 5.2.7, and exemplified herein in Example 6.8.

An exemplary high throughput assay for characterizing immunoglobulins comprising variant Fc regions may comprise: introducing a variant Fc region of the invention, e.g., by standard recombinant DNA technology methods, in a 4-4-20 antibody; characterizing the specific binding of the 4-4-20 antibody comprising the variant Fc region to an FcγR (e.g., FcγRIIIA, FcγRIIB) in an ELISA assay; characterizing the 4-4-20 antibody comprising the variant Fc region in an ADCC assay (using methods disclosed herein) wherein the target cells are opsonized with the 4-4-20 antibody comprising the variant Fc region; the variant Fc region may then be cloned into a second immunoglobulin, e.g., 4D5, 2H7, and that second immunoglobulin characterized in an ADCC assay, wherein the target cells are opsonized with the second antibody comprising the variant Fc region. The second antibody comprising the variant Fc region is then further analyzed using an ELISA-based assay to confirm the specific binding to an FcγR.

Preferably, a variant Fc region of the invention binds FcγRIIIA and/or FcγRIIA with a higher affinity than a wild type Fc region as determined in an ELISA assay. Most preferably, a variant Fc region of the invention binds FcγRIIIA and/or FcγRIIA with a higher affinity and binds FcγRIIB with a lower affinity than a wild type Fc region as determined in an ELISA assay. In some embodiments, the variant Fc region binds FcγRIIIA and/or FcγRIIA with at least 2-fold higher, at least 4-fold higher, more preferably at least 6-fold higher, most preferably at least 8 to 10-fold higher affinity than a wild type Fc region binds FcγRIIIA and/or FcγRIIA and binds FcγRIIB with at least 2-fold lower, at least 4-fold lower, more preferably at least 6-fold lower, most preferably at least 8 to 10-fold lower affinity than a wild type Fc region binds FcγRIIB as determined in an ELISA assay.

The immunoglobulin comprising the variant Fc regions may be analyzed at any point using a surface plasmon based resonance based assay, e.g., BIAcore, for defining the kinetic parameters of the Fc-FcγR interaction, using methods disclosed herein and known to those of skill in the art. Preferably, the Kd of a variant Fc region of the invention for binding to a monomeric FcγRIIIA and/or FcγRIIA as determined by BIAcore analysis is about 100 nM, preferably about 70 nM, most preferably about 40 nM.; and the Kd of the variant Fc region of the invention for binding a dimeric FcγRIIB is about 80 nM, about 100 nM, more preferably about 200 nM.

In most preferred embodiments, the immunoglobulin comprising the variant Fc regions is further characterized in an animal model for interaction with an FcγR. Preferred animal models for use in the methods of the invention are, for example, transgenic mice expressing human FcγRs, e.g., any mouse model described in U.S. Pat. No. 5,877,397, and U.S. Pat. No. 6,676,927 which are incorporated herein by reference in their entirety. Transgenic mice for use in the methods of the invention include, but are not limited to, nude knockout FcγRIIIA mice carrying human FcγRIIIA; nude knockout FcγRIIIA mice carrying human FcγRIIA; nude knockout FcγRIIIA mice carrying human FcγRIIB and human FcγRIIIA; nude knockout FcγRIIIA mice carrying human FcγRIIB and human FcγRIIA; nude knockout FcγRIIIA and FcγRIIA mice carrying human FcγRIIIA and FcγRIIA and nude knockout FcγRIIIA, FcγRIIA and FcγRIIB mice carrying human FcγRIIIA, FcγRIIA and FcγRIIB.

4.2.1 Design Strategies

The present invention encompasses engineering methods to generate Fc variants including but not limited to computational design strategies, library generation methods, and experimental production and screening methods. These strategies may be applied individually or in various combinations to engineer the Fc variants of the instant invention.

In most preferred embodiments, the engineering methods of the invention comprise methods in which amino acids at the interface between an Fc region and the Fc ligand are not modified. Fc ligands include but are not limited to FcγRs, C1q, FcRn, C3, mannose receptor, protein A, protein G, mannose receptor, and undiscovered molecules that bind Fc. Amino acids at the interface between an Fc region and an Fc ligand is defined as those amino acids that make a direct and/or indirect contact between the Fc region and the ligand, play a structural role in determining the conformation of the interface, or are within at least 3 angstroms, preferably at least 2 angstroms of each other as determined by structural analysis, such as x-ray crystallography and molecular modeling The amino acids at the interface between an Fc region and an Fc ligand include those amino acids that make a direct contact with an FcγR based on crystallographic and structural analysis of Fc-FcγR interactions such as those disclosed by Sondermann et al., (2000, Nature, 406: 267-273; which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that does not make a direct contact with an FcγR based on structural and crystallographic analysis, e.g., is not within the Fc-FcγR binding site.

Preferably, the engineering methods of the invention do not modify any of the amino acids as identified by Shields et al., which are located in the CH2 domain of an Fc region proximal to the hinge region, e.g., Leu234-Pro238; Ala327, Pro329, and affect binding of an Fc region to all human FcγRs.

In other embodiments, the invention encompasses Fc variants with altered FcγR affinities and/or altered effector functions, such that the Fc variant does not have an amino acid modification at a position at the interface between an Fc region and the Fc ligand. Preferably, such Fc variants in combination with one or more other amino acid modifications which are at the interface between an Fc region and the Fc ligand have a further impact on the particular altered property, e.g. altered FcγR affinity. Modifying amino acids at the interface between Fc and an Fc ligand may be done using methods known in the art, for example based on structural analysis of Fc-ligand complexes. For example but not by way of limitation by exploring energetically favorable substitutions at Fc positions that impact the binding interface, variants can be engineered that sample new interface conformations, some of which may improve binding to the Fc ligand, some of which may reduce Fc ligand binding, and some of which may have other favorable properties. Such new interface conformations could be the result of, for example, direct interaction with Fc ligand residues that form the interface, or indirect effects caused by the amino acid modifications such as perturbation of side chain or backbone conformations The invention encompasses engineering Fc variants comprising any of the amino acid modifications disclosed herein in combination with other modifications in which the conformation of the Fc carbohydrate at position 297 is altered. The invention encompasses conformational and compositional changes in the N297 carbohydrate that result in a desired property, for example increased or reduced affinity for an FcγR. Such modifications may further enhance the phenotype of the original amino acid modification of the Fc variants of the invention. Although not intending to be bound by a particular mechanism of actions such a strategy is supported by the observation that the carbohydrate structure and conformation dramatically affect Fc-FcγR and Fc/C1q binding (Umaha et al., 1999, Nat Biotechnol 17:176-180; Davies et al., 2001, Biotechnol Bioeng 74:288-294; Mimura et al., 2001, J Biol Chem 276:45539; Radaev et al., 2001, J Biol Chem 276:16478-16483; Shields et al. 2002, J Biol Chem 277:26733-26740; Shinkawa et al., 2003, J Biol Chem 278: 3466-3473).

Another design strategy for generating Fc variants in accordance with the invention is provided in which the Fc region is reengineered to eliminate the structural and functional dependence on glycosylation. This design strategy involves the optimization of Fc structure, stability, solubility, and/or Fc function (for example affinity of Fc for one or more Fc ligands) in the absence of the N297 carbohydrate. In one approach, positions that are exposed to solvent in the absence of glycosylation are engineered such that they are stable, structurally consistent with Fc structure, and have no tendency to aggregate. Approaches for optimizing aglycosylated Fc may involve but are not limited to designing amino acid modifications that enhance aglycoslated Fc stability and/or solubility by incorporating polar and/or charged residues that face inward towards the Cg2-Cg2 dimer axis, and by designing amino acid modifications that directly enhance the aglycosylated Fc-FcγR interface or the interface of aglycosylated Fc with some other Fc ligand.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Such modifications may be in the CH1, CH2, or CH3 domains or a combination thereof. Preferably the Fc variants of the invention enhance the property of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:49634969; Armour et al., 1999, Eur J Immunol 29:2613-2624; Idusogie et al, 2000, J Immunol 164:41784184; Reddy et al, 2000, Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. No. 5,624,821; U.S. Pat. No. 5,885,573; U.S. Pat. No. 6,194,551; PCT WO 00/42072; PCT WO 99/58572; each of which is incorporated herein by reference in its entirety.

4.2.2 FcγR-Fc Binding Assay

An FcγR-Fc binding assay was developed for determining the binding of the molecules of the invention comprising variant Fc regions to FcγR, which allowed detection and quantitation of the interaction, despite the inherently weak affinity of the receptor for its ligand, e.g., in the micromolar range for FcγRIIB and FcγRIIIA The method involves the formation of an FcγR complex that has an improved avidity for an Fc region, relative to an uncomplexed FcγR. According to the invention, the preferred molecular complex is a tetrameric immune complex, comprising: (a) the soluble region of FcγR (e.g., the soluble region of FcγRIIIA, FcγRIIA or FcγRIIB); (b) a biotinylated 15 amino acid AVITAG™ sequence (AVITAG™) operably linked to the C-terminus of the soluble region of FcγR (e.g., the soluble region of FcγRIIIA, FcγRIIA or FcγRIIB); and (c) streptavidin-phycoerythrin (SA-PE); in a molar ratio to form a tetrameric FcγR complex (preferably in a 5:1 molar ratio). According to a preferred embodiment of the invention, the fusion protein is biotinylated enzymatically, using for example, the E. coli Bir A enzyme, a biotin ligase which specifically biotinylates a lysine residue in the 15 amino acid AVITAG™ sequence. In a specific embodiment of the invention, 85% of the fusion protein is biotinylated, as determined by standard methods known to those skilled in the art, including but not limited to streptavidin shift assay. According to preferred embodiments of the invention, the biotinylated soluble FcγR proteins are mixed with SA-PE in a 1×SA-PE:5× biotinylated soluble FcγR molar ratio to form a tetrameric FcγR complex.

In a preferred embodiment of the invention, polypeptides comprising Fc regions bind the tetrameric FcγR complexes, formed according to the methods of the invention, with at least an 8-fold higher affinity than the monomeric uncomplexed FcγR. The binding of polypeptides comprising Fc regions to the tetrameric FcγR complexes may be determined using standard techniques known to those skilled in the art, such as for example, fluorescence activated cell sorting (FACS), radioimmunoassays, ELISA assays, etc.

The invention encompasses the use of the immune complexes formed according to the methods described above, for determining the functionality of molecules comprising an Fc region in cell-based or cell-free assays.

As a matter of convenience, the reagents may be provided in an assay kit, i.e., a packaged combination of reagents for assaying the ability of molecules comprising variant Fc regions to bind FcγR tetrameric complexes. Other forms of molecular complexes for use in determining Fc-FcγR interactions are also contemplated for use in the methods of the invention, e.g., fusion proteins formed as described in U.S. Provisional Application 60/439,709, filed on Jan. 13, 2003; which is incorporated herein by reference in its entirety.

4.2.3 Mutagenesis and Construction of Yeast Display Libraries

Molecular interactions between the IgG Fc and Fc receptors have been previously studied by both structural and genetic techniques. These studies identified amino acid residues that are critical for functional binding of Fc to different FcγR. None of these changes have been shown to improve human FcγR mediated efficacy of therapeutic antibodies in animal models. A complete analysis of all potential amino acid changes at these residues or other potentially important residues has not been reported. The platform described herein has the ability to construct mutant libraries with all possible amino acid changes, screen libraries using multiple functional assays, and finally analyze libraries in relevant humanized animal models.

The instant invention encompasses construction of multiple libraries based on both genetic and structural data known in the art or being developed. The method described and exemplified herein incorporates building individual libraries that contain mutants testing all 20 amino acid changes at between 3-6 residues in the Fc region. The complete set of mutations will be assembled in all possible combinations of mutations. The number of independent mutations generated is based on the number of sites being saturated during library assembly (Table 9 below). Library size will determine the choice of primary screen and therefore the choice of vector for initial cloning steps.

TABLE 9

Number of Independent mutants based on number of targeted sites.

| Library | # of residues | # independent mutants | Primary screen |
|---|---|---|---|
| Small | 3 or less | 8000 max. | ELISA |
| Large | 4-6 | $1.6 \times 10^5$-$6.4 \times 10^7$ | Surface display |

The instant invention encompasses construction of combinatorial libraries, focusing on a limited number of critical residues (e.g., 3-6). Using a library of randomly mutagenized IgG1 Fc and the screening assays described and exemplified herein Fc variants will be identified. In the initial rounds, the best 5 mutations, based on both FcR binding profile and functional activity will be selected. It will take $20^5$ individual mutants to cover all possible amino acid changes and their combinations at five locations. A library with at least 10-fold coverage for each mutant will be generated. In addition regions will be chosen based on available information, e.g., crystal structure data, Mouse/Human isotype FcγR binding differences, genetic data, and additional sites identified by mutagenesis.

The biggest disadvantage of current site directed mutagenic protocols is production of bias populations, overrepresenting variations in some regions and under-representing or completely lacking mutations in others. The present invention overcomes this problem by generating unbiased arrays of desirable Fc mutants using a well-developed gene building technology to eliminate the bias introduced in library construction by PCR based approaches such as overlapping PCR and inverted PCR. The key distinctions of the approach of the present invention are: 1) Employment of equimolar mix of 20 individual oligos for every targeted codon instead of degenerated primers. This way each amino acid is represented by a single, most used codon, whereas degenerated primers over represent those amino acids encoded by more codons over those encoded by fewer codons. 2) Building mutants by a chain replacement approach. This insures unbiased introduction of all desirable changes into the final product.

Figure 25:
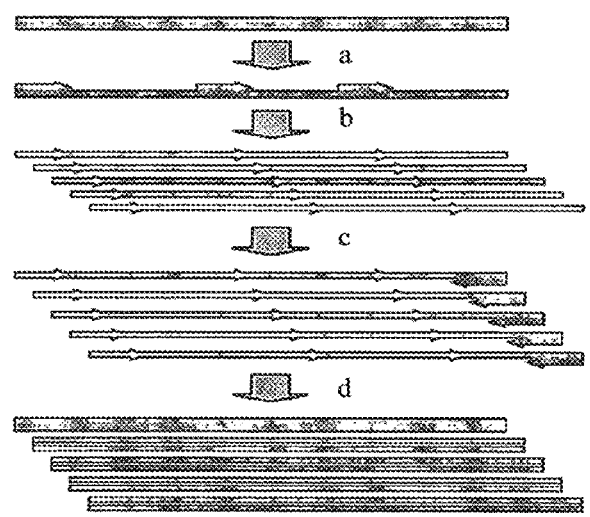

An exemplary protocol comprises of the following steps: 1) phosphorylated oligos, representing desirable changes at one or several locations, all complementary to the same strand, added to the template along with a thermostable, 5'>3' exonuclease deficient, DNA polymerase and ligase (FIG. 25, step a). 2) assembled mix undergoes a number of polymerization/ligation cycles, sufficient to generate desirable amount of product. Use of a 5'>3' exonuclease deficient DNA polymerase insures integrity of the primer sequence and its phosphate residue, when a thermostable ligase assembles individual primer-extended fragments into a contiguous single-stranded chain. Reaction cycles can continue until complete exhaustion of the oligos pool without introducing bias into the final product (FIG. 25, step b). 3) generated pool of single-stranded mutants is converted into double-stranded DNA by adding a reverse gene-specific primer to the reaction (FIG. 25, step c). 4) double-stranded product gets digested at the end-designed restriction sites and cloned into an appropriate expression vector (FIG. 25, step d).

To insure quality of the library, PCR amplified fragments will be analyzed by electrophoresis to determine the length of the final PCR products. The reaction will be characterized as successful if >99% of the PCR products are of the expected length. The final library will be cloned into an expression vector. A fraction of the mutant library will be sequenced to determine the rate of mutant codon incorporation. The number of fragments sequenced will be based on the number of target sites mutated and library validation will be determined by the observed rate of mutation at targeted sites (Table 10). The rate of vector without inserts should be less than 2%. The rate of mutation at non-targeted sites should be less than 8%. Libraries containing clones with >90% correct inserts will allow us to maintain screening timelines.

TABLE 10

Expected rates of Mutation for Libraries

| Targeted Residues | # of seq. reactions | Approx. rates of mutation for library validation |||||| 
|---|---|---|---|---|---|---|---|
| | | Single | Double | Triple | Quad. | Pent. | Hex. |
| 3 | 20 | 42% | 43% | 15% | NA | NA | NA |
| 4 | 50 | 29% | 43% | 21% | 7% | NA | NA |
| 5 | 75 | 18% | 35% | 32% | 11% | 4% | NA |
| 6 | 100 | 12% | 20% | 40% | 20% | 6% | 2% |

In other embodiments, the invention the invention encompasses overlapping or inverted PCR for construction of libraries. In order to remain unbiased, individual primers for each codon will be used rather than degenerative primers. A similar validation scheme as disclosed supra will be employed.

Figure 26:
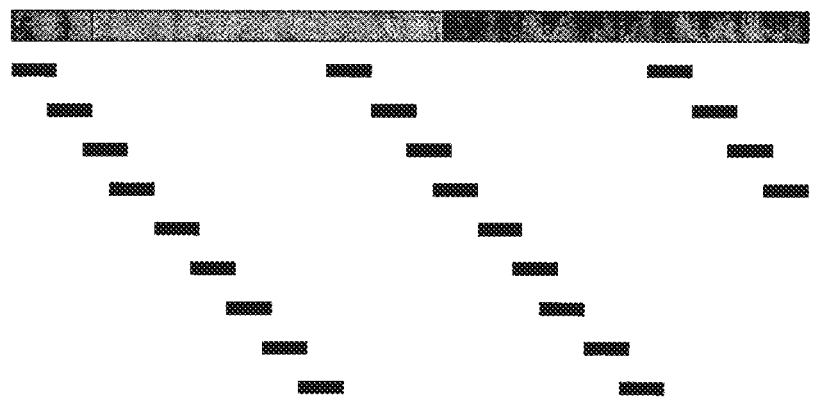

Most preferably automated protocols will be employed for high throughput library production. Automation allows for improved throughput, walk away operation, and an overall reduction in experimental error for tasks requiring tedious repetitive operations. Oligo synthesis capabilities is based on 2 Mermade DNA synthesizers (Bioautomation, Inc.) with a total output capability of 575 60 mer Oligos/12 hrs. Proprietary software handles all aspects of design, synthesis, and storage of the final oligonucleotides. Robotic liquid handlers will be employed to set up oligos for synthesis of full length Fc mutants and ligation reactions for incorporating the Fc mutants into antibody heavy chain expression vectors will be set up. After ligation it is estimated that it would take 1 FTE ~10 days to array the library clones and generate ~8000 minipreps, equivalent to a combinatorial library saturated at 3 sites. Subsequent to bacterial transformation a Qpix-2 clone picker robot will be used for picking colonies into 96 deep well plates. Culture growth will be done using a magnetic levitation stirrer, capable of incubating 12 plates and resulting in dense growth in 12-16 hr at 37° C. A Qiagen miniprep robot will be used to perform DNA preps at the rate of 4 96 well plates in 2.5 hrs. By overlapping tasks 5 such libraries could be constructed in 9 months with 1 FTE Affinity maturation requires the assembly of a new set of combinations of mutations, from a preselected mutant pool or members of a gene family, which can be enriched by a selection protocol. The process is repeated several times until the isolation of a mutant with the desired phenotype is achieved. The disadvantage of the current enzymatic approach, DNA shuffling, to accomplish this process is bias which can be introduced due to specific sites within gene that are hot spots for nucleases, dominance of specific mutants in the final reassembled pool and loss of some of the original mutants in the final pool. In order to overcome this shortcoming a build-a-gene (BAG) technology will be used to generate a highly complex library of Fc mutants containing random amino acid changes at all potential locations that may be important for receptor(s) binding. Sets of degenerated oligos covering specific regions of the IgG Fc will be used (See FIG. 26).

Oligos will be ~30 nt and degenerate oligos synthesized to change one (4 oligos) or two AAs (8 oligos) will be constructed. The oligos are designed to be overlapping with no gaps. It will take ~200 oligos to accommodate all single AA changes and ~2000 to change two AAs per oligonucleotide. All 2000+ oligos will be used individually and in combinations to generate arrays of Fc mutants using the protocol outlined above (A.20). We will use a home-written randomizer program and a robotic liquid handler for pooling selected combinations of mutant and wild type oligos. Large libraries will be cloned into vectors that will allow for screening using yeast surface display. This approach utilizes a magnetic bead selection followed by flow cytometry and has been successfully applied to libraries with a complexity>$10^9$ (Feldhaus et al., 2003, Nat. Biotech. 21(2): 163-170; which is incorporated herein by reference in its entirety). This limits the number of sites to test at any one pool to 7, resulting in ~$1.3 \times 10^9$ possible mutations/pool.

To insure quality of the library PCR amplified fragments will be analyzed by electrophoresis to determine the length of the final PCR products. The reaction will be characterized as successful if >99% of the PCR products are of the expected length. A fraction of the mutant library will be sequenced to determine the rate of mutant codon incorporation. The number of fragments sequenced will be based on the number of target sites mutated and library validation will be determined by the observed rate of mutation at targeted sites (Table 10). The rate of vectors without inserts should be less than 2%. The rate of mutation at non-targeted sites should be less than 8%.

The ability to generate the desired level of efficiency of mutagenesis by this approach will be determined by sequencing of a subset of clones. The alternative to BAG will be using a "DNA shuffle" protocol. This requires pooling all of the mutants, single, double, triple, etc. Following DNA preparation, Fc regions will be amplified by PCR using flanking primers that selectively amplify the mutated region of the Fc, ~700 bp. Novel mutants are constructed by reshuffling of mutations in the Fc via DNAseI treatment of the amplified DNA and isolation of 150-200 bp fragments (see, e.g., Stemmer et al., 1994, Proc. Natl. Acad. Sci. U.S.A. 91: 10747-51). Fragments will be religated, PCR amplified with nested primers and cloned into the yeast surface display vector, pYD1. The recombined library will be reselected in the yeast Fc display screen as described and exemplified herein.

BAG libraries will utilize most of the same equipment as the combinatorial library. However cloning will be in a vector suitable for yeast surface display and will not require arraying of individual clones as the yeast surface display will initially be employed for enrichment of large libraries. Subsequent to the appropriate level of enrichment individual clones will be arrayed.

An initial library of molecules comprising variant Fc regions is produced using any random based mutagenesis techniques known in the art. It will be appreciated by one of skill in the art that amino acid sequence variants of Fc regions may be obtained by any mutagenesis technique known to those skilled in the art. Some of these techniques are briefly described herein, however, it will be recognized that alternative procedures may produce an equivalent result. In a preferred embodiment, molecules of the invention comprising variant Fc regions are prepared by error-prone PCR as exemplified in Example 6, infra (See Leung et al., 1989, *Technique*, 1:11). It is especially preferred to have error rates of 2-3 bp/Kb for use in the methods of the invention. In one embodiment, using error prone PCR a mutation frequency of 2-3 mutations/kb is obtained.

Mutagenesis may be performed in accordance with any of the techniques known in the art including, but not limited to, synthesizing an oligonucleotide having one or more modifications within the sequence of the Fc region of an antibody or a polypeptide comprising an Fc region (e.g., the CH2 or CH3 domain) to be modified. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 30 to about 45 nucleotides or more in length is preferred, with about 10 to about 25 or more residues on both sides of the junction of the sequence being altered. A number of such primers introducing a variety of different mutations at one or more positions may be used to generate a library of mutants.

The technique of site-specific mutagenesis is well known in the art, as exemplified by various publications (see, e.g., Kunkel et al., *Methods Enzymol.*, 154:367-82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR™ with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.*, 18(6):1656, 1987, and Upender et al., *Biotechniques*, 18(1):29-30, 32, 1995, for PCR™-mediated mutagenesis procedures, which are hereby incorporated in their entireties. PCR™ employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques*, 16(3):410-2, 1994, which is hereby incorporated by reference in its entirety)

Another method for preparing variants for use in the invention, is cassette mutagenesis based on the technique described by Wells et al. (1985, *Gene*, 34: 315). The starting material is the plasmid comprising the desired DNA encoding the protein to be mutated (e.g., the DNA encoding a polypeptide comprising an Fc region). The codon(s) in the DNA sequence to be mutated are identified; there must be a unique restriction endonuclease site on each side of the identified mutations site(s). If no such restriction site exits, it may be generated by oligonucleotide directed mutagenesis. After the restriction sites have been introduced into the plasmid, the plasmid is cut at these sites and linearized. A double-stranded oligonucleotide encoding the sequence of the DNA between the restriction sites but containing the mutation is synthesized using standard procedures known to those skilled in the art. The double stranded oligonucleotide is referred to as the cassette. This cassette is designed to have 3' and 5' ends that are compatible with the ends of the linearized plasmid, such that it can be directly ligated to the plasmid.

Other methods known to those of skill in the art for producing sequence variants of the Fc region of an antibody or polypeptides comprising an Fc region can be used. For example, recombinant vectors encoding the amino acid sequence of the constant domain of an antibody or a fragment thereof may be treated with mutagenic agents, such as hydroxylamine, to obtain sequence variants.

Once a mutant library is produced according to the methods described, the mutagenized library is transformed into a yeast strain, preferably EBY100 (Invitrogen), MATa ura3-52 trpl leu2Δl his3Δ200 pep4::HIS3 prb1Δ1.6R can1 GAL:: GAL-AGA1 using a standard lithium acetate transformation protocol known to those skilled in the art (ref).

It will be appreciated by one of skill in the art, that once molecules of the invention with desired binding properties (e.g., molecules with variant Fc regions with at least one amino acid modification, which modification enhances the affinity of the variant Fc region for FcγRIIIA relative to a comparable molecule, comprising a wild-type Fc region) have been identified (See Section 5.1 and Table 2) according to the methods of the invention, other molecules (i.e. therapeutic antibodies) may be engineered using standard recombinant DNA techniques and any known mutagenesis techniques, as described in this section to produce engineered molecules carrying the identified mutation sites.

4.2.4 Yeast Surface Display

The preferred method for screening and identifying molecules comprising variant Fc regions with altered FcγR affinities (i.e., enhanced FcγRIIIA affinity and/or FcγRIIA) is yeast surface display technology (for review see Boder and Wittrup, 2000, *Methods in Enzymology*, 328: 430-444, which is incorporated herein by reference in its entirety) which addresses the deficiency in the prior art for screening binding interactions of extracellular post-translationally modified proteins. Specifically, the yeast surface display is a genetic method whereby polypeptides comprising Fc mutants are expressed on the yeast cell wall in a form accessible for interacting with FcγR. Yeast surface display of the mutant Fc containing polypeptides of the invention may be performed in accordance with any of the techniques known to those skilled in the art. See U.S. Pat. Nos. 6,423,538; 6,114,147; and 6,300, 065, all of which are incorporated herein by reference in their entirety. See Boder et al., 1997 *Nat. Biotechnol.*, 15:553-7; Boder et al., 1998 *Biotechnol. Prog.*, 14:55-62; Boder et al., 2000 *Methods Enzymol.*, 328:430-44; Boder et al., 2000 *Proc. Natl. Acad. Sci. U.S.A.*, 2000, 97:10701-5; Shusta et al., 1998 *Nat. Biotechnol.*, 1998, 16:773-7; Shusta et al., 1999 *J. Mol. Biol.*, 292:949-56; Shusta et al., 1999 *Curr. Opin. Biotechnol.*, 10:117-22; Shusta et al., 2000 *Nat. Biotechnol.*, 18:754-9; Wittrup et al., 1994 *Ann. N.Y. Acad. Sci.*, 745:321-30; Wittrup et al., 1994 *Cytometry*, 16:206-13; Wittrup, 1995 *Curr. Opin. Biotechnol.*, 6:203-8; Wittrup, 1999 *Trends Biotechnol.*, 17:423-4; Wittrup, 2000 *Nat. Biotechnol.*, 18:1039-40; Wittrup, 2001 *Curr. Opin. Biotechnol.*, 12:395-9.

Yeast Surface Display will be used to enrich libraries containing >$10^7$ independent clones. This approach will provide the ability to enrich large libraries >20-fold in single sort. Fc mutant libraries with >10,000 independent mutants (4 or more sites) will be cloned into the appropriate vectors for yeast surface display and enriched by FACS sorting until <8000 mutants are able to be tested by other biochemical and functional assays as described below.

The invention provides methods for constructing an Fc mutant library in yeast for displaying molecules comprising Fc regions, which have been mutated as described in Section 5.2.2. Preferably, the Fc mutant libraries for use in the methods of the invention contain at least $10^7$ cells, up to $10^9$ cells. One exemplary method for constructing a Fc library for use in the methods of the invention comprises the following: nucleic acids encoding molecules comprising Fc regions are cloned into the multiple cloning site of a vector derived from a yeast replicating vector, e.g., pCT302; such that the Fc encoding nucleic acids are expressed under the control of the GAL1 galactose-inducible promoter and in-frame with a nucleotide sequence encoding Aga2p, the mating agglutinin cell wall protein. In a preferred embodiment, nucleic acids encoding molecules comprising Fc regions are cloned C-terminal to the Aga2p coding region, such that a Fc-region Aga2p fusion protein is encoded. A fusion protein comprising the Aga2p protein and polypeptides comprising Fc regions will be secreted extracellularly and displayed on the cell wall via disulfide linkage to the Aga1p protein, an integral cell wall protein, using the preferred construct of the invention. In an alternative embodiment, the constructs may further comprise nucleotide sequences encoding epitope tags. Any epitope tag nucleotide coding sequence known to those skilled in the art can be used in accordance with the invention, including, but not limited to nucleotide sequences encoding hemagglutinin (HA), c-myc Xpress TAG, His-TAG, or VSTAG. The presence of the fusion protein on the yeast cell surface may be detected using FACS analysis, confocal fluorescence microscopy or standard immunostaining methods, all of which are known to those skilled in the art. In one embodiment, the presence of the Fc fusion proteins of the invention on the yeast cell surface are detected using Fc-specific monoclonal antibodies (CH3 specific), including but not limited to IgG1 Fc-specific monoclonal antibody, HP6017 (Sigma), JL512 (Immunotech), and any antibody disclosed in Partridge et al., 1986, *Molecular Immunology*, 23 (12): 1365-72, which is incorporated herein by reference in its entirety. In another embodiment, the presence of the Fc fusion proteins of the invention are detected by immunofluorescent labeling of epitope tags using techniques known to those skilled in the art. It is particularly useful in the methods of the invention, to use nucleotide sequences encoding epitope tags to flank the nucleic acids encoding the Fc fusion proteins, as an internal control, to detect if the fusion proteins are displayed on the cell wall in a partially proteolyzed form.

4.2.5 Screening of Yeast Display Libraries

The invention encompasses screening the yeast display libraries using immunological based assays including but not limited to cell based assays, solution based assays, and solid phase based assays.

In some embodiments, the invention encompasses identification of Fc mutants with altered FcγR affinities using affinity maturation methods which are known to those skilled in the art and encompassed herein. Briefly, affinity maturation creates novel alleles by randomly recombining individual mutations present in a mutant library, see, e.g., Hawkins et al., 1992, *J. Mol. Biol.* 226: 889-896; Stemmer et al., 1994 *Nature*, 370: 389-91; both of which are incorporated herein by reference in their entireties. It has been used successfully to increase the affinity of antibodies, T cell receptors and other proteins. The invention encompasses using mutations that show increased FcγR binding as a baseline to construct new mutant libraries with enhanced phenotypes. Using the methods of the invention, a population of IgG1 Fc mutants enriched by yeast surface display for increased binding to an FcγR, e.g., FcγRIIIA, may be selected. Following DNA preparation, Fc regions can be amplified by PCR using flanking primers that selectively amplify the mutated region of the Fc, which is about ~700 bp using methods known to one skilled in the art and exemplified or disclosed herein. Novel mutants can thus be constructed by reshuffling of mutations in the Fc region for example via DNAseI treatment of the amplified DNA and isolation of fragments using methods such as those disclosed by Stemmer et al., 1994 *Proc. Natl. Acad. Sci. USA* 91: 10747-51, which is incorporated herein by reference in its entirety. Fragments can then be religated, PCR amplified with nested primers and cloned into the yeast display vector, e.g., pYD1 using methods known to one skilled in the art. The recombined library can then be reselected in the yeast Fc display screen. As the $K_D$ decreases, below 10 nM, conditions can be established to allow for further increases in affinity based on the reduction of the off rate of the FcγRIIIA ligand from the Fc receptor using methods known in the art such as those disclosed in Boder et al., 1998, *Biotechnol. Prog.* 14: 55-62, which is incorporated herein by reference in its entirety. The invention encompasses a kinetic screen of the yeast library. A kinetic screen may be established by labeling of the Fc displaying cells to saturation with a labeled ligand, e.g., a fluorescent ligand followed by incubation with an excess of non-labeled ligand for a predetermined period. After termination of the reaction by the addition of excess buffer (e.g., 1×PBS, 0.5 mg/ml BSA) cells will be analyzed by FACS and sort gates set for selection. After each round of enrichment individual mutants can be tested for fold increases in affinity and sequenced for diversity. The in vitro recombination process can be repeated. In some embodiments, the in vitro is repeated at least 3 times.

Selection of the Fc variants of the invention may be done using any FcγR including but not limited to polymorphic variants of FcγR. In some embodiments, selection of the Fc variants is done using a polymorphic variant of FcγRIIIA which contains a phenylalanine at position 158. In other embodiments, selection of the Fc variants is done using a polymorphic variant of FcγRIIIA which contains a valine at position 158. FcγRIIIA 158V displays a higher affinity for IgG1 than 158F and an increased ADCC activity (see, e.g., Koene et al., 1997, *Blood*, 90:1109-14; Wu et al., 1997, *J. Clin. Invest.* 100: 1059-70, both of which are incorporated herein by reference in their entireties); this residue in fact directly interacts with the lower hinge region of IgG1 as recently shown by IgG1-FcγRIIIA co-crystallization studies, see, e.g., Sonderman et al., 2000, *Nature*, 100: 1059-70, which is incorporated herein by reference in its entirety. Studies have shown that in some cases therapeutic antibodies have improved efficacy in FcγRIIIA-158V homozygous patients. For example, humanized anti-CD20 monoclonal antibody Rituximab was therapeutically more effective in FcγRIIIA158V homozygous patients compared to FcγRIIIA 158F homozygous patients (See, e.g., Cartron et al., 2002 *Blood*, 99(3): 754-8). Although not intending to be bound by a particular mechanism of action, selection of Fc variants of the invention with FcγRIIIA 158F allotype may provide for variants that once engineered into therapeutic antibodies will be clinically more efficacious for FcγRIIIA 158F homozygous patients.

The invention encompasses screening yeast libraries based on FcγRIIB depletion and FcγRIIIA selection so that Fc mutants are selected that not only have an enhanced affinity for FcγRIIIA but also have a reduced affinity for FcγRIIB. Yeast libraries may be enriched for clones that have a reduced affinity for FcγRIIB by sequential depletion methods, for example, by incubating the yeast library with magnetic beads coated with FcγRIIB. FcγRIIB depletion is preferably carried out sequentially so that the library is enriched in clones that have a reduced affinity for FcγRIIB. In some embodiments, the FcγRIIB depletion step results in a population of cells so that only 30%, preferably only 10%, more preferably only 5%, most preferably less than 1% bind FcγRIIB. In some embodiments, FcγRIIB depletion is carried out in at least 3 cycles, at least 4 cycles, at least 6 cycles. The FcγRIIB depletion step is preferably combined with an FcγRIIIA selection step, for example using FACS sorting so that Fc variants with an enhanced affinity for FcγRIIIA are selected.

4.2.5.1 FACS Assays; Solid Phased Assays and Immunological Based Assays

The invention encompasses characterization of the mutant Fc fusion proteins that are displayed on the yeast surface cell wall, according to the methods described in Section 5.2.3. One aspect of the invention provides a method for selecting mutant Fc fusion proteins with a desirable binding property, specifically, the ability of the mutant Fc fusion protein to bind FcγRIIIA and/or FcγRIIA with a greater affinity than a comparable polypeptide comprising a wild-type Fc region binds FcγRIIIA and/or FcγRIIA. In another embodiment, the invention provides a method for selecting mutant Fc fusion proteins with a desirable binding property, specifically, the ability of the mutant Fc fusion protein to bind FcγRIIIA and/or FcγRIIA with a greater affinity than a comparable polypeptide comprising a wild-type Fc region binds FcγRIIIA and/or FcγRIIA, and further the ability of the mutant Fc fusion protein to bind FcγRIIB with a lower affinity than a comparable polypeptide comprising a wild-type Fc region binds FcγRIIB. It will be appreciated by one skilled in the art, that the methods of the invention can be used for identifying and screening any mutations in the Fc regions of molecules, with any desired binding characteristic.

Yeast cells displaying the mutant Fc fusion proteins can be screened and characterized by any biochemical or immunological based assays known to those skilled in the art for assessing binding interactions.

Preferably, fluorescence activated cell sorting (FACS), using any of the techniques known to those skilled in the art, is used for screening the mutant Fc fusion proteins displayed on the yeast cell surface for binding FcγRIIIA, preferably the FcγRIIIA tetrameric complex, or optionally FcγRIIB. Flow sorters are capable of rapidly examining a large number of individual cells that contain library inserts (e.g., 10-100 million cells per hour) (Shapiro et al., *Practical Flow Cytometry*, 1995). Additionally, specific parameters used for optimization including, but not limited to, ligand concentration (i.e., FcγRIIIA tetrameric complex), kinetic competition time, or FACS stringency may be varied in order to select for the cells which display Fc fusion proteins with specific binding properties, e.g., higher affinity for FcγRIIIA compared to a comparable polypeptide comprising a wild-type Fc region. Flow cytometers for sorting and examining biological cells are well known in the art. Known flow cytometers are described, for example, in U.S. Pat. Nos. 4,347,935; 5,464,581; 5,483,469; 5,602,039; 5,643,796; and 6,211,477; the entire contents of which are incorporated by reference herein. Other known flow cytometers are the FACS Vantage™ system manufactured by Becton Dickinson and Company, and the COPAS™ system manufactured by Union Biometrica.

According to a preferred embodiment of the invention, yeast cells are analyzed by fluorescence activated cell sorting (FACS). In most preferred embodiments, the FACS analysis of the yeast cells is done in an iterative manner, at least twice, at least three times, or at least 5 times. Between each round of selection cells are regrown and induced so the Fc regions are displayed on the maximum number of yeast cell surfaces. Although not intending to be bound by a particular mode of action, this iterative process helps enrich the population of the cells with a particular phenotype, e.g., high binding to FcγRIIIA.

In preferred embodiments, screening for Fc variants of the invention comprises a selection process that has multiple rounds of screening, e.g., at least two rounds of screening. In one embodiment, screening for Fc variants that have an enhanced affinity for FcγRIIIA may comprise the following steps: in the first round of screening, a library of yeast cells, e.g., a naïve library of $10^7$ cells is enriched by FACS, preferably in an iterative manner, using for example labeled tetrameric FcγRIIIA to select for Fc variants that have an enhanced affinity for FcγRIIIA; the variant Fc region that is selected with the desired phenotype, e.g., enhanced binding to FcγRIIIA, is then introduced into an antibody, e.g., a 4-4-20 antibody, and the engineered antibody is assayed using a secondary screen, e.g., ELISA for binding to an FcγR. In the second round of screening, a single mutation library may be generated based on the first screen so that the Fc region harbors the variant displaying the enhanced affinity for FcγRIIIA; and enriched by FACS using for example labeled monomeric FcγRIIIA in both the presence and absence of unlabeled receptor; and the variant Fc region is then introduced into an antibody, e.g., a 4-4-20 antibody, and the engineered antibody is assayed using a secondary screen, e.g., ELISA for binding to an FcγR. In some embodiments, the secondary screen may further comprise characterizing the antibodies comprising Fc variants in an ADCC or BIAcore based assay using methods disclosed herein The invention encompasses FACS screening of the mutant yeast library under equilibrium or kinetic conditions. When the screening is performed under equilibrium conditions, an excess of the yeast library carrying Fc mutants is incubated with FcγRIIIA, preferably labeled FcγRIIIA at a concentration 5-10 fold below the Kd, for at least one hour to allow binding of Fc mutants to FcγRIIIA under equilibrium conditions. When the screening is performed under kinetic conditions, the mutant yeast library is incubated with labeled FcγRIIIA; the cells are then incubated with equimolar unlabeled FcγRIIIA for a pre-selected time, bound FcγRIIIA is then monitored.

One exemplary method of analyzing the yeast cells expressing mutant Fc fusion proteins with FACS is costaining the cells with FcγRIIIA-tetrameric complex which has been labeled with a fluorescent label such as, PE and an anti-Fc antibody, such as F(ab)$_2$ anti-Fc which has been fluorescently labeled. Fluorescence measurements of a yeast library produced according to the methods of the invention preferably involves comparisons with controls; for example, yeast cells that lack the insert encoding molecules comprising an Fc region (negative control). The flow sorter has the ability not only to measure fluorescence signals in cells at a rapid rate, but also to collect cells that have specified fluorescent properties. This feature may be employed in a preferred embodiment of the invention to enrich the initial library population for cells expressing Fc fusion proteins with specific binding characteristics, e.g., higher affinity for FcγRIIIA compared to a comparable polypeptide comprising a wild-type Fc region. In a preferred embodiment of the invention, yeast cells are analyzed by FACS and sort gates established to select for cells that show the highest affinity for FcγRIIIA relative to the amount of Fc expression on the yeast cell surface. According to a preferred embodiment, four consecutive sorts are established, wherein the gates for each successive sort is 5.5%, 1%, 0.2%, and 0.1%. It is preferred that the yeast display library formed according to the methods of the invention be oversampled by at least 10-fold to improve the probability of isolating rare clones (e.g., analyze ~$10^8$ cells from a library of $10^7$ clones). Alternatively, 2-5 sorts are established to select for cells of the desired phenotype. Sort gates can be established empirically by one skilled in the art.

In other preferred embodiments, mutant Fc fusion proteins displayed on the yeast cell surface are screened using solid phase based assays, for example assays using magnetic beads, e.g., supplied by Dynal, preferably in a high through put manner for binding to an FcγR, e.g., FcγRIIIA In one embodiment, magnetic bead assays may be used to identify mutants with enhanced affinity for FcγRIIIA and/or reduced affinity for FcγRIIB. An exemplary assay to identify mutants with enhanced affinity for FcγRIIIA and reduced affinity for FcγRIIB may comprise selecting mutants by a sequential solid phase depletion using magnetic beads coated with FcγRIIB followed by selection with magnetic beads coated with FcγRIIIA For example one assay may comprise the following steps: incubating the library of yeast cells generated in accordance with the methods of the invention with magnetic beads coated with FcγRIIB; separating yeast cells bound to beads from the non bound fraction by placing the mixture in a magnetic field, removing the non-bound yeast cells and placing them in a fresh media; binding the yeast cells to beads coated with FcγRIIIA, separating yeast cells bound to beads from the non bound fraction by placing the mixture in a magnetic field, removing the non-bound yeast cells; removing the bound cells by rigorous vortexing; growing the recovered cells in glucose containing media; re-inducing in selective media containing galactose. The selection process is repeated at least once. Inserts containing the Fc domain are then amplified using common methodologies known in the art, e.g., PCR, and introduced into an antibody by methods already described for further characterization.

In an alternative embodiment, a non-yeast based system is used to characterize the binding properties of the molecules of the invention. One exemplary system for characterizing the molecules of the invention comprises a mammalian expression vector containing the heavy chain of the anti-fluorescein monoclonal antibody 4-4-20, into which the nucleic acids encoding the molecules of the invention with variant Fc regions are cloned. The resulting recombinant clone is expressed in a mammalian host cell line (i.e., human kidney cell line 293H), and the resulting recombinant immunoglobulin is analyzed for binding to FcγR using any standard assay known to those in the art, including but not limited to ELISA and FACS.

Molecules of the present invention (e.g., antibodies, fusion proteins, conjugated molecules) may be characterized in a variety of ways. In particular, molecules of the invention comprising modified Fc regions may be assayed for the ability to immunospecifically bind to a ligand, e.g., FcγRIIIA tetrameric complex. Such an assay may be performed in solution (e.g., Houghten, Bio/Techniques, 13:412-421, 1992), on beads (Lam, Nature, 354:82-84, 1991, on chips (Fodor, Nature, 364:555-556, 1993), on bacteria (U.S. Pat. No. 5,223, 409), on spores (U.S. Pat. Nos. 5,571,698; 5,403,484; and 5,223,409), on plasmids (Cull et al., Proc. Natl. Acad. Sci. USA, 89:1865-1869, 1992) or on phage (Scott and Smith, Science, 249:386-390, 1990; Devlin, Science, 249:404-406, 1990; Cwirla et al., Proc. Natl. Acad. Sci. USA, 87:6378-6382, 1990; and Felici, J. Mol. Biol., 222:301-310, 1991) (each of these references is incorporated by reference herein in its entirety). Molecules that have been identified to immunospecifically bind to an ligand, e.g., FcγRIIIA can then be assayed for their specificity and affinity for the ligand.

Molecules of the invention that have been engineered to comprise modified Fc regions (e.g., therapeutic antibodies) or have been identified in the yeast display system to have the desired phenotype (see Section 5.1) may be assayed for immunospecific binding to an antigen (e.g., cancer antigen and cross-reactivity with other antigens (e.g., FcγR) by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

The binding affinity of the molecules of the present invention comprising modified Fc regions to a ligand, e.g., FcγR tetrameric complex and the off-rate of the interaction can be determined by competitive binding assays. One example of a competitive binding assay is a radioimmunoassay comprising the incubation of labeled ligand, such as tetrameric FcγR (e.g., $^3$H or $^{125}$I) with a molecule of interest (e.g., molecules of the present invention comprising modified Fc regions) in the presence of increasing amounts of unlabeled ligand, such as tetrameric FcγR, and the detection of the molecule bound to the labeled ligand. The affinity of the molecule of the present invention for the ligand and the binding off-rates can be determined from the saturation data by scatchard analysis.

In a preferred embodiment, BIAcore kinetic analysis is used to determine the binding on and off rates of molecules of the present invention to a ligand such as FcγR. BIAcore kinetic analysis comprises analyzing the binding and dissociation of a ligand from chips with immobilized molecules (e.g., molecules comprising modified Fc regions) on their surface.

4.2.6 Sequencing of Mutants

Any of a variety of sequencing reactions known in the art can be used to directly sequence the molecules of the invention comprising variant Fc regions. Examples of sequencing reactions include those based on techniques developed by Maxim and Gilbert (Proc. Natl. Acad. Sci. USA, 74:560, 1977) or Sanger (Proc. Natl. Acad. Sci. USA, 74:5463, 1977). It is also contemplated that any of a variety of automated sequencing procedures can be utilized (Bio/Techniques, 19:448, 1995), including sequencing by mass spectrometry (see, e.g., PCT Publication No. WO 94/16101, Cohen et al., Adv. Chromatogr., 36:127-162, 1996, and Griffin et al., Appl. Biochem. Biotechnol., 38:147-159, 1993).

4.2.7 Functional Assays of Molecules with Variant Fc Regions

The invention encompasses characterization of the molecules of the invention (e.g., an antibody comprising a variant Fc region identified by the yeast display technology described supra; or therapeutic monoclonal antibodies engineered according to the methods of the invention) using assays known to those skilled in the art for identifying the effector cell function of the molecules. In particular, the invention encompasses characterizing the molecules of the invention for FcγR-mediated effector cell function. Examples of effector cell functions that can be assayed in accordance with the invention, include but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (For effector cell assays, see Perussia et al., 2000, *Methods Mol. Biol.* 121: 179-92; Baggiolini et al., 1998 *Experientia*, 44(10): 841-8; Lehmann et al., 2000 *J. Immunol. Methods*, 243(1-2): 229-42; Brown E J. 1994, *Methods Cell Biol.*, 45: 147-64; Munn et al., 1990 *J. Exp. Med.*, 172: 231-237, Abdul-Majid et al., 2002 *Scand. J. Immunol.* 55: 70-81; Ding et al., 1998, *Immunity* 8:403-411, each of which is incorporated by reference herein in its entirety).

In one embodiment, the molecules of the invention can be assayed for FcγR-mediated phagocytosis in human monocytes. Alternatively, the FcγR-mediated phagocytosis of the molecules of the invention may be assayed in other phagocytes, e.g., neutrophils (polymorphonuclear leuckocytes; PMN); human peripheral blood monocytes, monocyte-derived macrophages, which can be obtained using standard procedures known to those skilled in the art (e.g., see Brown E J. 1994, *Methods Cell Biol.*, 45: 147-164). In one embodiment, the function of the molecules of the invention is characterized by measuring the ability of THP-1 cells to phagocytose fluoresceinated IgG-opsonized sheep red blood cells (SRBC) by methods previously described (Tridandapani et al., 2000, *J. Biol. Chem.* 275: 20480-7). For example, an exemplary assay for measuring phagocytosis of the molecules of the invention comprising variant Fc regions with enhanced affinities for FcγRIIIA, comprises of: treating THP-1 cells with a molecule of the invention or with a control antibody that does not bind to FcγRIIIA, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate the functionality of the molecule of the invention. It can be appreciated by one skilled in the art that this exemplary assay can be used to assay any of the molecules identified by the methods of the invention.

Another exemplary assay for determining the phagocytosis of the molecules of the invention is an antibody-dependent opsonophagocytosis assay (ADCP) which can comprise the following: coating a target bioparticle such as *Escherichia coli*-labeled FITC (Molecular Probes) or *Staphylococcus aureus*-FITC with (i) wild-type 4-4-20 antibody, an antibody to fluorescein (See Bedzyk et al., 1989, *J. Biol. Chem.*, 264 (3): 1565-1569, which is incorporated herein by reference in its entirety), as the control antibody for FcγR-dependent ADCP; or (ii) 4-4-20 antibody harboring the D265A mutation that knocks out binding to FcγRIII, as a background control for FcγR-dependent ADCP (iii) 4-4-20 antibody carrying variant Fc regions identified by the methods of the invention and produced as exemplified in Example 6.6; and forming the opsonized particle; adding any of the osponized particles described (i-iii) to THP-1 effector cells (a monocytic cell line available from ATCC) in a 60:1 ratio to allow FcγR-mediated phagocytosis to occur; preferably incubating the cells and *E. coli*-FITC/antibody at 37° C. for 1.5 hour; adding trypan blue after incubation (preferably at room temperature for 2-3 min.) to the cells to quench the fluorescence of the bacteria that are adhered to the outside of the cell surface without being internalized; transferring cells into a FACS buffer (e.g., 0.1%, BSA in PBS, 0.1%, sodium azide), analyzing the fluorescence of the THP1 cells using FACS (e.g., BD FACS Calibur). Preferably, the THP-1 cells used in the assay are analyzed by FACS for expression of FcγR on the cell surface. THP-1 cells express both CD32A and CD64. CD64 is a high affinity FcγR that is blocked in conducting the ADCP assay in accordance with the methods of the invention. The THP-1 cells are preferably blocked with 100 ng/mL soluble IgG1 or 10% human serum. To analyze the extent of ADCP, the gate is preferably set on THP-1 cells and median fluorescence intensity is measured. The ADCP activity for individual mutants is calculated and reported as a normalized value to the wild type chMab 4-4-20 obtained. The opsonized particles are added to THP-1 cells such that the ratio of the opsonized particles to THP-1 cells is 30:1 or 60:1. In most preferred embodiments, the ADCP assay is conducted with controls, such as *E. coli*-FITC in medium, *E. coli*-FITC and THP-1 cells (to serve as FcγR-independent ADCP activity), *E. coli*-FITC, THP-1 cells and wild-type 4-4-20 antibody (to serve as FcγR-dependent ADCP activity), *E coli*-FITC, THP-1 cells, 4-4-20 D265A (to serve as the background control for FcγR-dependent ADCP activity).

In another embodiment, the molecules of the invention can be assayed for FcγR-mediated ADCC activity in effector cells, e.g., natural killer cells, using any of the standard methods known to those skilled in the art (See e.g., Perussia et al., 2000, *Methods Mol. Biol.* 121: 179-92). An exemplary assay for determining ADCC activity of the molecules of the invention is based on a $^{51}$Cr release assay comprising of: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell necrosis); opsonizing the target cells with the molecules of the invention comprising variant Fc regions; combining the opsonized radiolabeled target cells with effector cells in a microtitre plate at an appropriate ratio of target cells to effector cells; incubating the mixture of cells for 16-18 hours at 37° C.; collecting supernatants; and analyzing radioactivity. The cytotoxicity of the molecules of the invention can then be determined, for example using the following formula: % lysis=(experimental cpm−target leak cpm)/(detergent lysis cpm−target leak cpm)×100%. Alternatively, % lysis=(ADCC−AICC)/(maximum release−spontaneous release). Specific lysis can be calculated using the formula: specific lysis=% lysis with the molecules of the invention−% lysis in the absence of the molecules of the invention. A graph can be generated by varying either the target:effector cell ratio or antibody concentration.

In yet another embodiment, the molecules of the invention are characterized for antibody dependent cellular cytotoxicity (ADCC) see, e.g., Ding et al., *Immunity*, 1998, 8:403-11; which is incorporated herein by reference in its entirety.

Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. Preferred effector cells for use in the methods of the invention express different FcγR activating receptors. The invention encompasses, effector cells, THP-1, expressing FcγRI, FcγRIIA and FcγRIIB, and monocyte derived primary macrophages derived from whole human blood expressing both FcγRIIIA and FcγRIIB, to determine if Fc antibody mutants show increased ADCC activity and phagocytosis relative to wild type IgG1 antibodies.

The human monocyte cell line, THP-1, activates phagocytosis through expression of the high affinity receptor FcγRI and the low affinity receptor FcγRIIA (Fleit et al., 1991, *J. Leuk. Biol.* 49: 556). THP-1 cells do not constitutively express FcγRIIA or FcγRIIB. Stimulation of these cells with cytokines effects the FcR expression pattern (Pricop et al., 2000 *J. Immunol.* 166: 531-7). Growth of THP-1 cells in the presence of the cytokine IL4 induces FcγRIIB expression and causes a reduction in FcγRIIA and FcγRI expression. FcγRIIB expression can also be enhanced by increased cell density (Tridandapani et al., 2002, *J. Biol. Chem.* 277: 5082-9). In contrast, it has been reported that IFNγ can lead to expression of FcγRIIIA (Pearse et al., 1993 *PNAS USA* 90: 4314-8). The presence or absence of receptors on the cell surface can be determined by FACS using common methods known to one skilled in the art. Cytokine induced expression of FcγR on the cell surface provides a system to test both activation and inhibition in the presence of FcγRIIB. If THP-1 cells are unable to express the FcγRIIB the invention also encompasses another human monocyte cell line, U937. These cells have been shown to terminally differentiate into macrophages in the presence of IFNγ and TNF (Koren et al., 1979, *Nature* 279: 328-331).

FcγR dependent tumor cell killing is mediated by macrophage and NK cells in mouse tumor models (Clynes et al., 1998, *PNAS USA* 95: 652-656). The invention encompasses the use of elutriated monocytes from donors as effector cells to analyze the efficiency Fc mutants to trigger cell cytotoxicity of target cells in both phagocytosis and ADCC assays. Expression patterns of FcγRI, FcγRIIIA, and FcγRIIB are affected by different growth conditions. FcγR expression from frozen elutriated monocytes, fresh elutriated monocytes, monocytes maintained in 10% FBS, and monocytes cultured in FBS+ GM-CSF and or in human serum may be determined using common methods known to those skilled in the art. For example, cells can be stained with FcγR specific antibodies and analyzed by FACS to determine FcR profiles. Conditions that best mimic macrophage in vivo FcγR expression is then used for the methods of the invention.

In some embodiments, the invention encompasses the use of mouse cells especially when human cells with the right FcγR profiles are unable to be obtained. In some embodiments, the invention encompasses the mouse macrophage cell line RAW264.7 (ATCC) which can be transfected with human FcγRIIIA and stable transfectants isolated using methods known in the art, see, e.g., Ralph et al., *J. Immunol.* 119: 950-4). Transfectants can be quantitated for FcγRIIIA expression by FACS analysis using routine experimentation and high expressors can be used in the ADCC assays of the invention. In other embodiments, the invention encompasses isolation of spleen peritoneal macrophage expressing human FcγR from knockout transgenic mice such as those disclosed herein.

Lymphocytes may be harvested from peripheral blood of donors (PBM) using a Ficoll-Paque gradient (Pharmacia). Within the isolated mononuclear population of cells the majority of the ADCC activity occurs via the natural killer cells (NK) containing FcγRIIIA but not FcγRIIB on their surface. Results with these cells indicate the efficacy of the mutants on triggering NK cell ADCC and establish the reagents to test with elutriated monocytes.

Target cells used in the ADCC assays of the invention include, but are not limited to, breast cancer cell lines, e.g., SK-BR-3 with ATCC accession number HTB-30 (see, e.g., Tremp et al., 1976, *Cancer Res.* 33-41); B-lymphocytes; cells derived from Burkitts lymphoma, e.g., Raji cells with ATCC accession number CCL-86 (see, e.g., Epstein et al., 1965, *J. Natl. Cancer Inst.* 34: 231-240), and Daudi cells with ATCC accession number CCL-213 (see, e.g., Klein et al., 1968, *Cancer Res.* 28: 1300-10). The target cells must be recognized by the antigen binding site of the immunoglobulin to be assayed.

The ADCC assay is based on the ability of NK cells to mediate cell death via an apoptotic pathway. NK cells mediate cell death in part by FcγRIIIA's recognition of IgG bound to an antigen on a cell surface. The ADCC assays used in accordance with the methods of the invention may be radioactive based assays or fluorescence based assays. The ADCC assay used to characterize the molecules of the invention comprising variant Fc regions comprises labeling target cells, e.g., SK-BR-3, MCF-7, OVCAR3, Raji, Daudi cells, opsonizing target cells with an antibody that recognizes a cell surface receptor on the target cell via its antigen binding site; combining the labeled opsonized target cells and the effector cells at an appropriate ratio, which can be determined by routine experimentation; harvesting the cells; detecting the label in the supernatant of the lysed target cells, using an appropriate detection scheme based on the label used. The target cells may be labeled either with a radioactive label or a fluorescent label, using standard methods known in the art. For example the labels include, but are not limited to, [$^{51}$Cr] $Na_2CrO_4$; and the acetoxymethyl ester of the fluorescence enhancing ligand, 2,2':6',2"-terpyridine-6-6"-dicarboxylate (TDA).

In a specific preferred embodiment, a time resolved fluorimetric assay is used for measuring ADCC activity against target cells that have been labeled with the acetoxymethyl ester of the fluorescence enhancing ligand, 2,2':6',2"-terpyridine-6-6"-dicarboxylate (TDA). Such fluorimetric assays are known in the art, e.g., see, Blomberg et al., 1996, *Journal of Immunological Methods*, 193: 199-206; which is incorporated herein by reference in its entirety. Briefly, target cells are labeled with the membrane permeable acetoxymethyl diester of TDA (bis(acetoxymethyl) 2,2':6',2"-terpyridine-6-6"-dicarboxylate, (BATDA), which rapidly diffuses across the cell membrane of viable cells. Intracellular esterases split off the ester groups and the regenerated membrane impermeable TDA molecule is trapped inside the cell. After incubation of effector and target cells, e.g., for at least two hours, up to 3.5 hours, at 37° C., under 5% $CO_2$, the TDA released from the lysed target cells is chelated with Eu3+ and the fluorescence of the Europium-TDA chelates formed is quantitated in a time-resolved fluorometer (e.g., Victor 1420, Perkin Elmer/Wallac).

In another specific embodiment, the ADCC assay used to characterize the molecules of the invention comprising variant Fc regions comprises the following steps: Preferably 4–5×10$^6$ target cells (e.g., SK-BR-3, MCF-7, OVCAR3, Raji cells) are labeled with bis(acetoxymethyl) 2,2':6',2"-terpyridine-t-6"-dicarboxylate (DELFIA BATDA Reagent, Perkin Elmer/Wallac). For optimal labeling efficiency, the number of target cells used in the ADCC assay should preferably not exceed 5×10$^6$. BATDA reagent is added to the cells and the mixture is incubated at 37° C. preferably under 5% $CO_2$, for at least 30 minutes. The cells are then washed with a physiological buffer, e.g., PBS with 0.125 mM sulfinpyrazole, and media containing 0.125 mM sulfinpyrazole. The labeled target cells are then opsonized (coated) with a molecule of the invention comprising a variant Fc region, i.e., an immunoglobulin comprising a variant Fc region of the invention, including, but not limited to, a polyclonal antibody, a monoclonal antibody, a bispecific antibody, a multi-specific antibody, a humanized antibody, or a chimeric antibody. In preferred embodiments, the immunoglobulin comprising a variant Fc region used in the ADCC assay is specific for a cell surface receptor, a tumor antigen, or a cancer antigen. The immunoglobulin into which a variant Fc region of the invention is introduced may specifically bind any cancer or tumor antigen, such as those listed in section 5.4. Additionally, the immunoglobulin into which a variant Fc region of the invention is introduced may be any therapeutic antibody specific for a cancer antigen, such as those listed in section 5.4. In some embodiments, the immunoglobulin comprising a variant Fc region used in the ADCC assay is an anti-fluoresceine monoclonal antibody, 4-4-20 (Kranz et al., 1982 *J. Biol. Chem.* 257(12): 6987-6995) a mouse-human chimeric anti-CD20 monoclonal antibody 2H7 (Liu et al., 1987, *Journal of Immunology*, 139: 3521-6); or a humanized antibody (Ab4D5) against the human epidermal growth factor receptor 2 (p185 HER2) (Carter et al. (1992, *Proc. Natl. Acad. Sci. USA* 89: 4285-9). The target cells in the ADCC assay are chosen according to the immunoglobulin into which a variant Fc region of the invention has been introduced so that the immunoglobulin binds a cell surface receptor of the target cell specifically. Preferably, the ADCC assays of the invention are performed using more than one engineered antibody, e.g., anti Her2/neu, 4-4-20, 2B6, Rituxan, and 2H7, harboring the Fc variants of the invention. In a most preferred embodiment, the Fc variants of the invention are introduced into at least 3 antibodies and their ADCC activities are tested. Although not intending to be bound by a particular mechanism of action, examining at least 3 antibodies in these functional assays will diminish the chance of eliminating a viable Fc mutation erroneously.

Opsonized target cells are added to effector cells, e.g., PBMC, to produce effector:target ratios of approximately 50:1, 75:1, or 100:1. In a specific embodiment, when the immunoglobulin comprising a variant Fc region has the variable domain of 4-4-20, the effector:target is 75:1. The effector and target cells are incubated for at least two hours, up to 3.5 hours, at 37° C., under 5% $CO_2$. Cell supernatants are harvested and added to an acidic europium solution (e.g., DELFIA Europium Solution, Perkin Elmer/Wallac). The fluorescence of the Europium-TDA chelates formed is quantitated in a time-resolved fluorometer (e.g., Victor 1420, Perkin Elmer/Wallac). Maximal release (MR) and spontaneous release (SR) are determined by incubation of target cells with 1% TX-100 and media alone, respectively. Antibody independent cellular cytotoxicity (AICC) is measured by incubation of target and effector cells in the absence of antibody. Each assay is preferably performed in triplicate. The mean percentage specific lysis is calculated as: Experimental release (ADCC)−AICC)/(MR−SR)×100.

The invention encompasses characterization of the Fc variants in both NK-dependent and macrophage dependent ADCC assays. Fc variants of the invention have altered phenotypes such as an altered effector function as assayed in an NK dependent or macrophage dependent assay.

The invention encompasses assays known in the art and exemplified herein, to bind C1q and mediate complement dependent cytotoxicity (CDC). To determine C1q binding, a C1q binding ELISA may be performed. An exemplary assay may comprise the following: assay plates may be coated overnight at 4 C with polypeptide variant or starting polypeptide (control) in coating buffer. The plates may then be washed and blocked. Following washing, an aliquot of human C1q may be added to each well and incubated for 2 hrs at room temperature. Following a further wash, 100 uL of a sheep anti-complement C1q peroxidase conjugated antibody may be added to each well and incubated for 1 hour at room temperature. The plate may again be washed with wash buffer and 100 ul of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 ul of 4.5 NH2SO4. The absorbance may then read at (492-405) nm.

A preferred variant in accordance with the invention is one that displays a significant reduction in C1q binding, as detected and measured in this assay or a similar assay. Preferably the molecule comprising an Fc variant displays about 50 fold reduction, about 60 fold, about 80 fold, or about 90 fold reduction in C1q binding compared to a control antibody having a nonmutated IgG1 Fc region. In the most preferred embodiment, the molecule comprising an Fc variant does not bind C1q, i.e. the variant displays about 100 fold or more reduction in C1q binding compared to the control antibody.

Another exemplary variant is one which has a better binding affinity for human C1q than the molecule comprising wild type Fc region. Such a molecule may display, for example, about two-fold or more, and preferably about five-fold or more, improvement in human C1q binding compared to the parent molecule comprising wild type Fc region. For example, human C1q binding may be about two-fold to about 500-fold, and preferably from about two-fold or from about five-fold to about 1000-fold improved compared to the molecule comprising wild type Fc region.

To assess complement activation, a complement dependent cytotoxicity (CDC) assay may be performed, e.g. as described in Gazzano-Santoro et al., *J. Immunol. Methods* 202:163 (1996), which is incorporated herein by reference in its entirety. Briefly, various concentrations of the molecule comprising a variant Fc region and human complement may be diluted with buffer. Cells which express the antigen to which the molecule comprising a variant Fc region binds may be diluted to a density of about $1 \times 10^6$ cells/ml. Mixtures of the molecule comprising a variant Fc region, diluted human complement and cells expressing the antigen may be added to a flat bottom tissue culture 96 well plate and allowed to incubate for 2 hrs at 37 C and 5% CO2 to facilitate complement mediated cell lysis. 50 uL of alamar blue (Accumed International) may then be added to each well and incubated overnight at 37 C. The absorbance is measured using a 96-well fluorometer with excitation at 530 nm and emission at 590 nm. The results may be expressed in relative fluorescence units (RFU). The sample concentrations may be computed from a standard curve and the percent activity as compared to nonvariant molecule, i.e., a molecule comprising wild type Fc region, is reported for the variant of interest.

In some embodiments, an Fc variant of the invention does not activate complement. Preferably the variant does not appear to have any CDC activity in the above CDC assay. The invention also pertains to a variant with enhanced CDC compared to a parent molecule (a molecule comprising wild type Fc region), e.g., displaying about two-fold to about 100-fold improvement in CDC activity in vitro or in vivo (e.g., at the IC50 values for each molecule being compared). Complement assays may be performed with guinea pig, rabbit or human serum. Complement lysis of target cells may be detected by monitoring the release of intracellular enzymes such as lactate dehydrogenase (LDH), as described in Korzeniewski et al., 1983 *Immunol. Methods* 64(3): 313-20; and Decker et al., 1988 *J. Immunol. Methods* 115(1): 61-9, each of which is incorporated herein by reference in its entirety; or the release of an intracellular label such as europium, chromium 51 or indium 111 in which target cells are labeled as described herein.

4.2.8 Other Assays

The molecules of the invention comprising variant Fc regions may also be assayed using any surface plasmon resonance based assays known in the art for characterizing the kinetic parameters of Fc-FcγR interaction binding. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occurs is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

In some embodiments, the kinetic parameters of the binding of molecules of the invention comprising variant Fc regions, e.g., immunoglobulins comprising variant Fc region, to an FcγR may be determined using a BIAcore instrument (e.g., BIAcore instrument 1000, BIAcore Inc., Piscataway, N.J.). Any FcγR can be used to assess the interaction with the molecules of the invention comprising variant Fc regions. In a specific embodiment the FcγR is FcγRIIIA, preferably a soluble monomeric FcγRIIIA For example, in one embodiment, the soluble monomeric FcγRIIIA is the extracellular region of FcγRIIIA joined to the linker-AVITAG sequence (see, U.S. Provisional Application No. 60/439,498, filed on Jan. 9, 2003 and U.S. Provisional Application No. 60/456,041 filed on Mar. 19, 2003, which are incorporated herein by reference in their entireties). In another specific embodiment, the FcγR is FcγRIIB, preferably a soluble dimeric FcγRIIB. For example in one embodiment, the soluble dimeric FcγRIIB protein is prepared in accordance with the methodology described in U.S. Provisional application No. 60/439,709 filed on Jan. 13, 2003, which is incorporated herein by reference in its entirety.

An exemplary assay for determining the kinetic parameters of a molecule comprising a variant Fc region, wherein the molecule is the 4-4-20 antibody, to an FcγR using a BIAcore instrument comprises the following: BSA-FITC is immobilized on one of the four flow cells of a sensor chip surface, preferably through amine coupling chemistry such that about 5000 response units (RU) of BSA-FITC is immobilized on the surface. Once a suitable surface is prepared, 4-4-20 antibodies carrying the Fc mutations are passed over the surface, preferably by one minute injections of a 20 μg/mL solution at a 5 μL/mL flow rate. The level of 4-4-20 antibodies bound to the surface ranges between 400 and 700 RU. Next, dilution series of the receptor (FcγRIIA and FcγRIIB-Fc fusion protein) in HBS-P buffer (20 mM HEPES, 150 mM NaCl, 3 mM EDTA, pH 7.5) are injected onto the surface at 100 μL/min Antibody regeneration between different receptor dilutions is carried out preferably by single 5 second injections of 100 mM $NaHCO_3$ pH 9.4; 3M NaCl. Any regeneration technique known in the art is contemplated in the method of the invention.

Once an entire data set is collected, the resulting binding curves are globally fitted using computer algorithms supplied by the SPR instrument manufacturer, e.g., BIAcore, Inc. (Piscataway, N.J.). These algorithms calculate both the $K_{on}$ and $K_{off}$, from which the apparent equilibrium binding constant, $K_d$ is deduced as the ratio of the two rate constants (i.e., $K_{off}/K_{on}$). More detailed treatments of how the individual rate constants are derived can be found in the BIAevaluaion Software Handbook (BIAcore, Inc., Piscataway, N.J.). The analysis of the generated data may be done using any method known in the art. For a review of the various methods of interpretation of the kinetic data generated see Myszka, 1997, *Current Opinion in Biotechnology* 8: 50-7; Fisher et al., 1994, *Current Opinion in Biotechnology* 5: 389-95; O'Shannessy, 1994, *Current Opinion in Biotechnology*, 5:65-71; Chaiken et al., 1992, *Analytical Biochemistry*, 201: 197-210; Morton et al., 1995, *Analytical Biochemistry* 227: 176-85; O'Shannessy et al., 1996, *Analytical Biochemistry* 236: 275-83; all of which are incorporated herein by reference in their entirety.

In preferred embodiments, the kinetic parameters determined using an SPR analysis, e.g., BIAcore, may be used as a predictive measure of how a molecule of the invention will function in a functional assay, e.g., ADCC. An exemplary method for predicting the efficacy of a molecule of the invention based on kinetic parameters obtained from an SPR analysis may comprise the following: determining the $K_{off}$ values for binding of a molecule of the invention to FcγRIIIA and FcγRIIB; plotting (1) $K_{off}$ (wt)/$K_{off}$ (mut) for FcγRIIIA; (2) $K_{off}$(mut)/$K_{off}$(wt) for FcγRIIB against the ADCC data. Numbers higher than one show a decreased dissociation rate for FcγRIIIA and an increased dissociation rate for FcγRIIB relative to wild type; and possess and enhanced ADCC function.

4.3 Methods of Recombinantly Producing Molecules of the Invention 4.3.1 Polynucleotides Encoding Molecules of the Invention The present invention also includes polynucleotides that encode the molecules, including the polypeptides and antibodies, of the invention identified by the methods of the invention. The polynucleotides encoding the molecules of the invention may be obtained, and the nucleotide sequence of the polynucleotides determined, by any method known in the art.

Once the nucleotide sequence of the molecules (e.g., antibodies) that are identified by the methods of the invention is determined, the nucleotide sequence may be manipulated using methods well known in the art, e.g., recombinant DNA techniques, site directed mutagenesis, PCR, etc. (see, for example, the techniques described in Sambrook et al., 2001, *Molecular Cloning, A Laboratory Manual*, 3rd Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties), to generate, for example, antibodies having a different amino acid sequence, for example by generating amino acid substitutions, deletions, and/or insertions.

In a specific embodiment, when the nucleic acids encode antibodies, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278:457-479 for a listing of human framework regions).

In another embodiment, human libraries or any other libraries available in the art, can be screened by standard techniques known in the art, to clone the nucleic acids encoding the molecules of the invention.

4.3.2 Recombinant Expression Of Molecules of the Invention

Once a nucleic acid sequence encoding molecules of the invention (i.e., antibodies) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al. eds., 1998, *Current Protocols in Molecular Biology*, John Wiley & Sons, NY).

An expression vector comprising the nucleotide sequence of a molecule identified by the methods of the invention (i.e., an antibody) can be transferred to a host cell by conventional techniques (e.g., electroporation, liposomal transfection, and calcium phosphate precipitation) and the transfected cells are then cultured by conventional techniques to produce the molecules of the invention. In specific embodiments, the expression of the molecules of the invention is regulated by a constitutive, an inducible or a tissue, specific promoter.

The host cells used to express the molecules identified by the methods of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, *Gene* 45:101; Cockett et al., 1990, *Bio/Technology* 8:2).

A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the molecules identified by the methods of the invention; yeast (e.g., *Saccharomyces Pichia*) transformed with recombinant yeast expression vectors containing sequences encoding the molecules identified by the methods of the invention; insect cell systems infected with recombinant virus expression vectors (e.g., baculovirus) containing the sequences encoding the molecules identified by the methods of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules identified by the methods of the invention; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11: 223), hypoxanthine-guanine phosphoribosyltransferase (Szybalska & Szybalski, 1992, *Proc. Natl. Acad. Sci. USA* 48: 202), and adenine phosphoribosyltransferase (Lowy et al., 1980, *Cell* 22: 817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78: 1527); gpt, which confers resistance to mycophenolic acid (Mulligan & Berg, 1981, *Proc. Natl. Acad. Sci. USA* 78: 2072); neo, which confers resistance to the aminoglycoside G-418 *Clinical Pharmacy* 12: 488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1; and hygro, which confers resistance to hygromycin (Santerre et al., 1984, *Gene* 30:147).

The expression levels of an antibody of the invention can be increased by vector amplification (for a review, see Bebbington and Hentschel, *The use of vectors based on gene amplification for the expression of cloned genes in mammalian cells in DNA cloning*, Vol. 3 (Academic Press, New York, 1987). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once a molecule of the invention (i.e., antibodies) has been recombinantly expressed, it may be purified by any method known in the art for purification of polypeptides or antibodies, for example, by chromatography (e.g., ion exchange, affinity, particularly by affinity for the specific antigen after Protein A, and sizing column chromatography), centrifugation, differential solubility, or by any other standard technique for the purification of polypeptides or antibodies.

4.4 Prophylactic and Therapeutic Methods

The present invention encompasses administering one or more of the molecules of the invention (e.g., antibodies) to an animal, preferably a mammal, and most preferably a human, for preventing, treating, or ameliorating one or more symptoms associated with a disease, disorder, or infection. The molecules of the invention are particularly useful for the treatment or prevention of a disease or disorder where an enhanced efficacy of effector cell function (e.g., ADCC) mediated by FcγR is desired. The methods and compositions of the invention are particularly useful for the treatment or prevention of primary or metastatic neoplastic disease (i.e., cancer), and infectious diseases. Molecules of the invention may be provided in pharmaceutically acceptable compositions as known in the art or as described herein. As detailed below, the molecules of the invention can be used in methods of treating or preventing cancer (particularly in passive immunotherapy), autoimmune disease, inflammatory disorders or infectious diseases.

The molecules of the invention may also be advantageously utilized in combination with other therapeutic agents known in the art for the treatment or prevention of a cancer, autoimmune disease, inflammatory disorders or infectious diseases. In a specific embodiment, molecules of the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The molecules of the invention may also be advantageously utilized in combination with one or more drugs used to treat a disease, disorder, or infection such as, for example anti-cancer agents, anti-inflammatory agents or anti-viral agents, e.g., as detailed in sections 5.4.1.2 and 5.4.2.1 below.

4.4.1 Cancers

The invention encompasses methods and composition for treatment or prevention of cancer or metastasis in a subject comprising administering to the subject a therapeutically effective amount of one or more molecules comprising a variant Fc region.

Molecules of the invention (i.e., polypeptides, antibodies) comprising variant Fc regions can be used to prevent, inhibit or reduce the growth of primary tumors or metastasis of cancerous cells. In one embodiment, the molecule of the invention comprises a variant Fc that binds FcγRIIIA and/or FcγRIIA with a greater affinity than a comparable polypeptide comprising a wild type Fc region binds FcγRIIIA and/or FcγRIIA, and/or said variant Fc region has an enhanced effector function, e.g., ADCC, CDC, phagocytosis, opsonization, etc. Such molecules can be used alone to treat or prevent cancer. In another embodiment, the molecule of the invention comprises a variant Fc region that binds FcγRIIIA and/or FcγRIIA with a greater affinity than a comparable polypeptide comprising a wild type Fc region binds FcγRIIIA and/or FcγRIIA, and further binds FcγRIIB with a lower affinity than a comparable polypeptide comprising a wild-type Fc region binds FcγRIIB, and/or said variant Fc region has an enhanced effector function, e.g., ADCC, CDC, phagocytosis, opsonization, etc. Such molecules can also be used alone to treat or prevent cancer.

In some embodiments, the invention encompasses methods and compositions for the treatment or prevention of cancer in a subject with FcγR polymorphisms such as those homozygous for the FγRIIIA-158V or FcγRIIIA-158F alleles. In some embodiments, the invention encompasses engineering therapeutic antibodies, e.g., tumor specific monoclonal antibodies in accordance with the methods of the invention such that the engineered antibodies have enhanced efficacy in patients homozygous for the low affinity allele of FcγRIIIA (158F). In other embodiments, the invention encompasses engineering therapeutic antibodies, e.g., tumor specific monoclonal antibodies in accordance with the methods of the invention such that the engineered antibodies have enhanced efficacy in patients homozygous for the high affinity allele of FcγRIIIA (158V).

In some embodiments, the engineered antibodies of the invention are particularly effective in treating and/or preventing non-Hodgkin's lymphoma (NHL). The engineered antibodies of the invention are therapeutically more effective than current therapeutic regimens for NHL, including but not limited to chemotherapy, and immunotherapy using anti-CD20 mAb, Rituximab. The efficacy of anti-CD20 monoclonal antibodies however depends on the FcγR polymorphism of the subject (Carton et al., 2002 *Blood,* 99: 754-8; Weng et al., 2003 *J Clin Oncol.* 21(21):3940-7 both of which are incorporated herein by reference in their entireties). These receptors are expressed on the surface of the effector cells and mediate ADCC. High affinity alleles, of the low affinity activating receptors, improve the effector cells' ability to mediate ADCC. The methods of the invention allow engineering anti-CD20 antibodies harboring Fc mutations to enhance their affinity to FcγR on effector cells via their altered Fc domains. The engineered antibodies of the invention provide better immunotherapy reagents for patients regardless of their FcγR polymorphism.

An exemplary method for determining the efficacy of the engineered anti-CD20 antibodies in a subject may include the following: Plasmids harboring chimeric anti-HER2/neu heavy chain genes with Fc mutations that show substantially increased killing in ADCC can be used as a backbone to transfer in the variable domain from the Rituximab heavy chain gene. The variable region from the anti-HER2/neu Fc variant is replaced with the variable region from Rituximab. Plasmids containing wild type Fc domains or a D265A mutation to abrogate FcR binding, or the anti-CD20 Fc variants are transiently cotransfected with the Rituximab light chain gene into 293H cells, conditioned media and the antibody is purified over a protein G column using routine methods.

Anti-CD20 mAbs harboring the Fc variants are tested by ADCC using a cultured B cell line to determine the ability of the Fc mutations to enhance ADCC. Standard ADCC is performed using methods disclosed herein. Lymphocytes are harvested from peripheral blood using a Ficoll-Paque gradient (Pharmacia). Target Daudi cells, a B-cell line expressing CD20, are loaded with Europium (PerkinElmer) and incubated with effectors for 4 hrs at 37° C. Released Europium is detected using a fluorescent plate reader (Wallac). The resulting ADCC data indicates the efficacy of the Fc variants to trigger NK cell mediated cytotoxicity and establish which anti-CD20 Fc variants can be tested with both patient samples and elutriated monocytes. Fc variants showing the greatest potential for enhancing the efficacy of the anti-CD20 antibody are then tested in an ADCC assay using PBMCs from patients. PBMC from healthy donors are used as effector cells. In vitro ADCC assays using anti-CD20 variants and Rituximab are performed in primary lymphoma cells from patients with follicular lymphoma. The specific FcγR polymorphism of the donors is determined and cataloged using methods known in the art. ADCC assay is performed by effector cells from patients with different FcγRIIIA and FcγRIIA genotypes.

According to an aspect of the invention, molecules (e.g., antibodies) of the invention comprising variant Fc regions enhance the efficacy of cancer immunotherapy by increasing the potency of the antibody effector function relative to a molecule containing the wild-type Fc region, e.g., ADCC, CDC, phagocytosis, opsonization, etc. In a specific embodiment, antibody dependent cellular toxicity and/or phagocytosis of tumor cells is enhanced using the molecules of the invention with variant Fc regions. Molecules of the invention may enhance the efficacy of immunotherapy cancer treatment by enhancing at least one antibody-mediated effector function. In one particular embodiment, a molecule of the invention comprising a variant Fc region enhances the efficacy of immunotherapy treatment by enhancing the complement dependent cascade. In another embodiment of the invention, the molecule of the invention comprising a variant Fc region enhances the efficacy of immunotherapy treatment by enhancing the phagocytosis and/or opsonization of the targeted tumor cells. In another embodiment of the invention, the molecule of the invention comprising a variant Fc region enhances the efficacy of treatment by enhancing antibody-dependent cell-mediated cytotoxicity ("ADCC") in destruction of the targeted tumor cells.

The invention further contemplates engineering therapeutic antibodies (e.g., tumor specific monoclonal antibodies) for enhancing the therapeutic efficacy of the therapeutic antibody, for example, by enhancing the effector function of the therapeutic antibody (e.g., ADCC). Preferably the therapeutic antibody is a cytotoxic and/or opsonizing antibody. It will be appreciated by one of skill in the art, that once molecules of the invention with desired binding properties (e.g., molecules with variant Fc regions with at least one amino acid modification, which modification enhances the affinity of the variant Fc region for FcγRIIIA and/or FcγRIIA relative to a comparable molecule, comprising a wild-type Fc region) have been identified (See Section 5.2 and Table 8) according to the methods of the invention, therapeutic antibodies may be engineered using standard recombinant DNA techniques and any known mutagenesis techniques, as described in Section 5.2.2 to produce engineered therapeutic carrying the identified mutation sites with the desired binding properties. Any of the therapeutic antibodies listed in Table 9A that have demonstrated therapeutic utility in cancer treatment, may be engineered according to the methods of the invention, for example, by modifying the Fc region to have an enhanced affinity for FcγRIIIA and/or FcγRIIA compared to a therapeutic antibody having a wild-type Fc region, and used for the treatment and or prevention of a cancer characterized by a cancer antigen. Other therapeutic antibodies include those against pathogenic agents such as those against *Streptococcus pneumoniae* Serotype 6B, see, e.g., Sun et al., 1999, Infection and Immunity, 67(3): 1172-9.

The Fc variants of the invention may be incorporated into therapeutic antibodies such as those disclosed herein or other Fc fusion clinical candidates, i.e., a molecule comprising an Fc regions which has been approved for us in clinical trials or any other molecule that may benefit from the Fc variants of the instant invention, humanized, affinity matured, modified or engineered versions thereof.

The invention also encompasses engineering any other polypeptide comprising an Fc region which has therapeutic utility, including but not limited to ENBREL, according to the methods of the invention, in order to enhance the therapeutic efficacy of such polypeptides, for example, by enhancing the effector function of the polypeptide comprising an Fc region.

TABLE 9A

THERAPEUTIC ANTIBODIES THAT CAN BE ENGINEERED ACCORDING TO THE METHODS OF THE INVENTION

| Company | Product | Disease | Target |
| --- | --- | --- | --- |
| Abgenix | ABX-EGF ™ | Cancer | EGF receptor |
| AltaRex | OvaRex ™ | ovarian cancer | tumor antigen CA125 |
| | BravaRex ™ | metastatic cancers | tumor antigen MUC1 |
| Antisoma | Theragyn ™ (pemtumomabytrrium-90) | ovarian cancer | PEM antigen |
| | Therex ™ | breast cancer | PEM antigen |
| Boehringer Ingelheim | Blvatuzumab | head & neck cancer | CD44 |
| Centocor/J&J | Panorex ™ | Colorectal cancer | 17-1A |
| | ReoPro ™ | PTCA | gp IIIb/IIIa |
| | ReoPro ™ | Acute MI | gp IIIb/IIIa |
| | ReoPro ™ | Ischemic stroke | gp IIIb/IIIa |
| Corixa | Bexocar ™ | NHL | CD20 |
| CRC Technology | MAb, idiotypic 105AD7 ™ | colorectal cancer vaccine | gp72 |
| Crucell | Anti-EpCAM | cancer | Ep-CAM |
| Cytoclonal | MAb, lung cancer | non-small cell lung cancer | NA |
| Genentech | Herceptin ® | metastatic breast cancer | HER-2 |
| | Herceptin ® | early stage breast cancer | HER-2 |
| | Rituxan ® | Relapsed/refractory low-grade or follicular NHL | CD20 |
| | Rituxan ® | intermediate & high-grade NHL | CD20 |
| | MAb-VEGF | NSCLC, metastatic | VEGF |
| | MAb-VEGF | Colorectal cancer, metastatic | VEGF |
| | AMD Fab | age-related macular degeneration | CD18 |
| | E-26 (2$^{nd}$ gen. IgE) | allergic asthma & rhinitis | IgE |
| IDEC | Zevalin ™ (Rituxan ® + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |

TABLE 9A-continued

THERAPEUTIC ANTIBODIES THAT CAN BE ENGINEERED ACCORDING TO THE METHODS OF THE INVENTION

| Company | Product | Disease | Target |
|---|---|---|---|
| | Cetuximab + cisplatin & radiation | newly diagnosed or recurrent head & neck cancer | EGF receptor |
| | Cetuximab + gemcitabine | newly diagnosed metastatic pancreatic carcinoma | EGF receptor |
| | Cetuximab + cisplatin + 5FU or Taxol | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metasteses) | EGF receptor |
| | Cetuximab + radiation | locally advanced head & neck carcinoma | EGF receptor |
| | BEC2 ™ + Bacillus Calmette Guerin | small cell lung carcinoma | mimics ganglioside GD3 |
| | BEC2 ™ + Bacillus Calmette Guerin | melanoma | mimics ganglioside GD3 |
| | IMC-1C11 ™ | colorectal cancer with liver metasteses | VEGF-receptor |
| ImmonoGen | nuC242-DM1 ™ | Colorectal, gastric, and pancreatic cancer | nuC242 |
| ImmunoMedics | LymphoCide ™ | Non-Hodgkins lymphoma | CD22 |
| | LymphoCide Y-90 ™ | Non-Hodgkins lymphoma | CD22 |
| | CEA-Cide ™ | metastatic solid tumors | CEA |
| | CEA-Cide Y-90 ™ | metastatic solid tumors | CEA |
| | CEA-Scan ™ (Tc-99m-labeled arcitumomab) | colorectal cancer (radioimaging) | CEA |
| | CEA-Scan ™ (Tc-99m-labeled arcitumomab) | Breast cancer (radioimaging) | CEA |
| | CEA-Scan ™ (Tc-99m-labeled arcitumomab) | lung cancer (radioimaging) | CEA |
| | CEA-Scan ™ (Tc-99m-labeled arcitumomab) | intraoperative tumors (radio imaging) | CEA |
| | LeukoScan ™ (Tc-99m-labeled sulesomab) | soft tissue infection (radioimaging) | CEA |
| | LymphoScan ™ (Tc-99m-labeled) | lymphomas (radioimaging) | CD22 |
| | AFP-Scan ™ (Tc-99m-labeled) | liver 7 gem-cell cancers (radioimaging) | AFP |
| Intracel | HumaRAD-HN ™ (+ yttrium-90) | head & neck cancer | NA |
| | HumaSPECT ™ | colorectal imaging | NA |
| Medarex | MDX-101 ™ (CTLA-4) | Prostate and other cancers | CTLA-4 |
| | MDX-210 ™ (her-2 overexpression) | Prostate cancer | HER-2 |
| | MDX-210 ™ /MAK | Cancer | HER-2 |
| MedImmune | Vitaxin ™ | Cancer | $\alpha v \beta_3$ |
| Merck KGaA | MAb 425 ™ | Various cancers | EGF receptor |
| | IS-IL-2 | Various cancers | Ep-CAM |
| Millennium | Campath ™ (alemtuzumab) | chronic lymphocytic leukemia | CD52 |

TABLE 9A-continued

THERAPEUTIC ANTIBODIES THAT CAN BE ENGINEERED
ACCORDING TO THE METHODS OF THE INVENTION

| Company | Product | Disease | Target |
|---|---|---|---|
| NeoRx | CD20-streptavidin (+ biotin-yttrium 90) | Non-Hodgkins lymphoma | CD20 |
|  | Avidicin ™ (albumin + NRLU13) | metastatic cancer | NA |
| Peregrine | Oncolym ™ (+ iodine-131) | Non-Hodgkins lymphoma | HLA-DR 10 beta |
|  | Cotara ™ (+ iodine-131) | unresectable malignant glioma | DNA-associated proteins |
| Pharmacia Corporation | C215 ™ (+ staphylococcal enterotoxin) | pancreatic cancer | NA |
|  | MAb, lung/kidney cancer | lung & kidney cancer | NA |
|  | nacolomab tafenatox (C242 + staphylococcal enterotoxin) | colon & pancreatic cancer | NA |
| Protein Design Labs | Nuvion ™ | T cell malignancies | CD3 |
|  | SMART M195 ™ | AML | CD33 |
|  | SMART 1D10 ™ | NHL | HLA-DR antigen |
| Titan | CEAVac ™ | colorectal cancer, advanced | CEA |
|  | TriGem ™ | metastatic melanoma & small cell lung cancer | GD2-ganglioside |
|  | TriAb ™ | metastatic breast cancer | MUC-1 |
| Trilex | CEAVac ™ | colorectal cancer, advanced | CEA |
|  | TriGem ™ | metastatic melanoma & small cell lung cancer | GD2-ganglioside |
|  | TriAb ™ | metastatic breast cancer | MUC-1 |
| Viventia Biotech | NovoMAb-G2 ™ radiolabeled | Non-Hodgkins lymphoma | NA |
|  | Monopharm C ™ | colorectal & pancreatic carcinoma | SK-1 antigen |
|  | GlioMAb-H ™ (+ gelonin toxin) | gliorna, melanoma & neuroblastoma | NA |
| Xoma | Rituxan ® | Relapsed/refractory low-grade or follicular NHL | CD20 |
|  | Rituxan ® | intermediate & high-grade NHL | CD20 |
|  | ING-1 ™ | adenomcarcinoma | Ep-CAM |

Accordingly, the invention provides methods of preventing or treating cancer characterized by a cancer antigen, using a therapeutic antibody that binds a cancer antigen and is cytotoxic and has been modified at one or more sites in the Fc region, according to the invention, to bind FcγRIIIA and/or FcγRIIA with a higher affinity than the parent therapeutic antibody, and/or mediates effector function (e.g., ADCC, phagocytosis) more effectively. In another embodiment, the invention provides methods of preventing or treating cancer characterized by a cancer antigen, using a therapeutic antibody that binds a cancer antigen and is cytotoxic, and has been engineered according to the invention to bind FcγRIIIA and/or FcγRIIA with a higher affinity and bind FcγRIIB with a lower affinity than the parent therapeutic antibody, and/or mediates effector function (e.g., ADCC, phagocytosis) more effectively. The therapeutic antibodies that have been engineered according to the invention are useful for prevention or treatment of cancer, since they have an enhanced cytotoxic activity (e.g., enhanced tumor cell killing and/or enhanced for example, ADCC activity or CDC activity).

Cancers associated with a cancer antigen may be treated or prevented by administration of a therapeutic antibody that binds a cancer antigen and is cytotoxic, and has been engineered according to the methods of the invention to have, for example, an enhanced effector function. In one particular embodiment, the therapeutic antibodies engineered according to the methods of the invention enhance the antibody-mediated cytotoxic effect of the antibody directed at the particular cancer antigen. For example, but not by way of limitation, cancers associated with the following cancer antigens may be treated or prevented by the methods and compositions of the invention: KS1/4 pan-carcinoma antigen (Perez and Walker, 1990, *J. Immunol.* 142:32-37; Bumal, 1988, *Hybridoma* 7(4):407-415), ovarian carcinoma antigen (CA125) (Yu et al., 1991, *Cancer Res.* 51(2):48-475), prostatic acid phosphate (Tailor et al., 1990, *Nucl. Acids Res.* 18(1):4928), prostate specific antigen (Henttu and Vihko, 1989, *Biochem. Biophys. Res. Comm.* 10(2):903-910; Israeli et al., 1993, *Cancer Res.* 53:227-230), melanoma-associated antigen p97 (Estin et al., 1989, *J. Natl. Cancer Instit.* 81(6): 445-44), melanoma antigen gp75 (Vijayasardahl et al., 1990, *J. Exp. Med.* 171(4):1375-1380), high molecular weight melanoma antigen (HMW-MAA) (Natali et al., 1987, *Cancer* 59:55-3; Mittelman et al., 1990, *J. Clin. Invest.* 86:2136-2144)), prostate specific membrane antigen, carcinoembryonic antigen (CEA) (Foon et al., 1994, *Proc. Am. Soc. Clin. Oncol.* 13:294), polymorphic epithelial mucin antigen, human milk fat globule antigen, Colorectal tumor-associated antigens such as: CEA, TAG-72 (Yokata et al., 1992, *Cancer Res.* 52:3402-3408), CO017-1A (Ragnhammar et al., 1993, *Int. J. Cancer* 53:751-758); GICA 19-9 (Herlyn et al., 1982, *J. Clin. Immunol.* 2:135), CTA-1 and LEA, Burkitt's lymphoma antigen-38.13, CD19 (Ghetie et al., 1994, *Blood* 83:1329-1336), human B-lymphoma antigen-CD20 (Reff et al., 1994, *Blood* 83:435-445), CD33 (Sgouros et al., 1993, *J. Nucl. Med.* 34:422-430), melanoma specific antigens such as ganglioside GD2 (Saleh et al., 1993, *J. Immunol.*, 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12:1036-1044), ganglioside GM3 (Hoon et al., 1993, *Cancer Res.* 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46:3917-3923), antigens of fibrosarcoma, human leukemia T cell antigen-Gp37 (Bhattacharya-Chatterjee et al., 1988, *J. of Immun.* 141:1398-1403), neoglycoprotein, sphingolipids, breast cancer antigen such as EGFR (Epidermal growth factor receptor), HER2 antigen (p185$^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, *Science* 245:301-304), differentiation antigen (Feizi, 1985, *Nature* 314:53-57) such as I antigen found in fetal erythrocytes and primary endoderm, I(Ma) found in gastric adencarcinomas, M18 and M39 found in breast epithelium, SSEA-1 found in myeloid cells, VEP8, VEP9, My1, VIM-D5, and $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma, CO-514 (blood group Le$^a$) found in adenocarcinoma, NS-10 found in adenocarcinomas, CO-43 (blood group Le$^b$), G49, EGF receptor, (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson, 1998, *The Cancer Journal* 4:62).

Cancers and related disorders that can be treated or prevented by methods and compositions of the present invention include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and ciliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma, gallbladder cancers including but not limited to, adenocarcinoma; cholangiocarcinomas including but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, superficial spreading melanoma, nodular melanoma, lentigo malignant melanoma, acral lentiginous melanoma; kidney cancers including but not limited to, renal cell cancer, adenocarcinoma, hypernephroma, fibrosarcoma, transitional cell cancer (renal pelvis and/or uterer); Wilms' tumor; bladder cancers including but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, prostate, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

In a specific embodiment, a molecule of the invention (e.g., an antibody comprising a variant Fc region, or a therapeutic monoclonal antibody engineered according to the methods of the invention) inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in the absence of said molecule of the invention.

4.4.1.1 Combination Therapy

The invention further encompasses administering the molecules of the invention in combination with other therapies known to those skilled in the art for the treatment or prevention of cancer, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more anti-cancer agents, therapeutic antibodies (e.g., antibodies listed in Table 9A), or other agents known to those skilled in the art for the treatment and/or prevention of cancer (See Section 5.4.1.2).

In certain embodiments, one or more molecule of the invention is administered to a mammal, preferably a human, concurrently with one or more other therapeutic agents useful for the treatment of cancer. The term "concurrently" is not limited to the administration of prophylactic or therapeutic agents at exactly the same time, but rather it is meant that a molecule of the invention and the other agent are administered to a mammal in a sequence and within a time interval such that the molecule of the invention can act together with the other agent to provide an increased benefit than if they were administered otherwise. For example, each prophylactic or therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

In other embodiments, the prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active. One skilled in the art would be able to determine such a time frame by determining the half life of the administered agents.

In certain embodiments, the prophylactic or therapeutic agents of the invention are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic agents are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

In other embodiments, courses of treatment are administered concurrently to a mammal, i.e., individual doses of the therapeutics are administered separately yet within a time interval such that molecules of the invention can work together with the other agent or agents. For example, one component may be administered one time per week in combination with the other components that may be administered one time every two weeks or one time every three weeks. In other words, the dosing regimens for the therapeutics are carried out concurrently even if the therapeutics are not administered simultaneously or within the same patient visit.

When used in combination with other prophylactic and/or therapeutic agents, the molecules of the invention and the prophylactic and/or therapeutic agent can act additively or, more preferably, synergistically. In one embodiment, a molecule of the invention is administered concurrently with one or more therapeutic agents in the same pharmaceutical composition. In another embodiment, a molecule of the invention is administered concurrently with one or more other therapeutic agents in separate pharmaceutical compositions. In still another embodiment, a molecule of the invention is administered prior to or subsequent to administration of another prophylactic or therapeutic agent. The invention contemplates administration of a molecule of the invention in combination with other prophylactic or therapeutic agents by the same or different routes of administration, e.g., oral and parenteral. In certain embodiments, when a molecule of the invention is administered concurrently with another prophylactic or therapeutic agent that potentially produces adverse side effects including, but not limited to, toxicity, the prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

4.4.1.2 Other Therapeutic/Prophylactic Agents

In a specific embodiment, the methods of the invention encompass the administration of one or more molecules of the invention with one or more therapeutic agents used for the treatment and/or prevention of cancer. In one embodiment, angiogenesis inhibitors may be administered in combination with the molecules of the invention. Angiogenesis inhibitors that can be used in the methods and compositions of the invention include but are not limited to: Angiostatin (plasminogen fragment); antiangiogenic antithrombin III; Angiozyme™; ABT-627; Bay 12-9566™; Benefin™; Bevacizumab; BMS-275291 ™; cartilage-derived inhibitor (CDI); CAI; CD59 complement fragment; CEP-7055™; Col 3; Combretastatin A-4; Endostatin (collagen XVIII fragment); Fibronectin fragment; Gro-beta; Halofuginone; Heparinases; Heparin hexasaccharide fragment; HMV833™; Human chorionic gonadotropin (hCG); IM-862™; Interferon alpha/beta/gamma; Interferon inducible protein (IP-10); Interleukin-12; Kringle 5 (plasminogen fragment); Marimastat™; Metalloproteinase inhibitors (TIMPs); 2-Methoxyestradiol; MMI 270 (CGS 27023A); MoAb IMC-1C11™; Neovastat™; NM-3; Panzem™; PI-88; Placental ribonuclease inhibitor; Plasminogen activator inhibitor; Platelet factor-4 (PF4); Prinomastat™; Prolactin 16 kD fragment; Proliferin-related protein (PRP); PTK 787/ZK 222594; Retinoids; Solimastat™; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Anti-cancer agents that can be used in combination with the molecules of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine;

dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in methods of the invention include but are not limited to ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Smart M195 which is a humanized anti-CD33 IgG antibody (Protein Design Lab/Kanebo); LYMPHOCIDE™ which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVAT™ is a humanized anti-CD40L IgG antibody (Biogen); ANTEGREN™ is a humanized anti-VLA-4 IgG antibody (Elan); and CAT-152 is a human anti-TGF-$β_2$ antibody (Cambridge Ab Tech). Other examples of therapeutic antibodies that can be used in accordance with the invention are presented in Table 9A.

4.4.2 Autoimmune Disease and Inflammatory Diseases

In some embodiments, molecules of the invention comprise a variant Fc region, having one or more amino acid modifications in one or more regions, which modification increases the affinity of the variant Fc region for FcγRIIB but decreases the affinity of the variant Fc region for FcγRIIIA and/or FcγRIIA. Molecules of the invention with such binding characteristics are useful in regulating the immune response, e.g., in inhibiting the immune response in connection with autoimmune diseases or inflammatory diseases. Although not intending to be bound by any mechanism of action, molecules of the invention with an enhanced affinity for FcγRIIB and a decreased affinity for FcγRIIIA and/or FcγRIIA may lead to dampening of the activating response to FcγR and inhibition of cellular responsiveness.

In some embodiments, a molecule of the invention comprising a variant Fc region is not an immunoglobulin, and comprises at least one amino acid modification which modification increases the affinity of the variant Fc region for FcγRIIB relative to a molecule comprising a wild-type Fc region. In other embodiments, said molecule further comprises one or more amino acid modifications, which modifications decreases the affinity of the molecule for an activating FcγR. In some embodiments, the molecule is a soluble (i.e., not membrane bound) Fc region. The invention contemplates other amino acid modifications within the soluble Fc region which modulate its affinity for various Fc receptors, including those known to one skilled in the art as described herein. In other embodiments, the molecule (e.g., the Fc region comprising at least one or more amino acid modification) is modified using techniques known to one skilled in the art and as described herein to increase the in vivo half life of the Fc region. Such molecules have therapeutic utility in treating and/or preventing an autoimmune disorder. Although not intending to be bound by any mechanism of actions, such molecules with enhanced affinity for FcγRIIB will lead to a dampening of the activating receptors and thus a dampening of the immune response and have therapeutic efficacy for treating and/or preventing an autoimmune disorder.

In certain embodiments, the one or more amino acid modifications, which increase the affinity of the variant Fc region for FcγRIIB but decrease the affinity of the variant Fc region for FcγRIIIA comprise a substitution at position 246 with threonine and at position 396 with histidine; or a substitution at position 268 with aspartic acid and at position 318 with aspartic acid; or a substitution at position 217 with serine, at position 378 with valine, and at position 408 with arginine; or a substitution at position 375 with cysteine and at position 396 with leucine; or a substitution at position 246 with isolcucine and at position 334 with asparagine. In one embodiment, the one or more amino acid modifications, which increase the affinity of the variant Fc region for FcγRIIB but decrease the affinity of the variant Fc region for FcγRIIIA comprise a substitution at position 247 with leucine. In another embodiment, the one or more amino acid modification, which increases the affinity of the variant Fc region for FcγRIIB but decreases the affinity of the variant Fc region for FcγRIIIA comprise a substitution at position 372 with tyrosine. In yet another embodiment, the one or more amino acid modification, which increases the affinity of the variant Fc region for FcγRIIB but decreases the affinity of the variant Fc region for FcγRIIIA comprise a substitution at position 326 with glutamic acid. In one embodiment, the one or more amino acid modification, which increases the affinity of the variant Fc region for FcγRIIB but decreases the affinity of the variant Fc region for FcγRIIIA comprise a substitution at position 224 with leucine.

The variant Fc regions that have an enhanced affinity for FcγRIIB and a decreased affinity for FcγRIIIA and/or FcγRIIA relative to a comparable molecule comprising a wild-type Fc region, may be used to treat or prevent autoimmune diseases or inflammatory diseases. The present invention provides methods of preventing, treating, or managing one or more symptoms associated with an autoimmune or inflammatory disorder in a subject, comprising administering to said subject a therapeutically or prophylactically effective amount of one or more molecules of the invention with variant Fc regions that have an enhanced affinity for FcγRIIB and a decreased affinity for FcγRIIIA and or FcγRIIA relative to a comparable molecule comprising a wild type Fc region.

The invention also provides methods for preventing, treating, or managing one or more symptoms associated with an inflammatory disorder in a subject further comprising, administering to said subject a therapeutically or prophylactically effective amount of one or more anti-inflammatory agents. The invention also provides methods for preventing, treating, or managing one or more symptoms associated with an autoimmune disease further comprising, administering to said subject a therapeutically or prophylactically effective amount of one or more immunomodulatory agents. Section 5.4.2.1 provides non-limiting examples of anti-inflammatory agents and immunomodulatory agents.

Examples of autoimmune disorders that may be treated by administering the molecules of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteritis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described herein in Section 2.2.2, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

Molecules of the invention with variant Fc regions that have an enhanced affinity for FcγRIIB and a decreased affinity for FcγRIIIA relative to a comparable molecule comprising a wild-type Fc region can also be used to reduce the inflammation experienced by animals, particularly mammals, with inflammatory disorders. In a specific embodiment, a molecule of the invention reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal, which is not administered the said molecule.

Molecules of the invention with variant Fc regions that have an enhanced affinity for FcγRIIB and a decreased affinity for FcγRIIIA relative to a comparable molecule comprising a wild-type Fc region can also be used to prevent the rejection of transplants.

The invention further contemplates engineering any of the antibodies known in the art for the treatment and/or prevention of autoimmune disease or inflammatory disease, so that the antibodies comprise a variant Fc region comprising one or more amino acid modifications, which have been identified by the methods of the invention to have an enhanced affinity for FcγRIIB and a decreased affinity for FcγRIIIA relative to a comparable molecule comprising a wild type Fc region. A non-limiting example of the antibodies that are used for the treatment or prevention of inflammatory disorders which can be engineered according to the invention is presented in Table 10A, and a non-limiting example of the antibodies that are used for the treatment or prevention of autoimmune disorder is presented in Table 10B.

TABLE 10A

ANTIBODIES FOR INFLAMMATORY DISEASES AND AUTOIMMUNE DISEASES THAT CAN ENGINEERED IN ACCORDANCE WITH THE INVENTION.

| Antibody Name | Target Antigen | Product Type | Isotype | Sponsors | Indication |
|---|---|---|---|---|---|
| 5G1.1 | Complement (C5) | Humanized | IgG | Alexion Pharm Inc | Rheumatoid Arthritis |
| 5G1.1 | Complement (C5) | Humanized | IgG | Alexion Pharm Inc | SLE |
| 5G1.1 | Complement (C5) | Humanized | IgG | Alexion Pharm Inc | Nephritis |
| 5G1.1-SC | Complement (C5) | Humanized | ScFv | Alexion Pharm Inc | Cardiopulmonary Bypass |
| 5G1.1-SC | Complement (C5) | Humanized | ScFv | Alexion Pharm Inc | Myocardial Infarction |
| 5G1.1-SC | Complement (C5) | Humanized | ScFv | Alexion Pharm Inc | Angioplasty |
| ABX-CBL | CBL | Human | | Abgenix Inc | GvHD |
| ABX-CBL | CD147 | Murine | IgG | Abgenix Inc | Allograft rejection |
| ABX-IL8 | IL-8 | Human | IgG2 | Abgenix Inc | Psoriasis |
| Antegren | VLA-4 | Humanized | IgG | Athena/Elan | Multiple Sclerosis |
| Anti-CD11a | CD11a | Humanized | IgG1 | Genentech Inc/Xoma | Psoriasis |
| Anti-CD18 | CD18 | Humanized | Fab'2 | Genentech Inc | Myocardial infarction |
| Anti-LFA1 | CD18 | Murine | Fab'2 | Pasteur-Merieux/ Immunotech | Allograft rejection |
| Antova | CD40L | Humanized | IgG | Biogen | Allograft rejection |
| Antova | CD40L | Humanized | IgG | Biogen | SLE |
| BTI-322 | CD2 | Rat | IgG | Medimmune Inc | GvHD, Psoriasis |
| CDP571 | TNF-alpha | Humanized | IgG4 | Celltech | Crohn's |
| CDP571 | TNF-alpha | Humanized | IgG4 | Celltech | Rheumatoid Arthritis |
| CDP850 | E-selectin | Humanized | | Celltech | Psoriasis |
| Corsevin M | Fact VII | Chimeric | | Centocor | Anticoagulant |
| D2E7 | TNF-alpha | Human | | CAT/BASF | Rheumatoid Arthritis |
| Hu23F2G | CD11/18 | Humanized | | ICOS Pharm Inc | Multiple Sclerosis |
| Hu23F2G | CD11/18 | Humanized | IgG | ICOS Pharm Inc | Stroke |
| IC14 | CD14 | | | ICOS Pharm Inc | Toxic shock |
| ICM3 | ICAM-3 | Humanized | | ICOS Pharm Inc | Psoriasis |
| IDEC-114 | CD80 | Primatised | | IDEC Pharm/Mitsubishi | Psoriasis |
| IDEC-131 | CD40L | Humanized | | IDEC Pharm/Eisai | SLE |
| IDEC-131 | CD40L | Humanized | | IDEC Pharm/Eisai | Multiple Sclerosis |
| IDEC-151 | CD4 | Primatised | IgG1 | IDEC Pharm/Glaxo SmithKline | Rheumatoid Arthritis |
| IDEC-152 | CD23 | Primatised | | IDEC Pharm | Asthma/Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 | beta2-integrin | Humanized | IgG | Millennium Inc (LeukoSite Inc.) | Stroke |
| LDP-01 | beta2-integrin | Humanized | IgG | Millennium Inc (LeukoSite Inc.) | Allograft rejection |
| LDP-02 | alpha4beta7 | Humanized | | Millennium Inc (LeukoSite Inc.) | Ulcerative Colitis |
| MAK-195F | TNF alpha | Murine | Fab'2 | Knoll Pharm, BASF | Toxic shock |
| MDX-33 | CD64 (FcR) | Human | | Medarex/Centeon | Autoimmune haematogical disorders |

TABLE 10A-continued

ANTIBODIES FOR INFLAMMATORY DISEASES AND AUTOIMMUNE DISEASES THAT CAN ENGINEERED IN ACCORDANCE WITH THE INVENTION.

| Antibody Name | Target Antigen | Product Type | Isotype | Sponsors | Indication |
|---|---|---|---|---|---|
| MDX-CD4 | CD4 | Human | IgG | Medarex/Eisai/Genmab | Rheumatoid Arthritis |
| MEDI-507 | CD2 | Humanized | | Medimmune Inc | Psoriasis |
| MEDI-507 | CD2 | Humanized | | Medimmune Inc | GvHD |
| OKT4A | CD4 | Humanized | IgG | Ortho Biotech | Allograft rejection |
| OrthoClone OKT4A | CD4 | Humanized | IgG | Ortho Biotech | Autoimmune disease |
| Orthoclone/anti-CD3 OKT3 | CD3 | Murine | mIgG2a | Ortho Biotech | Allograft rejection |
| RepPro/Abciximab | gpIIbIIIa | Chimeric | Fab | Centocor/Lilly | Complications of coronary angioplasty |
| rhuMab-E25 | IgE | Humanized | IgG1 | Genentech/Novartis/Tanox Biosystems | Asthma/Allergy |
| SB-240563 | IL5 | Humanized | | GlaxoSmithKline | Asthma/Allergy |
| SB-240683 | IL-4 | Humanized | | GlaxoSmithKline | Asthma/Allergy |
| SCH55700 | IL-5 | Humanized | | Celltech/Schering | Asthma/Allergy |
| Simulect | CD25 | Chimeric | IgG1 | Novartis Pharm | Allograft rejection |
| SMART a-CD3 | CD3 | Humanized | | Protein Design Lab | Autoimmune disease |
| SMART a-CD3 | CD3 | Humanized | | Protein Design Lab | Allograft rejection |
| SMART a-CD3 | CD3 | Humanized | IgG | Protein Design Lab | Psoriasis |
| Zenapax | CD25 | Humanized | IgG1 | Protein Design Lab/Hoffman-La Roche | Allograft rejection |

TABLE 10B

ANTIBODIES FOR AUTOIMMUNE DISORDERS THAT CAN BE ENGINEERED IN ACCORDANCE WITH THE INVENTION

| Antibody | Indication | Target Antigen |
|---|---|---|
| ABX-RB2 | | antibody to CBL antigen on T cells, B cells and NK cells fully human antibody from the Xenomouse |
| 5c8 (Anti CD-40 ligand antibody) | Phase II trials were halted in Oct. 99 examine "adverse events" | CD-40 |
| IDEC 131 | systemic lupus erythyematous (SLE) | anti CD40 humanized |
| IDEC 151 | rheumatoid arthritis | primatized; anti-CD4 |
| IDEC 152 | Asthma | primatized; anti-CD23 |
| IDEC 114 | Psoriasis | primatized anti-CD80 |
| MEDI-507 | rheumatoid arthritis; multiple sclerosis Crohn's disease Psoriasis | anti-CD2 |
| LDP-02 (anti-b7 mAb) | inflammatory bowel disease Chron's disease ulcerative colitis | a4b7 integrin receptor on white blood cells (leukocytes) |
| SMART Anti-Gamma Interferon antibody | autoimmune disorders | Anti-Gamma Interferon |
| Verteportin | rheumatoid arthritis | |
| MDX-33 | blood disorders caused by autoimmune reactions Idiopathic Thrombocytopenia Purpurea (ITP) autoimmune hemolytic anemia | monoclonal antibody against FcRI receptors |

TABLE 10B-continued

ANTIBODIES FOR AUTOIMMUNE DISORDERS THAT CAN BE ENGINEERED IN ACCORDANCE WITH THE INVENTION

| Antibody | Indication | Target Antigen |
|---|---|---|
| MDX-CD4 | treat rheumatoid arthritis and other autoimmunity | monoclonal antibody against CD4 receptor molecule |
| VX-497 | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 | rheumatoid arthritis | inhibitor of ICE interleukin-1 beta (converting enzyme controls pathways leading to aggressive immune response) |
| VX-745 | specific to inflammation involved in chemical signalling of immune response onset and progression of inflammation | inhibitor of P38MAP kinase mitogen activated protein kinase |
| Enbrel (etanercept) | | targets TNF (tumor necrosis factor) |
| IL-8 | | fully human monoclonal antibody against IL-8 (interleukin 8) |
| Apogen MP4 | | recombinant antigen selectively destroys disease associated T-cells induces apoptosis T-cells eliminated by programmed cell death no longer attack body's own cells specific apogens target specific T-cells |

4.4.2.1 Immunomodulatory Agents and Anti-Inflammatory Agents

The present invention provides methods of treatment for autoimmune diseases and inflammatory diseases comprising administration of the molecules with variant Fc regions having an enhanced affinity for FcγRIIB and a decreased affinity for FcγRIIIA and/or FcγRIIA in conjunction with other treatment agents. Examples of immunomodulatory agents include, but are not limited to, methothrexate, ENBREL, REMICADE™, leflunomide, cyclophosphamide, cyclosporine A, and macrolide antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINET™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

4.4.3 Infectious Disease

The invention also encompasses methods for treating or preventing an infectious disease in a subject comprising administering a therapeutically or prophylactically effective amount of one or more molecules of the invention. Infectious diseases that can be treated or prevented by the molecules of the invention are caused by infectious agents including but not limited to viruses, bacteria, fungi, protozae, and viruses.

Viral diseases that can be treated or prevented using the molecules of the invention in conjunction with the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases that can be treated or prevented using the molecules of the invention in conjunction with the methods of the present invention, that are caused by bacteria include, but are not limited to, *mycobacteria rickettsia, mycoplasma, neisseria, S. pneumonia, Borrelia burgdorferi* (Lyme disease), *Bacillus antracis* (anthrax), tetanus, *streptococcus, staphylo-*

*coccus, mycobacterium*, tetanus, pertissus, cholera, plague, diptheria, *chlamydia, S. aureus* and *legionella*.

Protozoal diseases that can be treated or prevented using the molecules of the invention in conjunction with the methods of the present invention, that are caused by protozoa include, but are not limited to, *leishmania*, kokzidioa, *trypanosoma* or malaria.

Parasitic diseases that can be treated or prevented using the molecules of the invention in conjunction with the methods of the present invention, that are caused by parasites include, but are not limited to, *chlamydia* and *rickettsia*.

According to one aspect of the invention, molecules of the invention comprising variant Fc regions have an enhanced antibody effector function towards an infectious agent, e.g., a pathogenic protein, relative to a comparable molecule comprising a wild-type Fc region. Examples of infectious agents include but are not limited to bacteria (e.g., *Escherichia coli, Klebsiella pneumoniae, Staphylococcus aureus, Enterococcus faecials, Candida albicans, Proteus vulgaris, Staphylococcus viridans*, and *Pseudomonas aeruginosa*), a pathogen (e.g., B-lymphotropic papovavirus (LPV); *Bordatella pertussis*; Borna Disease virus (BDV); Bovine coronavirus; Choriomeningitis virus; Dengue virus; a virus, *E. coli*; Ebola; Echovirus 1; Echovirus-11 (EV); Endotoxin (LPS); Enteric bacteria; Enteric Orphan virus; Enteroviruses; Feline leukemia virus; Foot and mouth disease virus; Gibbon ape leukemia virus (GALV); Gram-negative bacteria; *Heliobacter pylori*; Hepatitis B virus (HBV); Herpes Simplex Virus; HIV-1; Human cytomegalovirus; Human coronovirus; Influenza A, B & C; *Legionella; Leishmania mexicana; Listeria monocytogenes*; Measles virus; Meningococcus; Morbilliviruses; Mouse hepatitis virus; Murine leukemia virus; Murine gamma herpes virus; Murine retrovirus; Murine coronavirus mouse hepatitis virus; *Mycobacterium avium*-M; *Neisseria gonorrhoeae*; Newcastle disease virus; Parvovirus B19; *Plasmodium falciparum*; Pox Virus; *Pseudomonas*; Rotavirus; *Samonella typhiurium; Shigella; Streptococci*; T-cell lymphotropic virus 1; Vaccinia virus).

In a specific embodiment, molecules of the invention enhance the efficacy of treatment of an infectious disease by enhancing phagocytosis and/or opsonization of the infectious agent causing the infectious disease. In another specific embodiment, molecules of the invention enhance the efficacy of treatment of an infectious disease by enhancing ADCC of infected cells causing the infectious disease.

In some embodiments, the molecules of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with antibiotics known to those skilled in the art for the treatment and or prevention of an infectious disease. Antibiotics that can be used in combination with the molecules of the invention include, but are not limited to, macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

In certain embodiments, the molecules of the invention can be administered in combination with a therapeutically or prophylactically effective amount of one or more antifungal agents. Antifungal agents that can be used in combination with the molecules of the invention include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

In some embodiments, the molecules of the invention can be administered in combination with a therapeutically or prophylactically effective amount of one or more anti-viral agent. Useful anti-viral agents that can be used in combination with the molecules of the invention include, but are not limited to, protease inhibitors, nucleoside reverse transcriptase inhibitors, non-nucleoside reverse transcriptase inhibitors and nucleoside analogs. Examples of antiviral agents include but are not limited to zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, the alpha-interferons; adefovir, clevadine, entecavir, pleconaril.

4.5 Vaccine Therapy

The invention further encompasses using a composition of the invention to induce an immune response against an antigenic or immunogenic agent, including but not limited to cancer antigens and infectious disease antigens (examples of which are disclosed infra). The vaccine compositions of the invention comprise one or more antigenic or immunogenic agents to which an immune response is desired, wherein the one or more antigenic or immunogenic agents is coated with a variant antibody of the invention that has an enhanced affinity to FcγRIIIA Although not intending to be bound by a particular mechanism of action, coating an antigenic or immunogenic agent with a variant antibody of the invention that has an enhanced affinity to FcγRIIIA, enhances the immune response to the desired antigenic or immunogenic agent by inducing humoral and cell-mediated responses. The vaccine compositions of the invention are particularly effective in eliciting an immune response, preferably a protective immune response against the antigenic or immunogenic agent.

In some embodiments, the antigenic or immunogenic agent in the vaccine compositions of the invention comprise a virus against which an immune response is desired. The viruses may be recombinant or chimeric, and are preferably attenuated. Production of recombinant, chimeric, and attenuated viruses may be performed using standard methods known to one skilled in the art. The invention encompasses a live recombinant viral vaccine or an inactivated recombinant viral vaccine to be formulated in accordance with the invention. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus is non-pathogenic to the subject to which it is administered. In this regard, the use of genetically engineered viruses for vaccine purposes may require the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaptation can be made into deletion mutations. These mutations should be more stable than the point mutations associated with cold or temperature sensitive mutants and reversion frequencies should be extremely low. Recombinant DNA technologies for engineering recombinant viruses are known in the art and encompassed in the invention. For example, techniques for modifying negative strand RNA viruses are known in the art, see, e.g., U.S. Pat. No. 5,166,057, which is incorporated herein by reference in its entirety.

Alternatively, chimeric viruses with "suicide" characteristics may be constructed for use in the intradermal vaccine formulations of the invention. Such viruses would go through only one or a few rounds of replication within the host. When used as a vaccine, the recombinant virus would go through limited replication cycle(s) and induce a sufficient level of immune response but it would not go further in the human host and cause disease. Alternatively, inactivated (killed) virus may be formulated in accordance with the invention. Inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled.

In certain embodiments, completely foreign epitopes, including antigens derived from other viral or non-viral pathogens can be engineered into the virus for use in the intradermal vaccine formulations of the invention. For example, antigens of non-related viruses such as HIV (gp160, gp120, gp41) parasite antigens (e.g., malaria), bacterial or fungal antigens or tumor antigens can be engineered into the attenuated strain.

Virtually any heterologous gene sequence may be constructed into the chimeric viruses of the invention for use in the intradermal vaccine formulations. Preferably, heterologous gene sequences are moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to, influenza and parainfluenza hemagglutinin neuraminidase and fusion glycoproteins such as the HN and F genes of human PIV3. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

In yet other embodiments, the invention encompasses pathogenic cells or viruses, preferably attenuated viruses, which express the variant antibody on their surface.

In alternative embodiments, the vaccine compositions of the invention comprise a fusion polypeptide wherein an antigenic or immunogenic agent is operatively linked to a variant antibody of the invention that has an enhanced affinity for FcγRIIIA Engineering fusion polypeptides for use in the vaccine compositions of the invention is performed using routine recombinant DNA technology methods and is within the level of ordinary skill.

The invention further encompasses methods to induce tolerance in a subject by administering a composition of the invention. Preferably a composition suitable for inducing tolerance in a subject comprises an antigenic or immunogenic agent coated with a variant antibody of the invention, wherein the variant antibody has a higher affinity to FcγRIIB. Although not intending to be bound by a particular mechanism of action, such compositions are effective in inducing tolerance by activating the FcγRIIB meditated inhibitory pathway.

4.6 Compositions and Methods of Administering

The invention provides methods and pharmaceutical compositions comprising molecules of the invention (i.e., antibodies, polypeptides) comprising variant Fc regions. The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, an antibody, a fusion protein, or a conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human. In yet another preferred embodiment, the antibody of the invention is from the same species as the subject.

Various delivery systems are known and can be used to administer a composition comprising molecules of the invention (i.e., antibodies, polypeptides), comprising variant Fc regions, e.g., encapsulation in liposomes, microparticles, microcapsules, recombinant cells capable of expressing the antibody or fusion protein, receptor-mediated endocytosis (See, e.g., Wu and Wu, 1987, *J. Biol. Chem.* 262:4429-4432), construction of a nucleic acid as part of a retroviral or other vector, etc. Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the molecules of the invention (i.e., antibodies, polypeptides) comprising variant Fc regions, are packaged in a hermetically sealed container such as an ampoule or sachette indicating the quantity of antibody. In one embodiment, the molecules of the invention are supplied as a dry sterilized lyophilized powder or water free concentrate in a hermetically sealed container and can be reconstituted, e.g., with water or saline to the appropriate concentration for administration to a subject. Preferably, the molecules of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized molecules of the invention should be stored at between 2 and 8° C. in their original container and the molecules should be administered within 12 hours, preferably within 6 hours, within 5 hours, within 3 hours, or within 1 hour after being reconstituted. In an alternative embodiment, molecules of the invention are supplied in liquid form in a hermetically sealed container indicating the quantity and concentration of the molecule, fusion protein, or conjugated molecule. Preferably, the liquid form of the molecules of the invention are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the molecules.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of the molecules of the invention administered to a patient are 0.01 mg to 1000 mg/day, when used as single agent therapy. In another embodiment the molecules of the invention are used in combination with other therapeutic compositions and the dosage administered to a patient are lower than when said molecules are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer, *Science* 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 3 17-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in its entirety. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., *Medical Applications of Controlled Release*, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; See also Levy et al., 1985, *Science* 228:190; During et al., 1989, Ann. Neurol. 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage and frequency of administration of antibodies of the invention may be reduced also by enhancing uptake and tissue penetration (e.g., into the lung) of the antibodies or fusion proteins by modifications such as, for example, lipidation.

Treatment of a subject with a therapeutically or prophylactically effective amount of molecules of the invention can include a single treatment or, preferably, can include a series of treatments. In a preferred example, a subject is treated with molecules of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

4.6.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of one or more molecules of the invention and a pharmaceutically acceptable carrier.

In one particular embodiment, the pharmaceutical composition comprises a therapeutically effective amount of one or more molecules of the invention comprising a variant Fc region, wherein said variant Fc region binds FcγRIIIA and/or FcγRIIA with a greater affinity than a comparable molecule comprising a wild-type Fc region binds FcγRIIIA and/or FcγRIIA and/or said variant Fc region mediates an effector function at least 2-fold more effectively than a comparable molecule comprising a wild-type Fc region, and a pharmaceutically acceptable carrier. In another embodiment, the pharmaceutical composition comprises a therapeutically effective amount of one or more molecules of the invention comprising a variant Fc region, wherein said variant Fc region binds FcγRIIIA with a greater affinity than a comparable molecule comprising a wild-type Fc region binds FcγRIIIA, and said variant Fc region binds FcγRIIB with a lower affinity than a comparable molecule comprising a wild-type Fc region binds FcγRIIB, and/or said variant Fc region mediates an effector function at least 2-fold more effectively than a comparable molecule comprising a wild-type Fc region, and a pharmaceutically acceptable carrier. In another embodiment, said pharmaceutical compositions further comprise one or more anti-cancer agents.

The invention also encompasses pharmaceutical compositions comprising a therapeutic antibody (e.g., tumor specific monoclonal antibody) that is specific for a particular cancer antigen, comprising one or more amino acid modifications in the Fc region as determined in accordance with the instant invention, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

4.6.2 Gene Therapy

In a specific embodiment, nucleic acids comprising sequences encoding molecules of the invention, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available in the art can be used according to the present invention. Exemplary methods are described below.

For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, Science 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990).

In a preferred aspect, a composition of the invention comprises nucleic acids encoding an antibody, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, 1989, *Proc. Natl. Acad. Sci. USA* 86:8932-8935; and Zijlstra et al., 1989, *Nature* 342:435-438).

In another preferred aspect, a composition of the invention comprises nucleic acids encoding a fusion protein, said nucleic acids being a part of an expression vector that expresses the fusion protein in a suitable host. In particular, such nucleic acids have promoters, preferably heterologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (See, e.g., Wu and Wu, 1987, *J. Biol. Chem.* 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (See, e.g., PCT Publications WO 92/06180; WO 92/22635; W092/20316; W093/14188; WO 93/20221). Alternatively, the nucleic acid can be introduced intracellularly and incorporated within host cell DNA for expression, by homologous recombination (Koller and Smithies, 1989, *Proc. Natl. Acad. Sci. USA* 86:8932-8935; and Zijlstra et al., 1989, *Nature* 342:435-438).

In a specific embodiment, viral vectors that contain nucleic acid sequences encoding a molecule of the invention (e.g., an antibody or a fusion protein) are used. For example, a retroviral vector can be used (See Miller et al., 1993, *Meth. Enzymol.* 217:581-599). These retroviral vectors contain the components necessary for the correct packaging of the viral genome and integration into the host cell DNA. The nucleic acid sequences encoding the antibody or a fusion protein to be used in gene therapy are cloned into one or more vectors, which facilitates delivery of the nucleotide sequence into a subject. More detail about retroviral vectors can be found in Boesen et al., (1994, *Biotherapy* 6:291-302), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, *J. Clin. Invest.* 93:644-651; Klein et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (*Current Opinion in Genetics and Development* 3:499-503, 1993, present a review of adenovirus-based gene therapy. Bout et al., (*Human Gene Therapy*, 5:3-10, 1994) demonstrated the use of adenovirus vectors to transfer genes to the respiratory epithelia of rhesus monkeys. Other instances of the use of adenoviruses in gene therapy can be found in Rosenfeld et al., 1991, *Science* 252:431-434; Rosenfeld et al., 1992, *Cell* 68:143-155; Mastrangeli et al., 1993, *J. Clin. Invest.* 91:225-234; PCT Publication WO94/12649; and Wang et al., 1995, *Gene Therapy* 2:775-783. In a preferred embodiment, adenovirus vectors are used.

Adeno-associated virus (AAV) has also been proposed for use in gene therapy (see, e.g., Walsh et al., 1993, *Proc. Soc. Exp. Biol. Med.* 204:289-300 and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to, transfection, electroporation, microinjection, infection with a viral or bacteriophage vector, containing the nucleic acid sequences, cell fusion, chromosome-mediated gene transfer, microcellmediated gene transfer, spheroplast fusion, etc. Numerous techniques are known in the art for the introduction of foreign genes into cells (See, e.g., Loeffler and Behr, 1993, *Meth. Enzymol.* 217:599-618, Cohen et al., 1993, *Meth. Enzymol.* 217:618-644; and *Clin. Pharma. Ther.* 29:69-92, 1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody or a fusion protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (See e.g., PCT Publication WO 94/08598; Stemple and Anderson, 1992, *Cell* 7 1:973-985; Rheinwald, 1980, *Meth. Cell Bio.* 21A:229; and Pittelkow and Scott, 1986, *Mayo Clinic Proc.* 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

4.6.3 Kits

The invention provides a pharmaceutical pack or kit comprising one or more containers filled with the molecules of the invention (i.e., antibodies, polypeptides comprising variant Fc regions). Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

4.7 Characterization and Demonstration of Therapeutic Utility

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans. For example, assays which can be used to determine whether administration of a specific pharmaceutical composition is desired, include cell culture assays in which a patient tissue sample is grown in culture, and exposed to or otherwise contacted with a pharmaceutical composition of the invention, and the effect of such composition upon the tissue sample is observed. The tissue sample can be obtained by biopsy from the patient. This test allows the identification of the therapeutically most effective prophylactic or therapeutic molecule(s) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary. Said aspects include the temporal regime of administering the prophylactic and/or therapeutic agents, and whether such agents are administered separately or as an admixture.

Preferred animal models for use in the methods of the invention are, for example, transgenic mice expressing human FcγRs on mouse effector cells, e.g., any mouse model described in U.S. Pat. No. 5,877,396 (which is incorporated herein by reference in its entirety) can be used in the present invention. Transgenic mice for use in the methods of the invention include, but are not limited to, mice carrying human FcγRIIIA; mice carrying human FcγRIIA; mice carrying human Fc'RIIB and human FcγRIIIA; mice carrying human FcγRIIB and human FcγRIIA.

Preferably, mutations showing the highest levels of activity in the functional assays described above will be tested for use in animal model studies prior to use in humans. Antibodies harboring the Fc mutants identified using the methods of the invention and tested in ADCC assays, including ch4D5 and ch520C9, two anti-Erb-B2 antibodies, and chCC49, an anti-TAG72 antibody, are preferred for use in animal models since they have been used previously in xenograft mouse model (Hudsiak et al., 1989, *Mol. Cell. Biol.* 9: 1165-72; Lewis et al., 1993, *Cancer Immunol. Immunother.* 37: 255-63; Bergman et al., 2001 *Clin. Cancer Res.* 7: 2050-6; Johnson et al., 1995, *Anticancer Res.* 1387-93). Sufficient quantities of antibodies may be prepared for use in animal models using methods described supra, for example using mammalian expression systems and IgG purification methods disclosed and exemplified herein. A typical experiment requires at least about 5.4 mg of mutant antibody. This calculation is based on average quantities of wild type antibody required to protect 8-10 30 g mice following a loading dose of 4 g/g and a weekly maintenance dose, 2 µg/g, for ten weeks. invention encompasses tumor cell lines as a source for xenograft tumors, such as SK-BR-3, BT474 and HT29 cells which are derived from patients with breast adenocarcinoma. These cells have both Erb-B2 and the prolactin receptors on their surface. The SK-BR-3 cells have been used successfully in both ADCC and xenograft tumor models. In other assays OVCAR3 cells derived from a human ovarian adenocarcinoma may be used. These cells express the antigen TAG72 on the cell surface and can be used in conjunction with the chCC49 antibody. The use of different antibodies and multiple tumor models will circumvent loss of any specific mutations due to an antibody specific Fc mutant incompatibility.

Mouse xenograft models may be used for examining efficacy of mouse antibodies generated against a tumor specific target based on the affinity and specificity of the CDR regions of the antibody molecule and the ability of the Fc region of the antibody to elicit an immune response (Wu et al., 2001, *Trends Cell Biol.* 11: S2-9). Transgenic mice expressing human FcγRs on mouse effector cells are unique and are tailor-made animal models to test the efficacy of human Fc-FcγR interactions. Pairs of FcγRIIIA, FcγRIIIB and FcγRIIA transgenic mouse lines generated in the lab of Dr. Jeffrey Ravetch (Through a licensing agreement with Rockefeller U. and Sloan Kettering Cancer center) can be used such as those listed in the Table 11 below.

TABLE 11

Mice Strains

| Strain Background | Human FcR |
|---|---|
| Nude/CD16A KO | none |
| Nude/CD16A KO | FcγRIIIA |
| Nude/CD16A KO | FcγRIIA |
| Nude/CD16A KO | FcγRIIA and IIIA |
| Nude/CD32B KO | none |
| Nude/CD32B KO | FcγRIIB |

Preferably Fc mutants showing both enhanced binding to FcγRIIIA and reduced binding to FcγRIIB, increased activity in ADCC and phagocytosis assays are tested in animal model experiments. The animal model experiments examine the increase in efficacy of Fc mutant bearing antibodies in FcγRIIIA transgenic, nude mCD16A knockout mice compared to a control which has been administered native antibody. Preferably, groups of 8-10 mice are examined using a standard protocol. An exemplary animal model experiment may comprise the following steps: in a breast cancer model, ~$2 \times 10^6$ SK-BR-3 cells are injected subcutaneously on day 1 with 0.1 mL PBS mixed with Matrigel (Becton Dickinson). Initially a wild type chimeric antibody and isotype control are administered to establish a curve for the predetermined therapeutic dose, intravenous injection of 4D5 on day 1 with an initial dose of 4 µg/g followed by weekly injections of 2 µg/g. Tumor volume is monitored for 6-8 weeks to measure progress of the disease. Tumor volume should increase linearly with time in animals injected with the isotype control. In contrast very little tumor growth should occur in the group injected with 4D5. Results from the standard dose study are used to set an upper limit for experiments testing the Fc mutants. These studies are done using subtherapeutic doses of the Fc mutant containing antibodies. A one tenth dose was used on xenograft models in experiments done in FcγRIIB knockout mice, see, Clynes et al., 2000, *Nat. Med.* 6: 443-6, with a resultant block in tumor cell growth. Since the mutants of the invention preferrably show an increase in FcγRIIIA activation and reduction in FcγRIIB binding the mutants are examined at one tenth therapeutic dose. Examination of tumor size at different intervals indicates the efficacy of the antibodies at the lower dose. Statistical analysis of the data using t test provides a way of determining if the data is significant. Fc mutants that show increased efficacy are tested at incrementally lower doses to determine the smallest possible dose as a measure of their efficacy.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," *Inflammation*, 24(2): 141-155, (2000). Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol Med.* 111, 544-547, (1962). This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al., 1992, Scand. *J. Gastroentrol.* 27:529-537; Strober, 1985, *Dig. Dis. Sci.* 30 (12 Suppl): 3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for autoimmune disorders can also be used to assess the efficacy of the combination therapies of invention. Animal models for autoimmune disorders such as type 1 diabetes, thyroid autoimmunity, sytemic lupus eruthematosus, and glomerulonephritis have been developed (Flanders et al., 1999, *Autoimmunity* 29:235-246; Krogh et al., 1999, *Biochimie* 81:511-515; Foster, 1999, *Semin. Nephrol.* 19:12-24).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice or nude mice with human xenografts, animal models, such as hamsters, rabbits, etc. known in the art and described in *Relevance of Tumor Models for Anticancer Drug Development* (1999, eds. Fiebig and Burger); *Contributions to Oncology* (1999, Karger); *The Nude Mouse in Oncology Research* (1991, eds. Boven and Winograd); and *Anticancer Drug Development Guide* (1997 ed. Teicher), herein incorporated by reference in their entireties.

Preferred animal models for determining the therapeutic efficacy of the molecules of the invention are mouse xenograft models. Tumor cell lines that can be used as a source for xenograft tumors include but are not limited to, SKBR3 and MCF7 cells, which can be derived from patients with breast adenocarcinoma. These cells have both erbB2 and prolactin receptors. SKBR3 cells have been used routinely in the art as ADCC and xenograft tumor models. Alternatively, OVCAR3 cells derived from a human ovarian adenocarcinoma can be used as a source for xenograft tumors.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

5. EXAMPLES

Using a yeast display system, mutant human IgG1 heavy chain Fc regions were screened for modified affinity to different Fc receptors. In particular, a mutant Fc library was generated by error prone PCR (Genemorph, Stratagene), and then the mutant Fc proteins were fused to the Aga2p cell wall protein, which allowed the fusion protein to be secreted extracellularly and displayed on the yeast cell wall.

Soluble forms of the human receptors (FcγRIIIA and FcγRIIB) were cloned. Detection of the IgG1 Fc domains on the yeast cell surface, however, is hindered due to the low affinity of FcγR for its ligand. In order to circumvent this limitation, soluble FcγR tetrameric complexes were formed using an AVITAG sequence which could be enzymatically biotinylated and subsequently reacted with streptavidin conjugated to phycoerythrin (SA-PE; Molecular Probes) to form soluble tetrameric FcγR complexes. ELISA assays confirmed that the soluble FcγR tetrameric complexes had a higher avidity for human IgG1 relative to the monomeric FcγR. Fc fusion proteins on the yeast cell surface also bound the soluble FcγR tetrameric complexes as assessed by FACS analysis.

The differential binding of the Fc fusion proteins expressed on the yeast cell surface to soluble tetrameric FcγR complexes was monitored by a FACS analysis. Fc fusion proteins with altered affinities for one or more soluble tetrameric FcγR complexes were thus identified and were then incorporated into a complete immunoglobulin and expressed in mammalian cells. The mammalian expressed product was used in ELISA assays to confirm the results obtained in the yeast surface display system. Finally, the mutant Fc regions were sequenced to confirm the altered residue(s).

5.1 Cloning, Expression and Purification of FcγRIIIA

Materials and Methods

Soluble FcγRIIB and FcγRIIIA were cloned as follows. The cDNA clones for the human FcγR genes (FcγRIIB and FcγRIIIA) were obtained (gift from Ravetch lab). Soluble region of the FcγRIIIA gene (amino acids 7-203) was amplified by PCR (Table 12), digested with BamHI/HindIII and ligated into the pET25vector (Novagen). This vector was digested with SalI/NotI and a 370 by fragment was gel isolated. The vector hu3A, (gift from J. Ravetch) was digested with BamHI/SalI and a 270 by fragment containing the N-terminus of FcγRIIIA was isolated. Both fragments were coligated into pcDNA3.1 cut with BamH/NotI to create pcDNA3-FcγRIIIA (amino acids 1-203). The soluble region of FcγRIIB (amino acids 33-180) was amplified by PCR (Table 12), digested with BglII/HindIII and ligated into pET25b(+) (Novagen). This vector was digested with BamHI/NotI and a 140 bp fragment was gel isolated. The vector huRIIb1 (gift from J. Ravetch) was digested with BamHI/EcoRI and a 440 bp N-terminal FcγRIIB fragment was isolated. Both of these fragments were coligated into pcDNA3.1 cut with BamHI/NotI to create pcDNA3-FcγRIIB (amino acids 1-180). Recombinant clones were transfected into 293H cells, supernatants were collected from cell cultures, and soluble recombinant FcγR (rFcγR) proteins were purified on an IgG sepharose column.

Results

Recombinant Soluble FcγRIIIA (rFcγRIIIA) and Recombinant Soluble FcγRIIB (rFcγRIIB) were Purified to Homogeneity Subsequent to expression and purification of the recombinant soluble FcγR proteins on an IgG sepharose column, the purity and apparent molecular weight of the recombinant purified soluble receptor proteins were determined by SDS-PAGE. As shown in FIG. 1, soluble rFcγRIIIA (FIG. 1, lane 1) had the expected apparent molecular weight of ~35 KDa and soluble rFcγRIIB (FIG. 1, lane 4) had the expected apparent molecular weight of ~20 KDa. As shown in FIG. 1, soluble rFcγRIIIA migrates as a diffuse "fuzzy" band which has been attributed to the high degree of glycosylation normally found on FcγRIIIA (Jefferis, et al., 1995 *Immunol Lett.* 44, 111-117).

5.1.1 Characterization of Purified Recombinant Soluble FcγRIIIA

Materials and Methods

Purified soluble rFcγRIIIA, which was obtained as described above, was analyzed for direct binding against human monomeric or aggregated IgG using an ELISA assay. The plate is coated with 10 ng of soluble rFcγRIIIA overnight in 1×PBS. Subsequent to coating, the plate is washed three times in 1×PBS/0.1% Tween 20. Human IgG, either biotinylated monomeric IgG or biotinylated aggregated IgG, is added to the wells at a concentration ranging from 0.03 mg/mL to 2 mg/mL, and allowed to bind to the soluble rFcγRIIIA The reaction is carried out for one hour at 37° C. The plate is washed again three times with 1×PBS/0.1% Tween 20. The binding of human IgG to soluble rFcγRIIIA is detected with streptavidin horseradish peroxidase conjugate by monitoring the absorbance at 650 nm. The absorbance at 650 nm is proportional to the bound aggregated IgG.

In a blocking ELISA experiment, the ability of an FcγRIIIA monoclonal antibody, 3G8, a mouse anti-FcγRIIIA antibody (Pharmingen), to block the binding of the receptor to aggregated IgG is monitored. The washing and incubation conditions were the same as described above, except that prior to IgG addition, a 5-fold molar excess of 3G8 was added and allowed to incubate for 30 minutes at 37° C.

Results

Purified, Recombinant Soluble FcγRIIIA Binds Aggregated IgG Specifically

The direct binding of purified recombinant soluble FcγRIIIA to aggregated and monomeric IgG was tested using an ELISA assay (FIG. 2). At an IgG concentration of 2 mg/ml, strong binding to the aggregated IgG was observed. However, at a similar concentration, no binding was detected to the monomeric IgG. The binding to aggregated IgG was blocked by 3G8, a mouse anti-FcγRIIIA monoclonal antibody that blocks the ligand binding site, indicating that the aggregated IgG binding is via that of the normal FcγRIIIA ligand binding site (FIG. 2). Soluble rFcγRIIB was also characterized and shown to bind to IgG with similar characteristics as the soluble rFcγRIIIA (data not shown).

5.2 Formation of Soluble FcγR Tetrameric Complexes

Materials and Methods

Construction of Plasmids for Expression of Soluble FcRγIIIA and FcRγIIB Fused to the AVITAG Peptide.

To generate soluble FcγR tetrameric complexes, the soluble region of the human FcRgIIIA gene (amino acids 7-203) was amplified by PCR (Table 12), digested with BamHI/HindIII and ligated into the pET25b(+) (Novagen). This vector was digested with SalI/NotI, and a 370 bp fragment was isolated by agarose gel electrophoresis. The vector hu3A, (gift from J. Ravetch) was digested with BamHI/SalI, and a 270 bp fragment containing the N-terminus of FcRγIIIA was isolated. Both fragments were coligated into pcDNA3.1 (Invitrogen), which had been digested with BamH/NotI to create pcDNA3-FcRgIIIA (amino acids 1-203).

The soluble region of FcRγIIB (amino acids 33-180) was amplified by PCR (Table I), digested with BglII/HindIII and ligated into pET25b(+) (Novagen). This vector was digested with BamHI/NotI, and a 140 bp fragment was isolated by agarose gel electrophoresis. The vector huRIIb$_1$ (gift from J. Ravetch) was digested with BamHI/EcoRI, and a 440 by FcRγIIB N-terminal fragment was isolated. Both of these fragments were co-ligated into pcDNA3.1, which had been digested with BamHI/NotI to create pcDNA3-FcRγIIB (amino acids 1-180). Subsequently, the linker-AVITAG sequence was fused to the C-terminus of both FcγRIIIA and FcγRIIB. To generate the FcγRIIIA-linker-avitag and FcγRIIB-linker-avitag constructs, the pcDNA3.1 FcγRIIIA and FcγRIIB constructs were digested with Not I and XbaI (both cut in the vector sequence) and a 86 base pair double stranded oligonucleotide consisting of NotI site at the 5' end and XbaI at the 3' end was ligated into the vector. This 86 bp fragment was generated by annealing two 5' phosphorylated reverse complement oligonucleotides (shown in Table 12 as 5' and 3' linker.avitag primers) with the restrictions sites for NotI and XbaI already pre-designed. Equal volumes of each primer at 100 ng per ul were mixed and the DNA heated to 90° C. for 15 minutes and cooled at room temperature for an hour to anneal. This created a double-stranded DNA fragment ready to be ligated to the pcDNA3.1-FcγRIIIA and FcγRIIB constructs digested with the respective enzymes. Therefore, the pcDNA3.1-FcRγIIIA-linker-AVITAG and pcDNA3.1-FcRγIIB-linker-AVITAG, were constructed.

TABLE 12

PRIMERS USED FOR CONSTRUCTION OF FcγR AND IgG VECTORS

| Oligomer | Sequence |
|---|---|
| 5' linker.avitag (SEQ. ID NO. 1) | GGCCGCAGGTGGTGGTGGTTCTGGTGGTGGT GGTTCTGGTCTGAACGACATCTTCGAGGCTC AGAAAA TCGAATGGCACGAATGAT |
| 3' linker.avitag (SEQ. ID NO. 2) | CTAGATCATTCGTGCCATTCGATTTTCTGAG CCTCGAAGATGTCGTTCAGACCAGAACCACC ACCACCAGAACCACCACCACCTGC |
| FcRIIIA left (SEQ. ID NO. 3) | G TTG GAT CCT CCA ACT GCT CTG CTA CTT CTA GTT T |
| FcRIIIA right (SEQ. ID NO. 4) | GAA AAG CTT AAA GAA TGA TGA GAT GGT TGA CAC T |
| FcRIIB right (SEQ. ID NO. 5) | GAA GTC GAC AAT GAT CCC CAT TGG TGA AGA G |
| FcRIIB left (SEQ. ID NO. 6) | G TTA GAT CTT GCT GTG CTA TTC CTG GCT CC |
| IgG1 right (SEQ. ID NO. 7) | ATA GTC GAC CAC TGA TTT ACC CGG AGA |
| IgG1 left (SEQ. ID NO. 8) | GGAA TTC AAC ACC AAG GTG GAC AAG AAA GTT |
| mcr025; ch1 (f') (SEQ. ID NO. 9) | AAA GGATCC GCG AGC TCA GCC TCC ACC AAG G |
| H021 (SEQ. ID NO. 10) | GTCTGCTCGAAGCATTAACC |

Biotinylation by BirA

Soluble Fc receptors (FcγR) fused to the 15 amino acid AVITAG sequence (Avidity, CO) (Schatz P. J., 1993, Bio-techology, 11:1138-1143) at the C-terminus of the protein cloned into pcDNA3.1 were generated by transiently transfecting 293H cells using Lipofectamine 2000 reagent (Invitrogen, CA). Supernatants were collected from the cultures and soluble FcR proteins were purified by passing the supernatants over an IgG sepharose column. Concentration of the soluble FcR-AVITAG fusion protein was quantitated by absorbance at 280 nm. The AVITAG present on the soluble FcR proteins was biotinylated according to the manufacturer's protocol (Avidity, CO) with the E. coli BirA enzyme, a biotin ligase. A 1:100 final dilution of a cocktail of protease inhibitors (Sigma catalog #P8849) and 1 mg/ml final concentration of Leupeptin (Sigma L-8511) were added to the mixture to prevent degradation of the proteins. The BirA reaction was incubated at room temperature overnight, following which the solution was concentrated using a Biomax 10K-ultrafiltration device (Millipore) by centrifugation at 3500 rpm at 4° C. The protein was loaded onto an FPLC Superdex 200 HR 10/30 column (Pharmacia Biotech) in Tris-HCl (20 mM, pH 8.0), 50 mM NaCl to separate the labeled soluble FcγR from free biotin.

Determination of the Extent of Biotinylation by Streptavidin Shift Assay

Approximately 80-85% of the protein was biotinylated by the BirA enzyme (Avidity, CO). The streptavidin-shift assay was used to determine the extent of biotinylation of the protein. Biotinylated protein was incubated with streptavidin (MW 60,000 Daltons) in different ratios. Unbiotinylated protein alone and streptavidin alone are included as controls to determine the extent of biotinylation. The incubation is carried out either on ice for 2 hours or overnight at 4° C. Samples are analyzed on a 4-12% SDS-PAGE Bis-Tris (Invitrogen, CA) with reducing agent and without boiling of the samples. Streptavidin bound biotinylated protein migrates as a high molecular weight band. The extent of biotinylation is estimated by the amount of monomeric protein left in the sample. Absence of monomeric low molecular weight species and presence of a complex with molecular weight greater than streptavidin alone indicates a high degree of biotinylation.

Formation of FcγR Tetrameric Complexes

Formation of FcγR tetrameric complexes was performed according to previously established methodologies for MHC class I tetramers (See Busch, D. H. et al., 1998 Immunity 8:353-362; Altman, J. D. et al., 1996, Science 274: 94-96). The concentration of the biotinylated monomeric FcγR was calculated based on absorbance at 280 nm. One molecule of streptavidin-phycoerythrin (SA-PE) (Molecular Probes, OR) has the capacity to bind 4 molecules of biotin. A 5:1 molar ratio of monomeric biotinylated FcγR to SA-PE (5× monomeric biotinylated FcγR: 1×SA-PE) was used to ensure an excess of biotinylated protein. The calculated molecular weight of SA-PE is 300,000 Daltons, therefore 303 mL of a 1 mg/mL solution of streptavidin-PE has 1 nmole of SA-PE, which was added to 5 nmole of protein. Efficient formation of tetrameric protein requires SA-PE to be added in step-wise increments. Half the amount of SA-PE was added upfront, and the remaining SA-PE was added in small aliquots every 20-30 minutes at 4° C. in the dark. The intervals for the addition of the remaining SA-PE are flexible. After the addition of SA-PE was complete, the solution was concentrated and loaded over an FPLC size exclusion column as above in phosphate buffered saline, at pH 7.4. The fraction that eluted in the void volume with a molecular weight greater than SA-PE alone was collected. Protease inhibitors were replenished to prevent protein degradation. The solution was concentrated and additional protease inhibitors were added to the final complex for storage. The final concentration of the soluble FcγR tetrameric complex was calculated based on the starting concentration of the biotinylated monomeric protein. For example, if 500 µg of biotinylated protein was used to make the tetrameric complex and the final concentrated tetramers were in a volume of 500 µL, the concentration is estimated to be approximately 1 mg/mL (The losses incurred during concentration are not taken into account as it is difficult to accurately determine how much is lost during each step of the formation of the tetramers. It is also not possible to take an absorbance at 280 nm to measure the concentration due to interference from the PE). Soluble FcγR tetrameric complexes were dispensed in small aliquots at −80° C. for long term storage with protease inhibitors. Sodium azide was not added to these preparations as the tetramers were used for screening a yeast display library. On thawing an aliquot, the tetramers were stored at 4° C. for up to 1 week.

ELISA Assay for Characterizing the Tetrameric FcγR Complexes

An ELISA was used to characterize the tetrameric FcγR complexes. Maxisorb F96 well plate (Nunc) was coated with 25 ng of human IgG in PBS buffer, and incuvated overnight at 4° C. The plates were washed with PBS/0.5% BSA/0.1% Tween 20 (wash and diluent buffer) before adding the combination of FcγRIIIA tetramers and test antibodies to determine blocking with 3G8, a mouse anti-human FcγRIIIA antibody as described below: The blocking step was performed as follows: soluble FcγRIIIA tetramers at a fixed 0.5 mg/ml final concentration were pre-incubated with antibodies for 1 h at room temperature in buffer, PBS/0.5% BSA/0.1% Tween 20. The final concentrations of the antibodies ranged from 60 mg/mL to 0.25 mg/mL. 3G8 is a mouse anti-human FcγRIIIA antibody, and for the purpose of this experiment, a chimeric version was used, i.e., the variable region of the antibody is a mouse anti-human FcγRIIIA and the constant region of the heavy and light chains is from the IgG1 human region. A chimeric 4.4.20. D265A was also used in this experiment, which is an anti-fluorescein antibody, such that the Fc region contains a mutation at position 265, where an aspartic acid is substituted with alanine in the human IgG1, which results in a reduced binding to FcγR. This antibody has been characterized previously (See Clynes et al., 2000, *Nat. Med.* 6: 443-446; Shields et al., 2001, *J. Biol. Chem.*, 276: 6591-6604). This antibody was used as negative isotype control.

The antibodies were allowed to bind to FcγRIIIA tetramers, by pre-incubation for 1 hour at room temperature. The mixture was then added to the IgG on the washed plate and incubated for and additional hour at room temperature. The plate was washed with buffer and DJ130c (a mouse anti-human FcγRIIIA antibody available from DAKO, Denmark; its epitope is distinct from that of the 3G8 antibody) at 1:5000 dilution was added and allowed to incubate for 1 hr. at room temperature in order to detect the bound FcγRIIIA tetramers. Unbound antibodies were washed out with buffer and the bound DJ130c was detected with goat anti-mouse peroxidase (Jackson laboratories). This reagent will not detect the human Fc. After washing out the unbound peroxidase-conjugated antibody, the substrate, TMB reagent (BioFx), was added to detect the extent of blocking with 3G8 versus the isotype control and the developed color was read at 650 nm.

For direct binding of soluble tetrameric FcγRIIIA to IgG by ELISA, maxisorb plates were coated with 25 ng IgG as described above. The soluble tetrameric FcγRIIIA were added from 20 mg/mL to 0.1 mg/mL and the biotinylated monomeric soluble tetrameric FcγRIIIA were added at concentrations ranging from 20 mg/mL to 0.16 mg/mL. Detection was the same as above with DJ130c, followed by goat anti-mouse-peroxidase antibody. Color developed with the TMB reagent and the plate was read at 650 nm.

Results

Soluble FcγRIIIA Tetrameric Complex Binds Monomeric Human IgG Via its Normal Ligand Binding Site Soluble FcγRIIIA-AVITAG fusion proteins were generated, isolated, and analyzed as described in the Material and Methods section using an ELISA assay and were shown to have similar properties as the non-AVITAG soluble FcγRIIIA protein (data not shown). The fusion proteins were biotinylated, and the tetrameric complexes were generated as described above.

The soluble FcγR tetrameric complex was then assessed for binding its ligand, monomeric human IgG, using an ELISA assay. Analysis by ELISA showed the soluble tetrameric FcγR complexes bind monomeric human IgG specifically. As shown in FIG. 3A, binding of soluble tetrameric FcγRIIIA to monomeric human IgG is blocked by 3G8, a mouse anti-human FcγIIIA monoclonal antibody, as monitored by the absorbance at 650 nm. On the other hand, the 4-4-20 monoclonal antibody harboring the D265A mutation was not able to block the binding of soluble tetrameric FcγRIIIA to monomeric human IgG (FIG. 3A). This experiment thus confirms that binding of the soluble tetrameric FcγRIIIA complex occurs through the native ligand binding site.

Figure 3B:
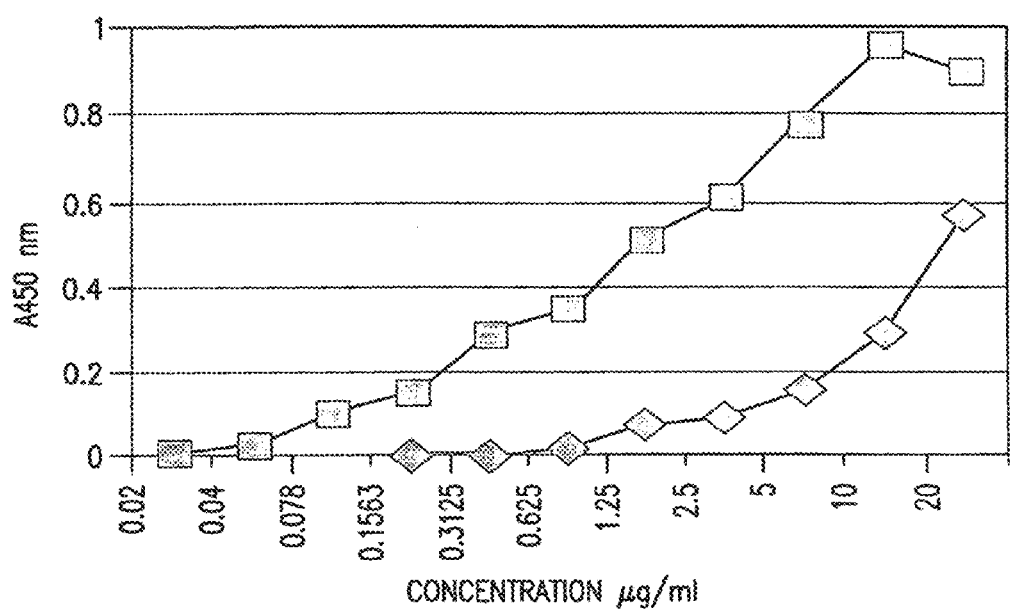

Soluble FcγRIIIA Tetrameric Complex Binds Monomeric Human IgG with a Greater Avidity than Monomeric Soluble FcγRIIIA The direct binding of soluble tetrameric FcγRIIIA to aggregated human IgG was assessed using an ELISA assay and compared to the direct binding of soluble monomeric FcγRIIIA to monometic human IgG. As shown in FIG. 3B, soluble tetrameric FcγRIIIA binds human IgG with a higher avidity (8-10 fold) than the soluble monomeric receptor, as monitored by the absorbance at 450 nm.

The binding of soluble FcγRIIIA tetrameric complex was also assayed using magnetic beads coated with Fc Fragment purified from IgG1 (FIG. 4). Soluble FcγRIIIA tetrameric complex binds to the IgG1 Fc-coated beads, under conditions in which monomer binding is not detected. Specificity of binding was shown by pre-incubating the receptor complex, with an anti-FcγRIIIA monoclonal antibody, LNK16, which blocks Fc binding. This assay further confirms that soluble FcγRIIIA tetrameric complex binds monomeric IgG through its normal ligand binding site, and the avidity of the receptor is increased due to multiple binding sites within the complex.

5.3 Construction of Yeast Strain for Display of Mutant IgG1 Fc Domains

Materials and Methods

The pYD1 vector (Invitrogen) is derived directly from a yeast replicating vector, pCT302 (Shusta, et al., 2000 *Nat. Biotechnol.* 18: 754-759, that has been successfully used to display T-cell receptors and a number of scFVs. This plasmid is centromeric and harbors the TRP1 gene enabling a relatively constant copy number of 1-2 plasmids per cell in a trpl yeast strain. Directional cloning into the polylinker places the gene of interest under the control of the GAL1 promoter and in-frame with AGA2. Fusion of the IgG Fc domain to the yeast Aga2p results in the extracellular secretion of the Aga2-Fc fusion protein and subsequent display of the Fc protein on the cell wall via disulfide bonding to the yeast Aga 1p protein, which is an integral cell wall protein.

In order to optimize the display levels, different fragments from the IgG1 heavy chain were amplified by PCR and cloned into pYD1. Specifically, the Fc region of the IgG1 heavy chain (allotype IG1m(a); amino acids 206-447) was amplified by PCR (Table 1) from the IMAGE clone 182740, digested with EcoRI/SalI and ligated into the pYD1 vector (Invitrogen). The initial clone from IMAGE contained a deletion of a single nucleotide at position 319 which was corrected by in vitro site directed mutagenesis to construct pYD-GIF206 (Quickchange, Stratagene).

The CH1-CH3 fragment (amino acids 118-447) was amplified from the heavy chain clone of the MAb B6.2 in the pCINEO vector using a 5' oligo (mcr025; ch1(f)) and a 3' oligo (H021) (See Table 8). The fragment was digested with BamHI/NotI and ligated into the pYD1 vector to construct pYD-CH1.

FIG. 5, shows a schematic presentation of the constructs. The CH1-CH3 construct contains the CH1 domain in addition to the hinge-CH2-CH3 domains of the heavy chain, GIF206 contains 6 amino acid residues upstream of the hinge and GIF227 starts within the hinge region at an endogenous proteolytic cleavage site (Jendeberg et al., 1997 *J. Immunol. Meth.* 201: 25-34).

5.4 Immunolocalization and Characterization of Fc Domains on the Yeast Cell Wall Materials and Methods Constructs containing the Aga2p-Fc fusion proteins and a control vector, pYD1, lacking any insert, were transformed into the yeast strain EBY100 (Invitrogen), MATa ura3-52 trpl leu2Δl his3Δ200 pep4::HIS3 prb1Δ1.6R can1 GAL::GAL-AGA1, using a standard lithium acetate yeast transformation protocol (Gietz et al., 1992 *Nucleic Acids Res.* 20: 1425) Subsequently, tryptophan prototrophs were selected on defined media. Amplification of independent cell populations and induction of Aga1p and the Aga2p-Fc fusion proteins were accomplished by growth in glucose, followed by growth in media containing galactose as the primary carbon source for 24-48 hrs at 20° C. Growth in galactose induces expression of the Aga2-Fc fusion proteins via the GALL promoter, which subsequently leads to the display of the Fc fusion proteins on the yeast cell surface.

Results

Figure 6A:
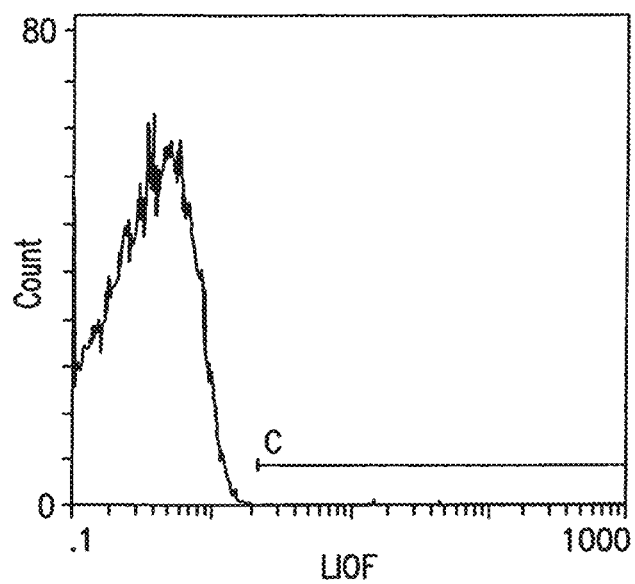
Figure 6B:
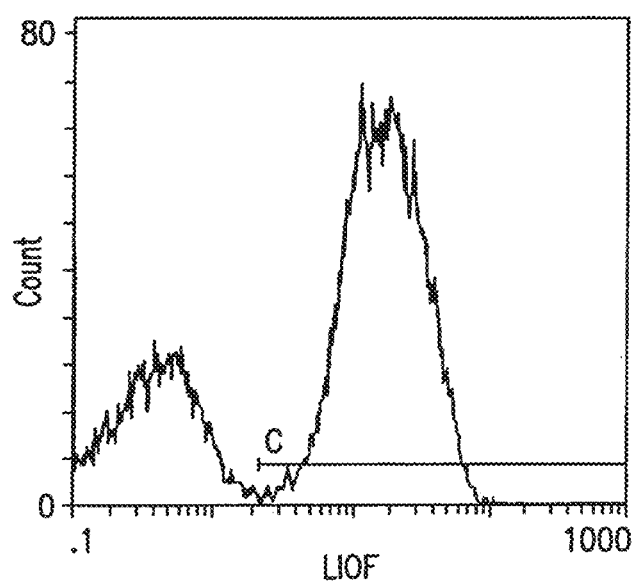
Figure 6C:
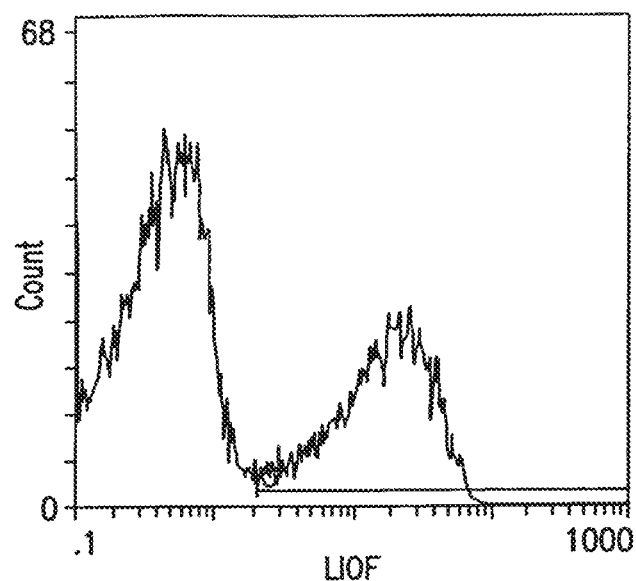
Figure 6D:
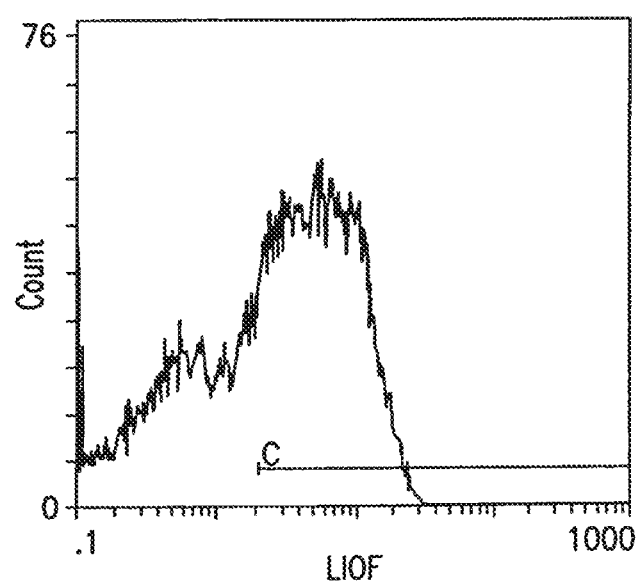
Figure 6E:
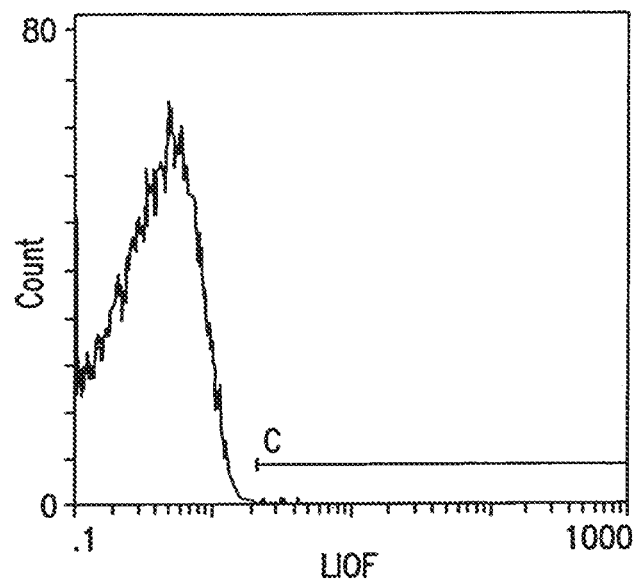
Figure 6F:
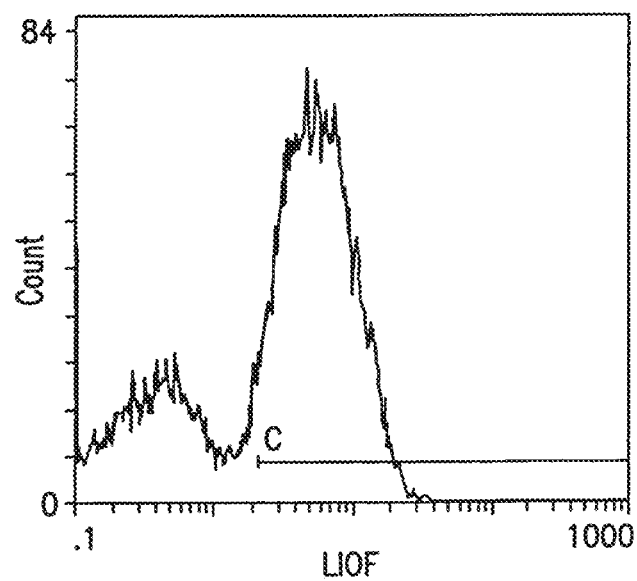
Figure 6G:
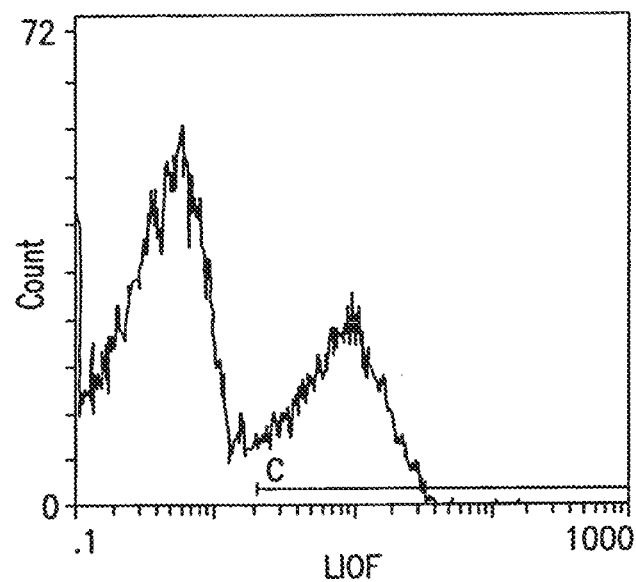
Figure 6H:
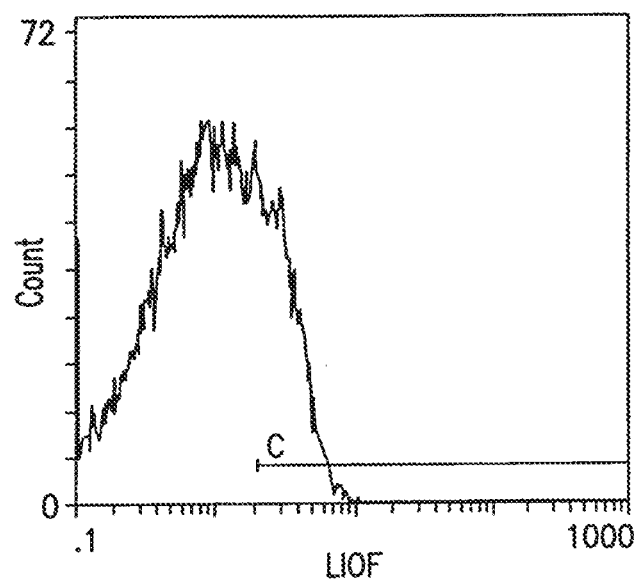

FACS Analysis of Fc Fusion Proteins Expression of Fc fusion proteins on the yeast cell surface was analyzed by immunostaining using a PE-conjugated polyclonal F(ab)$_2$ goat anti-human FcγR and HP6017 (Sigma) antibody (Jackson Immunoresearch Laboratories, Inc.). Fluorescence microscopy shows peripheral staining for the three Fc fusion proteins. The control strain, harboring vector alone, shows little or no staining (data not shown). FACS analysis was used to quantitate the staining (FIG. 6). The yeast strain containing the CH1-CH3 fusion demonstrated the highest percentage of cells stained with both antibodies (FIGS. 6B and F). The GIF227 construct showed the greatest mean fluorescence intensity (FIG. 6, panels C and G).

Characterization of the Binding of Fc Fusion Proteins Expressed on the Yeast Cell Surface The natural context of the Fc and FcγR proteins places the receptor on the cell surface and the Fc as the soluble ligand; however, the yeast Fc surface display reverses the geometry of the natural interaction. Detection of the IgG1 Fc proteins on the surface of the yeast cell wall is complicated by both the low affinity of the FcγR for its ligand and the reverse geometry inherent in the display system. Although the latter point cannot be altered, the avidity of the ligand was improved as explained above by forming soluble FcγR tetrameric complexes, which allows detection of FcγR binding to the Fc fusion proteins expressed on the surface yeast cell wall.

To characterize the binding of soluble tetrameric FcγR complexes to the surface displayed Fc fusion proteins, yeast cells expressing different Fc constructs were incubated with the soluble rFcγRIIIA tetrameric complex and analyzed by FACS. Yeast cells harboring pYD-CH1, displaying the wild type CH1-CH3 construct were bound by the soluble rFcγRIIIA tetrameric complex as shown by FACS analysis. The GIF206 and GIF227 strains, however, showed little or no binding to the soluble rFcγRIIIA tetrameric complex as shown by FACS analysis (data not shown).

Mutations in the Fc region that block binding to the FcγRs have been identified (Shields et al., 2001; *J Biol. Chem.* 276: 6591-6604). One of these mutations, D265A, was incorporated into pYD-CH1 and this mutant was expressed on the yeast cell surface. These cells were incubated with the soluble FcγRIIIA tetrameric complex using a high concentration of ligand (0.15 mM of Fc; 7.5 mM of D265A) FACS analysis indicated that soluble FcγRIIIA tetrameric complex bound to wild type Fc (FIG. 7A) but soluble FcγRIIIA tetrameric complex did not bind to the D265A-Fc mutant indicating that FcγR is interacting with the normal FcR binding site in the lower hinge-CH2 region (FIG. 7B).

Antibodies against the FcγRIIIA ligand binding site blocked binding of the soluble FcγRIIIA tetrameric complex to the wild type Fc protein displayed on the yeast cell surface wall, as analyzed by FACS (FIG. 8). The binding of soluble FcγRIIIA tetrameric complex was blocked by the 3G8 antibody, as well as the LNK16 antibody, another anti-FcγRIIIA monoclonal antibody (Advanced Immunological) (Tam et al., 1996 *J. Immunol.* 157: 1576-1581) and was not blocked by an irrelevant isotype control. Therefore, binding of soluble FcγRIIIA tetrameric complex to the Fc proteins displayed on the yeast cell surface occurs through the normal ligand binding site. The limited binding of the FcγRIIIA tetrameric complex indicates that a subpopulation of cells have a correctly folded Fc that is accessible to FcγR. There are numerous reasons why only a subpopulation of cells may be able to bind the ligand, for example, they may be at different stages of cell cycle or the fusion proteins may not have been exported.

In order to determine the dissociation constant of the FcγRIIIA-tetramer binding to the Fc fusion proteins on the yeast cell surface, the binding of a range of FcγRIIIA tetrameric complex was analyzed using FACS. FcγRIIIA tetrameric complex was titrated at concentrations of 1.4 µM to 0.0006 µM. Using the mean fluorescence intensity as a measure of binding affinity and nonlinear regression analysis, the $K_D$ was determined to be 0.006 µM (+/−0.001) (data not shown).

5.5 Construction of Fc Mutant Library

A mutant Fc library was constructed using primers flanking the Fc fragment in the Fc-CH1 construct and error-prone PCR (Genemorph, Stratagene). The CH1-CH3 insert in vector pYD-CHI was amplified using a mutagenic PCR (Genemorph, Stratagene). Five reactions were carried out using the pYD-upstream and pYD-downstream primers (Invitrogen). The resultant amplified fragment was digested with XHOI/BamHI and ligated into pYD1. The ligation reaction was then transformed into XL10 ultracompetent cells (Stratagene), which resulted in ~1×10$^6$ transformants, with 80% of the transformants containing inserts.

Sequence analysis of 28 random plasmids from the library indicated a mutation frequency ~2-3 mutations/kb with a breakdown of 40% conserved nucleotide changes and 60% of the mutations resulting in amino acid changes.

The library was transformed into the yeast strain EBY100, MATa ura3-52 trp 1 leu2Δ1 his3Δ200 pep4::HIS3 prb1Δ1.6R can 1 GAL GAL-AGA 1::URA3 to a high efficiency, ~3.3× 10$^5$ transformants/ug, in 30 independent transformation reactions to create a total of ~10$^7$ yeast transformants (Gietz, et al., 1992, *Nucleic Acids Res.* 20: 1425). The library was pooled and amplified by growth in glucose.

5.6 Selection and Analysis of Fc Mutants
Materials and Methods
ELISA Assay for Screening Fc Mutants ELISA plates (Nunc F96 MaxiSorp Immunoplate) were coated with 50 ml/well of 0.5 mg/ml BSA-FITC in carbonate buffer at 4° C., and allowed to incubate overnight. Plates were washed with 1×PBS/0.1% Tween 20 (PBST) 3 times. 200 ml/well of PBST/0.5% BSA was added and the plates were incubated for 30 mins at room temperature. Plates were washed three additional times with PBST. 50 ml/well of 1:4 diluted 4-4-20 antibody (approximately 3 mg/mL which would lead to a final concentration of 0.7-0.8 mg/well) either wild type or containing an Fc mutant, was added from conditional medium in PBST/0.5% BSA and allowed to incubate for 2 hrs at room temperature. Plates were washed with PBST three times. Purified, biotinylated monomeric FcγRIIIA at 3 mg/ml (in PBST/0.5% BSA) was added (50 µl/well) to the plates and allowed to incubate for 1.5 hours at room temperature. Plates were washed with PBST three times. 50 ml/well of a 1:5000 dilution of Streptavidin-HRP (Pharmacia, RPN 123v) in PBST/0.5% BSA was added and the plates were incubated for 30 minutes at room temperature. Plates were washed with PBST three times. 80 ml/well of TMB reagent (BioFX) was then added to the plates, and allowed to incubate for 10-15 minutes at room temperature in a dark place. The reactions were finally stopped by adding 40 ml/well of stop solution (0.18 M sulfuric acid). Plates were then monitored for absorbance at 450 nm. After the first screen, the interesting candidates were further confirmed by serial titration of 4-4-20-Fc mutants in the immuno-complex based binding ELISA. A few modifications were made in this ELISA. For coating the plates, 2 mg/ml BSA-FITC was used. Based on IgG quantitation results, diluted 4-4-20Fc (wild type or mutants) from conditional medium was added to a final concentration of 1, 0.5, 0.25, 0.125, 0.063, and 0 mg/ml in PBST-/0.5% BSA.

FACs Screen for the Cell Surface Displayed Fc Proteins

Cells were grown in at least 10 mls of HSM-Trp-Ura pH 5.5 with glucose for 16-24 hrs or until $OD_{600}$ was greater than 2.0. Cells were spun down at 2000 rpm for 5 minutes. Cells were resuspended in an equal volume of HSM-Trp-Ura, pH 7.0 with galactose. In a 125 ml flask, 36 mls of galactose media was added, and inoculated with 9 mls of culture, which was incubated at 20° C. with shaking for 24-48 hrs. Growth was monitored by measuring $OD_{600}$ at 8-16 hr intervals. Cells were harvested at 2K rpm for 5 minutes, and resuspended in an equal volume of 1×PBS, pH 7.4.

Equilibrium screen: An appropriate amount of cells was incubated while maintaining an excess of ligand. For example, it is preferred to start with a number of cells needed to ensure 10-fold coverage of the library. For the first sort with a library containing $10^7$ transformants, $10^8$ cells should be used. In fact it is best to start with $10^9$ cells to compensate for loss during the staining protocol.

Incubation was typically done in a 1.5 mL tube in volumes of 20-100 mls for 1 hour at 4° C. in the dark on a rotator (incubation buffer: 1×PBS pH7.4; 1 mg/ml BSA). Cells were washed once in 500 ml of incubation buffer and spun down at 4K rpm for 2.5 minutes. Cells were resuspended in 100 ml incubation buffer and incubated with the second staining reagent. For Fc-CH1, a F(ab)₂ goat anti-hFc F(ab)₂-FITC antibody (Jackson Immunoresearch Laboratories, Inc.) can be used to stain for CH1 expression. Staining was done with 1 mL for 30 minutes. Cells were washed additionally in 500 mL of incubation buffer and spun down at 4K rpm for 2.5 minutes, resuspended in 1 mL IX PBS 1 mg/mL BSA and analyzed by FACS.

Typical equilibrium screen sort gates and number of cells collected are shown in Table 13.

TABLE 13

SORT GATES AND NUMBER OF CELLS SORTED

| Sort | Gate | total cells screened | cells collected |
|------|------|---------------------|-----------------|
| 1$^{st}$ | 5% | $10^8$ | $5 \times 10^6$ |
| 2$^{nd}$ | 1% | $10^7$ | $1 \times 10^5$ |
| 3$^{rd}$ | 0.2% | $10^7$ | $2 \times 10^4$ |
| 4$^{th}$ | 0.2% | $10^7$ | $2 \times 10^4$ |

After the 3rd and 4th sorts, cells were plated directly on -trp-ura plates to identify individual mutants. This typically recovered ~200-400 colonies per plate. After collection the cells were placed in 10 mLs of glucose media in a 50 mL conical tube and grown at 30° C. The whole procedure was repeated iteratively.

Results
FACS Analysis of Fc Mutants

After induction in galactose media, cells were harvested and co-stained with soluble FcγRIIIA tetrameric complex-PE labeled and F(ab₂) of mouse anti-human Fc-FITC labeled (Jackson Immunoresearch Laboratories, Inc.). Cells were analyzed by FACS and sort gates were used to select the cells that showed the highest affinity for the soluble FcγRIIIA tetrameric complex relative to the amount of Fc expression on the cell surface (FIG. 9). For example, a cell containing a mutant Fc that binds better to the soluble FcγRIIIA tetrameric complex may express fewer Fc fusion proteins on the yeast cell surface, and this cell will be in the lower left hand corner of the sort gate.

Four consecutive sorts were done to enrich for those mutants that showed the highest affinity for the soluble FcγRIIIA tetrameric complex. The gates for each successive sort were 5.5%, 1%, 0.2% and 0.1%. After the last sort, cells were plated onto selective media and individual colonies were isolated. Each individual colony represented a clonal population of cells harboring a single Fc mutant within the Aga2-Fc fusion protein. Initially 32 independent colonies were picked and tested by FACS for binding to soluble FcγRIIIA tetrameric complex (FIG. 10). Eighteen mutants showed an increase in binding intensity as measured by the percentage of cells bound by soluble FcγRIIIA tetrameric complex and the mean fluorescence intensity of the bound cells.

Mutations showing an increase in binding to FcγRIIIA were also tested for binding to soluble FcγRIIB tetrameric complex (FIG. 10). Most mutations that lead to an increase in binding to the soluble FcγRIIIA tetrameric complex also resulted in detection of FcγRIIB tetrameric complex staining (FIG. 10). Based on both previous physical and genetic data, some mutations that increase binding to FcγRIIIA, are expected to also increase binding to FcγRIIB (Shields et al., 2001, *J Biol. Chem.* 276: 6591-6604; Sondermann et al., 2000, *Nature* 406: 267-273).

Analysis of Mutants in a 4-4-20 MAb Produced in a Human Cell Line.

Isolation and analysis of mutations in the yeast system allows for fast identification of novel mutant alleles. The use of a heterologous system to isolate mutations could result in the identification of mutations that enhance binding through an alteration that results in misfolding or alteration in glycosylation that is specific to yeast. To analyze the Fc mutations in an immunoglobulin molecule that is produced in human cells, the mutants were subcloned into a mammalian expression vector, containing the heavy chain of the anti-fluorescein monoclonal antibody, 4-4-20 (Kranz et al., 1982 *J. Biol. Chem.*, 257(12): 6987-6995). The mutant 4-4-20 heavy chains were transiently coexpressed with the light chain clones in the human kidney cell line (293H). Supernatants were collected and analyzed by ELISA (FIG. 11).

According to the ELISA assay, the majority of the mutants that were identified as having an enhanced affinity for the soluble monomeric FcγRIIIA complex, in the secondary FACS analysis, also showed an increase in binding to the soluble FcγRIIIA tetrameric complex when present in the Fc region of the 4-4-20 monoclonal antibody produced in the human cell line (FIG. 11A). Two mutants, number 16 and number 19, however, showed a decrease in binding to the soluble FcγRIIIA monomeric complex.

Table 14, summarizes the mutations that have been identified and their corresponding binding characteristics to FcγRIIIA and FcγRIIB, as determined by both yeast display based assays and ELISA. In Table 14, the symbols represent the following: • corresponds to a 1-fold increase in affinity; + corresponds to a 50% increase in affinity; – corresponds to a 1-fold decrease in affinity; → corresponds to no change in affinity compared to a comparable molecule comprising a wild-type Fc region.

TABLE 14

MUTATIONS IDENTIFIED AND BINDING CHARACTERISTICS

| Clone # | Mutation sites | Domain | IIIA binding | IIB binding |
|---|---|---|---|---|
| 4 | A339V, Q347H | CH2, CH3 | + | + |
| 5 | L251P, S415I | CH2, CH3 | + | + |
| 7 | Aga2p-T43I | Note: This is a mutation in Aga2P that enhances display. | | Aga2p-T43I |
| 8 | V185M, K218N, R292L, D399E | CH1, hinge, CH2, CH3 | no change | – |
| 12 | K290E, L142P | CH1, CH2 | + | not tested |
| 16 | A141V, H268L, K288E, P291S | CH1, CH2 | – | not tested |
| 19 | L133M, P150Y, K205E, S383N, N384K | CH1, CH2, CH3 | – | not tested |
| 21 | P396L | CH3 | • | •+ |
| 25 | P396H | CH3 | ••• | •• |
| 6 | K392R | CH3 | no change | no change |
| 15 | R301C, M252L, S192T | CH1, CH2 | – | not tested |
| 17 | N315I | CH2 | no change | not tested |
| 18 | S132I | CH1 | no change | not tested |
| 26 | A162V | CH1 | no change | not tested |
| 27 | V348M, K334N, F275I, Y202M, K147T | CH1, Ch2 | + | + |
| 29 | H310Y, T289A, G337E | CH2 | – | not tested |
| 30 | S119F, G371S, Y407N, E258D | CH1, CH2, CH3 | + | no change |
| 31 | K409R, S166N | CH1, CH3 | no change | not tested |
| 20 | S408I, V215I, V125I | CH1, hinge, CH3 | + | no change |
| 24 | G385E, P247H | CH2, CH3 | ••• | + |
| 16 | V379M | CH3 | •• | no change |
| 17 | S219Y | Hinge | • | – |
| 18 | V282M | CH2 | • | – |

TABLE 14-continued

MUTATIONS IDENTIFIED AND BINDING CHARACTERISTICS

| Clone # | Mutation sites | Domain | IIIA binding | IIB binding |
|---|---|---|---|---|
| 31 | F275I, K334N, V348M | CH2 | + | no change |
| 35 | D401V | CH3 | + | no change |
| 37 | V280L, P395S | CH2 | + | – |
| 40 | K222N | Hinge | • | no change |
| 41 | K246T, Y319F | CH2 | • | no change |
| 42 | F243I, V379L | CH2, CH3 | •+ | – |
| 43 | K334E | CH2 | •+ | – |
| 44 | K246T, P396H | CH2, CH3 | • | ••+ |
| 45 | H268D, E318D | CH2 | •+ | ••••• |
| 49 | K288N, A330S, P396L | CH2, CH3 | ••••• | ••• |
| 50 | F243L, R255L, E318K | CH2 | • | – |
| 53 | K334E, T359N, T366S | CH2, CH3 | • | no change |
| 54 | I377F | CH3 | •+ | + |
| 57 | K334I | CH2 | • | no change |
| 58 | P244H, L358M, V379M, N384K, V397M | CH2, CH3 | •+ | •+ |
| 59 | K334E, T359N, T366S (independent isolate) | CH2, CH3 | •+ | no change |
| 61 | I377F (independent isolate) | CH3 | ••• | ••+ |
| 62 | P247L | CH2 | •• | ••+ |
| 64 | P217S, A378V, S408R | Hinge, CH3 | •• | •••••+ |
| 65 | P247L, I253N, K334N | CH2 | ••• | ••+ |
| 66 | K288M, K334E | CH2 | ••• | – |
| 67 | K334E, E380D | CH2, CH3 | •+ | – |
| 68 | P247L (independent isolate) | CH2 | + | •••• |
| 69 | T256S, V305I, K334E, N390S | CH2, CH3 | •+ | no change |
| 70 | K326E | CH2 | •+ | ••+ |
| 71 | F372Y | CH3 | + | •••••+ |
| 72 | K326E (independent isolate) | CH2 | + | •• |
| 74 | K334E, T359N, T366S (independent isolate) | CH2, CH3 | •• | no change |
| 75 | K334E (independent isolate) | CH2 | •••+ | no change |
| 76 | P396L (independent isolate) | CH3 | •+ | no change |
| 78 | K326E (independent isolate) | CH2 | •• | •••+ |
| 79 | K246I, K334N | CH2 | • | •••• |
| 80 | K334E (independent isolate) | CH2 | • | no change |
| 81 | T335N, K370E, A378, T394M, S424L | CH2, CH3 | • | no change |
| 82 | K320E, K326E | CH2 | • | • |
| 84 | H224L | Hinge | • | ••••• |
| 87 | S375C, P396L | CH3 | •+ | ••••+ |
| 89 | E233D, K334E | CH2 | •+ | no change |
| 91 | K334E (independent isolate) | CH2 | • | no change |
| 92 | K334E (independent isolate) | CH2 | • | no change |
| 94 | K334E, T359N, T366S, Q386R | CH2 | • | no change |

Analysis of soluble FcγRIIB tetrameric complex binding shows that 7 out of the 8 mutants that showed an increase in binding to the soluble FcγRIIIA tetrameric complex also had an increased binding to the soluble FcγRIIB tetrameric complex (FIG. 11B). One mutant, number 8, showed a decrease in binding to the soluble FcγRIIB tetrameric complex. Three of the mutants show no difference in binding to either the soluble FcγRIIIA tetrameric complex or the soluble FcγRIIB tetrameric complex, possibly due to mutations that result in yeast specific alterations.

5.7 ADCC Assay of Fc Mutants

Effector Cell Preparation:

Peripheral blood mononuclear cells (PBMC) were purified by Ficoll-Paque (Pharmacia, 17-1440-02) Ficoll-Paque density gradient centrifugation from normal peripheral human blood (Biowhittaker/Poietics, 1 W-406). Blood was shipped the same day at ambient temperature, and diluted 1:1 in PBS and glucose (1 g/1 L) and layered onto Ficoll in 15 mL conical tubes (3 mL Ficoll; 4 mL PBS/blood) or 50 mL conical tubes (15 mL: Ficoll; 20 mL PBS/blood). Centrifugation was done at 1500 rpm (400 rcf) for 40 minutes at room temperature. The PBMC layer was removed (approximately 4-6 mL from 50 mL conical tube) and diluted 1:10 in PBS (which contains no $Ca^{2+}$ or $Mg^{2+}$) in a 50 mL conical tube, and spun for an additional ten minutes at 1200 rpm (250 rcf) at room temperature. The supernatant was removed and the pellets were resuspended in 10-12 mL PBS (which contains no $Ca^{2+}$ or $Mg^{2+}$), transferred to 15 mL conical tubes, and spun for another 10 minutes at 1200 rpm at room temperature. The supernatant was removed and the pellets were resuspended in a minimum volume (1-2 mL) of media (Isocove's media (IMDM)+10% fetal bovine serum (FBS), 4 mM Gln, Penicillin/Streptomycin (P/S)). The resuspended PBMC were diluted to the appropriate volume for the ADCC assay; two fold dilutions were done in an ELISA 96 well plate (Nunc F96 MaxiSorp Immunoplate). The yield of PBMC was approximately $3-5 \times 10^7$ cells per 40-50 mL of whole blood.

Target Cell Preparation:

Target cells used in the assay were SK-BR-3 (ATCC Accession number HTB-30; Trempe et al., 1976, Cancer Res. 33-41), Raji (ATCC Accession number CCL-86; Epstein et al., 1965, J. Natl. Cancer Inst. 34: 231-40), or Daudi cells (ATCC Accession number CCL-213; Klein et al., 1968, Cancer Res. 28: 1300-10) (resuspended in 0.5 mL IMDM media) and they were labeled with europium chelate bis(acetoxymethyl) 2,2":6',2" terpyridine 6,6' dicarboxylate (BATDA reagent; Perkin Elmer DELFIA reagent; C136-100). K562 cells (ATCC Accession number CCL-243) were used as control cells for NK activity. The Daudi and Raji cells were spun down; the SK-BR-3 cells were trypsinized for 2-5 minutes at 37° C., 5% $CO_2$ and the media was neutralized prior to being spun down at 200-350 G. The number of target cells used in the assays was about $4-5 \times 10^6$ cells and it did not exceed $5 \times 10^6$ since labeling efficiency was best with as few as $2 \times 10^6$ cells. Once the cells were spun down, the media was aspirated to 0.5 mL in 15 mL Falcon tubes. 2.5 μl of BATDA reagent was added and the mixture was incubated at 37° C., 5% $CO_2$ for 30 minutes. Cells were washed twice in 10 mL PBS and 0.125 mM sulfinpyrazole ("SP"; SIGMA S-9509); and twice in 10 mL assay media (cell media+0.125 mM sulfinpyrazole). Cells were resuspended in 1 mL assay media, counted and diluted.

When SK-BR-3 cells were used as target cells after the first PBS/SP wash, the PBS/SP was aspirated and 500 μg/mL of FITC was added (PIERCE 461110) in IMDM media containing SP, Gln, and P/S and incubated for 30 minutes at 37° C., 5% $CO_2$. Cells were washed twice with assay media; resuspended in 1 mL assay media, counted and diluted.

Antibody Opsonization:

Once target cells were prepared as described supra, they were opsonized with the appropriate antibodies. In the case of Fc variants, 50 μL of $1 \times 10^5$ cells/mL were added to 2× concentration of the antibody harboring the Fc variant. Final concentrations were as follows: Ch-4-4-20 final concentration was 0.5-1 μg/mL; and Ch4D5 final concentration was 30 ng/mL-1 ng/mL.

Opsonized target cells were added to effector cells to produce an effector:target ratio of 75:1 in the case of the 4-4-20 antibodies with Fc variants. In the case of the Ch4D5 antibodies with Fc variants, effector:target ratio of 50:1 or 75:1 were achieved. Effective PBMC gradient for the assay ranges from 100:1 to 1:1. Spontaneous release (SR) was measured by adding 100 μL, of assay media to the cells; maximal release (MR) was measured by adding 4% TX-100. Cells were spun down at 200 rpm in a Beckman centrifuge for 1 minute at room temperature at 57 G. Cells were incubated for 3-3.5 hours at 37° C., 5% $CO_2$. After incubation, the cells were spun at 1000 rpm in a Beckman centrifuge (about 220× g) for five minutes at 10° C. 20 μl of supernatant was collected; 2000 μL of Eu solution was added and the mixture was shaken for 15 minutes at room temperature at 120 rpm on a rotary shaker. The fluorescence was quantitated in a time resolved fluormeter (Victor 1420, Perkin Elmer)

Results

As described above, the variant Fc regions were subcloned into a mammalian expression vector, containing the heavy chain of the anti-fluoresceine monoclonal antibody, 4-4-20 (Kranz et al., 1982 J. Biol. Chem., 257(12): 6987-6995). The variant 4-4-20 heavy chains were transiently coexpressed with the light chain clones in the human kidney cell line (293H). Supernatants were collected and analyzed using the ADCC assay. FIG. 12 shows that ADCC activity of the mutants is concentration-dependent. As summarized in Table 8, five immunoglobulins with variant Fc regions had an enhanced ADCC activity relative to wild type ch 4-4-20. The five mutants were as follows: MGFc-27 (G316D, A378V, D399E); MGFc-31 (P247L, N421K); MGFc-10 (K288N, A330S, P396L); MGFc-28 (N315I, V379M, T394M); MGFc-29 (F243I, V379L, G420V).

Additional 4-4-20 immunoglobulins with variant Fc regions were assayed for their ADCC activity relative to a 4-4-20 immunoglobulin with a wild-type Fc region. These results are summarized in Table 15.

Figure 13B:
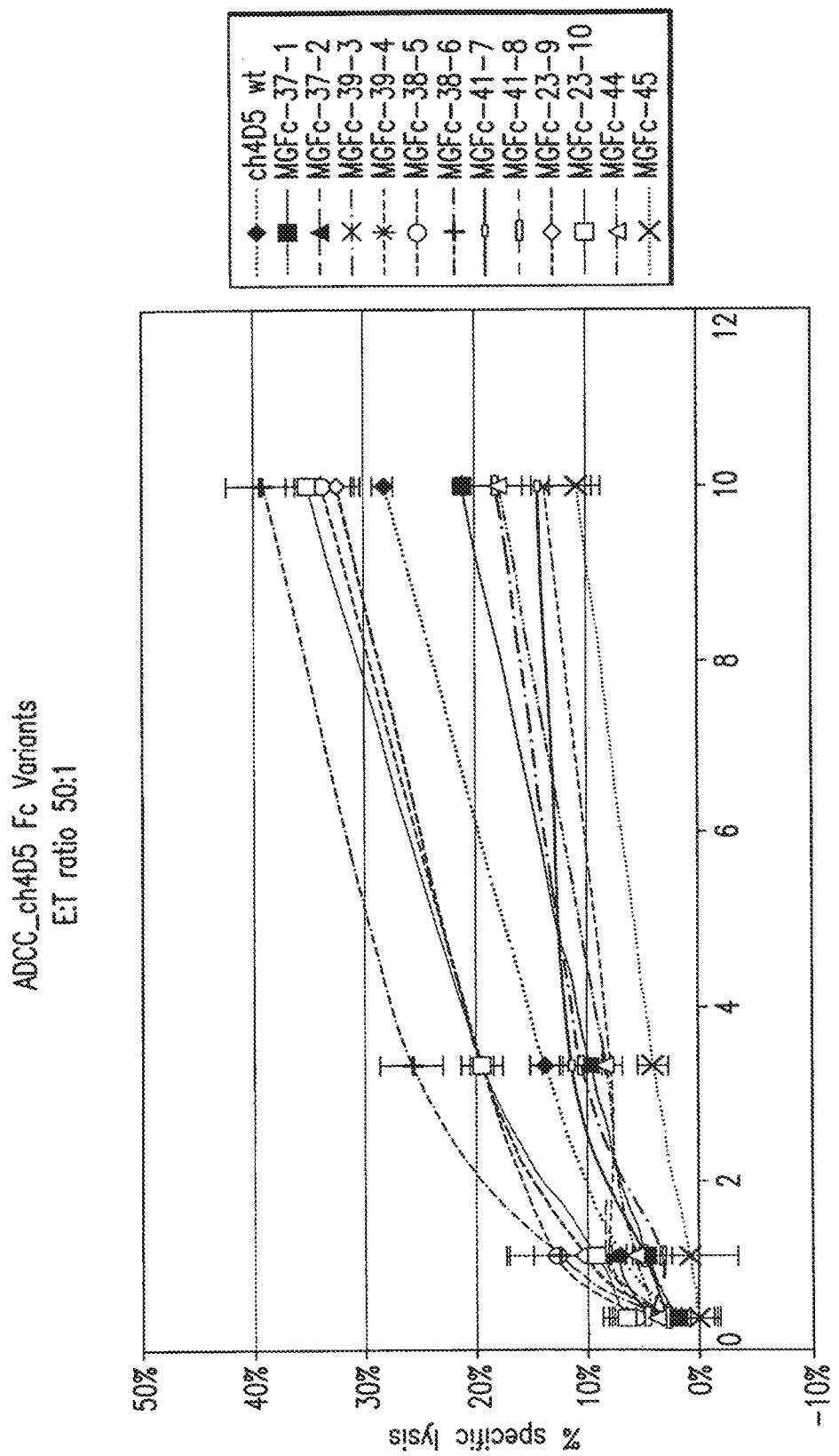

ADCC assays were also carried out using the same protocol as previously described for the 4-4-20 antibody, however, the variant Fc regions were cloned into a humanized antibody (Ab4D5) which is specific for the human epidermal growth factor receptor 2 (HER2/neu). In this case, SK-BR-3 cells were used as the target cells that were opsonized with a HER2/neu antibody carrying a variant Fc region. HER2/neu is endogenously expressed by the SK-BR-3 cells and therefore present on the surface these cells. FIG. 13 shows the ADCC activity of HER2/neu antibodies carrying variant Fc regions. Table 16 summarizes the results of ADCC activity of the mutants in the context of the HER2/neu antibody. Normalization was carried out by comparing the concentration of the mutant to the wildtype antibody required for a specific value of percent cell lysis.

As shown in FIG. 13A, MGFc-5 (V379M), MGFc-9 (P243I, V379L), MGFc-10 (K288N, A330S, P396L), MGFc-13 (K334E, T359N, T366S), and MGFc-27 (G316D, A378V, D399E) mutants that were cloned in to the humanized anti-HER2/neu antibody exhibited a higher % specific lysis of SK-BR-3 cells relative to the wild antibody.

TABLE 15

SUMMARY OF ADCC ACTIVITY OF MUTANTS

| | Fc Variant | | ADCC | | | |
|---|---|---|---|---|---|---|
| | | | 1 ug/ml | | 0.5 ug/ml | |
| Label | Ref | Amino Acid Variation | % specific lysis | Normalized | % specific lysis | Normalized |
| MGFc-27 | 2C4 | G316D, A378V, D399E | 33% | 2.24 | 22% | 3.60 |
| MGFc-31 | 3B9 | P247L, N421K | 30% | 2.05 | 17% | 2.90 |
| MGFc-10 | 1E1 | K288N, A330S, P396L | 24% | 1.66 | 10% | 1.67 |
| MGFc-28 | 2C5 | N315I, V379M, T394M | 20% | 1.37 | 10% | 1.69 |
| MGFc-29 | 3D11 | F243I, V379L, G420V | 20% | 1.35 | 7% | 1.17 |
| ch4-4-20 (P54008) | | | 15% | 1.00 | 6% | 1.00 |
| MGFc-35 | 3D2 | R255Q, K326E | 11% | 0.79 | 3% | 0.53 |
| MGFc-36 | 3D3 | K218R, G281D, G385R | 10% | 0.67 | 5% | 0.78 |
| MGFc-30 | 3A8 | F275Y | 9% | 0.64 | 2% | 0.37 |
| MGFc-32 | 3C8 | D280E, S354F, A431D, L441I | 9% | 0.62 | 4% | 0.75 |
| MGFc-33 | 3C9 | K317N, F423deleted | 3% | 0.18 | −1% | −0.22 |
| MGFc-34 | 3B10 | F241L, E258G | −1% | −0.08 | −4% | −0.71 |
| MGFc-26 | | D265A | 1% | 0.08 | −3% | −0.45 |

TABLE 16

SUMMARY OF MUTANTS

| Fc Variant | Amino Acid changes | FcR3A, $K_D$/Koff | FcR2B, $K_D$/$K_{off}$ | ELISA IIIA binding | ELISA IIB binding | Phagocytosis (mutant/WT) | 4-4-20 ADCC (mutant/wt) | Anti-HER2 ADCC (mutant/wt) |
|---|---|---|---|---|---|---|---|---|
| Wt | none | 198/0.170 | 94/.094 | 1 | 1 | 1 | 1 | 1 |
| MGFc 5 | V379M | 160/0.167 | 70/0.10 | 2X | N/C | 0.86 | 2.09 | 1.77 |
| MGFc 9 | P243I, V379L | 99.7/0.105 | 120/0.113 | 1.5X | reduced | ? | 2.25 | 2.04 |
| MGFc 10 | K288N, A330S, P396L | 128/0.115 | 33.4/0.050 | 5X | 3X | 1.2 | 2.96 | 2.50 |
| MGFc 11 | F243L, R255L | 90/0.075 | 74.7/0.09 | 1x | reduced | 0.8 | 2.38 | 1.00 |
| MGFc 13 | K334E, T359N, T366S | 55.20.128 | 72/0.11 | 1.5X | N/C | [ | 1.57 | 3.67 |
| MGFc 14 | K288M, K334E | 75.4/0.1 | 95.6/0.089 | 3X | reduced | [ | 1.74 | |
| MGFc 23 | K334E, R292L | 70.2/0.105 | 108/0.107 | | | [ | 2.09 | 1.6 |
| MGFc 27 | G316D, A378V, D399E | 72/0.117 | 46/0.06 | 1.5X | 14X | 1.4 | 3.60 | 6.88 |
| MGFc 28 | N315I, A379M, D399E | | | 1X | 9X | 1.37 | 1.69 | 1.00 |
| MGFc 29 | P243I, V379L, G420V | 108/0.082 | 93.4/.101 | 2.5X | 7X | 0.93 | 1.17 | 1.00 |
| MGFc 31 | P247L, N421K | 62/0.108 | 66/0.065 | 3X | N/C | 1.35 | 2.90 | 1.00 |
| MGFc 37 | K248M | 154/0.175 | 100/0.091 | 1.4X | reduced | 0.98 | 3.83 | 0.67 |
| MGFc 38 | K392T, P396L | 84/0.104 | 50/0.041 | 4.5X | 2.5X | 1.4 | 3.07 | 2.50 |
| MGFc 39 | E293V, Q295E, A327T | 195/0.198 | 86/0.074 | 1.4X | reduced | 1.5 | 4.29 | 0.50 |
| MGFc 40 | K248M | 180/0.186 | 110/0.09 | 1.4X | reduced | 1.14 | 4.03 | |
| MGFc 41 | H268N, P396L | 178/0.159 | 46.6/0.036 | 2.2X | 4.5X | 1.96 | 2.24 | 0.67 |
| MGFc 43 | Y319F, P352L, P396L | 125/0.139 | 55.7/0.041 | 3.5X | 2X | 1.58 | 1.09 | |

5.8 Analysis of Kinetic Parameters of Fc Mutants

Kinetic parameters of the binding of ch4-4-20 antibodies harboring Fc mutants to FcγRIIIA and FcγRIIB were analyzed using a BIAcore assay (BIAcore instrument 1000, BIAcore Inc., Piscataway, N.J.). The FcγRIIIA used in this assay was a soluble monomeric protein, the extracellular region of FcγRIIIA joined to the linker-AVITAG sequence as described in Section 6.2 supra. The FcγRIIB used in this assay was a soluble dimeric protein prepared in accordance with the methodology described in U.S. Provisional Application No. 60/439,709 filed on Jan. 13, 2003, which is incorporated herein by reference. Briefly, the FcγRIIB used was the extracellular domain of FcγRIIB fused to the hinge-CH2-CH3 domain of human IgG2.

BSA-FITC (36 μg/mL in 10 mM Acetate Buffer at pH 5.0) was immobilized on one of the four flow cells (flow cell 2) of a sensor chip surface through amine coupling chemistry (by modification of carboxymethyl groups with mixture of NHS/EDC) such that about 5000 response units (RU) of BSA-FITC was immobilized on the surface. Following this, the unreacted active esters were "capped off" with an injection of 1M Et-NH2. Once a suitable surface was prepared, ch 4-4-20 antibodies carrying the Fc mutations were passed over the surface by one minute injections of a 20 μg/mL solution at a 5 μL/mL flow rate. The level of ch-4-4-20 antibodies bound to the surface ranged between 400 and 700 RU. Next, dilution series of the receptor (FcγRIIIA and FcγRIIB-Fc fusion protein) in HBS-P buffer (10 mM HEPES, 150 mM NaCl, 0.005% Surfactant P20, 3 mM EDTA, pH 7.4) were injected onto the surface at 100 μL/min Antibody regeneration between different receptor dilutions was carried out by single 5 second injections of 100 mM NaHCO₃ pH 9.4; 3M NaCl.

The same dilutions of the receptor were also injected over a BSA-FITC surface without any ch-4-4-20 antibody at the beginning and at the end of the assay as reference injections.

Once an entire data set was collected, the resulting binding curves were globally fitted using computer algorithms supplied by the manufacturer, BIAcore, Inc. (Piscataway, N.J.). These algorithms calculate both the $K_{on}$ and $K_{off}$, from which the apparent equilibrium binding constant, $K_D$ is deduced as the ratio of the two rate constants (i.e., $K_{off}/K_{on}$). More detailed treatments of how the individual rate constants are derived can be found in the BIAevaluation Software Handbook (BIAcore, Inc., Piscataway, N.J.).

Binding curves for two different concentrations (200 nM and 800 nM for FcγRIIIA and 200 nM and 400 nM for FcγRIIB fusion protein) were aligned and responses adjusted to the same level of captured antibodies, and the reference curves were subtracted from the experimental curves. Association and dissociation phases were fitted separately. Dissociation rate constant was obtained for interval 32-34 sec of the dissociation phase; association phase fit was obtained by a 1:1 Langmuir model and base fit was selected on the basis $R_{max}$ and chi$^2$ criteria.

Results

Figure 14:
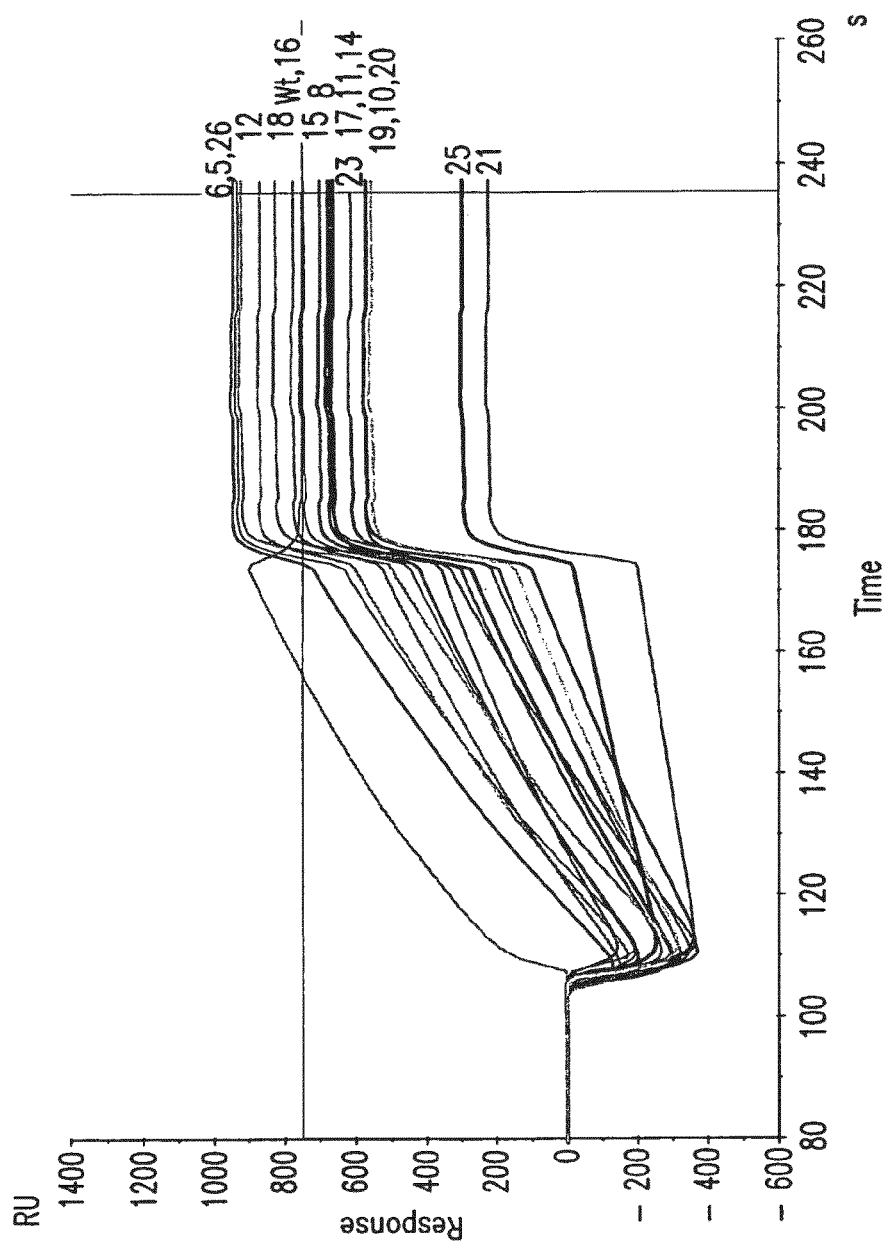

FIG. 14 shows the capture of ch 4-4-20 antibodies with mutant Fc regions on the BSA-FTIC-immobilized sensor chip. 6 μL of antibodies at a concentration of about 20 μg/mL were injected at 5 μL/min over the BSA-FITC surface. FIG. 15 is a sensogram of real time binding of FcγRIIIA to ch-4-4-20 antibodies carrying variant Fc regions. Binding of FcγRIIIA was analyzed at 200 nM concentration and resonance signal responses were normalized at the level of the response obtained for the wild type ch-4-4-20 antibody. Kinetic parameters for the binding of FcγRIIIA to ch-4-4-20 antibodies were obtained by fitting the data obtained at two different FcγRIIIA concentrations, 200 and 800 nM (FIG. 16). The solid line represents the association fit which was obtained based on the $K_{off}$ values calculated for the dissociation curves in interval 32-34 seconds. $K_D$ and $K_{off}$ represent the average calculated from the two different FcγRIIIA concentrations used. FIG. 17 is a sensogram of real time binding of FcγRIIB-Fc fusion protein to ch-4-4-20 antibodies carrying variant Fc regions. Binding of FcγRIIB-Fc fusion protein was analyzed at 200 nM concentration and resonance signal responses were normalized at the level of the response obtained for the wild type ch-4-4-20 antibody. Kinetic parameters for the binding of FcγRIIB-Fc fusion protein to ch-4-4-20 antibodies were obtained by fitting the data obtained at two different FcγRIIB-Fc fusion protein concentrations, 200 and 800 nM (FIG. 18). The solid line represents the association fit which was obtained based on the $K_{off}$ calculated for the dissociation curves in interval 32-34 seconds. $K_D$ and $K_{off}$ represent the average from the two different FcγRIIB-Fc fusion protein concentrations used.

The kinetic parameters ($K_{on}$ and $K_{off}$) that were determined from the BIAcore analysis correlated with the binding characteristic of the mutants as determined by an ELISA assay and the functional activity of the mutants as determined in an ADCC assay. Specifically, as seen in Table 17, mutants that had an enhanced ADCC activity relative to the wild-type protein, and had an enhanced binding to FcγRIIIA as determined by an ELISA assay had an improved $K_{off}$ for FcγRIIIA (i.e., a lower $K_{off}$). Therefore, a lower $K_{off}$ value for FcγRIIIA for a mutant Fc protein relative to a wild type protein may be likely to have an enhanced ADCC function. On the other hand, as seen in Table 18, mutants that had an enhanced ADCC activity relative to the wild-type protein, and had a reduced binding for FcγRIIB-Fc fusion protein as determined by an ELISA assay had a higher $K_{off}$ for FcγRIIB-Fc fusion protein.

Thus, the $K_{off}$ values for FcγRIIIA and FcγRIIB can be used as predictive measures of how a mutant will behave in a functional assay such as an ADCC assay. In fact, ratios of $K_{off}$ values for FcγRIIIA and FcγRIIB-Fc fusion protein of the mutants to the wild type protein were plotted against ADCC data (FIG. 19). Specifically, in the case of $K_{off}$ values for FcγRIIIA, the ratio of $K_{off}$(wt)/$K_{off}$(mutant) was plotted against the ADCC data; and in the case of $K_{off}$ values for FcγRIIB, the ratio of $K_{off}$(mut)/$K_{off}$(wt) was plotted against the ADCC data. Numbers higher than one (1) show a decreased dissociation rate for FcγRIIIA and an increased dissociation rate for FcγRIIB-Fc relative to wild type. Mutants that fall within the indicated box have a lower off rate for FcγRIIIA binding and a higher off-rate for FcγRIIB-Fc binding, and possess an enhanced ADCC function.

TABLE 17

Kinetic parameters of FcRIIIa binding to ch4-4-20Ab obtained by "separate fit" of 200 nM and 800 nM binding curves

| Ch4-4-20Ab | BIAcore Kd, nM | $K_{on}$ 1/Ms | $K_{off}$, 1/s | ELISA, OD | ADCC, % |
|---|---|---|---|---|---|
| Wt(0225) | 319 | 6.0 × 10$^5$ | 0.170 | 0.5 | 17.5 |
| Mut11(0225) | 90 | 8.22 × 10$^5$ | 0.075 | 0.37 | 32 |
| Mut5(0225) | 214 | 8.2 × 10$^5$ | 0.172 | 0.75 | 26 |
| Mut6(0225) | 264 | 6.67 × 10$^5$ | 0.175 | 0.6 | 23 |
| Mut8(0225) | 234 | 8.3 × 10$^5$ | 0.196 | 0.5 | 22 |
| Mut10(0225) | 128 | 9.04 × 10$^5$ | 0.115 | 1.0 | 41 |
| Mut12(0225) | 111 | 1.04 × 10$^6$ | 0.115 | 1.0 | 37 |
| Mut15(0225) | 67.9 | 1.97 × 10$^6$ | 0.133 | 1.0 | 15 |
| Mut16(0225) | 84.8 | 1.60 × 10$^6$ | 0.133 | 1.0 | 15 |
| Mut18(0225) | 92 | 1.23 × 10$^6$ | 0.112 | 1.0 | 28 |
| Mut25(0225) | 48.6 | 2.05 × 10$^6$ | 0.1 | 1.0 | 41 |
| Mut14(0225) | 75.4 | 1.37 × 10$^6$ | 0.1 | 1.1 | 28 |
| Mut17(0225) | 70.5 | 1.42 × 10$^6$ | 0.1 | 1.25 | 30 |
| Mut19(0225) | 100 | 1.20 × 10$^6$ | 0.120 | 0.75 | 11 |
| Mut20(0225) | 71.5 | 1.75 × 10$^6$ | 0.126 | 0.5 | 10 |
| Mut23(0225) | 70.2 | 1.43 × 10$^6$ | 0.105 | 1.25 | 25 |

Highlighted mutants do not fit to the group by ELISA or ADCC data.

TABLE 18

Kinetic parameters of FcRIIB-Fc binding to wild type and mutant ch4-4-20Ab obtained by "separate fit" of 200 nM and 800 nM binding curves.

| Ch4-4-20Ab | BIAcore Kd, nM | $K_{on}$ 1/Ms | $K_{off}$, 1/s | ELISA, OD | ADCC, % |
|---|---|---|---|---|---|
| Wt(0225) | 61.4 | | 0.085 | 0.4 | 17.5 |
| Mut11(0225) | 82.3 | | 0.1 | 0.08 | 32 |
| Mut5(0225) | 50 | | 0.057 | 0.6 | 26 |
| Mut6(0225) | 66.5 | | 0.060 | 0.35 | 23 |
| Mut8(0225) | 44.2 | | 0.068 | 0.25 | 22 |
| Mut10(0225) | 41.3 | | 0.05 | 1.2 | 41 |
| Mut12(0225) | 40.1 | | 0.051 | 0.4 | 37 |
| Mut15(0225) | 37.8 | | 0.040 | 1.55 | 15 |
| Mut16(0225) | 40 | | 0.043 | 1.55 | 15 |
| Mut18(0225) | 51.7 | | 0.043 | 1.25 | 28 |
| Mut25(0225) | | | 0.112 | 0.08 | 41 |
| Mut14(0225) | 95.6 | | 0.089 | 0.13 | 28 |
| Mut17(0225) | 55.3 | | 0.056 | 0.38 | 30 |
| Mut19(0225) | 45.3 | | 0.046 | 1.0 | 11 |
| Mut20(0225) | 24.1 | | 0.028 | 0.8 | 10 |
| Mut23(0225) | 108 | | 0.107 | 0.1 | 25 |

5.9 Screening for Fc Mutants Using Multiple Rounds of Enrichment Using a Solid Phase Assay The following mutant screens were aimed at identifying additional sets of mutants that show improved binding to FcγRIIIA and reduced binding to FcγRIIB. Secondary screening of selected Fc variants was performed by ELISA followed by testing for ADCC in the 4-4-20 system. Mutants were than selected primarily based on their ability to mediate ADCC via 4-4-20 using Fluorescein coated SK-BR3 cells as targets and isolated PBMC from human donors as the effector cell population. Fc mutants that showed a relative increase in ADCC, e.g., an enhancement by a factor of 2 were than cloned into anti-HER2/neu or anti-CD20 chAbs and tested in an ADCC assay using the appropriate tumor cells as targets. The mutants were also analyzed by BIAcore and their relative $K_{off}$ were determined.

Screen 1: Sequential Solid Phase Depletion and Selection Using Magnetic Beads Coated with FcγRIIB Followed by Selection with Magnetic Beads Coated with FcγRIIIA.

The aim of this screen was identification of Fc mutants that either no longer bind FcγRIIB or show reduced binding to FcγRIIB. A 10-fold excess of the naïve library (~$10^7$ cells) was incubated with magnetic beads ("My One", Dynal) coated with FcγRIIB. Yeast bound to beads were separated from the non-bound fraction by placing the tube containing the mixture in a magnetic field. Those yeast cells that were not bound to the beads were removed and placed in fresh media. They were next bound to beads that were coated with FcγRIIIA. Yeast bound to beads were separated from the nonbound fraction by placing the tube containing the mixture in a magnetic field. Nonbound yeast were removed and the bound cells were removed by vigorous vortexing. The recovered cells were regrown in glucose containing media and reinduced in selective media containing galactose. The selection process was repeated. The final culture was than used to harvest DNA. Inserts containing the Fc domain were amplified by PCR and cloned into 4-4-20. Approximately 90 Fc mutants were screened by 4-4-20 ELISA and ADCC assays and the resultant positive mutants are shown in Table 19.

TABLE 19

Mutants selected by sequential solid phase depletion and selection using Magnetic beads coated with FcγRIIB followed by selection with magnetic beads coated with FcγRIIIA.

| Mutant | Amino Acid changes |
| --- | --- |
| MgFc37 | K248M |
| MgFc38 | K392T, P396L |
| MgFc39 | E293V, Q295E, A327T |
| MgFc41 | H268N, P396LN |
| MgFc43 | Y319F, P352L, P396L |
| MgFc42 | D221E, D270E, V308A, Q311H, P396L, G402D |

Screens 2&3: Mutants Selected by FACS, Equilibrium and Kinetic Screening:

The first library screen identified a mutation at position 396, changing the amino acid from Proline to Leucine (P396L). This Fc variant showed increased binding to both FcγRIIIA and FcγRIIB. A second library was constructed using P396L as a base line. PCR mutagenesis was used to generate ~$10^7$ mutants each of which contained the P396L mutation and contained additional nucleotide changes. The P396L library was screened using two sets of conditions.

An equilibrium screen was performed using biotinylated FcγRIIIA-linker-avitag as a monomer, using methods already described. Approximately 10-fold excess of library ($10^8$ cells) was incubated in a 0.5 mL of approximately 7 nM FcγRIIIA for 1 hr. The mixture was sorted by FACS, selecting top 1.2% of binders. Selected yeast cells were grown in selective media containing glucose and reinduced in selective media containing galactose. The equilibrium screen was repeated a second time and the sort gate was set to collect the top 0.2% of binders. The selected yeast cells were then grown under selective conditions in glucose. This culture was than used to harvest DNA. Inserts containing the Fc domain were amplified by PCR and cloned into the nucleotide sequence encoding 4-4-20 variable domain using methods already described. Approximately 90 Fc mutants were screened by 4-4-20 ELISA and ADCC and the resultant positive mutants are shown in Table 20.

TABLE 20

Mutants selected by FACS using an Equilibrium screen with concentrations of FcRIIIA of approximately 7 nM.

| Mutant | Amino Acid changes |
| --- | --- |
| MgFc43b | K288R, T307A, K344E, P396L |
| MgFc44 | K334N, P396L |
| MgFc46 | P217S, P396L |
| MgFc47 | K210M, P396L |
| MgFc48 | V379M, P396L |
| MgFc49 | K261N, K210M, P396L |
| MgFc60 | P217S, P396L |

A kinetic screen was also implemented to identify mutants with improved $K_{off}$ in binding FcγRIIIA Conditions were established for screening the P396L library using a strain with the P396L Fc variant displayed on the yeast surface. Briefly cells grown under inducing conditions were incubated with 0.1 µM biotinylated FcγRIIIA-linker-avitag monomer for 1 hr. The cells were washed to remove the labeled ligand. Labeled cells were then incubated for different times with 0.1 µM unlabeled FcγRIIIA-linker-avitag monomer, washed and then stained with SA:PE for FACS analysis (FIG. 20). Cells were also stained with goat anti-human Fc to show that the Fc display was maintained during the experiment.

Figures 21A, 21B, 21C:
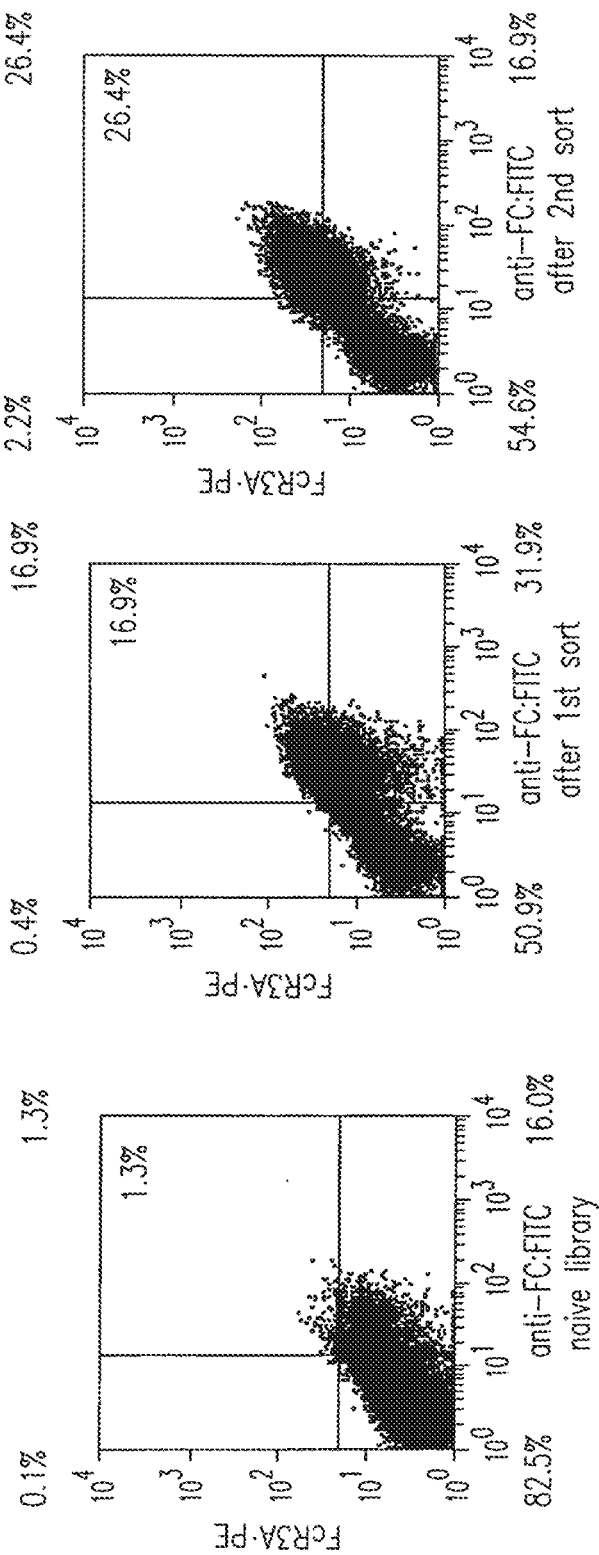

Based on the competition study it was determined that a 1 minute incubation resulted in approximately 50% loss of cell staining This time point was chosen for the kinetic screen using the P396L library. Approximately 10-fold excess of library ($10^8$ cells) was incubated with 0.1 µM biotinylated FcγRIIIA-linker-avitag monomer in a 0.5 mL volume. Cells were washed and then incubated for 1 minute with unlabeled ligand. Subsequently the cells were washed and labeled with SA:PE. The mixture was sorted by FACS, selecting the top 0.3% of binders. Selected yeast cells were grown in selective media containing glucose and reinduced in selective media containing galactose. The kinetic screen was repeated a second time and the sort gate was set to collect the top 0.2% of binders. The nonselected P396L library was compared to the yeast cells selected for improved binding by FACS (FIG. 21). The histograms show the percentage of cells that are costained with both Fc RIIIA/PE and goat anti-human Fc/FITC (upper right).

The selected yeast cells from the second sort were then grown under selective conditions in glucose. This culture was than used to harvest DNA. Inserts containing the Fc domain were amplified by PCR and cloned into the nucleotide sequence encoding 4-4-20 variable domain using methods described above. Approximately 90 Fc mutants were screened by 4-4-20 ELISA and ADCC and the resultant positive mutants are shown in Table 21.

TABLE 21

Mutants selected by FACS using a Kinetic screen using equimolar amounts of unlabeled CD16A for 1 minute.

| Mutants | Amino Acid changes |
| --- | --- |
| MgFc50 | P247S, P396L |
| MgFc51 | Q419H, P396L |
| MgFc52 | V240A, P396L |
| MgFc53 | L410H, P396L |
| MgFc54 | F243L, V305I, A378D, F404S, P396L |
| MgFc55 | R255I, P396L |
| MgFc57 | L242F, P396L |
| MgFc59 | K370E, P396L |

Screens 4 and 5: Combining the Solid Phase FcγRIIB Depletion Step with FcγRIIIA Selection by FACs Sort, Using the FcγRIIIA 158V Allele Analysis of Fc variants from Screen 1 showed that the mutations that were selected from the secondary screen had improved binding to both FcγRIIIA and FcγRIIB. Therefore, the data suggested that sequential depletion and selection using magnetic beads (solid phase) under the established conditions did not efficiently select for differential binding of FcγRIIIA and FcγRIIB. Therefore, in order to screen more effectively for mutants that bind FcγRIIIA, while having reduced or no binding to FcγRIIB, the solid phase FcγRIIB depletion step was combined with FcγRIIIA selection by FACs sort. This combination identified Fc variants that bind FcγRIIIA with greater or equal affinity than wild-type Fc.

A 10-fold excess of the naïve library (~$10^7$) was incubated with magnetic beads coated with FcγRIIB. Yeast bound to beads were separated from the non-bound fraction by placing the tube containing the mixture in a magnetic field. Those yeast cells that were not bound to the beads were removed and placed in fresh media and subsequently reinduced in media containing galactose. The FcγRIIB depletion by magnetic beads was repeated 5 times. The resulting yeast population was analyzed and found to show greater than 50% cell staining with goat anti-human Fc and a very small percentage of cells were stained with FcγRIIIA. These cells were then selected twice by a FACS sort using 0.1 µM biotinylated FcγRIIIA linker-avitag (data not shown). The FcγRIIIA was the 158V allotype. Yeast cells were analyzed for both FcγRIIIA and FcγRIIB binding after each sort and compared to binding by wild-type Fc domain (FIGS. 22A-B).

The selected yeast cells from the second sort were then grown under selective conditions in glucose. This culture was then used to harvest DNA. Inserts containing the Fc domain were amplified by PCR and cloned into the nucleotide sequence encoding 4-4-20 variable domain. Approximately 90 Fc mutants were screened by 4-4-20 ELISA and ADCC and the resultant positive mutants are shown in Table 22 (mutants 61-66).

TABLE 22

Mutants selected by magnetic bead depletion using beads coated with CD32B and final selection by FACS using FcγRIIIA 158Valine or 158Phenylalanine

| Mutants | Amino Acid Changes |
| --- | --- |
| MgFc61 | A330V |
| MgFc62 | R292G |
| MgFc63 | S298N, K360R, N361D |
| MgFc64 | E233G |
| MgFc65 | N276Y |
| MgFc66 | A330V, V427M |
| MgFc67 | V284M, S298N, K334E, R355W, R416T |

Screening of Fc Mutants Using the 158F Allele of FcγRIIIA:

Two different alleles of FcγRIIIA receptor exist that have different binding affinities for the IgG1 Fc domain (Koene et al., 1997, *Blood* 90: 1109-1114; Wu et al., 1997, *J. Clin. Invest.* 100: 1059-70). The 158F allele binds to the Fc domain with a binding constant 5-10 fold lower than the 158V allele. Previously all of the Fc screens using yeast display were done using the high binding 158V allele as a ligand. In this experiment, Fc mutants were selected from the FcγRIIB depleted yeast population using biotinylated FcγRIIIA158F-linker-avitag monomer as a ligand. The sort gate was set to select the top 0.25 percent FcγRIIIA 158F binders. The resulting enriched population was analyzed by FACS (FIG. 22B). Individual clones were then isolated and their binding to different FcγRs were analyzed by FACS (FIG. 22B). Analysis of individual clones from the population resulted in the identification of a single mutant harboring 5 mutations MgFc67 (V284M, S298N, K334E, R355W, R416S), which had an enhanced binding to FcγRIIIA and a reduced binding to FcγRIIB.

Secondary Screen of Mutants by an ADCC Assay for Screens 1, 2, and 3:

Mutants that were selected in the above screens were then analyzed using a standard ADCC assay to determine the relative rates of lysis mediated by ch4-4-20 harboring the Fc mutants. ch4-4-20 antibodies carrying the Fc variants were constructed using methods already described above. SK-BR3 cells were used as targets and effector cells were PBMC that were isolated from donors using a Ficoll gradient, as described supra (Section 6.7). The ADCC activity results for the mutants are summarized in Table 23.

As seen in Table 23, mutants isolated using the above primary and secondary screens based on FcγRIIB depletion and FcγRIIIA selection showed enhanced ADCC activity relative to wild-type.

TABLE 23

Analysis of ADCC mediated by 4-4-20 anti-Fluorescein antibody on SKBR3 cells coated with fluorescein.

| Mutant | Amino Acid Change | Relative rate of lysis |
| --- | --- | --- |
| MgFc37 | K248M | 3.83 |
| MgFc38 | K392T, P396L | 3.07 |
| MgFc39 | E293V, Q295E, A327T | 4.29 |
| MgFc41 | H268N, P396LN | 2.24 |
| MgFc43 | Y319F, P352L, P396L | 1.09 |
| MgFc42 | D221E, D270E, V308A, Q311H, P396L, G402D | 3.17 |
| MgFc43b | K288R, T307A, K344E, P396L | 3.3 |
| MgFc44 | K334N, P396L | 2.43 |
| MgFc46 | P217S, P396L | 2.04 |
| MgFc47 | K210M, P396L | 2.02 |
| MgFc48 | V379M, P396L | 2.01 |
| MgFc49 | K261N, K210M, P396L | 2.06 |
| MgFc50 | P247S, P396L | 2.1 |
| MgFc51 | Q419H, P396L | 2.24 |
| MgFc52 | V240A, P396L | 2.35 |
| MgFc53 | L410H, P396L | 2 |
| MgFc54 | F243L, V305I, A378D, F404S, P396L | 3.59 |
| MgFc55 | R255I, P396L | 2.79 |
| MgFc57 | L242F, P396L | 2.4 |
| MgFc59 | K370E, P396L | 2.47 |
| MgFc60 | P217S, P396L | 1.44 |

Mutants 37, 38, 39, 41, 43 were analyzed using 0.5 µg/mL ch4-4-20. All other antibodies were tested at 1 µg/mL. All rates were normalized to wild type ch4-4-20 (IgG1).

Mutants were additionally cloned into the heavy chain of antitumor monoclonal antibody 4D5 (anti-HER2/neu) and anti-CD20 monoclonal antibody 2H7 by replacing the Fc domain of these monoclonal antibodies. These chimeric monoclonal antibodies were expressed and purified and tested in an ADCC assay using standard methods by transient transfection into 293H cells and purification over protein G column. The chimeric 4D5 antibodies were tested in an ADCC assay using SK-BR3 cells as targets (FIG. 23), whereas the chimeric 2H7 antibodies were tested in an ADCC assay using Daudi cells as targets (FIG. 24).

Secondary Screen of Mutants Via BIAcore:

Mutants that were selected in the above screens were then analyzed by BIAcore to determine the kinetic parameters for binding FcγRIIIA(158V) and FcγRIIB. The method used was similar to that disclosed in Section 6.8, supra.

The data displayed are $K_{off}$ values relative to wild type off rates as determined from experiments using the Fc mutants in the ch4-4-20 monoclonal antibody. Relative numbers greater than one indicate a decrease in $K_{off}$ rate. Numbers less than one indicate an increase in off rate.

Mutants that showed a decrease in off rates for FcγRIIIA were MgFc38 (K392, P396L), MgFc43 (Y319F, P352L, P396L), MgFc42 (D221E, D270E, V308A, Q311H, P396L, G402D), MgFc43b (K288R, T307A, K344E, P396L), MgFc44 (K334N, P396L), MgFc46 (P217S, P396L), MgFc49 (K261N, K210M, P396L). Mutants that showed a decrease in off rate for FcγRIIB were, MgFc38 (K392, P396L), MgFc39 (E293V, Q295E, A327T), MgFc43 (K288R, T307A, K344E, P396L), MgFc44 (K334N, P396L). The Biacore data is summarized in Table 24.

TABLE 24

BIAcore data.

| Fc mutant | AA residues | FcγRIIIA158V (Koff WT/Mut) | FcγRIIB (Koff WT/Mut) |
|---|---|---|---|
| MgFc37 | K248M | 0.977 | 1.03 |
| MgFc38 | K392T, P396L | 1.64 | 2.3 |
| MgFc39 | E293V, Q295E, A327T | 0.86 | 1.3 |
| MgFc41 | H268N, P396LN | 0.92 | 1.04 |
| MgFc43 | Y319F, P352L, P396L | 1.23 | 2.29 |
| MgFc42 | D221E, D270E, V308A, Q311H, P396L, G402D | 1.38 | |
| MgFc43b | K288R, T307A, K344E, P396L | 1.27 | 0.89 |
| MgFc44 | K334N, P396L | 1.27 | 1.33 |
| MgFc46 | P217S, P396L | 1.17 | 0.95 |
| MgFc47 | K210M, P396L | | |
| MgFc48 | V379M, P396L | | |
| MgFc49 | K261N, K210M, P396L | 1.29 | 0.85 |
| MgFc50 | P247S, P396L | | |
| MgFc51 | Q419H, P396L | | |
| MgFc52 | V240A, P396L | | |
| MgFc53 | L410H, P396L | | |
| MgFc54 | F243L, V305I, A378D, F404S, P396L | | |
| MgFc55 | R255l, P396L | | |
| MgFc57 | L242F, P396L | | |
| MgFc59 | K370E, P396L | | |
| MgFc60 | P217S, P396L | | |
| MgFc61 | A330V | 1 | 0.61 |
| MgFc62 | R292G | 1 | 0.67 |
| MgFc63 | S298N, K360R, N361D | 1 | 0.67 |
| MgFc64 | E233G | 1 | 0.54 |
| MgFc65 | N276Y | 1 | 0.64 |
| MgFc66 | A330V, G427M, | 1 | 0.62 |
| MgFc67 | V284M, S298N, K334E, R355W, R416T | | |

5.10 PBMC Mediated ADCC Assays

Materials and Methods

Fc variants that show improved binding to FcγRIIIA were tested by PBMC based ADCC using 60:1 effector:target ratio. Two different tumor model systems were used as targets, SK-BR3 (anti-HER2/neu) and Daudi (anti-CD20). Percent specific Lysis was quantitated for each mutant. Linear regression analysis was used to plot the data setting the maximal percent lysis at 100%.

ADCC is activated on immune system effector cells via a signal transduction pathway that is triggered by an interaction between low affinity FcγR and an immune complex. Effector cell populations were derived from either primary blood or activated monocyte derived macrophages (MDM). Target cells were loaded with europium and incubated with chimeric MAb and subsequently incubated with effector cell populations. Europium works the same way as $^{51}Cr$, but it is non-radioactive and the released europium is detected in a fluorescent plate reader. Lymphocytes harvested from peripheral blood of donors (PBM) using a Ficoll-Paque gradient (Pharmacia) contain primarily natural killer cells (NK). The majority of the ADCC activity will occur via the NK containing FcγRIIIA but not FcγRIIB on their surface.

Experiments were performed using two different target cell populations, SK-BR-3 and Daudi, expressing HER2/neu and CD20, respectively. ADCC assays were set up using Ch4-4-20/FITC coated SK-BR-3, Ch4D5/SKBR3, and Rituxan/Daudi (data not shown). Chimeric MAbs were modified using Fc mutations identified. Fc mutants were cloned into Ch4D5. Purified Ab was used to opsonize SK-BR-3 cells or Daudi cells. Fc mutants were cloned into Ch4D5.

Results.

Fc mutants showed improved PBMC mediated ADCC activity in SK BR3 cells (FIG. 27). The plot shows linear regression analysis of a standard ADCC assay. Antibody was titrated over 3 logs using an effector to target ratio of 75:1. % lysis=(Experimental release−SR)/(MR−SR)*100.

Fc mutants showed improved PBMC mediated ADCC activity in Daudi cells (FIG. 28).

5.11 Monocyte Derived Macrophage (MDM) Based ADCC Assays

FcγR dependent tumor cell killing is mediated by macrophage and NK cells in mouse tumor models (Clynes et al., 1998, PNAS USA, 95: 652-6). Elutriated monocytes from donors were used as effector cells to analyze the efficiency Fc mutants to trigger cell cytotoxicity of target cells in ADCC assays. Expression patterns of FcγRI, FcγR3A, and FcγR2B are affected by different growth conditions. FcγR expression from frozen monocytes cultured in media containing different combinations of cytokines and human serum were examined by FACS using FcR specific MAbs. (FIG. 29). Cultured cells were stained with FcγR specific antibodies and analyzed by FACS to determine MDM FcγR profiles. Conditions that best mimic macrophage in vivo FcγR expression, i.e., showed the greatest fraction of cells expressing CD16 and CD32B were used in a monocyte derived macrophage (MDM) based ADCC assay. For the experiment in FIG. 29, frozen elutriated monocytes were grown for 8 days in DMEM and 20% FBS containing either M-CSF (condition 1) or GM-CSF (condition 2). For the experiment in FIG. 30, frozen elutriated monocytes were cultured for 2 days in DMEM and 20% FBS containing GM-CSF, IL-2 and IFNγ prior to ADCC assay. Serum free conditions have also been developed which allow for high levels of CD16 and CD32B expression (data not shown). Briefly, purified monocytes were grown for 6-8 days in Macrophage-SFM (Invitrogen) containing GM-CSF, M-CSF, IL-6, IL-10, and IL-1β. While the incidence of CD32B+/CD16+ cells in these cultures is highest using a mixture of cytokines, combinations of two of more cytokines will also enhance FcγR expression (M-CSF/IL-6, M-CSF/IL-10; or M-CSF/IL-1β). For ADCC assays, IFNγ is added for the final 24-48 hours.

MDM based ADCC required incubation times of >16 hrs to observe target cell killing. Target cells were loaded with Indium-111 which is retained for long incubations within the target cells. Indium release was quantitated using a gamma counter. All other reagents, Abs and target cells, were similar to the PBMC based ADCC assay. ADCC activity due to FcγRI can be efficiently blocked using the anti-FcRI blocking antibody (M21, Ancell). The assay conditions differ slightly from the PBMC based assay. 20:1 target to effector; 18-14 hr incubation at 37 C.

Fc mutants that show improved PBMC ADCC, increased binding to FcγRIIIA, or decreased binding to FcγRIIB were tested (FIG. 30).

5.12 Effect of Fc Mutants on Complement Activity

Fc mutants were originally identified based on their increased binding to FcγRIIIA. These mutants were subsequently validated for their improved affinity for all low affinity receptors and in many cases improved activity in ADCC mediated by PBMC. In vivo antibody mediated cytotoxicity can occur through multiple mechanisms. In addition to ADCC other possible mechanisms include complement dependent cytotoxicity (CDC) and apoptosis. The binding of C1q to the Fc region of an immunoglobulin initiates as cascade resulting in cell lysis by CDC. The interaction between C1q and the Fc has benn studies in a series of Fc mutants. The results of these experiments indicate that C1q and the low affinity FcR bind to overlapping regions of the Fc, however the exact contact residues within the Fc vary.

Mutants that showed improved ADCC in the PBMC based assay were examined for their effect in CDC. Antibodies were analyzed in the anti CD20 Ch-mAb, 2H7. We detected improved CDC for each mutant ch-mAb tested. Interestingly even though these mutants were selected for their improved ADCC they also show enhanced CDC Materials and Methods.

Figure 31:
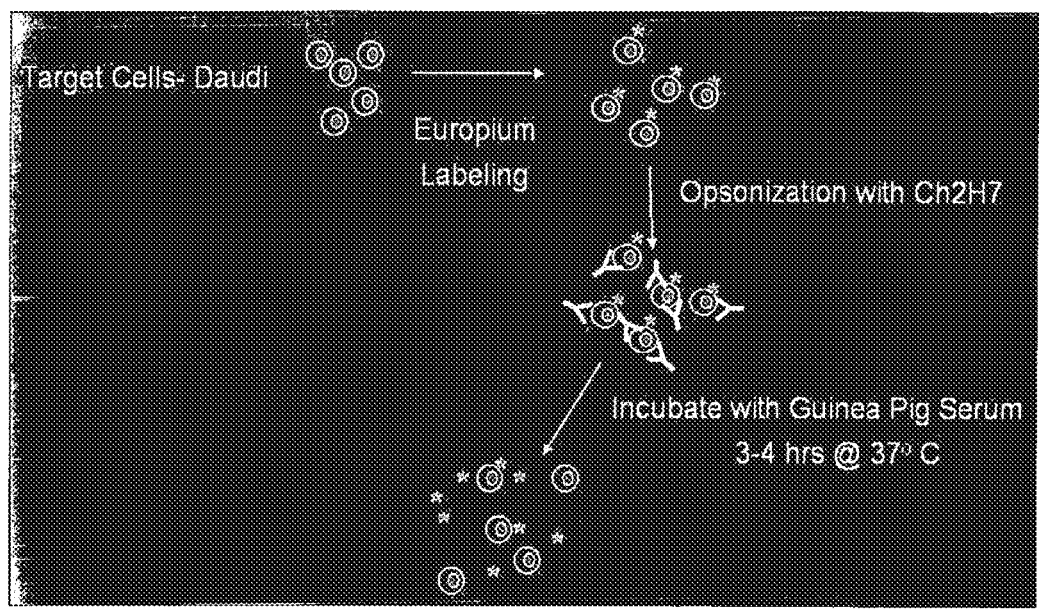

CDC assay was used to test the Fc mutants using anti-CD20 and Daudi cells as targets. Guinea Pig Serum was used as the source for complement (US Biological). The CDC assay was similar to PBMC based ADCC. Target cells were loaded with europium and opsonized with ChMAb. However complement, guinea pig serum, was added instead of effector cells. FIG. 31 shows a flow chart of the assay. Anti-CD20 ChMab over 3 orders of magnitude was titrated. % lysis was calculated. Daudi cells, $(3 \times 10^6)$ were labeled with BADTA reagent. $1 \times 10^4$ cells were aliquoted into wells in a 96 well plate. Antibodies were titrated into the wells using 3 fold dilutions. The opsonization reaction was allowed to proceed for 30-40 minutes at 37° C. in 5% $CO_2$. Guinea pig serum was added to a final conc. of 20%. The reaction was allowed to proceed for 3.5 hrs at 37° C. in 5% $CO_2$. Subsequently, 100 uls of cell media was added to the reaction and cells were spun down. For detection 20 uls of the supernatant was added to 200 uls of the Europium solution and the plates were read in the Victor2 (Wallac).

Figure 32:
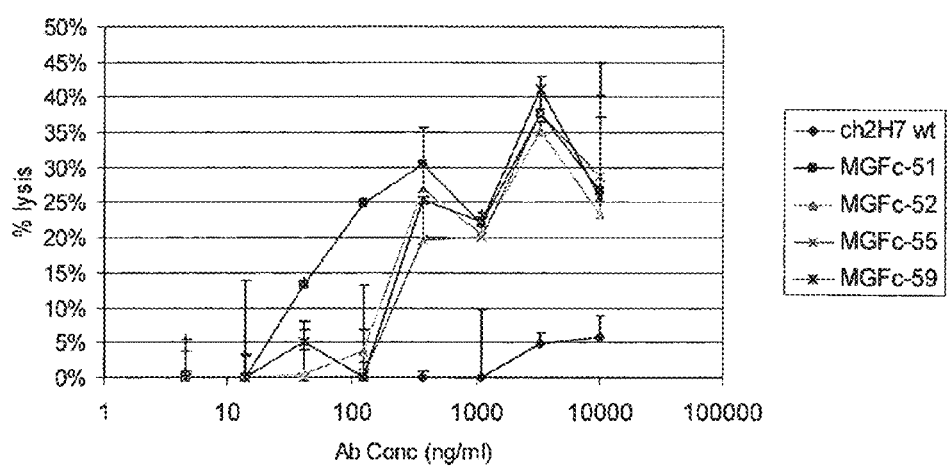

Results:

All mutants that show improved binding for either activating FcR or C1q were placed in the CDC assay (FIG. 32). Fc mutants that showed enhanced binding to FcγRIIIA also showed improved complement activity. Each of the mutants show enhanced complement activity compared to wild type. The mutants tested are double mutants. In each case one of the mutations present is P396L.

Figure 35:
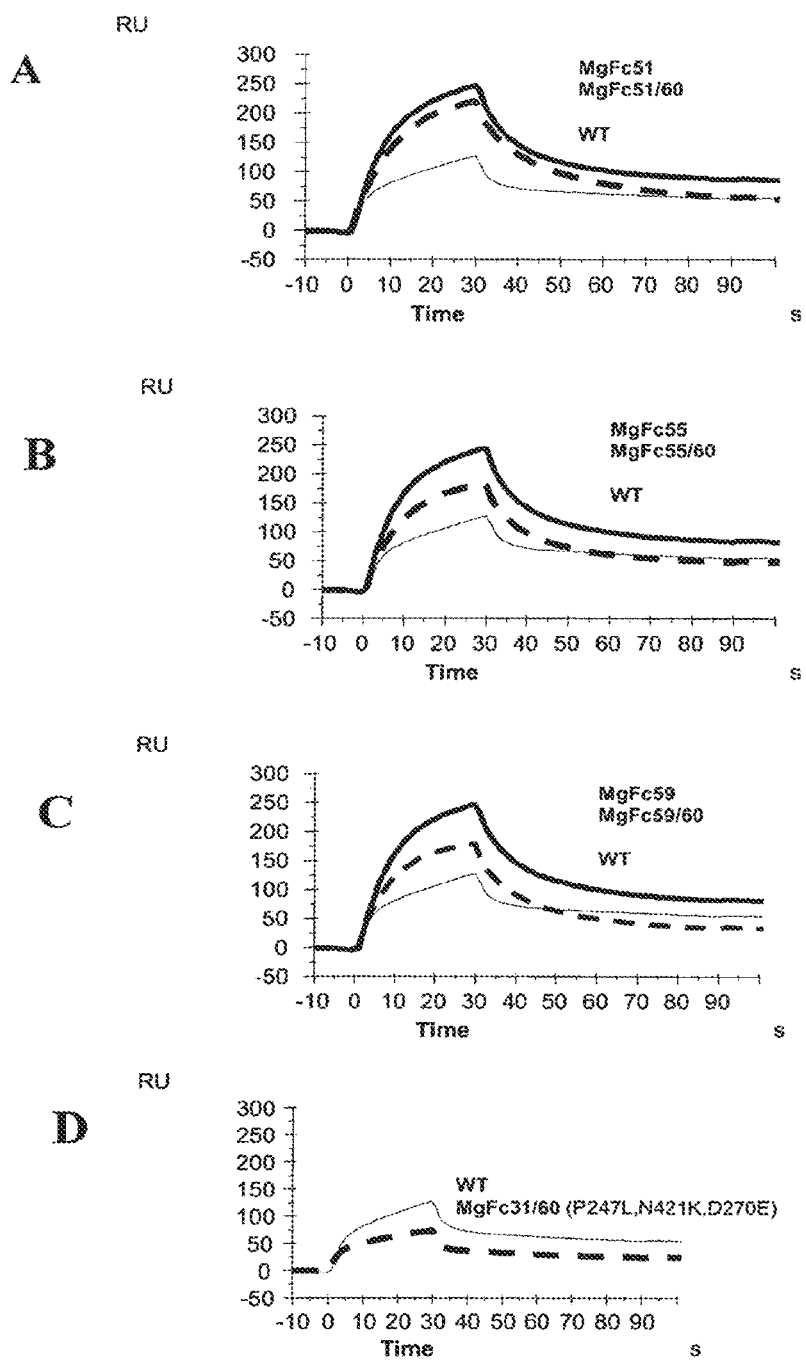

To determine whether the increase in CDC correlated with increased binding of C1q to IgG1 Fc binding between the two proteins was measured in realtime using surface plasmon resonance. In order to examine the binding between C1q and an IgG1 Fc the Fc variants were cloned into an anti-CD32B ch-mAb, 2B6. This allowed us to capture the wt and mutant antibodies to the glass slide via soluble CD32B protein (FIG. 34A). Three of the four mutants tested in CDC were also examined in the Biacore. All 3 showed greatly enhanced $K_{off}$ compare to wild type Fc (FIG. 34B). Biacore format for C1q binding to 2B6 mutants demonstrate enhanced binding of mutants with P396L mutation (FIG. 35). Mutation D270E can reduce C1q binding at different extent. A summary of the kinetic analysis of FcγR and C1q binding is depicted in the table 25 below.

TABLE 25

KINETIC ANALYSIS OF FcgR and C1q binding to mutant 2B6

| 2B6Mutants | 3aV158 | 3aF158 | 2bfcagl | 2aR131Fcagl | 2aH131Fcagl | C1q |
|---|---|---|---|---|---|---|
| WT | 0.192 | 0.434 | 0.056 | 0.070 | 0.053 | 0.124 |
| MgFc38 (K392T, P396L) | 0.114 | 0.243 | 0.024 | 0.028 | 0.024 | 0.096 |
| MgFc51 (Q419H, P396L) | 0.142 | 0.310 | 0.030 | 0.036 | 0.028 | 0.074 |
| MgFc55 (R255I, P396L) | 0.146 | 0.330 | 0.030 | 0.034 | 0.028 | 0.080 |
| MgFc59 (K370E, P396L) | 0.149 | 0.338 | 0.028 | 0.033 | 0.028 | 0.078 |
| MgFc31/60 | 0.084 | 0.238 | 0.094 | 0.127 | 0.034 | 0.210 |
| MgFc51/60 | 0.112 | 0.293 | 0.077 | 0.089 | 0.028 | 0.079 |
| MgFc55/60 | 0.113 | 0.288 | 0.078 | 0.099 | 0.025 | 0.108 |
| MgFc59/60 | 0.105 | 0.296 | 0.078 | 0.095 | 0.024 | 0.107 |

5.13 Designing Fc Variants with Decreased Binding to FcγRIIB

Based on a selection for Fc mutants that reduce binding to FcγRIIB and increase binding to FcγRIIA 131H a number of mutations including D270E was identified. Each mutation was tested individually for binding to the low affinity Fc receptors and their allelic variants.

D270E had the binding characteristics that suggested it would specifically reduce FcγRIIB binding. D270E was tested in combination with mutations that were previously identified based on their improved binding to all FcR.

Results.

Figure 36:
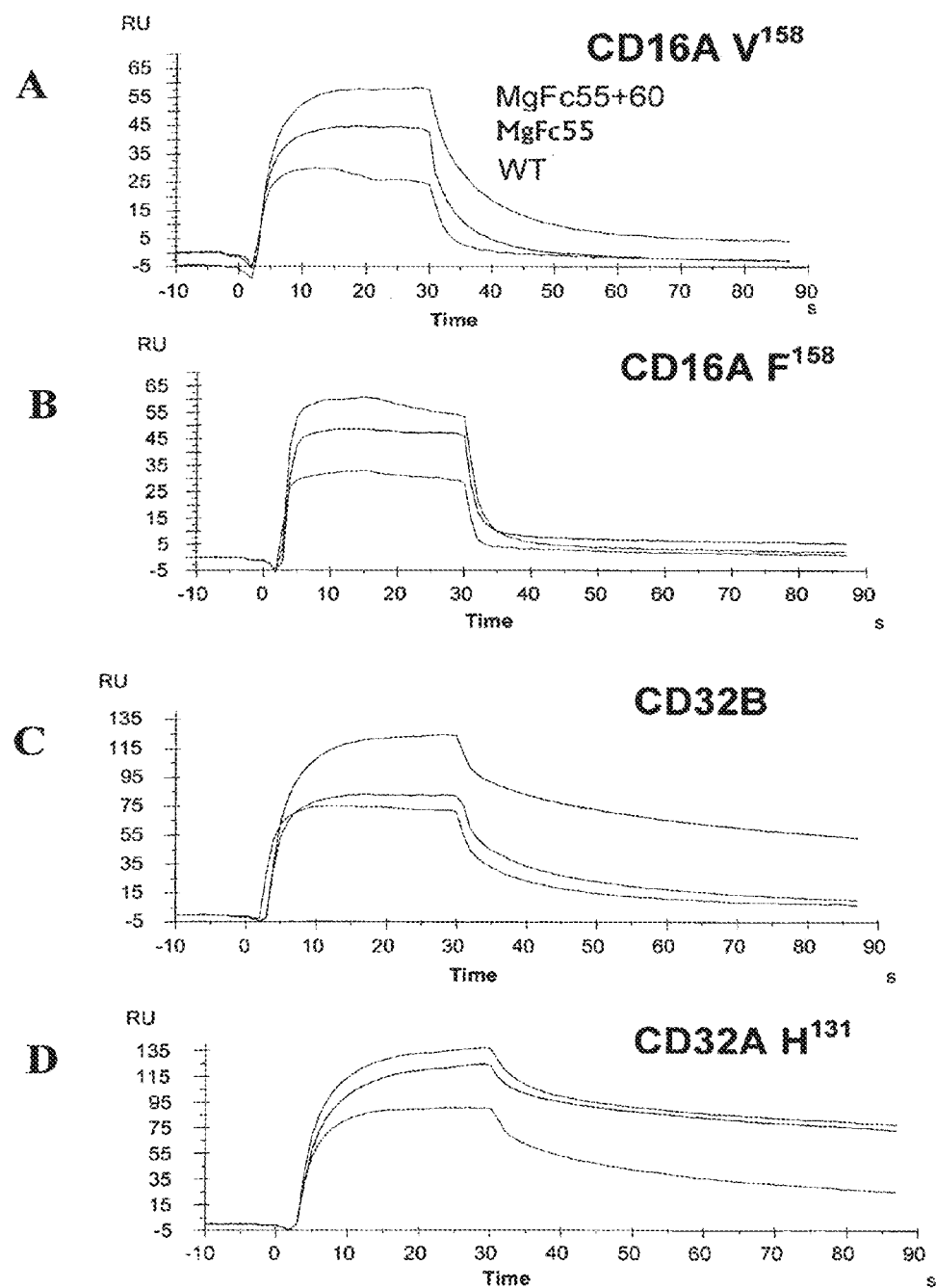
Figure 37:
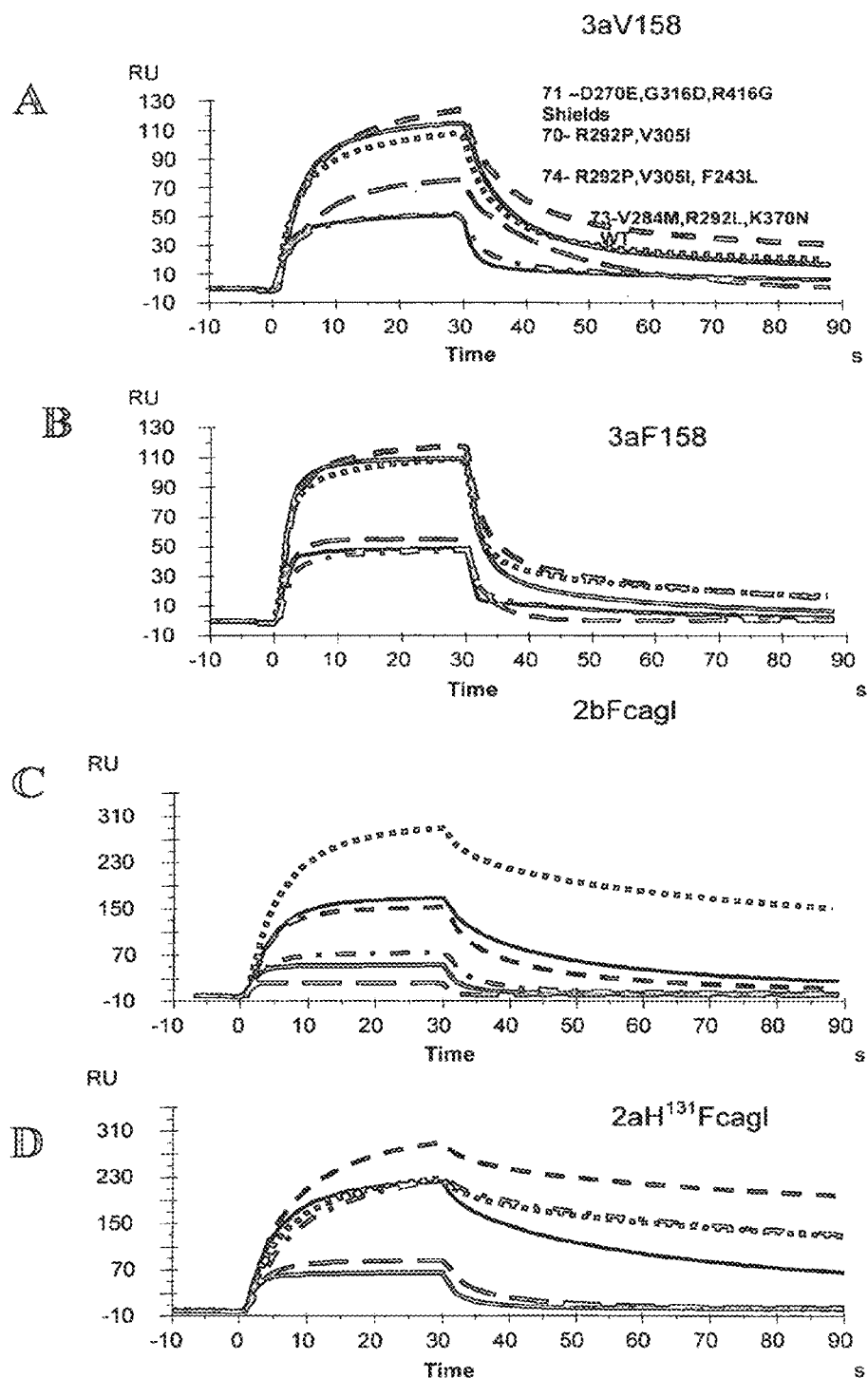

As shown in Tables 26 and 27 and FIGS. 36 and 37 addition of D270E mutation enhances FcγRIIIA and FcγRIIA H131 binding and reduces binding to FcγRIIB. FIG. 38 shows the plot of MDM ADCC data against the Koff as determined for CD32A H131H binding for select mutants.

TABLE 26

ADDITION OF D270E MUTATION ENHANCES FcγRIIIA AND FcγRIIA H131 BINDING AND REDUCES FcγRIIB BINDING

| 4D5Mutants | 3aV158 | 3aF158 | 2bfcagl | 2aR131Fcagl | 2aH131Fcagl |
|---|---|---|---|---|---|
| Wt pure | 0.175 | 0.408 | 0.078 | 0.067 | 0.046 |
| MgFc55 | 0.148 | 0.381 | 0.036 | 0.033 | 0.029 |
| MgFc55/60 | 0.120 | 0.320 | 0.092 | 0.087 | 0.013 |
| MgFc55/60 + R292G | 0.116 | 0.405 | 0.124 | 0.112 | 0.037 |

TABLE 26-continued

ADDITION OF D270E MUTATION ENHANCES
FcγRIIIA AND FcγRIIA H131 BINDING AND
REDUCES FcγRIIB BINDING

| 4D5Mutants | 3aV158 | 3aF158 | 2bfcagl | 2aR131Fcagl | 2aH131Fcagl |
|---|---|---|---|---|---|
| MgFc55/60 + Y300L | 0.106 | 0.304 | 0.092 | 0.087 | 0.015 |
| MgFc52 | 0.140 | 0.359 | 0.038 | 0.040 | 0.026 |
| MgFc52/60 | 0.122 | 0.315 | 0.094 | 0.087 | 0.013 |
| MgFc59 | 0.145 | 0.378 | 0.039 | 0.047 | 0.033 |
| MgFc59/60 | 0.117 | 0.273 | 0.088 | 0.082 | 0.012 |
| MgFc31 | 0.125 | 0.305 | 0.040 | 0.043 | 0.030 |
| MgFc31/60 | 0.085 | 0.215 | 0.139 | 0.132 | 0.020 |
| MgFc51 | 0.135 | 0.442 | 0.060 | 0.047 | 0.062 |
| MgFc51/60 | 0.098 | 0.264 | 0.118 | 0.106 | 0.023 |
| MgFc38 | 0.108 | 0.292 | 0.034 | 0.025 | 0.032 |
| MgFc38/60 | 0.089 | 0.232 | 0.101 | 0.093 | 0.021 |

TABLE 27

KINETIC CHARACTERISTICS OF 4D5 MUTANTS

| 4D5Mutants | 3aV158 | 3aF158 | 2bfcagl | 2aR131Fcagl | 2aH131Fcagl |
|---|---|---|---|---|---|
| MgFc70 | 0.101 | 0.250 | 0.030 | 0.025 | 0.025 |
| MgFc71 | 0.074 | 0.212 | 0.102 | 0.094 | 0.020 |
| MgFc73 | 0.132 | 0.306 | 0.190 | — | 0.024 |
| MgFc74 | 0.063 | 0.370 | n.b. | 0.311 | 0.166 |
| WT023stable | 0.150 | 0.419 | 0.071 | 0.068 | 0.043 |

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout this application various publications are cited. Their contents are hereby incorporated by reference into the present application in their entireties for all purposes.

What is claimed is:

1. A polypeptide having a variant Fc region wherein said variant Fc region:
   (A) contains a CH2 domain and a CH3 domain;
   (B) possesses an amino acid sequence that differs from the amino acid sequence of a wild-type Fc region by comprising amino acid modifications at positions 292, 305 and 243, relative to said wild-type Fc region, wherein said numbering is that of the EU index as in Kabat; and
   (C) binds to FcγR with an altered affinity relative to that of said wild-type Fc region.

2. The polypeptide of claim 1, wherein said modifications comprise the modifications R292P, V305I and F243L.

3. The polypeptide of claim 1, wherein said variant Fc region of said polypeptide additionally comprises a modification that enhances C1q binding, said modification being:
   (1) P247L and N421K;
   (2) R255L and P396L;
   (3) K370E and P396L;
   (4) K392T and P396L;
   (5) P396L and V240A; or
   (6) P396L and Q419H.

4. The polypeptide of claim 1, wherein said variant Fc region of said polypeptide additionally comprises a modification at position 297.

5. The polypeptide of claim 1, wherein said polypeptide is an antibody that contains said variant Fc region.

6. The antibody of claim 5, wherein said antibody is antibody produced by hybridoma clone: 1D5 (ATCC accession number PTA-5958), 1F2 (ATCC accession number PTA-5959), 2D11 (ATCC accession number PTA-5960), 2E1 (ATCC accession number PTA-5961) or 2H9 (ATCC accession number PTA-5962).

7. A composition comprising the polypeptide of claim 1, and a pharmaceutically acceptable carrier.

8. A composition comprising the antibody of claim 5, and a pharmaceutically acceptable carrier.

* * * * *

SEQUENCE LISTING

<160> NUMBER OF SEQ ID NOS: 10

<210> SEQ ID NO 1
<211> LENGTH: 86
<212> TYPE: DNA
<213> ORGANISM: Artificial Sequence
<220> FEATURE:
<223> OTHER INFORMATION: Primer: 5' linker.avitag

<400> SEQUENCE: 1
ggccgcaggt ggtggtggtt ctggtggtgg tggttctggt ctgaacgaca tcttcgaggc     60
tcagaaaatc gaatggcacg aatgat                                         86

<210> SEQ ID NO 2
<211> LENGTH: 86
<212> TYPE: DNA
<213> ORGANISM: Artificial Sequence
<220> FEATURE:
<223> OTHER INFORMATION: Primer: 3' linker.avitag

<400> SEQUENCE: 2
ctagatcatt cgtgccattc gattttctga gcctcgaaga tgtcgttcag accagaacca     60
ccaccaccag aaccaccacc acctgc                                         86

<210> SEQ ID NO 3
<211> LENGTH: 35
<212> TYPE: DNA
<213> ORGANISM: Artificial Sequence
<220> FEATURE:
<223> OTHER INFORMATION: Primer: FcR3A left

<400> SEQUENCE: 3
gttggatcct ccaactgctc tgctacttct agttt                               35

<210> SEQ ID NO 4
<211> LENGTH: 34
<212> TYPE: DNA

```
<213> ORGANISM: Artificial Sequence
<220> FEATURE:
<223> OTHER INFORMATION: Primer: FcR3A Right

<400> SEQUENCE: 4
gaaaagctta agaatgatg agatggttga cact                                    34

<210> SEQ ID NO 5
<211> LENGTH: 31
<212> TYPE: DNA
<213> ORGANISM: Artificial Sequence
<220> FEATURE:
<223> OTHER INFORMATION: Primer: FcR2B right

<400> SEQUENCE: 5
gaagtcgaca atgatcccca ttggtgaaga g                                      31

<210> SEQ ID NO 6
<211> LENGTH: 30
<212> TYPE: DNA
<213> ORGANISM: Artificial Sequence
<220> FEATURE:
<223> OTHER INFORMATION: Primer: FcR2B left

<400> SEQUENCE: 6
gttagatctt gctgtgctat tcctggctcc                                        30

<210> SEQ ID NO 7
<211> LENGTH: 27
<212> TYPE: DNA
<213> ORGANISM: Artificial Sequence
<220> FEATURE:
<223> OTHER INFORMATION: Primer: IgG1 right

<400> SEQUENCE: 7
atagtcgacc actgatttac ccggaga                                           27

<210> SEQ ID NO 8
<211> LENGTH: 31
<212> TYPE: DNA
<213> ORGANISM: Artificial Sequence
<220> FEATURE:
<223> OTHER INFORMATION: Primer: IgG1 left

<400> SEQUENCE: 8
ggaattcaac accaaggtgg acaagaaagt t                                      31

<210> SEQ ID NO 9
<211> LENGTH: 31
<212> TYPE: DNA
<213> ORGANISM: Artificial Sequence
<220> FEATURE:
<223> OTHER INFORMATION: Primer: mcr025;chl (f')

<400> SEQUENCE: 9
aaaggatccg cgagctcagc ctccaccaag g                                      31

<210> SEQ ID NO 10
<211> LENGTH: 20
<212> TYPE: DNA
<213> ORGANISM: Artificial Sequence
<220> FEATURE:
<223> OTHER INFORMATION: Primer: H021

<400> SEQUENCE: 10
gtctgctcga agcattaacc                                                   20
```